(12) United States Patent
Yu

(10) Patent No.: US 11,541,029 B2
(45) Date of Patent: Jan. 3, 2023

(54) HIGH PENETRATION COMPOSITIONS AND THEIR APPLICATIONS

(75) Inventor: Chongxi Yu, Plainfield, IL (US)

(73) Assignee: Techfields Pharma Co., Ltd., Suzhou (CN)

( * ) Notice: Subject to any disclaimer, the term of this patent is extended or adjusted under 35 U.S.C. 154(b) by 0 days.

(21) Appl. No.: 13/133,021

(22) PCT Filed: Dec. 4, 2009

(86) PCT No.: PCT/US2009/066884
§ 371 (c)(1),
(2), (4) Date: Jul. 22, 2011

(87) PCT Pub. No.: WO2010/065936
PCT Pub. Date: Jun. 10, 2010

(65) Prior Publication Data
US 2011/0269689 A1 Nov. 3, 2011

Related U.S. Application Data

(60) Provisional application No. 61/120,052, filed on Dec. 4, 2008.

(51) Int. Cl.
| | | |
|---|---|---|
| *C07C 15/30* | (2006.01) | |
| *C07C 15/38* | (2006.01) | |
| *A61K 8/31* | (2006.01) | |
| *A61K 31/015* | (2006.01) | |
| *A61K 31/352* | (2006.01) | |
| *C07D 215/18* | (2006.01) | |
| *A61K 47/54* | (2017.01) | |
| *C07D 209/42* | (2006.01) | |
| *C07D 295/088* | (2006.01) | |
| *C07D 211/34* | (2006.01) | |
| *C07D 231/14* | (2006.01) | |
| *C07D 313/14* | (2006.01) | |
| *C07D 417/04* | (2006.01) | |
| *C07D 491/048* | (2006.01) | |
| *C07D 501/22* | (2006.01) | |
| *C07D 277/56* | (2006.01) | |
| *C07D 207/34* | (2006.01) | |

(52) U.S. Cl.
CPC .............. *A61K 31/352* (2013.01); *A61K 8/31* (2013.01); *A61K 31/015* (2013.01); *A61K 47/54* (2017.08); *C07C 15/30* (2013.01); *C07C 15/38* (2013.01); *C07D 207/34* (2013.01); *C07D 209/42* (2013.01); *C07D 211/34* (2013.01); *C07D 215/18* (2013.01); *C07D 231/14* (2013.01); *C07D 277/56* (2013.01); *C07D 295/088* (2013.01); *C07D 313/14* (2013.01); *C07D 417/04* (2013.01); *C07D 491/048* (2013.01); *C07D 501/22* (2013.01); *Y02A 50/30* (2018.01)

(58) Field of Classification Search
CPC ........ A61K 8/31; A61K 31/015; C07C 15/30; C07C 15/38
See application file for complete search history.

(56) References Cited

U.S. PATENT DOCUMENTS

| | | | |
|---|---|---|---|
| 1,815,802 | A | 7/1931 | Schleicher et al. |
| 2,671,805 | A | 3/1954 | Krimmel et al. |
| 3,365,483 | A | 1/1968 | Jerzmanowska et al. |
| 3,420,871 | A | 1/1969 | Scherrer et al. |
| 3,476,791 | A | 11/1969 | Newman et al. |
| 3,488,380 | A | 1/1970 | Goldhamer et al. |
| 3,704,298 | A | 11/1972 | Zinnes et al. |
| 3,787,324 | A | 1/1974 | Zinnes et al. |
| 3,821,279 | A | 6/1974 | Kurono et al. |
| 3,822,258 | A | 7/1974 | Zinnes et al. |
| 3,956,363 | A | 5/1976 | Shen et al. |
| 3,957,764 | A | 5/1976 | Lund |
| 3,966,923 | A | 6/1976 | Serre |
| 4,006,181 | A | 2/1977 | Cousse et al. |

(Continued)

FOREIGN PATENT DOCUMENTS

| | | |
|---|---|---|
| AU | 2004201178 A1 | 4/2004 |
| CA | 1246446 | 12/1988 |

(Continued)

OTHER PUBLICATIONS

Amin et al., Journal of the American Pharmaceutical Association, 1948, 37, 243-245.*

(Continued)

*Primary Examiner* — Abigail Vanhorn
(74) *Attorney, Agent, or Firm* — Fox Rothschild LLP

(57) ABSTRACT

High penetration compositions (HPC) of a parent compound, which are capable of crossing biological barriers with high penetration efficiency. The HPCs are capable of being converted to parent drugs or parent drug-related compounds such as metabolites after crossing one or more biological barriers and thus can render treatments for the conditions that the parent drugs or parent drug-related compounds can. Additionally, the HPCs are capable of reaching areas that their parent drugs or parent drug-related compounds may not be able to access or to render a sufficient concentration at the target areas HPCs of NSAIA, for example, have demonstrated indications such as treating hair loss. A HPC can be administered to a subject through various administration routes, e.g., locally delivered to an action site of a condition with a high concentration or systematically administered to a biological subject and enter the general circulation with a faster rate.

5 Claims, 111 Drawing Sheets

(56) References Cited

U.S. PATENT DOCUMENTS

| | | |
|---|---|---|
| 4,012,508 A | 3/1977 | Burton |
| 4,035,376 A | 7/1977 | Janssen et al. |
| 4,044,049 A | 8/1977 | Ruyle et al. |
| 4,127,671 A | 11/1978 | Cognacq |
| 4,146,637 A | 3/1979 | Metz et al. |
| 4,150,137 A | 4/1979 | Noda et al. |
| 4,180,662 A | 12/1979 | Pfister et al. |
| 4,180,665 A | 12/1979 | Schwander et al. |
| 4,192,871 A * | 3/1980 | Phillipps .......... C07J 3/005 514/176 |
| 4,206,220 A | 6/1980 | Sloan |
| 4,207,332 A | 6/1980 | Hayashi et al. |
| 4,235,896 A * | 11/1980 | Mieville .......... C07C 45/45 514/217.03 |
| 4,244,948 A | 1/1981 | Boghosian et al. |
| 4,285,951 A | 8/1981 | Hoefle |
| 4,376,768 A | 3/1983 | Ozaki et al. |
| 4,472,431 A | 9/1984 | Toth |
| 4,543,353 A | 9/1985 | Faustini et al. |
| 4,551,452 A | 11/1985 | Marfat |
| 4,623,486 A | 11/1986 | Lombardino |
| 4,640,689 A | 2/1987 | Sibalis |
| 4,640,911 A | 2/1987 | Baschang et al. |
| 4,689,338 A | 8/1987 | Gerster |
| 4,743,704 A | 5/1988 | Nicolini |
| 4,746,509 A | 5/1988 | Haggiage et al. |
| 4,822,773 A | 4/1989 | Alexander et al. |
| 4,933,184 A | 6/1990 | Tsuk |
| 5,081,118 A | 1/1992 | Braisted et al. |
| 5,100,918 A | 3/1992 | Sunshine et al. |
| 5,134,165 A | 7/1992 | Hirsch-Kauffmann |
| 5,190,953 A | 3/1993 | Munson, Jr. et al. |
| 5,192,753 A | 3/1993 | McGeer et al. |
| 5,331,000 A | 7/1994 | Young et al. |
| 5,399,562 A | 3/1995 | Becker et al. |
| 5,510,385 A * | 4/1996 | Stroppolo .......... A61K 31/19 514/555 |
| 5,530,145 A | 6/1996 | Wang et al. |
| 5,570,559 A | 11/1996 | Lewis |
| 5,604,259 A | 2/1997 | Jee |
| 5,607,691 A | 3/1997 | Hale et al. |
| 5,654,337 A | 8/1997 | Roentsch et al. |
| 5,760,261 A | 6/1998 | Guttag |
| 5,861,170 A | 1/1999 | Kissel |
| 5,885,597 A | 3/1999 | Botknecht et al. |
| 5,902,110 A | 5/1999 | Alfano et al. |
| 6,011,049 A | 1/2000 | Whitcomb |
| 6,054,457 A | 4/2000 | Setoi et al. |
| 6,190,690 B1 | 2/2001 | Park et al. |
| 6,193,996 B1 | 2/2001 | Effing et al. |
| 6,262,121 B1 | 7/2001 | Kawaji et al. |
| 6,346,278 B1 | 2/2002 | Macrides et al. |
| 6,368,618 B1 | 4/2002 | Jun et al. |
| 6,416,772 B1 | 7/2002 | Van Engelen et al. |
| 6,444,234 B1 | 9/2002 | Kirby et al. |
| 6,528,040 B1 | 3/2003 | Pearson et al. |
| 6,592,891 B1 | 7/2003 | Donati et al. |
| 6,593,365 B1 | 7/2003 | Yung-Yu Hung et al. |
| 6,635,674 B1 | 10/2003 | Kaneko et al. |
| 6,638,528 B1 | 10/2003 | Kanios |
| 6,693,135 B2 | 2/2004 | Yeager et al. |
| 6,723,337 B1 | 4/2004 | Song et al. |
| 6,773,724 B2 | 8/2004 | Franckowiak et al. |
| 7,052,715 B2 | 5/2006 | Fishman |
| 7,256,210 B2 | 8/2007 | Man et al. |
| 2001/0038861 A1 | 11/2001 | Hsu et al. |
| 2002/0142607 A1 | 10/2002 | Gabriel et al. |
| 2003/0087962 A1 | 5/2003 | Demopulos et al. |
| 2004/0022837 A1 | 2/2004 | Hsu et al. |
| 2004/0192778 A1* | 9/2004 | Jardien .......... A61K 8/44 514/564 |
| 2004/0229920 A1 | 11/2004 | Garvey et al. |
| 2004/0254182 A1 | 12/2004 | Mulvihill et al. |
| 2004/0266870 A1 | 12/2004 | Allegretti et al. |
| 2005/0037922 A1 | 2/2005 | Bickers et al. |
| 2005/0049255 A1 | 3/2005 | Bictash et al. |
| 2005/0080067 A1 | 4/2005 | Allegretti et al. |
| 2005/0107463 A1 | 5/2005 | Woodward et al. |
| 2005/0272108 A1 | 12/2005 | Kalra et al. |
| 2006/0003428 A1 | 1/2006 | Tsai |
| 2006/0024365 A1 | 2/2006 | Vaya et al. |
| 2006/0058362 A1 | 3/2006 | Man et al. |
| 2006/0172002 A1 | 8/2006 | Takada et al. |

FOREIGN PATENT DOCUMENTS

| | | | |
|---|---|---|---|
| CA | 2614312 A1 | 1/2007 | |
| CN | 1244801 A | 2/2000 | |
| CN | 1538951 A | 10/2004 | |
| CN | 101312734 A | 11/2008 | |
| DE | 3023206 A1 | 1/1982 | |
| EP | 152379 A2 | 8/1985 | |
| EP | 0202062 A2 | 11/1986 | |
| EP | 237495 A2 | 9/1987 | |
| EP | 289262 A2 | 11/1988 | |
| EP | 0208404 B1 | 8/1990 | |
| EP | 0469450 | 5/1992 | |
| EP | 659442 A1 | 6/1995 | |
| EP | 1 120 416 A1 | 8/2001 | |
| ES | 2023585 A6 * | 1/1992 | |
| FR | 5342 M | 9/1967 | |
| FR | 1593024 A | 5/1970 | |
| FR | 2410641 A1 | 6/1979 | |
| GB | 958186 A | 5/1964 | |
| GB | 984471 | 2/1965 | |
| GB | 1000208 | 8/1965 | |
| GB | 1032564 A * | 6/1966 | .......... C07J 41/00 |
| GB | 1165300 | 9/1969 | |
| GB | 1187259 A | 4/1970 | |
| GB | 1 415 295 | 11/1975 | |
| GB | 2154585 A | 9/1985 | |
| JP | S5513275 A | 1/1980 | |
| JP | 57-183738 A | 11/1982 | |
| JP | 58049353 A * | 3/1983 | |
| JP | H04-30372 B2 | 5/1992 | |
| JP | 2004-525112 | 8/2004 | |
| JP | 2005-504121 | 2/2005 | |
| RU | 2165265 C2 | 4/2001 | |
| RU | 2 175 230 C1 | 10/2001 | |
| WO | WO 90/02141 A1 | 3/1990 | |
| WO | 90/08128 | 7/1990 | |
| WO | 93/07902 | 4/1993 | |
| WO | WO 93/14743 A2 | 8/1993 | |
| WO | WO 93/17677 A1 | 9/1993 | |
| WO | 1993/25197 | 12/1993 | |
| WO | WO 93/25703 A1 | 12/1993 | |
| WO | 1994/00449 | 1/1994 | |
| WO | 9400449 | 1/1994 | |
| WO | 1994/10167 | 5/1994 | |
| WO | 9410167 | 5/1994 | |
| WO | WO 94/20635 A1 | 9/1994 | |
| WO | WO 95/34813 | 12/1995 | |
| WO | 1996/028144 | 9/1996 | |
| WO | WO 97/27211 | 7/1997 | |
| WO | WO 97/44020 A1 | 11/1997 | |
| WO | WO 97/45113 A1 | 12/1997 | |
| WO | WO 98/33506 | 8/1998 | |
| WO | 1998/040061 | 9/1998 | |
| WO | WO 98/47502 A1 | 10/1998 | |
| WO | WO 99/45024 | 9/1999 | |
| WO | 2001/054481 A2 | 8/2001 | |
| WO | WO 01/58852 A2 | 8/2001 | |
| WO | WO 01/85143 A2 | 11/2001 | |
| WO | 2002/000167 A2 | 1/2002 | |
| WO | WO 02/68377 A1 | 9/2002 | |
| WO | WO 02/85297 A2 | 10/2002 | |
| WO | 2003/022270 A1 | 3/2003 | |
| WO | WO 03/29187 A1 | 4/2003 | |
| WO | 2003/061713 A1 | 7/2003 | |
| WO | 04000300 | 12/2003 | |
| WO | 04004648 | 1/2004 | |
| WO | 2004080423 A2 | 9/2004 | |
| WO | WO 05/68421 A1 | 7/2005 | |
| WO | WO 05/97099 A1 | 10/2005 | |

(56) References Cited

FOREIGN PATENT DOCUMENTS

| | | |
|---|---|---|
| WO | WO 06/74249 A1 | 7/2006 |
| WO | 2006/128184 | 11/2006 |
| WO | 06128184 A2 | 11/2006 |
| WO | WO 08/007171 A1 | 1/2008 |
| WO | WO 08/010025 A1 | 1/2008 |
| WO | WO 08/012602 A1 | 1/2008 |
| WO | WO 08/012603 A1 | 1/2008 |
| WO | WO 08/012605 A1 | 1/2008 |
| WO | WO 08/017903 A1 | 2/2008 |
| WO | WO 08/020270 A1 | 2/2008 |
| WO | 2008/026776 | 3/2008 |
| WO | WO 08/029199 A1 | 3/2008 |
| WO | WO 08/029200 A1 | 3/2008 |
| WO | WO 08/041054 A1 | 4/2008 |
| WO | WO 08/041059 A1 | 4/2008 |
| WO | WO 08/044095 A1 | 4/2008 |
| WO | WO 08/056207 A1 | 5/2008 |
| WO | WO 08/072032 A1 | 6/2008 |
| WO | WO 08/087493 A1 | 7/2008 |
| WO | WO 08/093173 A1 | 8/2008 |
| WO | 2008110351 A2 | 9/2008 |
| WO | WO 08/149181 A1 | 12/2008 |
| WO | WO-2008149181 A1 * | 12/2008 ........... C07D 403/12 |
| WO | WO 2008/021605 A1 | 1/2009 |
| WO | WO 2009108804 A2 * | 9/2009 ................ C07J 9/00 |

OTHER PUBLICATIONS

Benoit-Guyod et al., Chimica Therapeutica, 1968, 3(5), 336-42.*
Berge et al. "Pharmaceutical Salts." Journal of Pharmaceutical Sciences, 66(1): 1977:1-19.*
Heyl et al., Journal of the American Chemical Society, 1953, 75(8), pp. 1918-1920.*
Mork et al., Pharmaceutical Research, 1992, 9(4), p. 492-496.*
Khan et al., Steroids, 2006, 71, pp. 42-53.*
Souza et al., British Journal of Pharmacology, 143, pp. 132-142. (Year: 2004).*
Elmegeed et al., Egypt. J. Chem., 48(4), pp. 407-423. (Year: 2005).*
Bartzatt et al., Letters in Drug Design, 5, pp. 162-168. (Year: 2008).*
Holt et al., Inhibition of fatty acid amide hydrolase, a key endocannabinoid metabolizing enzyme, by analogues of ibuprofen and indomethacin, European Journal of Pharmacology, 565 (1-3), pp. 26-36. (Year: 2007).*
Guillard, Sophie, et al. "N-Acyltrifluoromethanesulfonamides as new chemoselective acylating agents for aliphatic and aromatic amines." Tetrahedron 62.24 (2006): 5608-5616. (Year: 2006).*
Bartzatt, Ronald, et al. "Bifunctional constructs of aspirin and ibuprofen (non-steroidal anti-inflammatory drugs; NSAIDs) that express antibacterial and alkylation activities." Biotechnology and applied biochemistry 37.3 (2003): 273-282. (Year: 2003).*
Cannon, J. G., "Analog Design," Burger's Medicinal Chemistry and Drug Discovery, Ch. 19, 5th Ed., vol. 1: Principles and Practice, Wiley-Interscience, 1995, pp. 783-802.
Brown, K., et al., "Nonsteroidal Antiinflammatory Agents. 1 2,4-Diphenylthiazole-5-acetic Acid and Related Compounds," J. Med. Chem. 17(11):1177-1181 (1975).
Agawa, T., et al., "Stabilities of Vitamin A Urethans," Kogyo Kagaku Zasshi 58:686-688 (1955).
Allegretti, M. et al., "2-Arylpropionic CXC Chemokine Receptor 1 (CXCR1) Ligands as Novel Noncompetitive CXCL8 Inhibitors," J. Medic. Chem. 48(13):4312-4331 (2005).
Altuntas, T. G., et al., "A Study on the Interation Between p60c-src Receptor Tyrosine Kinase and Arylcarboxylic and Arylacetic Acid Derivatives Based on Docking Modes and In Vitro Activity," Biol. Pharm. Bull. 27(1):61-65 (2004).
Andrews, J. M., "Determination of Minimum Inhibitory Concentrations," Journal of Antimicrobial Chemotherapy 48, suppl. S1: 5-16 (2001).

Apt, L., et al., "A Randomized Clinical Trial of the Nonsteroidal Eyedrop Diclofenac After Strabismus Surgery," Ophthalmology 105:1448-1454 (1998).
Arora, P., et al., "Design Development, Physicochemical, and In Vitro and In Vivo Evaluation of Transdermal Patches Containing Diclofenac Diethylammonium Salt," J. Pharm. Sci. 91:2076-2089 (2002).
Barcia, E., et al., "Influence of Medium and Temperature on the Hydrolysis Kenetics of Propacetamol Hydrochloride: Determination Using Derivative Spectrophotometry," Chem. Pharm. Bull. 53(3):277-280 (2005).
Battaglino, R., et al., "Fluoxetine Treatment Increases Trabecular Bone Formation in Mice (Fluoxetine Affects Bone Mass)," J. Cell Biochem. 100(6):1387-1394 (2007).
Berge, S. M., et al., "Pharmaceutical Salts," J. Pharm. Sci. 66:1-19 (1977).
Bundgaard, H., et al., "Prodrugs as Drug Delivery Systems IV: N-Mannich Bases as Potential Novel Prodrugs for Amides, Ureides, Amines, and Other NH-Acidic Compounds," J. Pharm. Sci. 69:44-46 (1980).
Campbell, C. L., et al., "Aspirin Dose for the Prevention of Cardiovascular Disease," JAMA 297(18):2018-2024 (2007).
Cevc, G., et al., "New, Highly Efficient Formulation of Diclofenac for the Topical, Transdermal Administration in Ultradeformable Drug Carriers, Transfersomes," Biochim. Biophys. Acta 1514:191-205 (2001).
Chanal, J. L., et al., Etude de la Distribution et de L'Elimination Chez le Rat de L'Acetyl Salicylate de Dimethyl Amino Ethyle Influence de la Position de Marquage au Carbone 14, Boll. Chim. Farm. 119:331-338 (1980).
Cwalina, G. E., et al., "Synthesis and Stability Studies of Certain Disubstituted Aminoacetoxybenzoic Acids," J. Organic Chem. 26:3344-3346 (1961).
D'Amour, F. E., et al., "A Method for Determining Loss of Pain Sensation," J. Pharmacol. Exp. Ther. 72:74-79 (1941).
Dalpiaz, A., et al., "Vitamin C and 6-Amino-Vitamin C Conjugates of Diclofenac: Synthesis and Evaluation," International Journal of Pharmaceutics 291 (1-2):171-181 (2005).
Database Caplus [Online] Chemical Abstracts Service, Columbus, OH, US; "Esters of .Omega.-Aminoaliphatic Acids and p-Acetamidophenol," retrieved from STN database accession No. 1969:3537.
Diven, W. F., et al., "Treatment of Experimental Acute Otitis Media with Ibuprofen and Ampicillin," Int. J. Pediatric Otorhinolaryngology 33:127-139 (1995).
Drachman, D. B., et al., "Cyclooxygenase 2 Inhibition Protects Motor Neurons and Prolongs Survival in a Transgenic Mouse Model of ALS," Ann. Neurol. 52:771-778 (2002).
Erlanson-Albertsson, C., et al., "Enterostatin—A Peptide Regulating Fat Intake," Obes. Rev. 5(4):360-372 (1997).
Funt, L. S., "Oral Ibuprofen and Minocycline for the Treatment of Resistant Acne Vulgaris," J. Amer. Acad. Dermatol. 13(3):524-525 (1985).
Gamache, D.A., et al., "Nepafenac, A Unique Nonsteroidal Prodrug with Potential Utility in the Treatment of Trauma-Induced Ocular Inflammation: I. Asssessment of Anti-Inflammatory Efficacy," Inflammation 24(4):357-370 (2000).
Gidoh, M., et al., "Derivatives of Several Acidic Anti-Inflammatory Drugs Showing Local Anesthetic Effects and Their Possible Use in the Treatment of Leprous Neuritis," Nippon Rai Gakkai Zasshi 52(3):156-64 (1983).
Ginaldi, L., et al., "Osteoporosis, Inflammation and Ageing," Immunity & Ageing 2:14 (2005).
Giraud, I., et al., "Application to a Cartilage Targeting Strategy: Synthesis and In Vivo Biodistribution of 14C-Labeled Quaternary Ammonium-Glucosamine Conjugates," Bioconjugate Chem. 11:212-218 (2000).
Gossel, T.A., "Aspirin's Role in Reducing Cardiac Mortality," U.S. Pharmacitst, Feb. 1988, pp. 34-41.
Gringauz, A., "Certain Disubstituted O-Aminoacetoxy- and Propoxybenzoic and Cinnamic Acids and Their Tert-Butyl Esters," J. Pharma. Sci. 59(3):422-225 (1970).

(56) References Cited

OTHER PUBLICATIONS

Hacking, M.A.P.J., et al., "Lipase Catalysed Acylation of Hydroxylamine and Hydrazine Derivatives," Journal of Molecular Catalysis B: Exzymatic 11:315-321 (2001).
Hengesh, E. J., Principles of Medicinal Chemistry, 4th Ed., p. 591, Williams & Wilkins, 1995.
Hennekens, C. H., et al., "Final Report on the Aspirin Component of the Ongoing Physicians' Health Study," N. Eng. J. Med. 321:129-135 (1989).
In't Veld, B. A., et al., "Nonsteroidal Antiinflammatory Drugs and the Risk of Alzheimer's Disease," N. Eng. J. Med. 345(21):1515-1521 (2001).
Jona, J. A., et al., "Design of Novel Prodrugs for the Enhancement of the Transdermal Penetration of Indomethacin," International Journal of Pharmaceuticals 123:127-136 (1995).
Jung, Y. J., et al., "Colon-Specific Prodrugs of 5-Aminosalicylic Acid: Synthesis and In Vitro/In Vivo Properties of Acidic Amino Acid Derivatives of 5-Aminosalicylic Acid," J. Pharm. Sci. 90:1767-1775 (2001).
Kawathekar, N., et al., "Synthesis, Biological Evaluation and QSAR Analysis of Some New Derivatives of Ketoprofen and Flurbiprofen," Indian J. Pharma.ceutical Sciences 60(6):346-352 (1998).
Kigasawa, K., et al., "Decomposition and Stabilization of Drugs. XVIII. Studies on the Stability of Carboxylic Acid Esters of Phenol and Their Effectiveness as Prodrug," J. Pharm. Soc. Japan 99(4):402-412 (1979).
Kisel, V.M., et al., "Condensed Isoquinolines. 15. Synthesis of 5,10-Dihydro[1,2,4]Triazolo[1,5-b]-Isoquinolines and Related Spiranes," Chemistry of Heterocyclic Compounds 38(10):1253-1262 (2002).
Kobayashi, M., et al., "A Model System for Convenient Fluorescent Labeling of Sugar Chain in Taka-Amylase A.," Biosci. Biotechnol. Biochem. 61 (11):1836-1839 (1997).
Korean Intellectual Property Office, International Preliminary Report on Patentability for PCT/IB2006/052318 dated May 7, 2007.
Korean Intellectual Property Office, International Preliminary Report on Patentability for PCT/IB2006/052461 dated Mar. 29, 2007.
Korean Intellectual Property Office, International Preliminary Report on Patentability for PCT/IB2006/052549 dated Apr. 23, 2007.
Korean Intellectual Property Office, International Preliminary Report on Patentability for PCT/IB2006/052563 dated Apr. 25, 2007.
Korean Intellectual Property Office, International Preliminary Report on Patentability for PCT/IB2006/052575 dated Apr. 25, 2007.
Korean Intellectual Property Office, International Search Report for PCT/IB2006/052732 dated May 2, 2007.
Korean Intellectual Property Office, International Search Report for PCT/IB2006/052815 dated May 3, 2007.
Korean Intellectual Property Office, International Preliminary Report on Patentability for PCT/IB2006/053090 dated May 12, 2007.
Korean Intellectual Property Office, International Preliminary Report on Patentability for PCT/IB2006/053594 dated Jun. 20, 2007.
Korean Intellectual Property Office, International Preliminary Report on Patentability for PCT/IB 2006/053619 dated Jun. 26, 2007.
Korean Intellectual Property Office, International Search Report for PCT/IB2006/053741 dated May 29, 2007.
Korean Intellectual Property Office, International Preliminary Report on Patentability for PCT/IB2006/053091 dated May 12, 2007.
Korean Intellectual Property Office, International Preliminary Report on Patetability for PCT/IB2007/052090 dated May 31, 2007.
Korean Intellectual Property Office, International Preliminary Report on Patentability for PCT/US2009/066884 dated Jun. 7, 2011.
Kovach, I. M., et al., "Amino Acid Esters of Phenols as Prodrugs: Synthesis and Stability of Glycine, beta-Aspartic Acid, and alpha-Aspartic Acid Esters of p-Acetamidophenol," J. Pharm. Sci. 70(8):881-885 (1981).
Machon, Z., et al., "Synthesis of Benzoylcholine Derivatives," Dissertationes Pharmaceuticae 17(4):491-496 (1965).
Madhu, C., et al., "Penetration of Natural Prostaglandins and Their Ester Prodrugs and Analogs Across Human Ocular Tissues in Vitro," Journal of Ocular Pharmacology 14(5):389-399 (1998).
Magnette, J.-L., et al., "Diclofenac Systemic Exposure is Not Increased when Topical Diclofenac is Applied to Ultraviolet-Induced Erythema," Eur. J. Clin. Pharmacol. 60:591-594 (2004).
McGeer, P.L., et al., "The Inflammatory Response System of Brain Implications for the Theray of Alzheimer and Other Neurodegenerative Diseases," Res. Rev. 21:195-218 (1995).
Milosovich, S., et al., "Testosteronyl-4-Dimethylaminobutyrate-HCI: A Prodrug with Improved Skin Penetration Rate," J. Pharm. Sci. 82(2):227-228 (1993).
Nebioglu, D., et al., "Synthesis and In Vitro Anti-Inflammatory Activities of Some New Diaryl Amine Derivatives as Prodrug of Diclofenac," J. Fac. Pharm. Gazi 10(1):69-81 (1993).
Nicolas, C., et al., "New Quaternary Ammonium Oxican Derivatives Targeted Toward Cartilage: Synthesis, Pharmacokinetic Studies, and Antiinflammatory Potency," J. Med. Chem. 42:5235-5240 (1999).
Nielsen, N. M., et al., "Evaluation of Glycolamide Esters and Various Other Esters of Aspirin as True Aspirin Prodrugs," J. Med. Chem. 32(3):727-734 (1989).
Non_steroidal_antiinflammatory_dr,2011, http://en.wikipedia.org/wiki/Non-steroidal_anti-inflammatory_drug.
Pan, D.S., et al., "Inhibitory Effect of Progesterone on Inflammatory Factors after Experimental Traumatic Brain Injury," Biomed. Environ. Sci. 20(5):432-438 (2007).
PDR Generics, 1996, 2nd Ed., Medical Economics, Montvale, New Jersey, p. 242-243.
PDR Generics, "Fenoprofen Calcium," 1996, second edition, Medical Economics, Montvale, NJ, p. 1289-1292.
PDR Generics, "Ketoprofen," 1996, second edition, Medical Economics, Montvale, NJ, p. 1810-1815.
Perioli, L., et al., "Potential Prodrugs of Non-Steroidal Anti-Inflammatory Agents for Targeted Drug Delivery to the CNS," European Journal of Medicinal Chemistry 39(8):715-727 (2004).
Ponte, C., et al., "Does Acetaminophen Interfere in the Antibiotic Treatment of Acute Otitis Media Caused by a Penicillin-Resistant Pneumococcus Strain? A Gerbil Model," Pediatric Res. 54(6):913-918 (2003).
Raisz, L., "Pathogenesis of Osteoporosis: Concepts, Conflicts, and Prospects," J. Clin. Invest. 115(12):3318-3325 (2005).
Rolka, D. B., et al., "Aspirin Use Among Adults with Diabetes," Diabetes Care 24(2):197-201 (2001).
Romundstad, L., et al., "Adding propacetamol to Ketorolac Increase the Tolerance to Painful Pressure," European Journal of Pain (Amsterdam, Netherlands) 10(3):177-183, ISSN:1090-3801 (2006).
Roof, R.L., et al., "Gender Differences in Acute CNS Trauma and Stroke: Neuroprotective Effects of Estrogen and Progesterone," J. Neurotrauma 17(5):367-388 (2000).
Rosenberg, E.W., et al., "Effect of Topical Applications of Heavy Suspensions of Killed Malassezia Ovalis on Rabbit Skin," Mycopathologia 72:147-154 (1980).
Roth, H. J., et al., "Synthesis of Polymer Bound Antiphlogistic Agents," Archiv der Pharmazie 321(5):273-276 (1988).
Salimbeni, A., et al., "New Esters of N-Arylanthranilic Acids," Farmaco, Edizione Scientifica 30(4):276-286 (1975).
Santos, C., et al., "Cyclization-Activated Prodrug. Synthesis, Reactivity and Toxicity of Dipeptide Esters of Paracetamol," Bioorganic & Medicial Chemistry Letters 15(6):1595-1598 (2005).
Scott, I. L., "Keystone Symposia: Inflammation and Cancer, Breckenridge, CO, USA, Feb. 27-Mar. 3, 2005," Technical Reports 10(13)1-17.
Selim, A. S. M., et al., "A New Method for the Direct Isolation of Glycine from Protein Hydrolyzates," Biochemical Journal 61(2):177-179 (1955).
Shanbhag, V. R., et al., "Ester and Amide Prodrugs of Ibuprofen and Naproxen: Synthesis, Anti-Inflammatory Activity, and Gastrointestinal Toxicity," Journal of Pharmaceutical Sciences 81 (2):149-54 (1992).
Sloan, K. B., et al., "Design for Optimized Topical Delivery: Prodrugs and a Paradigm Change," Pharmaceutical Research 23(12):2729-2747 (2006).
Sloan, K. B., et al., "Designing for Topical Delivery: Prodrugs Can Make the Difference," Medicinal Research Reviews 23(6):763-793 (2003).

(56) References Cited

OTHER PUBLICATIONS

Soine, T. O., et al., "Antispasmodics. I. Phenyl Esters of Beta-Dialkylaminopropionic Acids," J. Am. Pharm. Assoc. 41:236-238 (1952).

Song, N., et al., "Synthesis of a Derivative of Quaternary Ammonium-Ibuprofen," Journal of Ocean University of Qingdao 32(6):911-913 (2002).

Sorhede, M., et al., "Enterostatin: A Gut-Brain Peptide Regulating Fat Intake in Rat," J. Physiol. 87:273-275 (1993).

SpinalCordinjury,2011, http://www.mayoclinic.com/health/spinal-cord-injury/DS00460/DSECTION=treatments-and-drugs.

Terry, M. B., et al., "Association of Frequency and Duration of Aspirin Use and Hormone Receptor Status With Breast Cancer Risk," JAMA 291 (21):2433-2489 (2004).

Thun, M.J., et al., "Aspirin Use and Reduced Risk of Fatal Colon Cancer," N. Eng. J. Med., 325(23):1593-1596 (1991).

Tjebbes, G.W.A., et al., "d-Ibuprofen in Ocular Inflammation Induced by Paracentesis of the Rabbit Eye," Prostaglandins, Butterworth, Stoneham, MA, US 40(1):29-33 (1990).

Tozkoparan, B., et al., "6-Benzylidenethiazolo[3,2-b]-1,24-Triazole-5(6H)-Ones Sybstituted with Ibprofen: Synthesis, Characterization and Evaluation of Anti-Inflammatory Activity," Eur. J. Med. Chem. 35(7-8):743-750 (2000).

Tute, M. S., et al., Principles of Medicinal Chemistry, Eds., Williams & Wilkins, Media, PA, 1995, pp. 52.

Urbanska, H., et al., "Synthesis and Pharmacological Properties of Aminoalkyl Esters of Nicotinic Acid Derivatives," Acta Poloniae Pharmaceutica 36(6):657-665 (1979).

Venuti, M. C., et al., "Synthesis and Biological Evaluation of Omega-(N,N,N-Trialkylammonium)Alkyl Esters and Thioesters of Carboxylic Acid Nonsteroidal Antiinflammatory Agents," Pharmaceutical Research 6(10):867-873 (1989).

Warolin, C., et al., "Sur L'Activite Pharamacodynamique de L'Anhydride Acetylsalicylique et du Chlorhydrate D'Acetylsalicylate de N Diethylaminoethyle (1)," Therapie 21(1):245-59 (1966).

Wiwattanawongsa, K., et al., "Experimental and Computational Studies of Epithelial Transport of Mefenamic Acid Ester Prodrugs," Pharmaceutical Research 22(5):721-727 (2005).

Wolinski, J., et al., "Search for Anticholinargic Compounds. XX. Synthesis of Aminoalkyl O-, M-, and P-Hydroxybenzoates and O-, M-, and P-Acetoxybenzoates," Acta Poloniae Pharmaceutica 37(3):275-280 (1980).

Woods, H. F., et al., "Inhibition By Salicylate of Gluconeogenesis in the Isolated Perfused Rat Liver," Clin. Exp. Pharmacol. Physiol. 1(6):535-540 (1974).

Wright, D.W., et al., "ProTECT: A Randomized Clinical Trial of Progesterone for Acute Traumatic Brain Injury," Ann. Emerg. Med. 49(4):391-402 (2007).

Xiao, G., et al., "Improved Outcomes from the Administration of Progesterone for Patients with Acute Severe ttraumatic bbrain iinjury: A Randomized Controlled Trial," Crit. Care 12:R61 (2008).

Yadav, M.R., et al., "Synthesis and Pharmacological Evaluation of Some Dual-Acting Aminoalcohol Ester Derivatives of Flurbiprofen and 2-[1,1 '-Biphenyl-4-yl] Acetic Acid: A Potential Approach to Reduce Local Gastrointestinal Toxicity," Chem. & Biodiversity 3(11):1238-1248 (2006).

Yang, S., et al., "Specificity of RGS10A as a Key Component in the RANKL Signaling Mechanism for Osteoclast Differentiation," J. Cell Sci. 120:3362-3371 (2007).

Zovko, M., et al., "Macromolecular Prodrugs. IX. Synthesis of Polymer-Fenoprofen Conjugates," Int. J. Pharmaceutics 228:129-138 (2001).

Zovko, M., et al., "The Novel Ketoprofenamides: Synthesis and Spectroscopic Characterization," Croatica Chemica Acta 76(4):335-341 (2003).

Silverman, R.B., "The Organic Chemistry of Drug Design and Drug Action," Academic Press Inc. 1992, pp. 355-361.

Cannon, J. G.,"Analog Design," Burger's Medicinal Chemistry and Drug Discovery 5th Ed. 1:783-802 (1995).

Carrico, D., et al., "In Vitro and In Vivo Antimalarial of Peptidomimetic Protein Farnesyltransferase Inhibitors with Improved Membrane Permeability," Bioorg. Med. Chem. 12(24):6517-6526 (2004).

Halen, P. K., et al., "Synthesis and Pharmacological Evaluation of Some Dual-Acting Amino-Alcohol Ester Derivatives of Flurbiprofen and 2-[1,1'-Biphenyl-4-yl]Acetic Acid: A Potential Approach to Reduce Local Gastrointestinal Toxicity," Chemistry & Biodiversity 3(11): 1238-1248 (2006).

Halen, P. K., et al., "Combining Anticholinergic and Anti-Inflammatory Activities into a Single Moiety: A Novel Approach to Reduce Gastrointestinal Toxictiy of Ibuprofen and Ketoprofen," Chem. Biol. Drug Des. 70:450-455 (2007).

Ho, et al., "The Percutaneous Penetration of Prostaglandin E1 and Its Alkyl Esters," Journal of Controlled Release 58:349 (1999).

Horan, P. J., et al., "Antinociceptive Profile of Biphalin, a Dimeric Enkephalin Analog," J. Pharmacology & Experimental Therapeutics 265(3): 1446-1454 (1993).

Hovgaard, L., et al., "Drug Delivery Studies in Caco-2 Monolayers. Synthesis, Hydrolysis, and Transport of O-Cyclopropane Carboxylic Acid Ester Prodrugs of Various B-Blocking Agents," Pharm. Res. 12(3):387-392 (1995).

Hovgaard, L., et al., "Permeation Studies on O-Cyclopropanoyl Ester Prodrugs of B-Blockers in Caco-2 Cell Monolayers," Proceed. Intern: Symp. Control. Rel. Bioact. Mater. 20:238-239 (1993).

Toyooka, T., et al., "Fluoroescent Chiral Derivatization Reagents for Carboxylic Acid Enantiomers in High-Performance Liquid Chromatography," Caplus an 1992:523750 (1992).

Altucci, L., et al., "RAR and RXR Modulation in Cancer and Metabolic Disease," Nat. Rev. Drug Disc. 6:793-810 (2007).

Choi, I., et al., "9-Cis Retinoid Acid Promotes Lymphangiogenesis and Enhances Lymphatic Vessel Regeneration Therapeutic Implications of 9-Cis Retinoic Acid for Secondary Lymphedema," Circulation 125(7):872-882 (2012).

Dawson, M. I., et al., "The Retinoid X Receptors and Their Ligands," Biochim. Biophys. Acta 1821(1):21-56 (2012).

Duester, G., "Retonoic Acid Synthesis and Signaling during Early Organogenesis," Cell 134(6):921-931 (2008).

Georgala, S., et al., "Oral Isotretinoin in the Treatment of Recalcitrant Condylomata Acuminata of the Cervix: A Randomized Placebo Controlled Trial," Sex Transm. Infect. 80:216-218 (2000).

Knychalska-Karwan, Z., et al., "The Use of Edan in Stomatodynia," J. Stomatol. 38:10 (1985).

Laaksovirta, S., et al., "The Cytostatic effect of 9-Cis-Retinoic Acid, Tretinoin, and Isotretinoin on Three Different Human Bladder Cancer Cell Lines In Vitro," Urol. Res. 27:17-22 (1999).

Mao, J. T., et al., "A Pilot Study of All-trans-Retinoic Acid for the Treatment of Human Emphysema," Am. J. Respir. Crit. Care Med. 165:718-723 (2002).

Marshall, H., et al., "Retinoids and Hox Genes," FASEB J. 10:969-978 (1996).

Meng-er, H., et al., "Use of All-Trans Retinoic Acid in the Treatment of Acute Promyelocytic Leukemia," Blood 72 (2):567-572 (1988).

Moore, T., et al., "The Production of Experimental Vitamin A Deficiency in Rats and Mice," Lab. Animals 5:239-250 (1971).

Nelson, A. M., et al., "Neutrophil Gelatinase-Associated Lipocalin Mediates 13-cis Retinoic Acid-Induced Apoptosis of Human Sebaceous Gland Cells," J. Clin. Invest. 118:1468-1478 (2008).

Nelson, A. M., et al., "13-cis Retinoic Acid Induces Apoptosis and Cell Cycle Arrest in Human SEB-1 Sebocytes," J. Invest. Dermatol. 126:2178-2189 (2006).

Pendino, F., et al., "Retinoids Down-Regulate Telomerase and Telomere Length in a Pathway Distinct from leukemia Cell Differentiation," PNAS 98(12):6662-6667 (2001).

Sanz, M. A., "Treatment of Acute Promyelocytic Leukemia," Hematology 147-155 (2006).

Shalinsky, D. R., et al., "Enhanced Antitumor Efficacy of Cisplatin in Combination with ALRT1057 (9-Cis Retinoic Acid) in Human Oral Squamous Carcinoma Xenografts in Nude Mice," Clin. Cancer Res. 2:511-520 (1996).

Shimshoni, J. A., et al., "Stereoselective Formation and Metabolism of 4-Hydroxy-Retinoic Acid Enantiomers by Cytochrome P450 Enzymes," J. Biol. Chem. 287(50):42223-42232 (2012).

(56) References Cited

OTHER PUBLICATIONS

Van Beek, M. E. A. B., et al., "Spermatogenesis in Retinol-Deficient Rats Maintained on Retinoic Acid," J. Reprod. Fert. 94:327-336 (1992).

Zhao, Z., et al., "Effect of 9-cis-Retinoic Acid on Growth and RXR Expression in Human Breast Cancer Cells," Exp. Cell Res. 219(2):555-561 (1995).

Zhou, Q., et al., "Expression of Stimulated by Retinoic Acid Gene 8 (Stra8) in Spermatogenic Cells Induced by Retinoic Acid: An In Vivo Study in Vitamin A-Sufficient Postnatal Murine Testes," Biol. Reprod. 79:35-42 (2008).

Ahmed, S et al., "Evaluation of stereoselective transdermal transpor and concurrent cutaneous hydrolysis of several ester prodrugs of propranolol: mechanism of stereoselective permeation," Pharm. Res., 13(10): 1524-1529 (1998) (7 pages).

Otagiri, M. et al., Prodrug, Drug Delivery System, CMC Corporation, Jan. 31, 2000, p. 123-135 (43 pages).

Wang, X. et al., "New suprarolecular system binding to nucleic acids," Proc. SPIE 3863, 1999 International Conference on Biomedical Optics, 155 (Sep. 17, 1999) (7 pages).

VG Belikov, Pharmaceutical Chemistry, "Vysshaya shkola", 1993, pp. 43-45, Part 1, Moscow, Russia.

Office Action dated Oct. 6, 2016 in Russian Application No. 2011127186/04(040243).

Bock et al., "Relative non-steroidal anti-inflammatory drug (NSAID) antiproliferative activity is mediated through p21-induced G1 arrest and E2F inhibition," Molecular Carcinogenesis (2007); 46(10): 857-864.

Cheng et al., "Ketoprofen-inhibited N-Acetyltransferase Activity and Gene Expression in Human Colon Tumor Cells," Anticancer Research (2006); 26:1105-1112.

Blomgren et al., "In vitro capacity of various cyclooxygenase inhibitors to revert immune suppression caused by radiation therapy for breast cancer," Radiotherapy and Oncology (1990); 19: 329-335.

\* cited by examiner

Structure F-1

Structure F-2

Structure F-3

Structure F-4

Structure F-5

Structure F-6

Structure F-7

Structure F-8

Structure F-9

Structure F-10

Structure F-11

Structure F-12

Structure F-13

Structure F-14

Structure F-15

Structure F-16

Structure F-17

Structure F-18

Structure F-19

Structure F-20

Structure F-21

Structure F-22

Structure F-23

Structure F-24

Structure F-25

Structure F-26

Structure F-27

Structure F-28

Structure F-29

Structure F-30

Structure F-31

Structure F-32

Structure F-33

Structure F-34

Structure F-35

Structure F-36

Structure F-37

Structure F-38

Structure F-39

Structure F-40

Structure F-41

Structure F-42

Structure F-43

Structure F-44

Structure F-45

Structure F-46

Structure F-47

Structure F-48

Structure F-49

Structure F-50

Structure F-51

Structure F-52

Structure F-53

Structure F-54

Structure F-55

Structure F-56

Structure F-57

Structure F-58

Structure F-59

Structure F-60

Structure F-61

Structure F-62

Structure F-63

Structure F-64

Structure F-65

Structure F-66

Structure F-67

Structure F-68

Structure F-69

Structure F-70

Structure F-71

Structure F-72

Structure F-73

Structure F-74

Structure F-75

Structure F-76

Structure F-77

Structure F-78

Structure F-79

Structure F-80

Structure F-81

Structure F-82

Structure F-83

Structure F-84

Structure F-85

Structure F-86

Structure F-87

Structure F-88

Structure F-89

Structure F-90

Structure F-91

Structure F-92

Structure F-93

Structure F-94

Structure F-95

Structure F-96

Structure F-97

Structure F-98

Structure F-99

Structure F-100

Structure F-101

Structure F-102

Structure F-103

Structure F-104

Structure F-105

Structure F-106

Structure F-107

Structure F-108

Structure F-109

Structure F-110

Structure F-111

Structure F-112

Structure F-113

Structure F-114

Structure F-115

Structure F-116

Structure F-117

Structure F-118

Structure F-119

Structure F-120

Structure F-130

Structure F-131

Structure F-132

Structure F-133

Structure F-134

Structure F-135

Structure F-136

Structure F-137

Structure F-138

Structure F-139

Structure F-140

Structure F-141

Stucture F-142

Stucture F-143

Structure F-144

Structure F-145

Stucture F-146

Stucture F-147

Structure F-148

Structure F-149

Structure F-150

Structure F-151

Structure F-152

Structure F-153

Structure F-154

Structure F-155

Structure F-156

Structure F-157

Structure F-158

Structure F-159

Structure F-160

Structure F-161

Structure F-162

Structure F-163

Structure F-164

Structure F-165

Structure F-166

Structure F-167

Structure F-168

Structure F-169

Structure F-170

Structure F-171

Structure F-172

Structure F-173

Structure F-174

Structure F-175

Structure F-176

Structure F-177

Structure F-178

Structure F-179

Structure F-180

Structure F-181

Structure F-182

Structure F-183

Structure F-184

Structure F-185

Structure F-186

Structure F-187

Structure F-188

Structure F-189

Structure F-190

Structure F-191

Structure F-192

Structure F-193

Structure F-194

Structure F-195

Structure F-196

Structure F-197

Structure F-198

Structure F-199

Structure F-200

Structure F-201

Structure F-202

Structure F-203

Structure F-204

Structure F-205

Structure F-206

Structure F-207

Structure F-208

Structure F-209

Structure F-210

Structure F-211

Structure F-212

Structure F-213

Structure F-214

Structure F-215

Structure F-216

Structure F-217

Structure F-218

Structure F-219

Structure F2-1

Structure F2-2

Structure F2-3

Structure F2-4

Structure F2-5

Structure F2-6

Structure F2-7

Structure F2-8

Structure F2-9

Structure F2-10

Structure F2-11

Structure F2-12

Structure F2-37

Structure F2-38

Structure F2-39

Structure F2-40

Structure F2-41

Structure F2-42

Structure F2-43

Structure F2-44

Structure F2-45

Structure F2-46

Structure F2-47

Structure F2-48

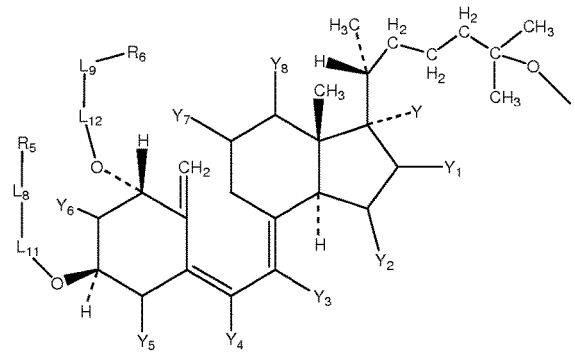
Structure F2-60
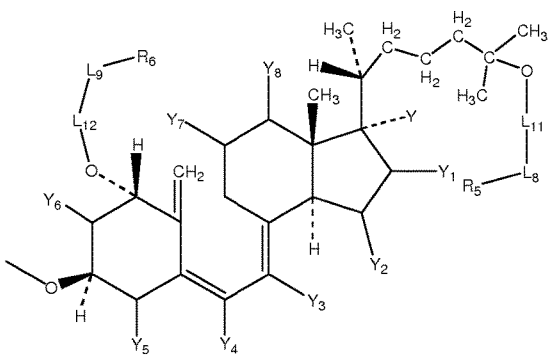
Structure F2-61
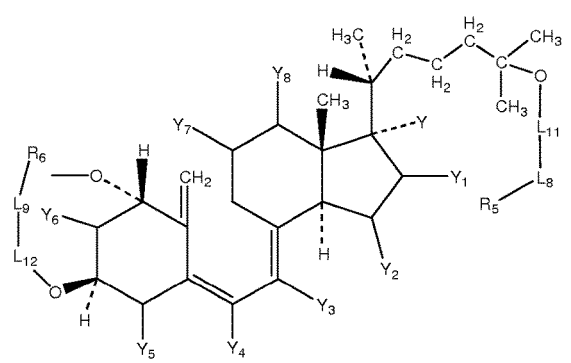
Structure F2-62
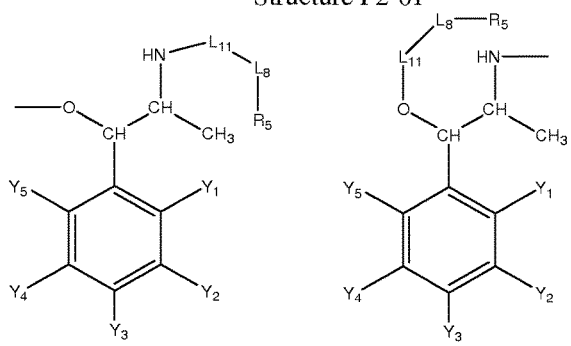
Structure F2-63    Structure F2-64
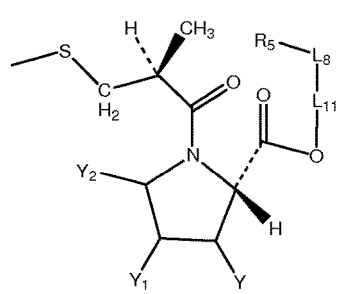
Structure F2-65
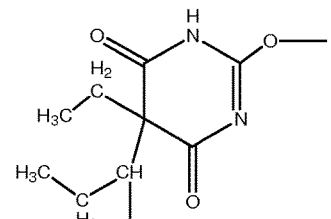
Structure F2-66
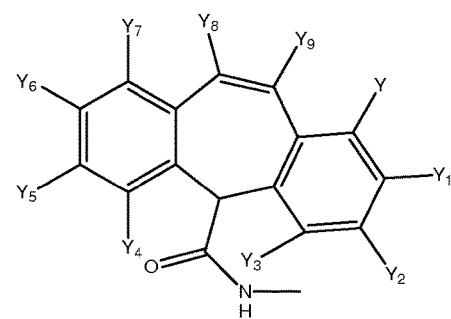
Structure F2-67
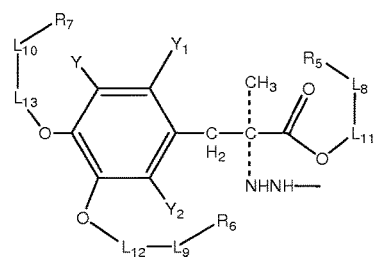
Structure F2-68
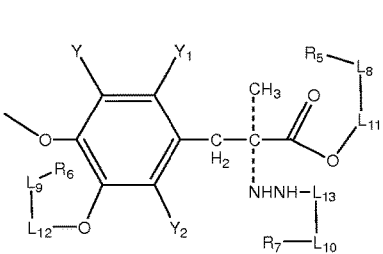
Structure F2-69
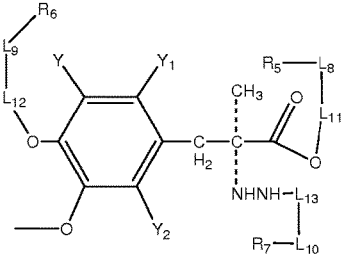
Structure F2-70
FIGURE 2  F Structure F2-71

Structure F2-72

Structure F2-73

Structure F2-74

Structure F2-75

Structure F2-76

Structure F2-77

Structure F2-78

Structure F2-79

Structure F2-80

Structure F2-81

Structure F2-82

Structure F2-83

Structure F2-84

Structure F2-85

Structure F2-86

Structure F2-87

Structure F2-88

Structure F2-89

Structure F2-90

Structure F2-91

Structure F2-92

Structure F2-93

Structure F2-94

Structure F2-95

Structure F2-96

Structure F2-97

Structure F2-98

Structure F2-99

Structure F2-100

Structure F2-101

Structure F2-102

Structure F2-103

Structure F2-131

Structure F2-132

Structure F2-133

Structure F2-134

Structure F2-135

Structure F2-136

Structure F2-137

Structure F2-138

Structure F2-139

Structure F2-140

Structure F2-141

Structure F2-142

Structure F2-143

Structure F2-144

Structure F2-145

Structure F2-146

Structure F2-147

Structure F2-148

Structure F2-149

Structure F2-162

Structure F2-163

Structure F2-164

Structure F2-165

Structure F2-166

Structure F2-167

Structure F2-168

Structure F2-169

Structure F2-170

Structure F2-171

Structure F2-172

Structure F2-173

Structure F2-187

Structure F2-188

Structure F2-189

Structure F2-190

Structure F2-191

Structure F2-192

Structure F2-193

Structure F2-194

Structure F2-195

Structure F2-196

Structure F2-197

Structure F2-198

Structure F2-211

Structure F2-212

Structure F2-213

Structure F2-214

Structure F2-215

Structure F2-216

Structure F2-217

Structure F2-218

Structure F2-219

Structure F2-220

Structure F2-221

Structure F2-222

Structure F2-223

Structure F2-224

Structure F2-225

Structure F2-226

Structure F2-227

Structure F2-228

Structure F2-229

Structure F2-230

Structure F2-231

Structure F2-232

Structure F2-233

Structure F2-234

Structure F2-235

Structure F2-236

Structure F2-237

Structure F2-238

Structure F2-239

Structure F2-240

Structure F2-241

Structure F2-242

Structure F2-243

Structure F2-244

Structure F2-245

Structure F2-246

Structure F2-247

Structure F2-248

Structure F2-249

Structure F2-250

Structure F2-251

Structure F2-252

Structure F2-253

Structure F2-254

Structure F2-255

Structure F2-256

Structure F2-257

Structure F2-258

Structure F2-259

Structure F2-260

Structure F2-261

Structure F2-262

Structure F2-263

Structure F2-264

Structure F2-265

Structure F2-266

Structure F2-267

Structure F2-269

Structure F2-268

Structure F2-270

Structure F2-271

Structure F2-272

Structure F2-273

Structure F2-274

Structure F2-275

Structure F2-276

Structure F2-277

Structure F2-278

Structure F2-279

Structure F2-280

Structure F2-281

Structure F2-282

Structure F2-283

Structure F2-284

Structure F2-285

Structure F2-286

Structure F2-287

Structure F2-288

Structure F2-289

Structure F2-290

Structure F2-291

Structure F2-305

Structure F2-306

Structure F2-307

Structure F2-308

Structure F2-309

Structure F2-310

Structure F2-311

Structure F2-312

Structure F2-326

Structure F2-327

Structure F2-328

Structure F2-329

Structure F2-330

Structure F2-331

Structure F2-332

Structure F2-333

Structure F2-334

Structure F2-335

Structure F2-336

Structure F2-337

Structure F2-354

Structure F2-355

Structure F2-356

Structure F2-357

Structure F2-358

Structure F2-359

Structure F2-360

Structure F2-361

Structure F2-362

Structure F2-363

Structure F2-364

Structure F2-365

Structure F2-366

Structure F2-367

Structure F2-368

Structure F2-369

Structure F2-370

Structure F2-371

Structure F2-372

Structure F2-373

Structure F2-374

Structure F2-390

Structure F2-391

Structure F2-392

Structure F2-393

Structure F2-394

Structure F2-395

Structure F2-396

Structure F2-397

Structure F2-398

Structure F2-399

Structure F2-400

Structure F2-401

Structure F2-402

Structure F2-403

Structure F2-404

Structure F2-405     Structure F2-406     Structure F2-407

Structure F2-408     Structure F2-409

Structure F2-410     Structure F2-411

Structure F2-412

Structure F2-413

Structure F2-414

Structure F2-415

Structure F2-416

Structure F2-417

Structure F2-418

Structure F2-419

Structure F2-420

Structure F2-421

Structure F2-422

Structure F2-423

Structure F2-424

Structure F2-425

Structure F2-426

Structure F2-427

Structure F2-428

Structure F2-429

Structure F2-430

Structure F2-431

Structure F2-432

Structure F2-433

Structure F2-434

Structure F2-435

Structure F2-436

Structure F2-437

Structure F2-438

Structure F3-1

Structure F3-2

Structure F3-3

Structure F3-4

Structure F3-5

Structure F3-6

Structure F3-7

Structure F3-8

Structure F3-9

Structure F3-10

Structure F3-11

Structure F3-12

Structure F3-13

Structure F3-14

Structure F3-15

Structure F3-16

Structure F3-17

Structure F3-18

Structure F3-19

Structure F3-20

Structure F3-21

Structure F3-22

Structure F3-23

Structure F3-24

Structure F3-25

Structure F3-26

Structure F3-27

Structure F3-28

Structure F3-29

Structure F3-30

Structure F3-31

Structure F3-32

Structure F3-33

Structure F3-34

Structure F3-35

Structure F3-36

Structure F3-37

Structure F3-38

Structure F3-39

Structure F3-40

Structure F3-41

Structure F3-42

Structure F3-43

Structure F3-44

Structure F4-1

Structure F4-2

Structure F4-3

Structure F4-4

Structure F4-5

Structure F4-6

Structure F4-7

Structure F4-8

Structure F4-9

Structure F4-10

Structure F4-11

Structure F4-12

Structure F4-13

Structure F4-14

Structure F4-15

Structure F4-16

Structure F4-17

Structure F4-18

Structure P-44

Structure P2-428

Structure P2-429

Structure P2-430

Structure P2-431

Structure P2-432

Structure P4-1

Structure P4-2

Structure P4-3

Structure P4-4

Structure P4-5

Structure P4-6

Structure P4-7

Structure P4-8

Structure P4-9

Structure P4-10

Structure P4-11

Structure P4-12

Structure P4-13

Structure P4-14

Structure P4-15

Structure P4-16

Structure P4-17

Structure P4-18

Structure P4-19

Structure P4-20

Structure P4-21

Structure P4-22

Structure P4-23

Structure P4-24

Structure P4-25

Structure P4-26

Structure P4-27

Structure P4-28

Structure P4-29

Structure P4-30

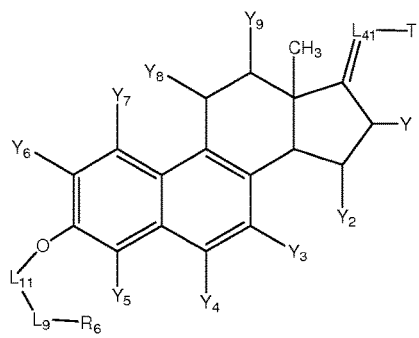
Structure P4-31
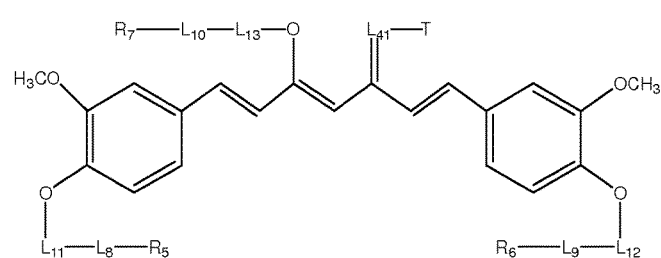
Structure P4-32

Structure D5-1

Structure D5-2

Structure D5-3

Structure D5-4

Structure D5-5

Structure D5-6

Structure D5-7

Structure D5-8

Structure D5-9

Structure D5-10

Structure D5-11

Structure D5-12

Structure D5-13

Structure D5-14

Structure D5-15

Structure D5-16

Structure D5-17

Structure D5-18

Structure D5-19

Structure D5-20

Structure D5-21

Structure D5-22

Structure D5-23

Structure D5-24

Structure D5-25

Structure D5-26

Structure D5-27

Structure D5-28

Structure D5-29

Structure D5-30

Structure D5-31

Structure D5-32

Structure D5-33

Structure D5-34

Structure D5-35

Structure D5-36

Structure D5-37

Structure D5-38

Structure D5-39

Structure D5-40

Structure D5-41

Structure D5-42

Structure D5-43   Structure D5-44   Structure D5-45

Structure D5-46   Structure D5-47   Structure D5-48

Structure D5-49   Structure D5-50   Structure D5-51

Structure D5-52   Structure D5-53   Structure D5-54

Structure D5-55

Structure D5-56

Structure D5-57

Structure D5-58

Structure D5-59

Structure D5-60

Structure D5-61

Structure D5-62

Structure D5-63

Structure D5-64

Structure D5-65

Structure D5-66

Structure D5-67        Structure D5-68        Structure D5-69

Structure D5-70        Structure D5-71        Structure D5-72

Structure D5-73        Structure D5-74        Structure D5-75

Structure D5-76        Structure D5-77        Structure D5-78

Structure D5-79

Structure D4-80

Structure D5-81

Structure D5-82

Structure D5-83

Structure D5-84

Structure D5-85

Structure D5-86

Structure D5-87

Structure D5-88

Structure D5-89

Structure D5-90

Structure D5-91

Structure D5-92

Structure D5-93

Structure D5-94

Structure D5-95

Structure D5-96

Structure D5-97

Structure D5-98

Structure D5-99

Structure D5-100

Structure D5-101

Structure D5-102

Structure D5-103

Structure D5-104

Structure D5-105

Structure D5-106

Structure D5-107

Structure D5-108

Structure D5-109

Structure D5-110

Structure D5-111

Structure D5-112

Structure D5-113

Structure D5-114

Structure D5-115

Structure D5-116

Structure D5-117

Structure D5-118

Structure D5-119

Structure D5-120

Structure D5-121

Structure D5-122

Structure D5-123

Structure D5-124

Structure D5-125

Structure D5-126

Structure D5-127

Structure D5-128

Structure D5-129

Structure D5-130

Structure D5-131

Structure D5-132

Structure D5-133

Structure D5-134

Structure D5-135

Structure D5-136

Structure D5-137

Structure D5-138

Structure D5-139

Structure D5-140

Structure D5-141

Structure D5-142

Structure D5-143

Structure D5-144

Structure D5-145

Structure D5-146

Structure D5-147

Structure D5-148

Structure D5-149

Structure D5-170

Structure D5-171

Structure D5-172

Structure D5-173

Structure D5-174

Structure D5-175

Structure D5-176

Structure D5-177

Structure D5-178

Structure D5-179

Structure D5-180

Structure D5-181

Structure D5-182

Structure D5-183

Structure D5-184

Structure D5-185

Structure D5-186

Structure D5-187

Structure D5-188

Structure D5-189

Structure D5-190

Structure D5-191

Structure D5-192

Structure D5-193

Structure D5-194

Structure D5-195

Structure D5-196

Structure D5-197

Structure D5-198

Structure D5-199

Structure D5-200

Structure D5-201

Structure D5-202 　　　　Structure D5-203 　　　　Structure D5-204

Structure D5-205 　　　　Structure D5-206 　　　　Structure D5-207

Structure D5-208 　　　　Structure D5-209 　　　　Structure D5-210

Structure D5-211 　　　　Structure D5-212 　　　　Structure D5-213

Structure D5-237
Structure D5-238
Structure D5-239
Structure D5-240
Structure D5-241
Structure D5-242
Structure D5-243

Picture 1:

Picture 2:

Picture 3:

Picture 4:

Picture 5:

Picture 6:

Picture 7:

Picture 8:

Picture 9:

HIGH PENETRATION COMPOSITIONS AND THEIR APPLICATIONS

PRIORITY CLAIM

The present application claims priority to U.S. Provisional Application 61/120,052, filed Dec. 4, 2008, which is incorporated herein by reference.

FIELD OF THE INVENTION

This invention relates to the field of compositions and pharmaceutical compositions that are capable of penetrating across one or more biological barriers and methods of using the pharmaceutical compositions for preventing, diagnosing and/or treating condition or disease in human, animals and plants.

BACKGROUND

Active agents or drugs that are effective in vitro may not be as effective in vivo due to the delivery difficulties in vivo, in particular, their limited penetration ability across one or more biological barriers before reaching the site of action where diseases occur in vivo.

Currently many drugs are administered through systematic route, such as oral or parenteral administration, to reach an action site of a condition or disease. Since higher dosage of drugs is required to reach a distal location in the systematic administration, drugs delivered by such route may cause adverse reactions.

For example, non-steroidal anti-inflammatory agents (NSAIAs) are widely used for treatment of acute or chronic conditions where pain and inflammation are present. Although NSAIAs are absorbed in the stomach and intestinal mucosa, oral administration usually accompanies adverse drug reactions such as gastrointestinal (GI) effects and renal effects. For instance, aspirin is known to cause gastric mucosal cell damage. The side effects of NSAIAs appear to be dose-dependent, and in many cases severe enough to pose the risk of dyspepsia, gastroduodenal bleeding, gastric ulcerations, gastritis, ulcer perforation, and even death.

Modifications of known NSAIAs have been reported to improve their efficacy and decrease their side effects. However, to treat inflammation or pain at distal areas, a much higher plasma concentration of an NSAIA is required when the drug is administered orally than when the drug is administered at the particular site of pain or injury (Fishman; Robert, U.S. Pat. No. 7,052,715).

Fishman and many others (Van Engelen et al. U.S. Pat. No. 6,416,772; Macrides et al. U.S. Pat. No. 6,346,278; Kirby et al. U.S. Pat. No. 6,444,234, Pearson et al. U.S. Pat. No. 6,528,040, and Botknecht et al. U.S. Pat. No. 5,885,597) have attempted to develop a delivery system for transdermal application through drug formulation to reduce the side effects associated with oral administration and achieve localized drug administration with reduced systematic exposure. It is very difficult, however, to deliver therapeutically effective plasma levels of these drugs by the formulation.

Prostaglandins and prostaglandin analogs have a wide variety of physiological functions and effects, and therefore have many medicinal uses. For example, prostaglandins and prostaglandin analogs can be used to induce childbirth or abortion; prevent closure of patent ductus arteriosus in newborns with particular cyanotic heart defects; prevent and treat peptic ulcers; as a vasodilator to treat severe Raynaud's phenomenon or ischemia of a limb or to treat pulmonary hypertension, which are treated traditionally via intravenous, subcutaneous or inhalation administration routes; treat glaucoma (e.g., in form of analogs such as bimatoprost ophthalmic solution, which is a synthetic prostamide analog with ocular hypotensive activity); and treat erectile dysfunction or in penile rehabilitation following surgery (e.g., PGE1 as alprostadil). However, prostaglandins and prostaglandin analogs are rapidly metabolized and inactivated by various oxidative and reductive pathways. For example, when taken orally, the drugs can be destroyed and/or inactivated in a few minutes by the first pass metabolism.

Mustards and mustard-related compounds have been used for treatment of various types of cancers and tumors. However, mustards and mustard-related compounds also cause adverse side effects such as nausea, vomiting, diarrhea, loss of appetite, hair loss and increased susceptibility to infection. Such side effects are often dose-dependent.

Peptides play various roles in a biological subject. For example, peptides and peptide-related compounds may be used to treat conditions such as obesity, infections, pain and sexual dysfunctions. However, peptides and peptide related compounds are rapidly proteolysized by proteolytic enzymes. When peptides and peptide related compounds are taken orally, they will be proteolysized in a few minutes. Other systematic administrations of peptides and peptide related compounds are painful, and in many cases require frequent and costly office visits to treat chronic conditions.

Beta-lactam and related compounds are widely used antibiotics. Oral administration has disadvantage of poor absorption of the antibiotics from GI tract. Intravenous, subcutaneous and intramuscular routes are not only painful, but also require administration by trained individuals and may incur other risks such as needle injury, infection, and other trauma. Along with the extensive use of antimicrobials, drug resistance becomes a common and serious problem as the pathogens mutate over time.

Therefore, there is a need to develop novel compositions that are capable of being delivered efficiently and effectively to an action site of a condition (e.g., a disease) to prevent, reduce or treat the condition in a biological subject with minimum side effects. Furthermore, new indications may be discovered due to the efficient and effective delivery of compositions or pharmaceutical compositions across biological barriers which have been difficult to cross.

SUMMARY OF THE INVENTION

One aspect of the present disclosure relates to a high penetration composition (HPC) comprising a functional unit covalently linked to a transportational unit through a linker.

In certain embodiments, a HPC of a parent drug comprises a functional unit that comprises a moiety of an agent wherein the delivery of the agent into a biological subject and/or transportation across one or more biological barrier are/is desired. The agent comprises the parent drug or a parent drug-related compound. The parent drug-related compound is a metabolite of the parent drug, a mimic/analog of the parent drug, or a compound that can be metabolized into the parent drug, a metabolite or a mimic/analog of the parent drug.

In certain embodiments, a parent drug or a parent drug-related compound comprises at least a functional group such as carboxyl, hydroxyl, thiol, amino, phosphate/phosphonate, carbonyl, or guanidino group. In certain embodiments, a parent drug or a parent drug-related compound comprises more than one functional group. In certain embodiments, a parent drug of a HPC is a non-steroidal anti-inflammatory agent (NSAIA). In certain embodiments, a parent drug of a HPC is a steroid, such as progesterone, desogestrel, and ethinylestradiol. In certain embodiments, a parent drug of a HPC is a peptide. In certain embodiments, a parent drug of a HPC is a mustard. In certain embodiments, a parent drug of a HPC is a beta-lactam antibiotics. In certain embodiments, a parent drug of a HPC is a antidiabetic drug such as glibornuide. In certain embodiments, a parent drug of a HPC is atenolol.

In certain embodiments, a functional unit may be hydrophilic, lipophilic, or amphiphilic (hydrophilic and lipophilic). The lipophilic moiety of the function unit may be inherent or achieved by converting its hydrophilic moieties to lipophilic moieties. For example, a lipophilic moiety of a functional unit is produced by converting one or more hydrophilic groups of the functional unit to lipophilic groups via traditional organic synthesis. Examples of the hydrophilic groups include, without limitation, carboxylic, hydroxyl, thiol, amine, phosphate/phosphonate and carbonyl groups. The lipophilic moieties produced via the modification of these hydrophilic groups include, without limitation, ethers, thioethers, esters, thioesters, carbonates, carbamates, amides, phosphates and oximes.

Examples of NSAIA include, but are not limited to, aspirin, diflunisal, salsalate, salicylic acid, ibuprofen, ketoprofen, fenoprofen, naproxen, suprofen, acetaminophen, α-methyl-(p-chlorobenzoyl)-5-methoxy-2-methylindole 3-acetic acid, flurbiprofen, carprofen, pranoprofen, benoxaprofen, alminoprofen, tiaprofenic acid, pirprofen, zaltoprofen, bermoprofen, loxoprofen, indoprofen, fenclorac, oxaprozin, fenbufen, orpanoxin, ketorolac, clidanac, tolmetin, zomepirac, etodolac, amfenac, bromofenac, alclofenac, fenclofenac, acemetacin, fentiazac, indomethacin, sulindac, lonazolac, bendazac, 6MNA, diclofenac, mefenamic acid, meclofenamic acid, flufenamic acid, niflumic acid, flunixin, piroxicam, sudoxicam, lornoxicam, tenoxicam, ampiroxicam, lomoxicam, isoxicam, cinnoxicam, and meloxicam.

Examples of prostaglandins and prostaglandin analogs include, but are not limited to, $PGA_1$, $PGA_2$, $PGA_3$, $PGB_1$, $PGB_2$, $PGB_3$, $PGD_1$, $PGD_2$, $PGD_3$, $PGE_1$, $PGE_2$, $PGE_3$, $PGF_{1\alpha}$, $PGF_{1\beta}$, $PGF_{2\alpha}$, $PGF_{2\beta}$, $PGF_{3\alpha}$, $PGG_2$, $PGH_1$, $PGH_2$, $PGI_2$ (prostacyclin), $PGI_3$, $PGJ_2$, $PGK_1$, $PGK_2$, carboprost, prostalene, misoprostol, gemeprost, sulprostone, fluprostenol cloprostenol, bimatoprost {(Z)-7-[(1R,2R,3R,5S)-3,5-Dihydroxy-2-[1E,3S]-3-hydroxy-5-phenyl-1-pentenyl]cyclopentyl}-5-N-ethylheptenamide}, latanoprost (13,14-dihydro-17-phenyl-18,19,20-trinor $PGF_{2\alpha}$, isopropyl ester), travoprost {(Z)-7-[(1 R,2R,3R,5S)-3,5-dihydroxy-2-[(1E,3R)-3-hydroxy-4-[(α,α,α-trifluoro-m-tolyl)oxy]-1-butenyl]cyclopentyl]-5-heptenoate}, and unoprostone (13,14-dihydro-15-keto-20-ethyl Prostaglandin $F_{2\alpha}$).

Examples of mustards include, but are not limited to, nitrogen mustards, nitrobenzyl mustards, phosphoramide mustard, isophosphoramide mustards and aldophosphamide.

Examples of peptides include, but are not limited to, peptide hormones (e.g. hyrotropin-releasing hormone, tuftsin (Thr-Lys-Pro-Arg), met-enkephaline (Tyr-Gly-Gly-Phe-Met), oxytocin, angiotensin, gastrin, somatostatin, dynorphin, endothelin, secretin, calcitonin, and insulin), enterostatins (e.g. Val-Pro-Asp-Pro-Arg (VPDPR), Val-Pro-Gly-Pro-Arg (VPGPR), and Ala-Pro-Gly-Pro-Arg (APGPR)), Melanocortin II (cyclo(1,6)-Ac-Nle-Asp-His-Phe-Arg-Trp-Lys-OH), opioid peptides (e.g. Met-enkephalin (H-Tyr-Gly-Gly-Phe-Met-OH), Leu-enkephalin (H-Tyr-Gly-Gly-Phe-Leu-OH), H-Tyr-D-Ala-Gly-N-Me-Phe-Met (O)—OL, and H-Tyr-D-Ala-Gly-Phe-Leu-OH), antimicrobial peptides (e.g. tachyplesins, histatin peptides and the derivatives), calcium binding peptides, competence stimulating peptides, peptide vaccines, and peptide mimics (e.g. α-helix mimics and β-sheet mimics).

Examples of beta-lactam antibiotics include, but are not limited to, penicillin derivatives, cephalosporins, penems, monobactams, carbapenems, beta-lactamase inhibitors and combinations thereof. Examples of penicillin derivatives include, but are not limited to, aminopenicillins (e.g. amoxicillin, ampicillin, and epicillin); carboxypenicillins (e.g. carbenicillin, ticarcillin, and temocillin); ureidopenicillins (e.g. azlocillin, piperacillin and mezlocillin); mecillinam, sulbenicillin, benzathine penicillin, penicillin G (benzylpenicillin), penicillin V (phenoxymethylpenicillin), penicillin O (allylmercaptomethylpenicillinic), procaine penicillin, oxacillin, methicillin, nafcillin, cloxacillin, dicloxacillin, flucloxacillin, pivampicillin, hetacillin, becampicillin, metampicillin, talampicillin, co-amoxiclav (amoxicillin plus clavulanic acid), and piperacillion. Examples of cephalosporins include, but are not limited to, cephalexin, cephalothin, cefazolin, cefaclor, cefuroxime, cefamandole, cefotetan, cefoxitin, ceforanide, ceftriaxone, cefotaxime, cefpodoxime proxetil, ceftazidime, cefepime, cefoperazone, ceftizoxime, cefixime and cefpirome. Examples of penems include, without limitation, faropenem. Examples of monobactams include, without limitation, aztreonam and tigemonam. Examples of carbapenems include, but are not limited to, biapenem, •doripenem, ertapenem, •imipenem, •meropenem, •and panipenem. Examples of beta-lactamase inhibitors include, but are not limited to, tazobactam ([2S-(2alpha,3beta,5alpha)]-3-Methyl-7-oxo-3-(1H-1,2,3-triazol-1-ylmethyl)-4-thia-1-azabicyclo[3.2.0]heptane-2-carboxylic acid 4,4-dioxide sodium salt), sulbactam (2S,5R)-3,3-dimethyl-7-oxo-4-thia-1-azabicyclo[3.2.0]heptane-2-carboxylic acid 4,4-dioxide sodium), and clavulanic acid ((2R,5R,Z)-3-(2-hydroxyethylidene)-7-oxo-4-oxa-1-azabicyclo[3.2.0] heptane-2-carboxylic acid). Other examples of antibiotics include, without limitation, [(N-benzyloxycarbonylamino) methyl]-phosphonic acid mono-(4-nitrophenyl) ester sodium salt, [(N-benzyloxycarbonylamino)methyl]-phosphonic acid mono-(3-pyridinyl) ester sodium salt, sulfanilamide (4-aminobenzenesulfonamide), sulfasalazine (6-oxo-3-(2-[4-(N-pyridin-2-ylsulfamoyl)phenyl]hydrazono) cyclohexa-1,4-dienecarboxylic acid), 1-cyclopropyl-6-fluoro-4-oxo-7-piperazin-1-yl-quinoline-3-carboxylic acid, nalidixic acid (1-ethyl-7-methyl-4-oxo-[1,8]naphthyridine-3-carboxylic acid), In certain embodiments, a transportational unit of a HPC comprises a protonatable amine group that is capable of facilitating the transportation or crossing of the HPC through one or more biological barriers (e.g., >about 10 times, >about 50 times, >about 100 times, >about 300 times, >about 500 times, >about 1,000 times, >about 10,000 times faster than the parent drug) In certain embodiments, the protonatable amine group is substantially protonated at the pH of the biological barriers the HPC penetrates through. In certain embodiment, the amine group can be reversibly protonated.

In certain embodiments, a linker covalently linking a functional unit and a transportational unit of a HPC comprises a bond that is capable of being cleaved after the HPC penetrates across one or more biological barriers. The cleavable bond comprises, for example, a covalent bond, an ether, thioether, amide, ester, thioester, carbonate, carbamate, phosphate or oxime bond.

Another aspect of the present disclosure relates to a pharmaceutical composition comprising one HPC and a pharmaceutically acceptable carrier.

Another aspect of the present disclosure relates to the use of a composition of the present disclosure in penetrating a biological barrier, such as skin, blood-brain barrier, blood milk barrier, blood-cerebrospinal fluid (CSF) barrier, and blood-synovial fluid (SF) barrier.

Another aspect of the present disclosure relates to method for diagnosing the onset, development, or remission of a condition in a biological subject by using a HPC of the present disclosure. In certain embodiments, the HPC or the functional unit of the HPC of the composition is detectable. In certain embodiments, the HPC or the functional unit of the HPC is inherently labeled, or labeled or conjugated to a detectable agent.

Another aspect of the present disclosure relates methods for screening a test functional unit, a test linker, or a test transportational unit with desired characters.

Another aspect of the present disclosure relates to a method for treating a condition in a biological subject by administering to the subject a composition in accordance with the present disclosure. In certain embodiments, the method relates to treating a condition in a subject treatable by a parent drug by administering to the subject a therapeutically effective amount of a HPC of the parent drug, or a pharmaceutical composition thereof. In certain embodiments, the HPC or the pharmaceutical composition of the HPC is administrated to a biological subject via various routes including, but not limited to, oral, enteral, buccal, nasal, topical, rectal, vaginal, aerosol, transmucosal, epidermal, transdermal, dermal, ophthalmic, pulmonary, subcutaneous, and/or parenteral routes. In certain embodiments, the HPC or the pharmaceutical composition of the HPC is administered orally, transdermally, topically, subcutaneously and/or parenterally.

In certain embodiments, conditions treatable by a HPC of a parent drug of the present disclosure or a pharmaceutical composition thereof include, treating conditions in a site that the parent drug is difficult to reach due to its lack of penetration ability. Examples of such conditions include, without limitation, spinal cord injury, myelin infection and related conditions (e.g. muscle disorders such as amyotrophic lateral sclerosis (ALS), oculopharyngeal muscular dystrophy (OPMD), myotonic dystrophy (MD), Duchenne muscular dystrophy (DMD), polymyositis (PM), dermatomyositis (DM) and inclusion body myositis (IBM)). In certain embodiments, conditions treatable by a HPC include autoimmune disorders (e.g. psoriasis, Crohn's disease, lupus erythematosus, discoid lupus erythematosus, systematic lupus erythematosus, multiple sclerosis, fibrosis (e.g. cystic fibrosis, liver fibrosis, pulmonary fibrosis, pancreas fibrosis, spleen fibrosis, gastrointestinal fibrosis, and fibrosis in other organ)), metabolite disorders (e.g. diabetes (type II), abnormal blood lipid level), thrombosis related conditions (e.g. stroke), neurodegenerative disease (e.g. Alzheimer's diseases and Parkinson's disease), cirrhosis, liver inflammation, hyperthyroidism, gallstones, ageing, undesired skin conditions (e.g. vitiligo, actinic keratosis, abnormal vascular skin lesions, birthmarks, moles (nevi), skin tags, aging spots (liver spots), pus-filled or reddish bumps, comedones, papules, pustules, nodules, epidermoid cysts, keratosis pilaris, sagging skin, wrinkles, crows feet, flesh-colored skin spots, rosacea, post-treatment skin), macular degeneration and age-related macular degeneration (AMD), cough, organ transplant rejection, cancer and tumor (e.g. gastric cancer, multiple myeloma, brain tumor, prostate cancer and bone cancer), grey and/or white hair, hair loss, bold, insufficient hair or eyelashes, pregnancy in women, embryo implantation, brain trama, and conditions in plants that are related to viral, fungus or insect infections.

In certain embodiments, conditions treatable by a NSAIA HPC or a pharmaceutical composition thereof include, but are not limited to, myelin infection and related conditions, cirrhosis, liver inflammation, hyperthyroidism, gallstones, ageing, undesired skin conditions (e.g. actinic keratosis, abnormal vascular skin lesions, birthmarks, moles (nevi), skin tags, aging spots (liver spots), pus-filled or reddish bumps, comedones, papules, pustules, nodules, epidermoid cysts, keratosis pilaris, sagging skin, wrinkles, crows feet, flesh-colored skin spots, rosacea, post-treatment skin), cough, organ transplant rejection, cancer and tumor (e.g. prostate cancer and bone cancer), grey and/or white hair, hair loss, bold, ageing, and conditions in plants that are related to viral, fungus or insect infections.

In accordance with the advantages of the present disclosure, without intending to be limited by any particular mechanism, a therapeutically effective amount of a HPC can be administered locally to a site of condition with a less dosage to achieve a higher local concentration. The advantages include, for example, avoidance of systematic administration and reduction of adverse effects (e.g., pain of injection, gastrointestinal/renal effects, and other side effect), possible novel treatment due to high local concentration of a HPC or the corresponding parent drug or an active metabolite thereof. HPCs can penetrate skin, blood-brain, blood-milk, and other membrane barriers many times faster and have a pharmacological effect many times stronger than their parent drugs. The present disclosure further includes, for example, systematic administration of a HPC to a biological subject to achieve faster and more efficient bioavailability, penetration of biological barriers (e.g., the blood brain barrier) which have not been crossed by parent agents significantly, and new indications thereof.

DETAILED DESCRIPTION OF THE INVENTION

Figure 1:
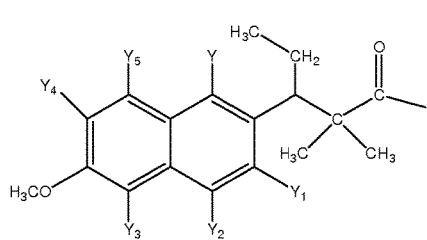
FIG. 1: Exemplary structures of functional unit F1.
Figure 1:
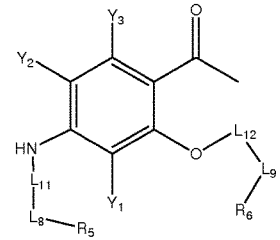
Figure 1:
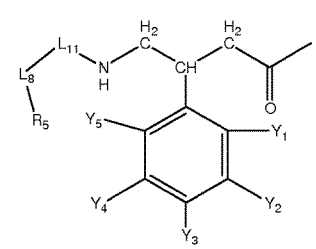
Figure 1:
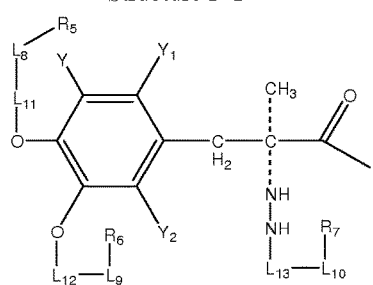
Figure 1:
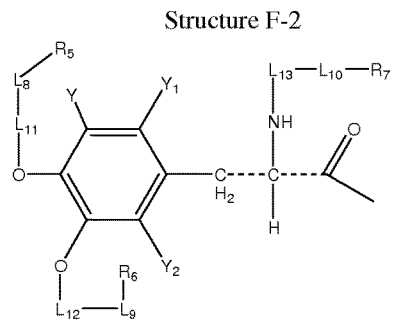
Figure 1:
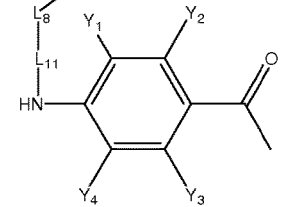
Figure 1:
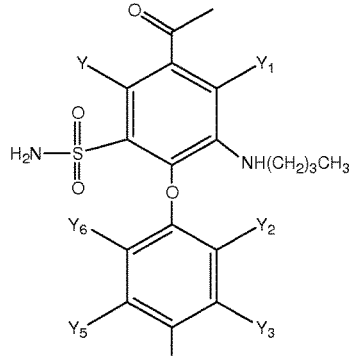
Figure 1:
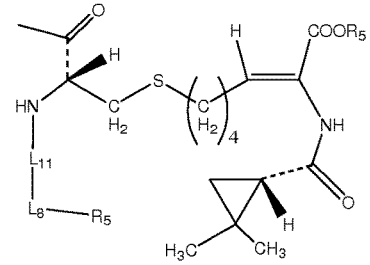
Figure 1:
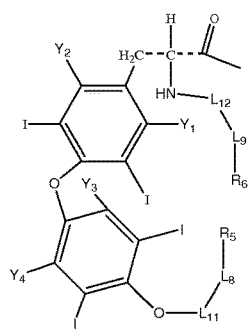
Figure 1:
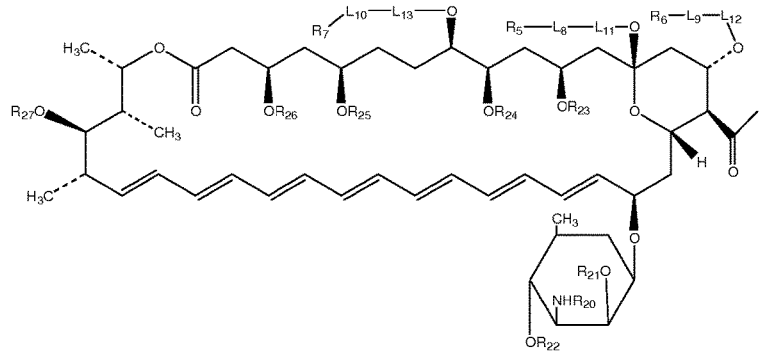
Figure 1:
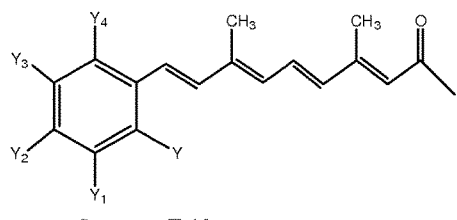
Figure 1:
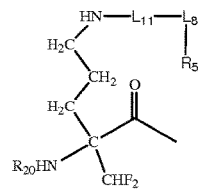
Figure 1:
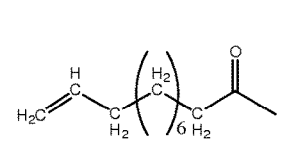
Figure 1:
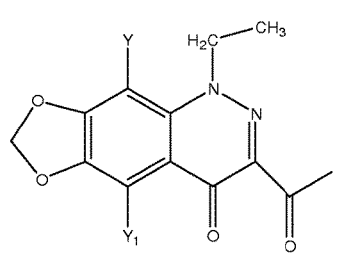
Figure 1:
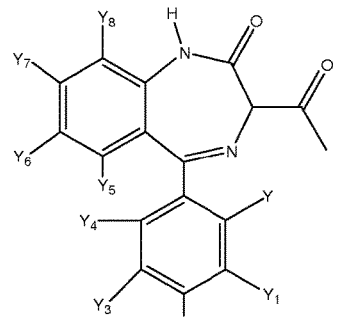
Figure 1:
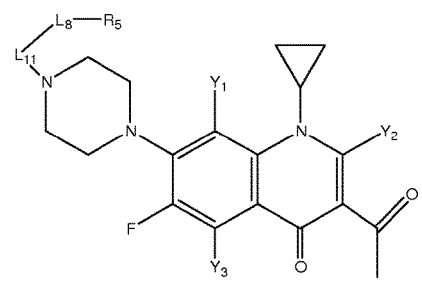
Figure 1:
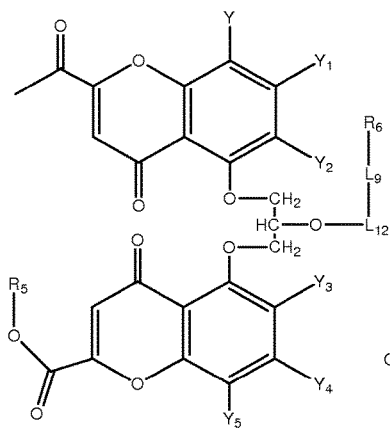
Figure 1:
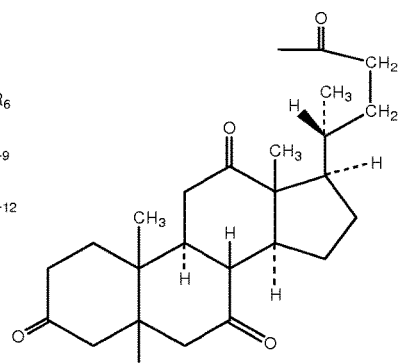
Figure 1:
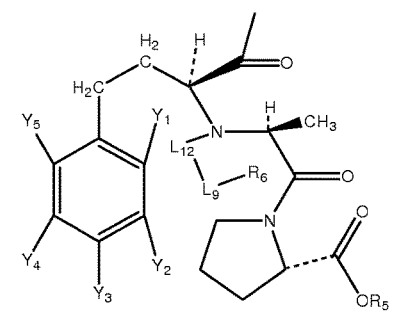
Figure 1:
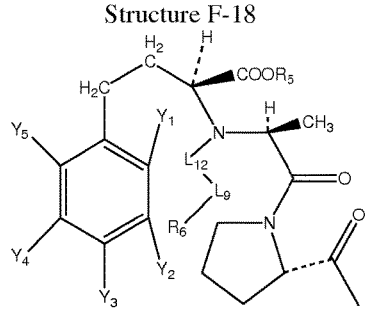
Figure 1:
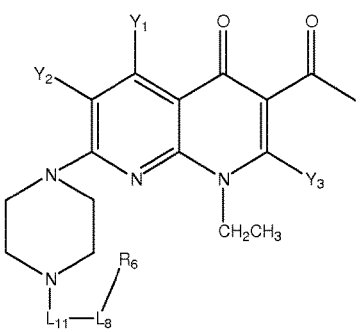
Figure 1:
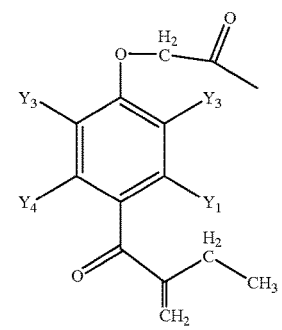
Figure 1:
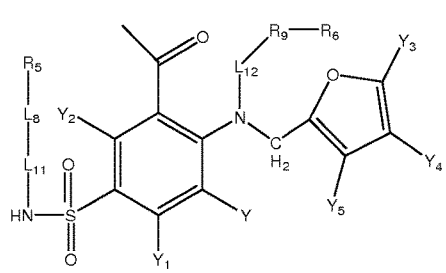
Figure 1:
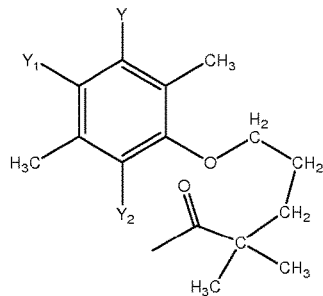
Figure 1:
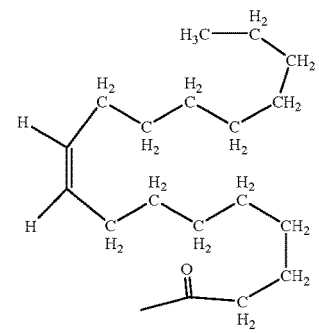
Figure 1:
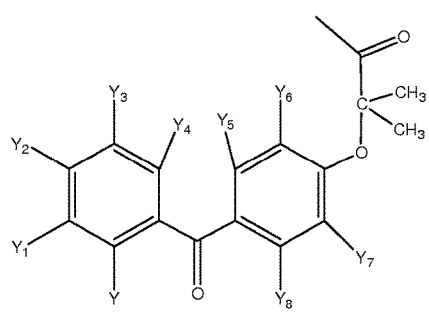
Figure 1:
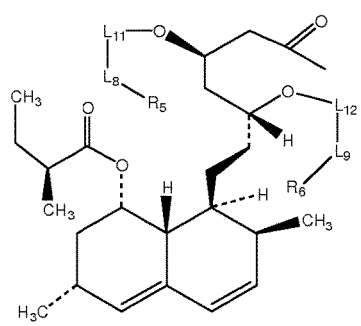
Figure 1:
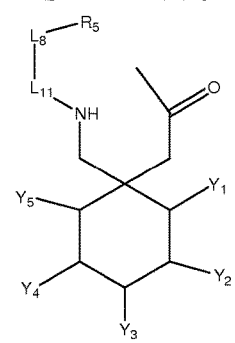
Figure 1:
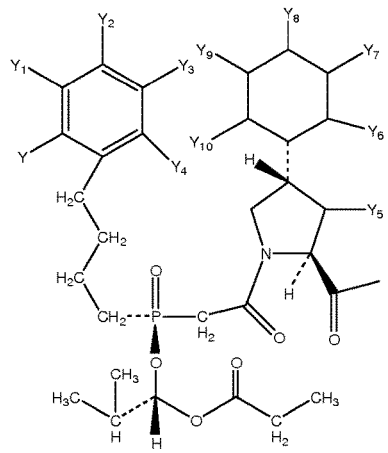
Figure 1:
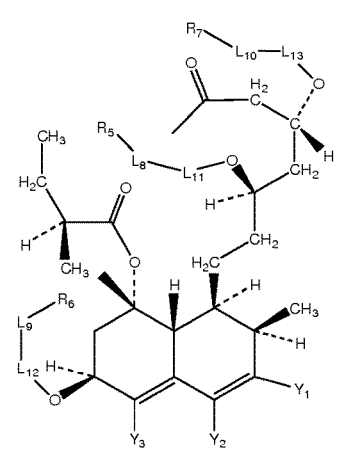
Figure 1:
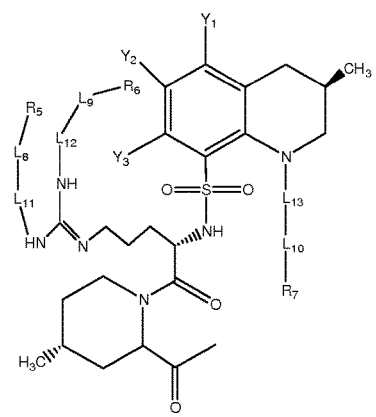
Figure 1:
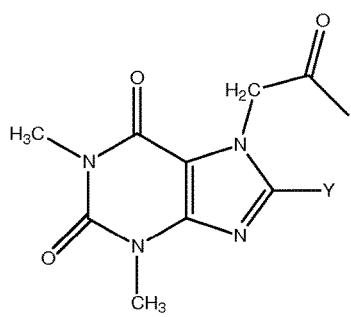
Figure 1:
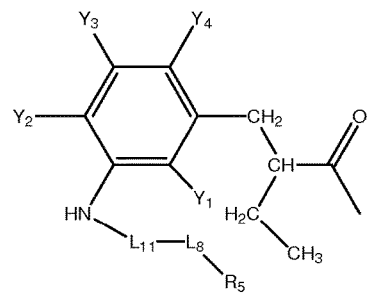
Figure 1:
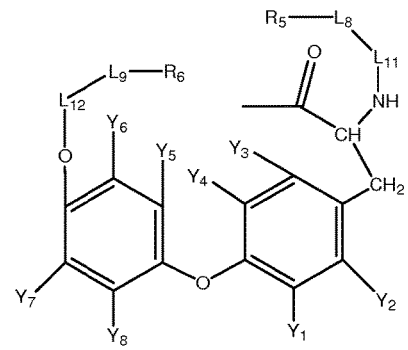
Figure 1:
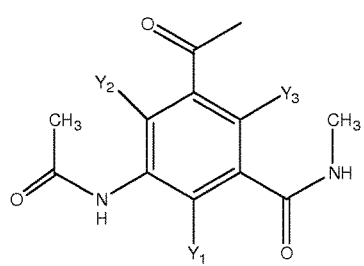
Figure 1:
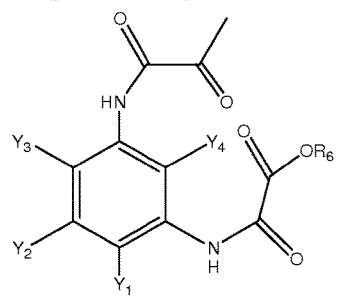
Figure 1:
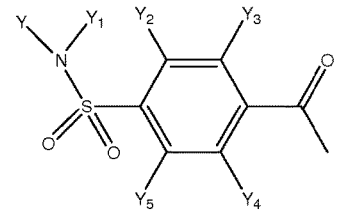
Figure 1:
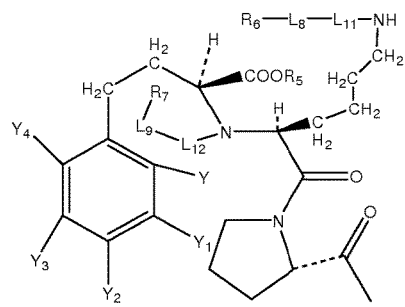
Figure 1:
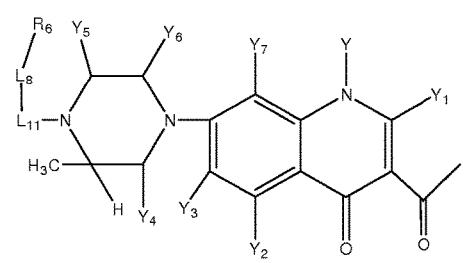
Figure 1:
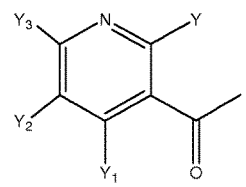
Figure 1:
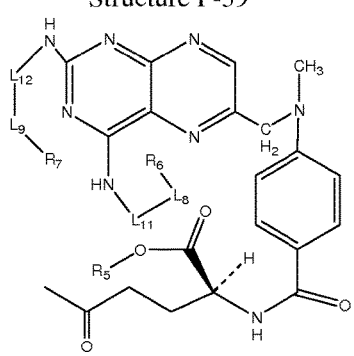
Figure 1:
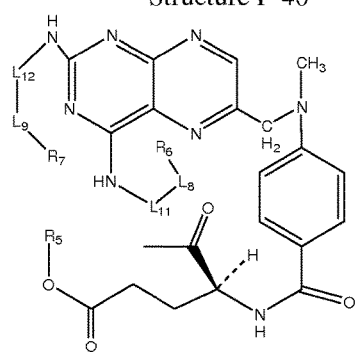
Figure 1:
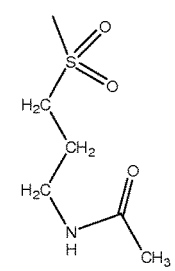
Figure 1:
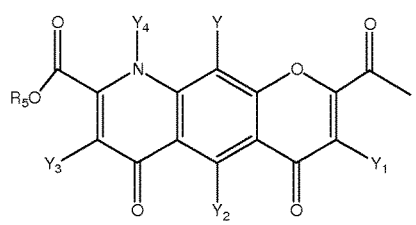
Figure 1:
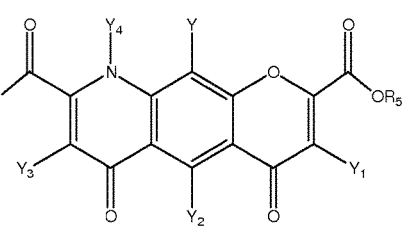
Figure 1:
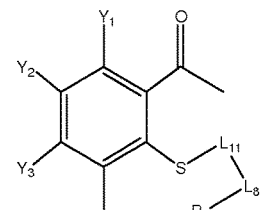
Figure 1:
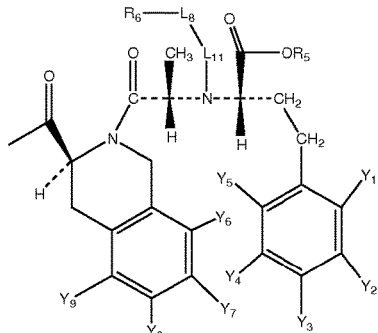
Figure 1:
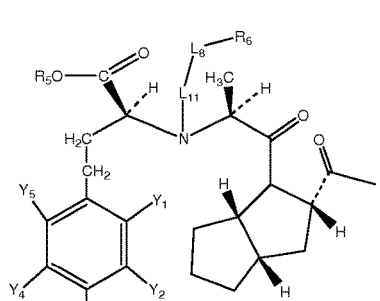
Figure 1:
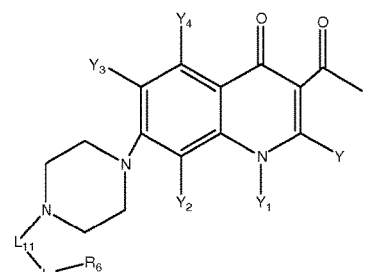
Figure 1:
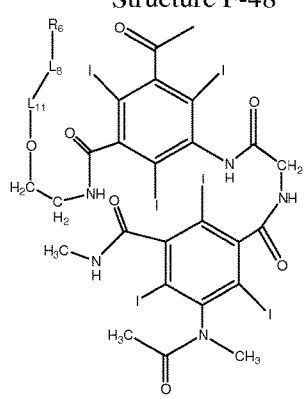
Figure 1:
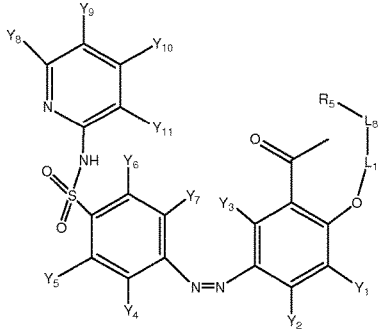
Figure 1:
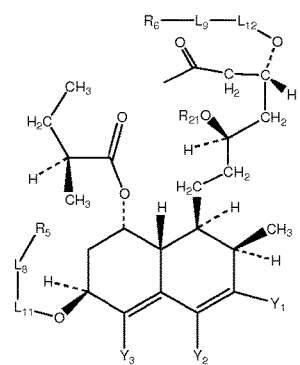
Figure 1:
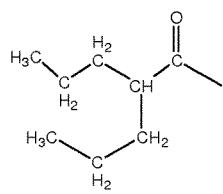
Figure 1:
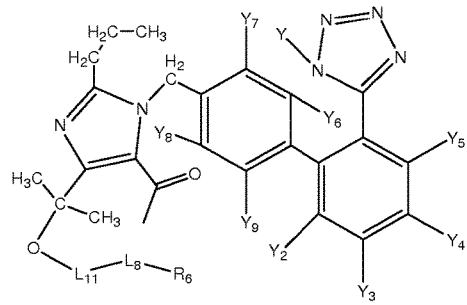
Figure 1:
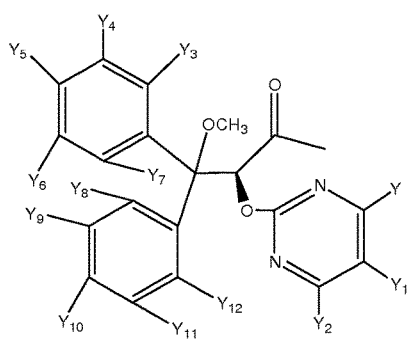
Figure 1:
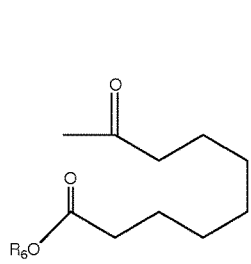
Figure 1:
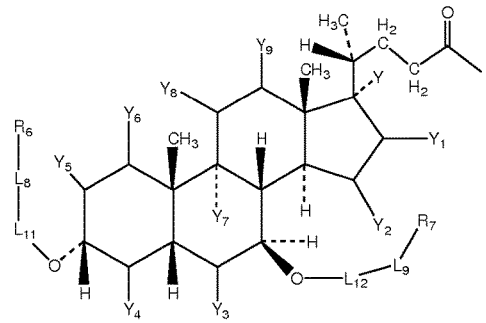
Figure 1:
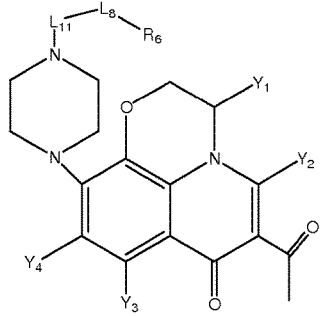
Figure 1:
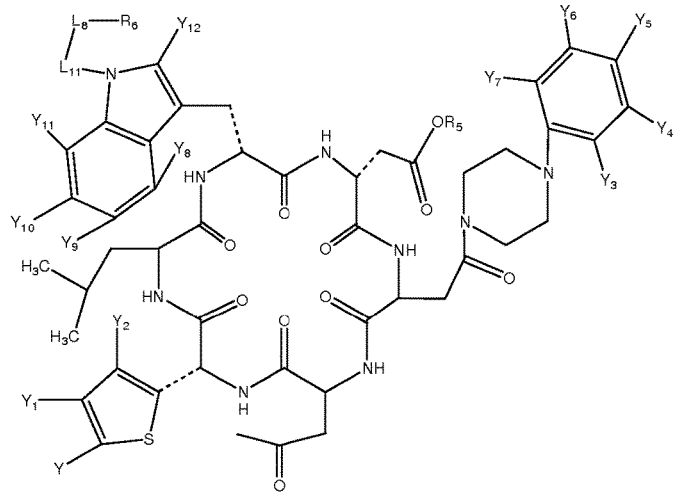
Figure 1:
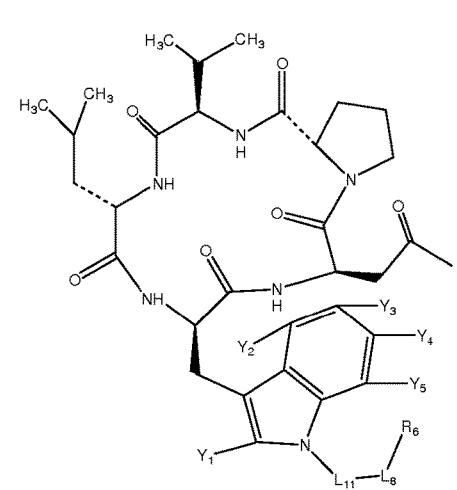
Figure 1:
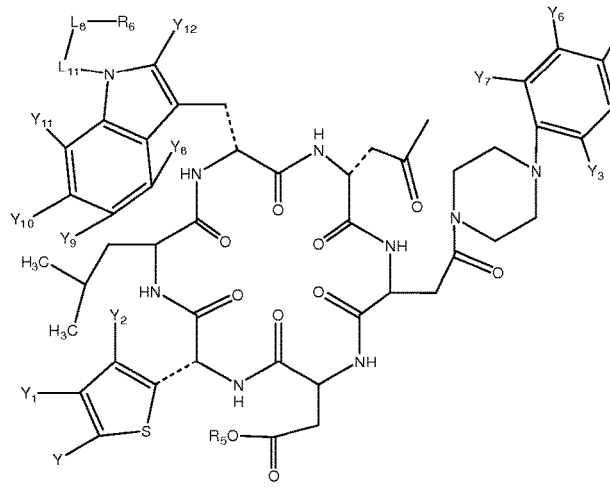
Figure 1:
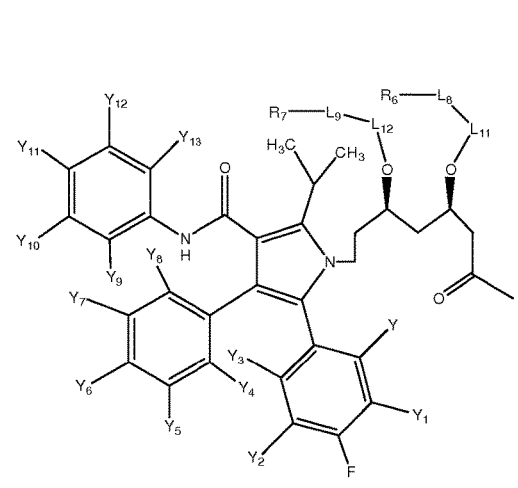
Figure 1:
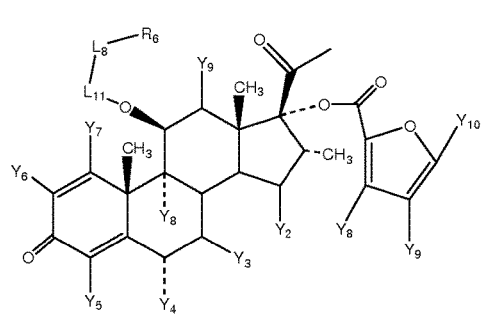
Figure 1:
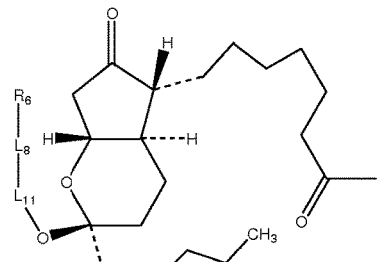
Figure 1:
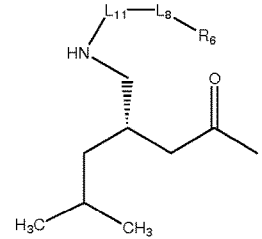
Figure 1:
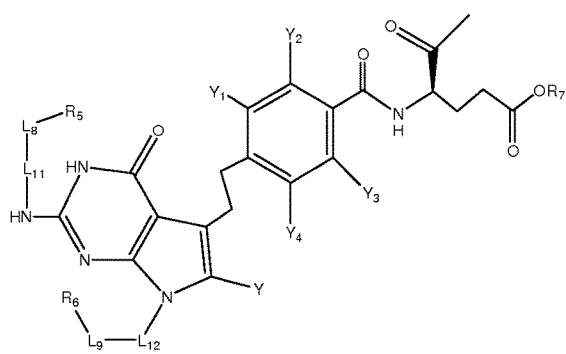
Figure 1:
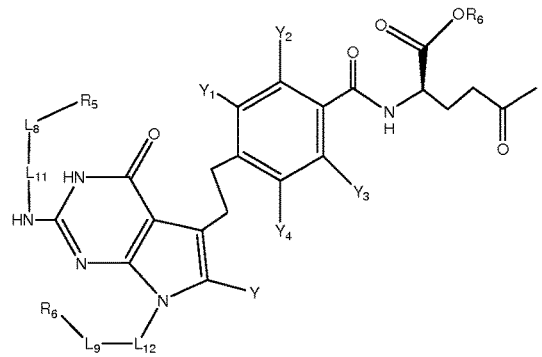
Figure 1:
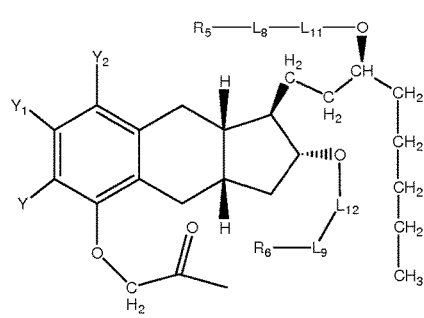
Figure 1:
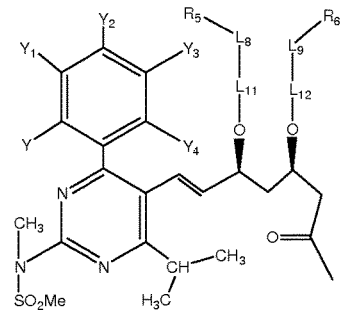
Figure 1:
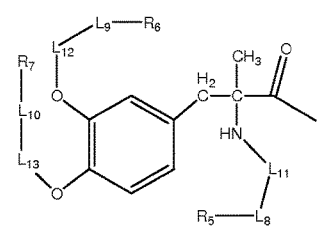
Figure 1:
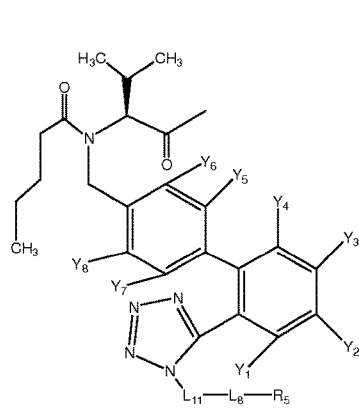
Figure 1:
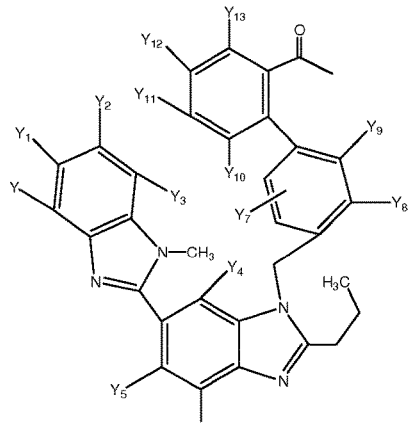
Figure 1:
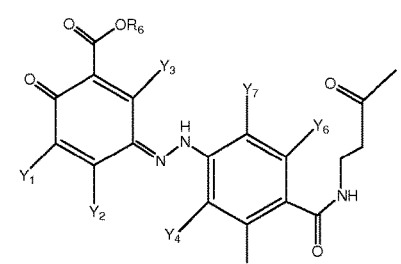
Figure 1:
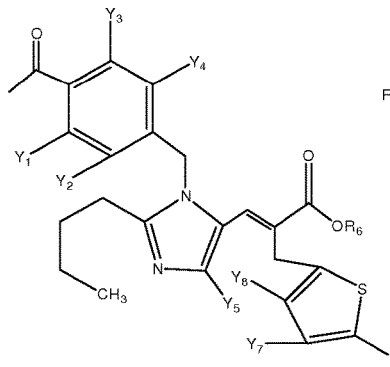
Figure 1:
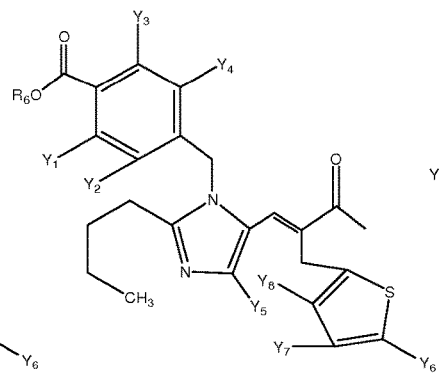
Figure 1:
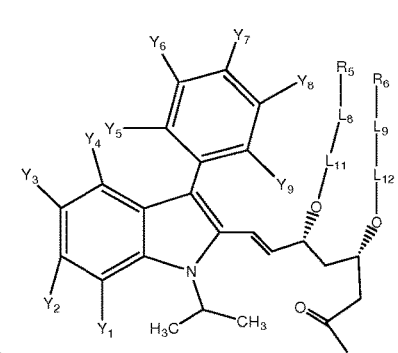
Figure 1:
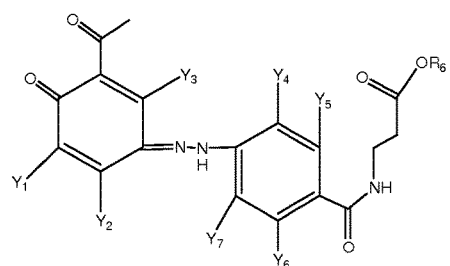
Figure 1:
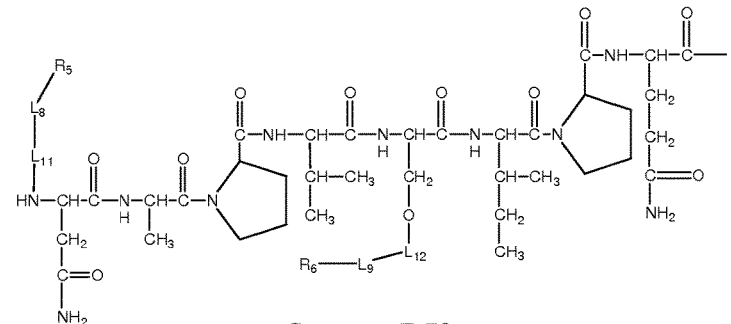
Figure 1:
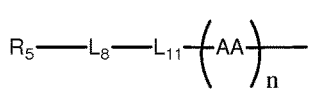
Figure 1:
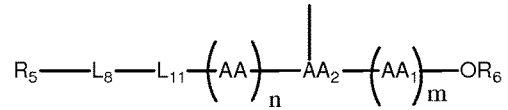
Figure 1:
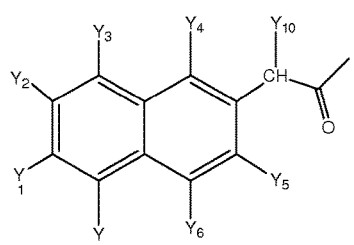
Figure 1:
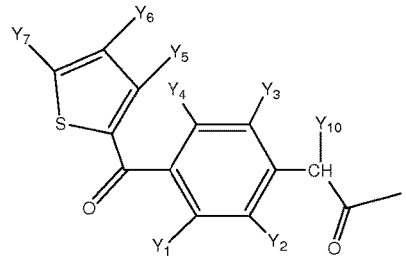
Figure 1:
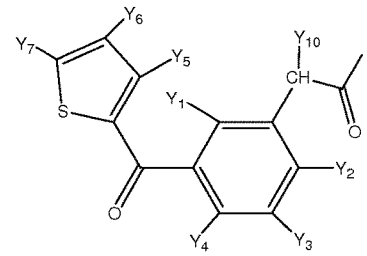
Figure 1:
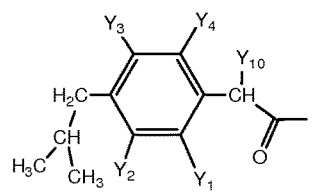
Figure 1:
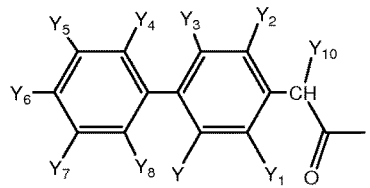
Figure 1:
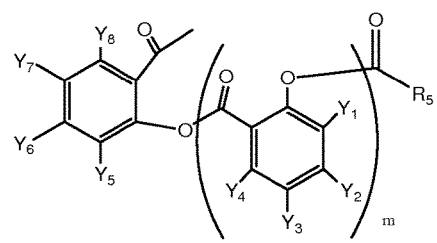
Figure 1:
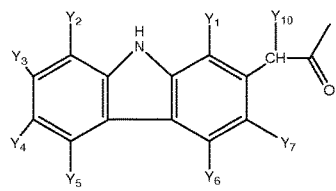
Figure 1:
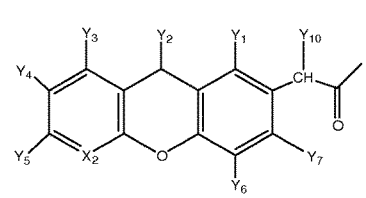
Figure 1:
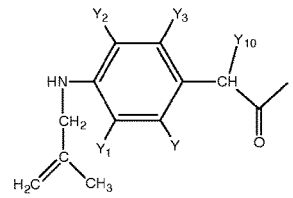
Figure 1:
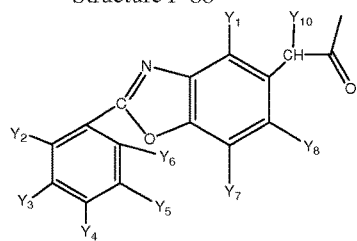
Figure 1:
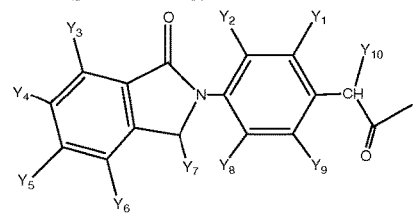
Figure 1:
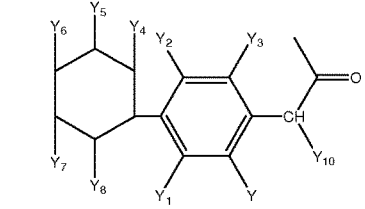
Figure 1:
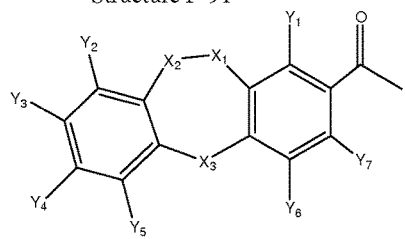
Figure 1:
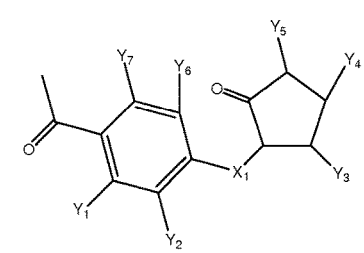
Figure 1:
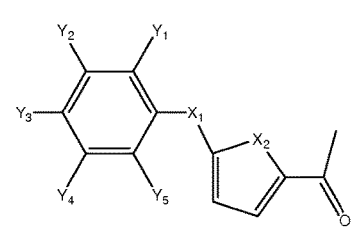
Figure 1:
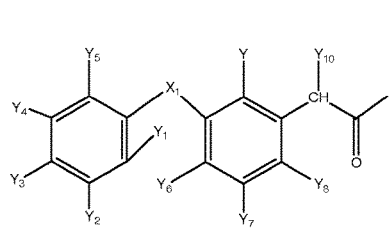
Figure 1:
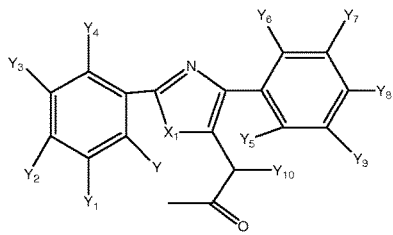
Figure 1:
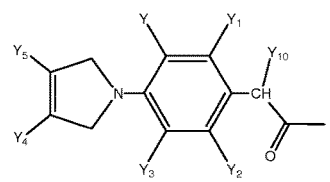
Figure 1:
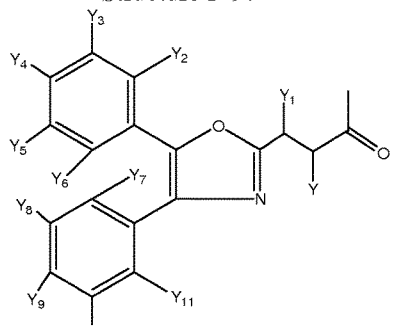
Figure 1:
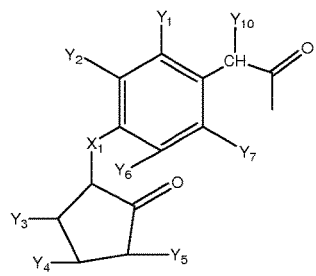
Figure 1:
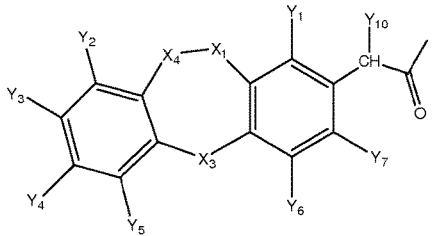
Figure 1:
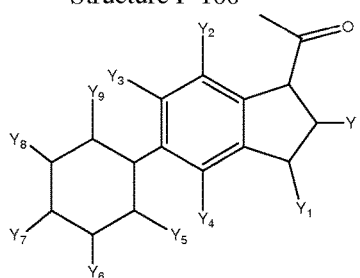
Figure 1:
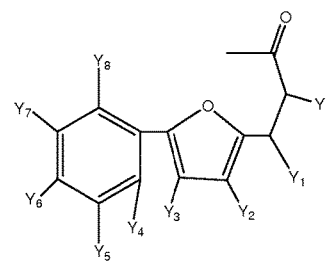
Figure 1:
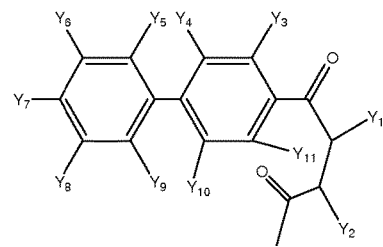
Figure 1:
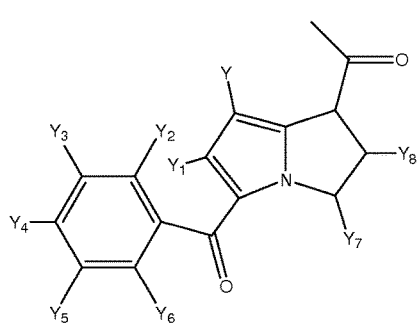
Figure 1:
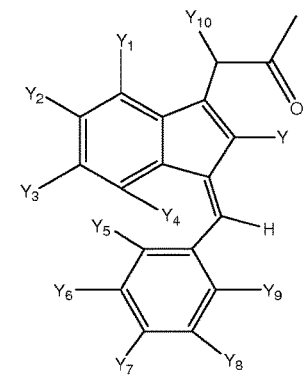
Figure 1:
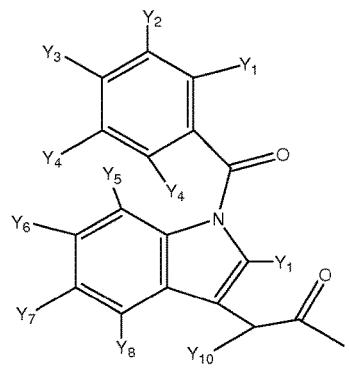
Figure 1:
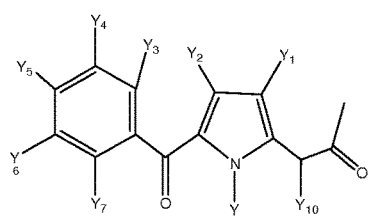
Figure 1:
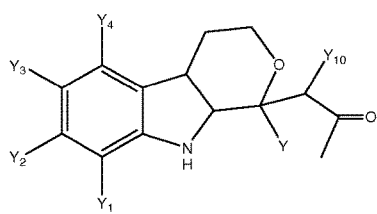
Figure 1:
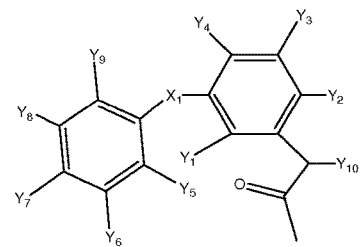
Figure 1:
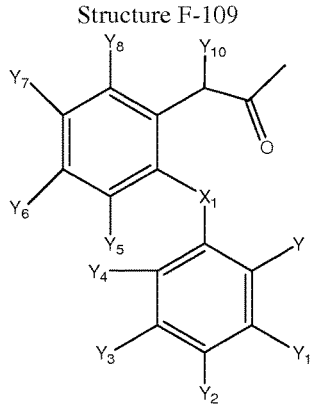
Figure 1:
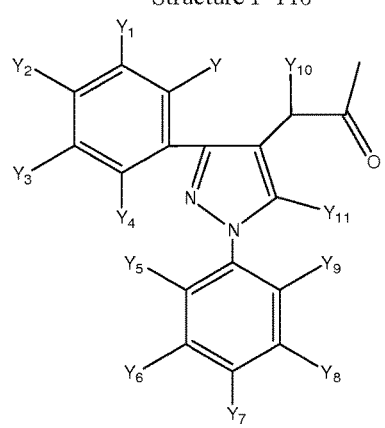
Figure 1:
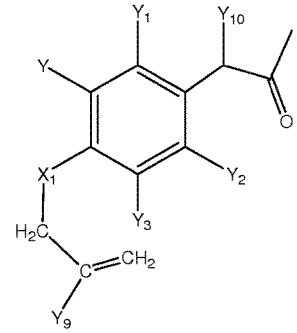
Figure 1:
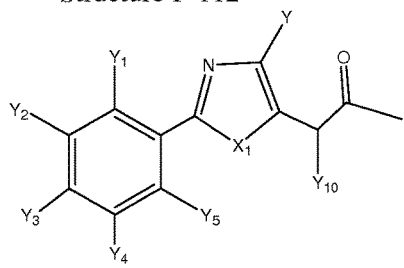
Figure 1:
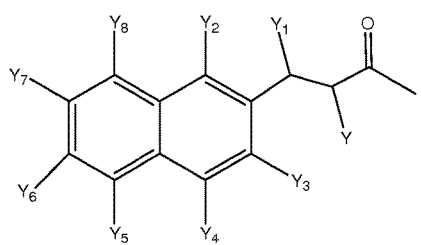
Figure 1:
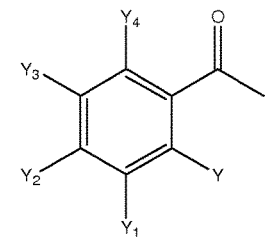
Figure 1:
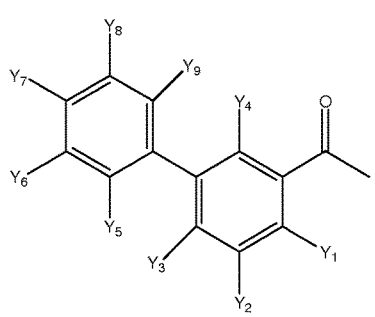
Figure 1:
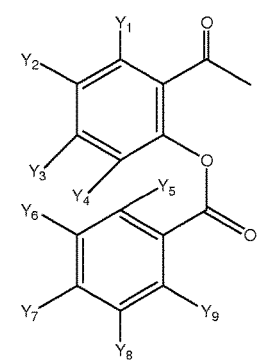
Figure 1:
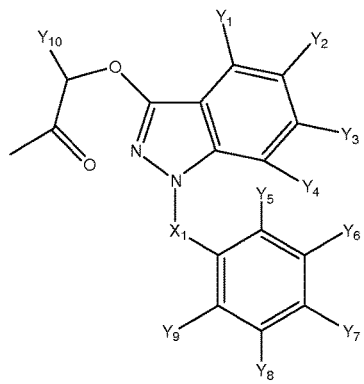
Figure 1:
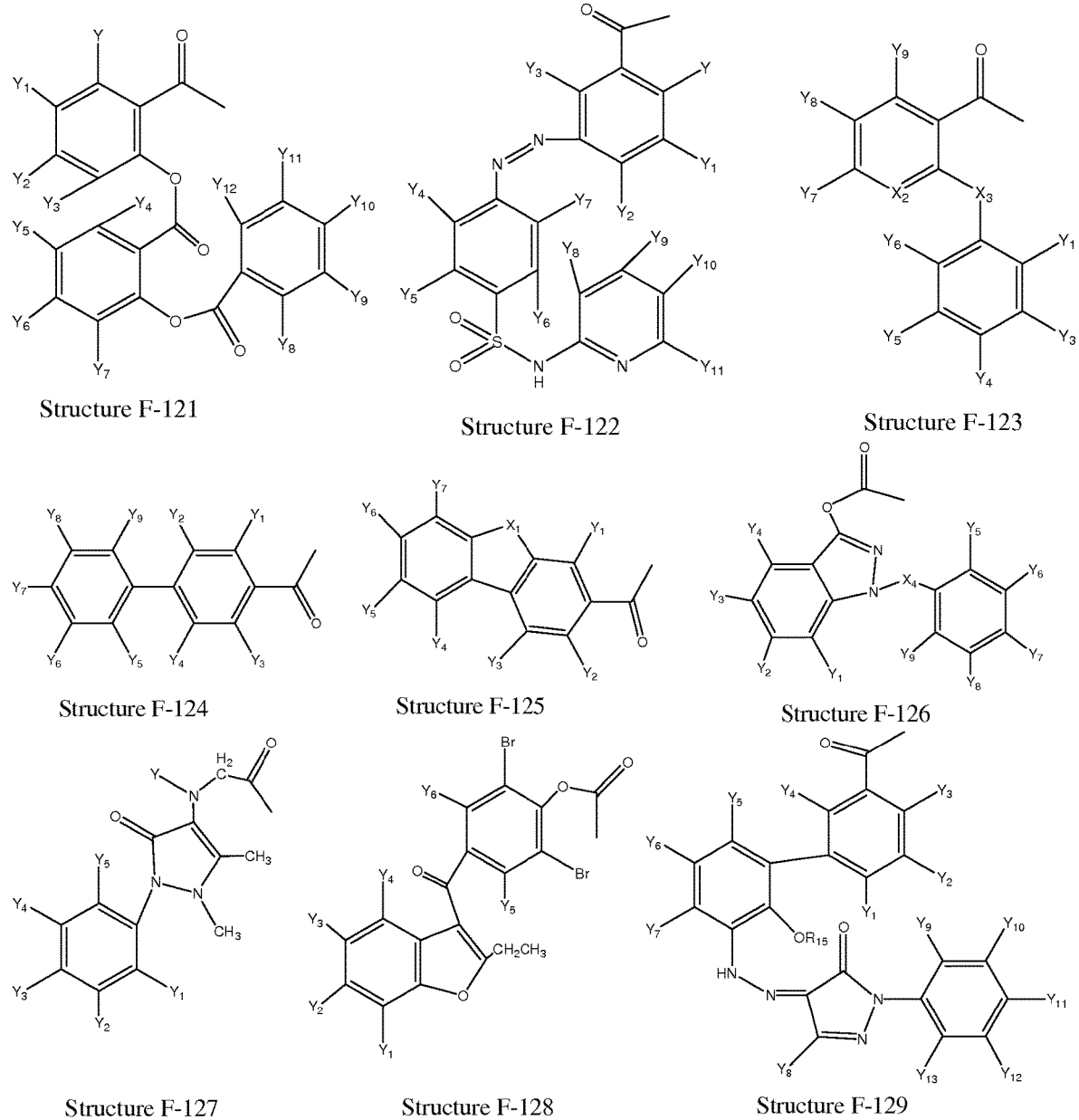
Figure 1:
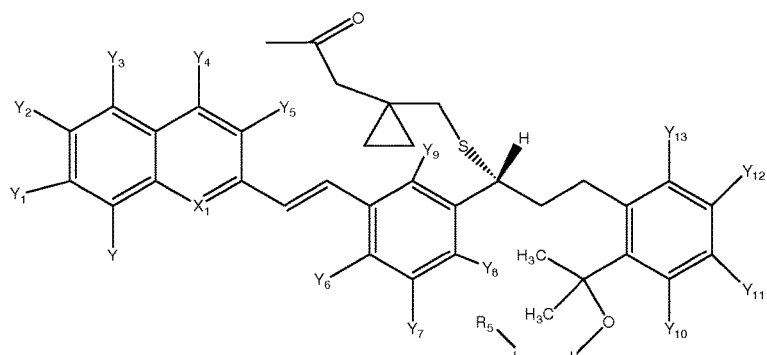
Figure 1:
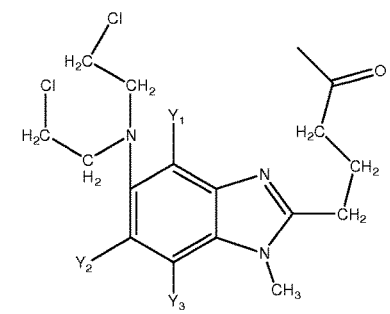
Figure 1:
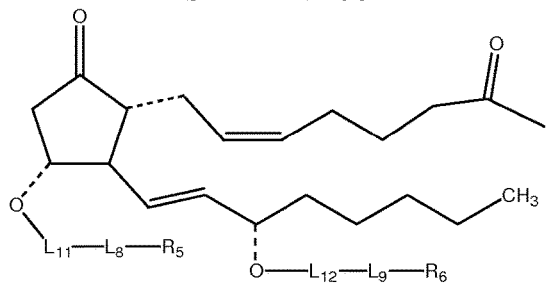
Figure 1:
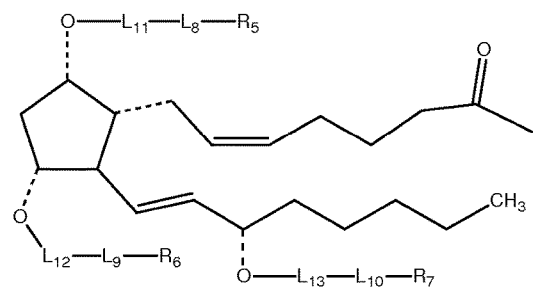
Figure 1:
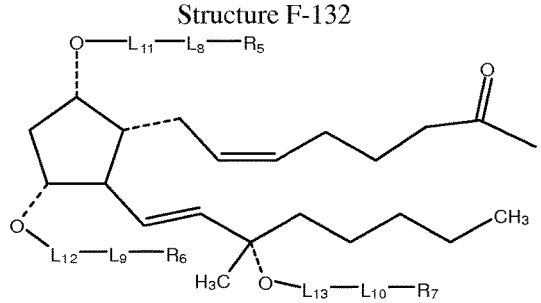
Figure 1:
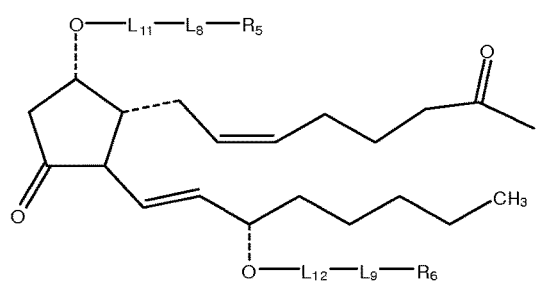
Figure 1:
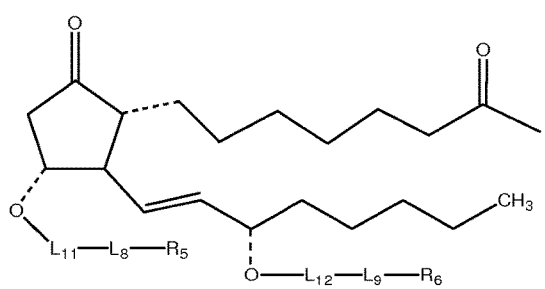
Figure 1:
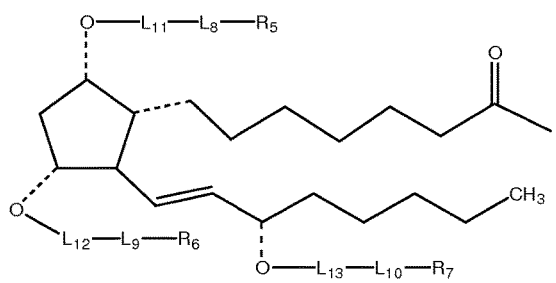
Figure 1:
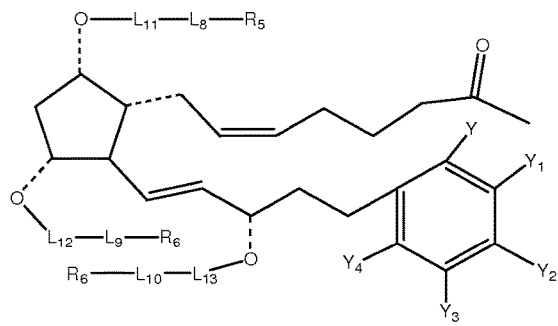
Figure 1:
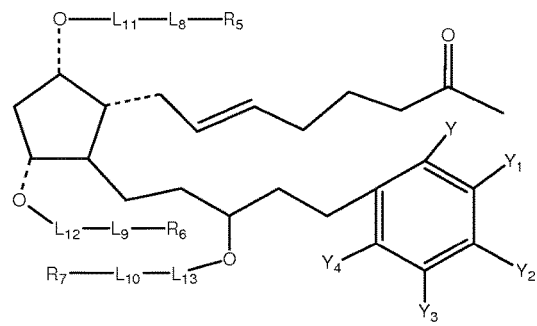
Figure 1:
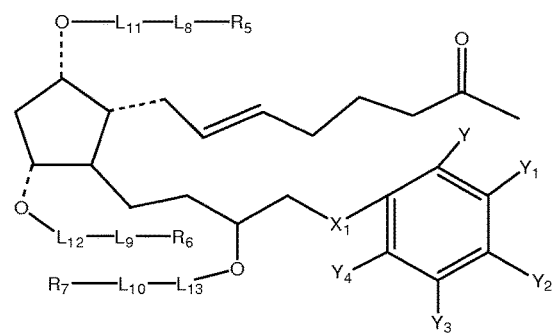
Figure 1:
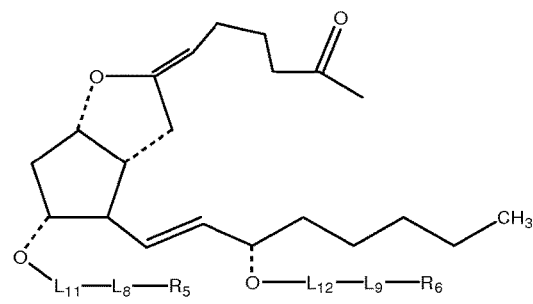
Figure 1:
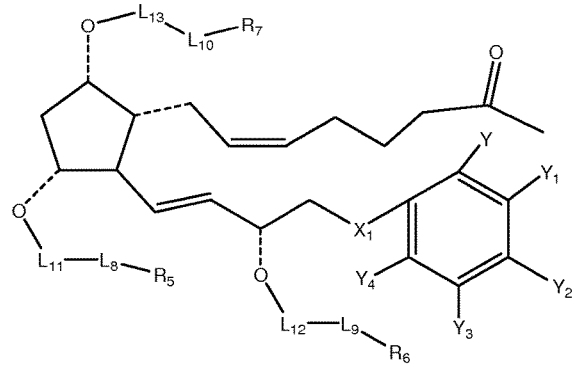
Figure 1:
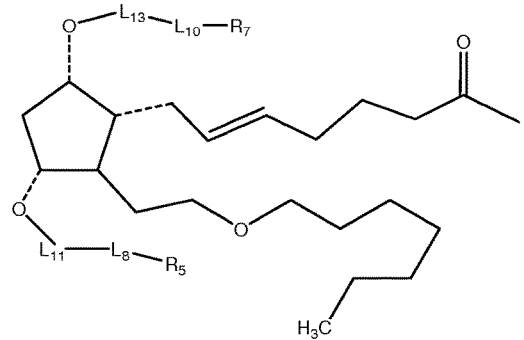
Figure 1:
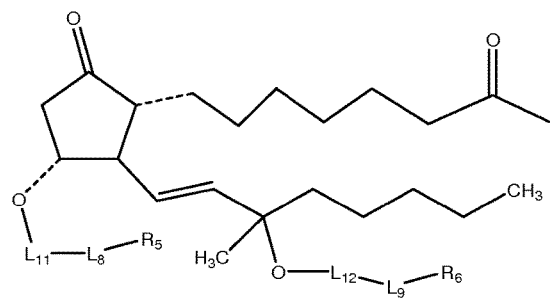
Figure 1:
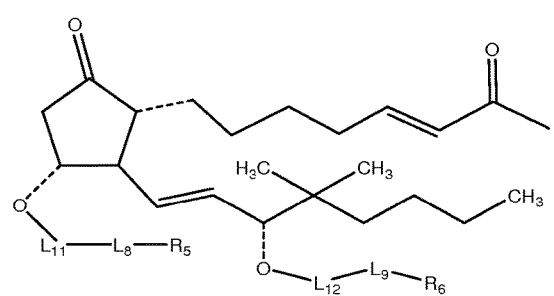
Figure 1:
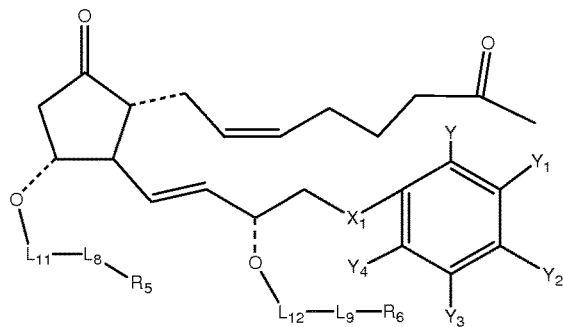
Figure 1:
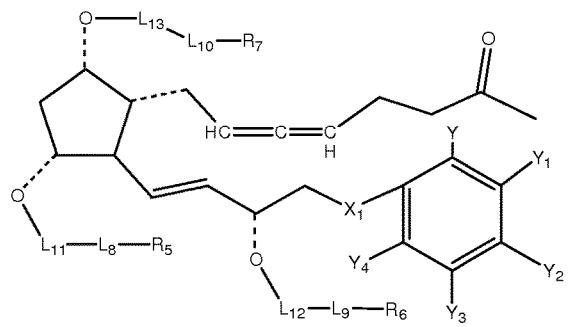
Figure 1:
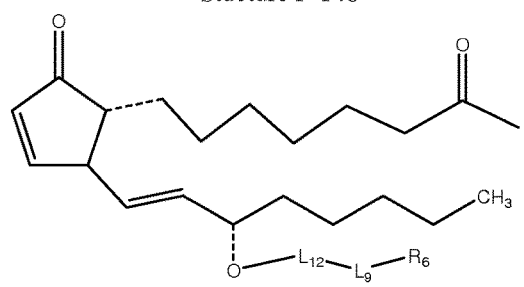
Figure 1:
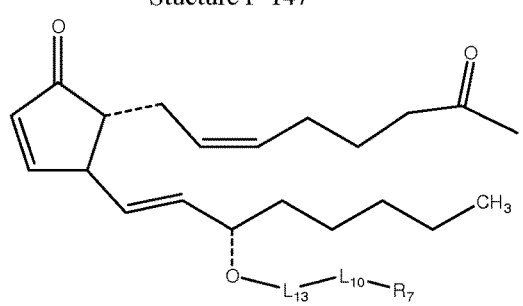
Figure 1:
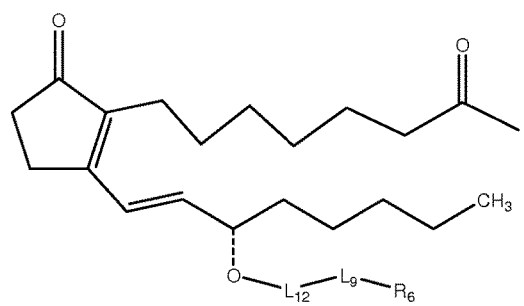
Figure 1:
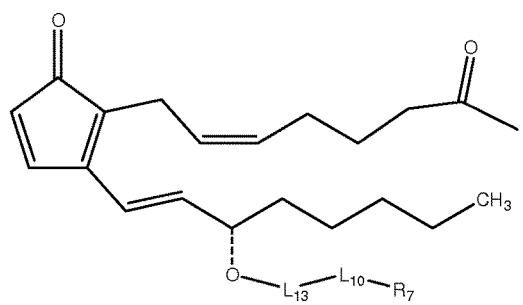
Figure 1:
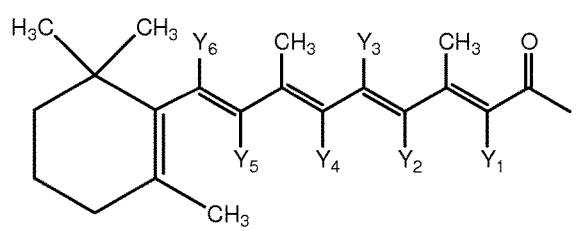
Figure 1:
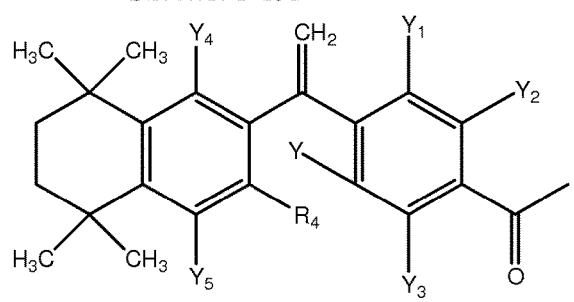
Figure 1:
Figure 1:
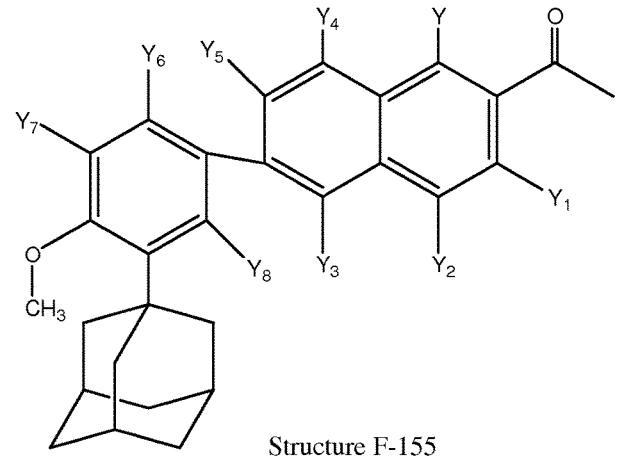
Figure 1:
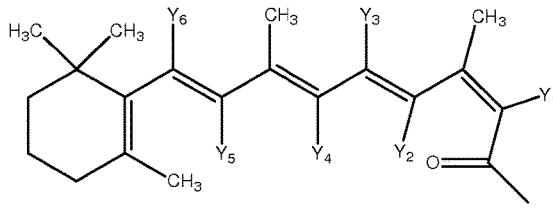
Figure 1:
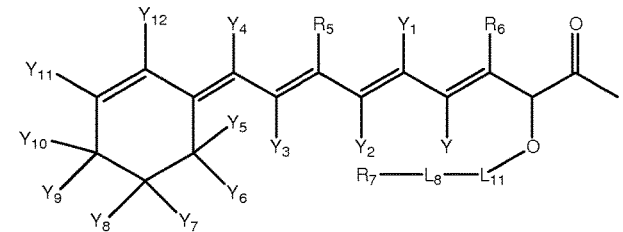
Figure 1:
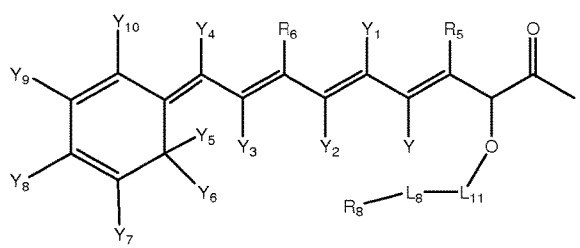
Figure 1:
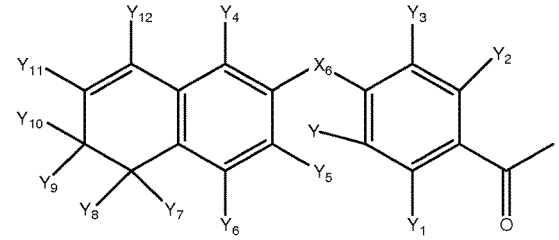
Figure 1:
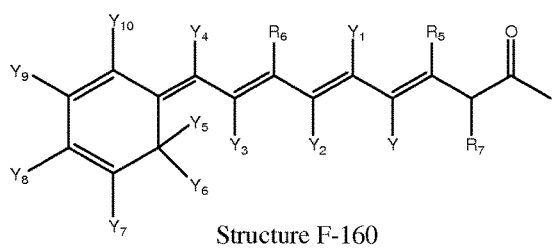
Figure 1:
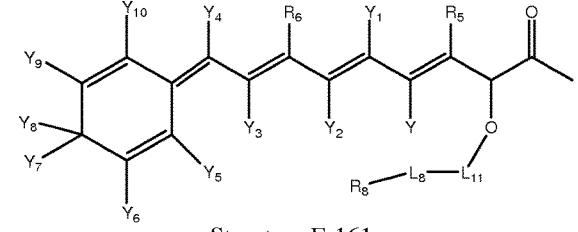
Figure 1:
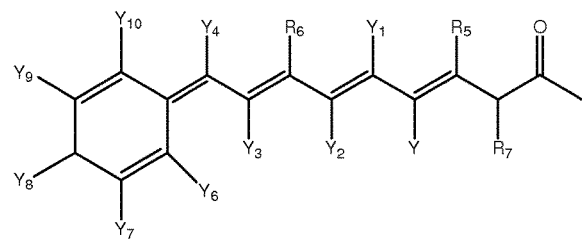
Figure 1:
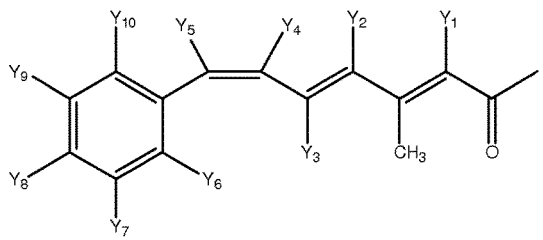
Figure 1:
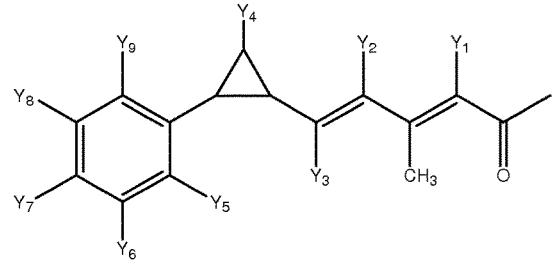
Figure 1:
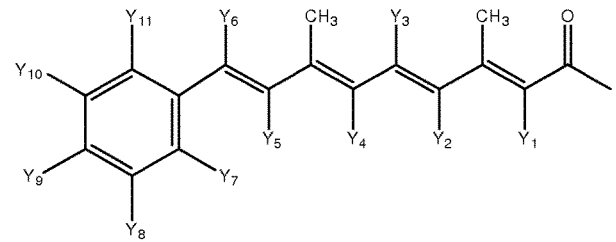
Figure 1:
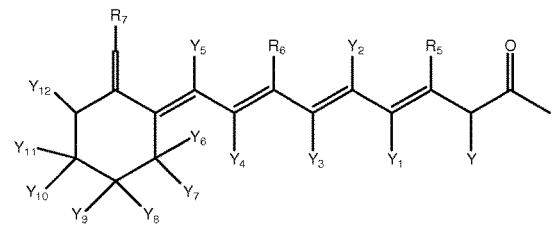
Figure 1:
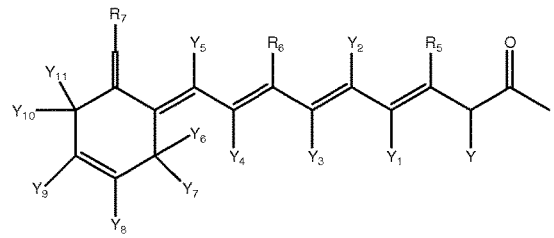
Figure 1:
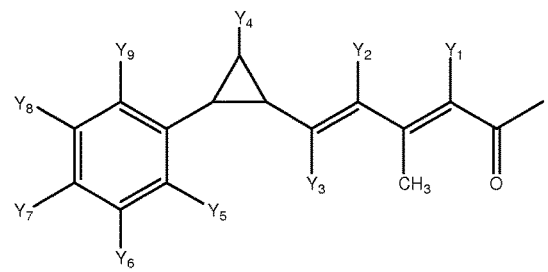
Figure 1:
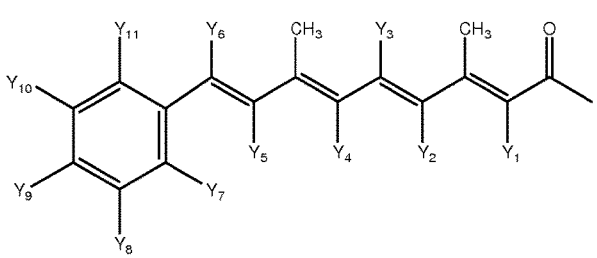
Figure 1:
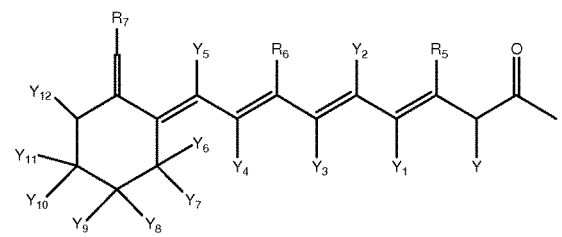
Figure 1:
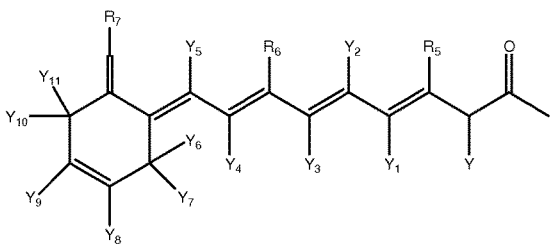
Figure 1:
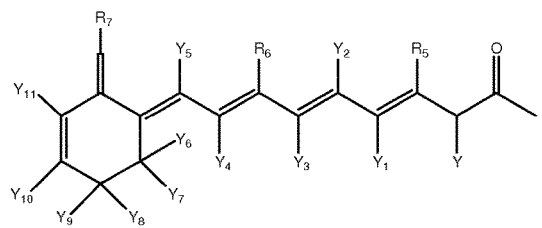
Figure 1:
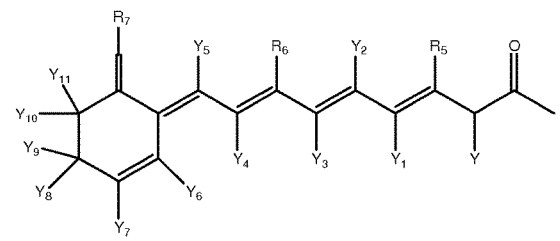
Figure 1:
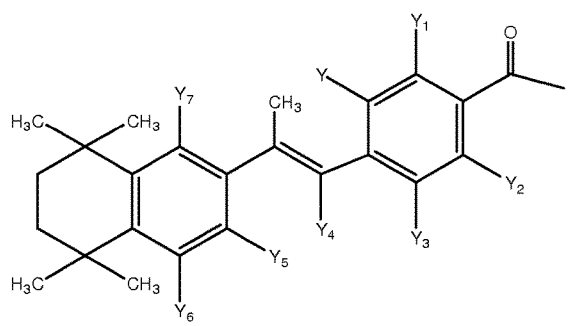
Figure 1:
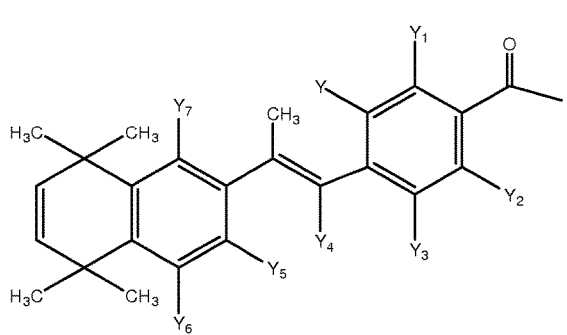
Figure 1:
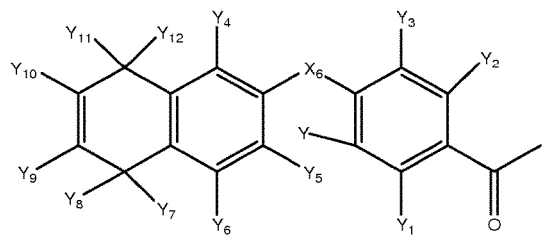
Figure 1:
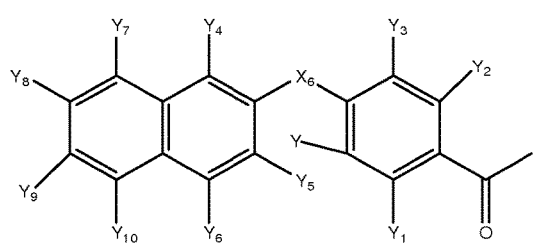
Figure 1:
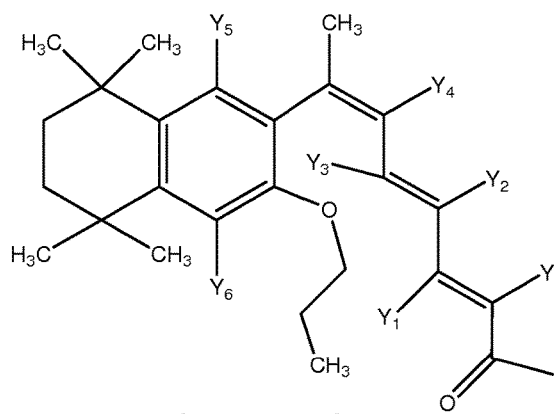
Figure 1:
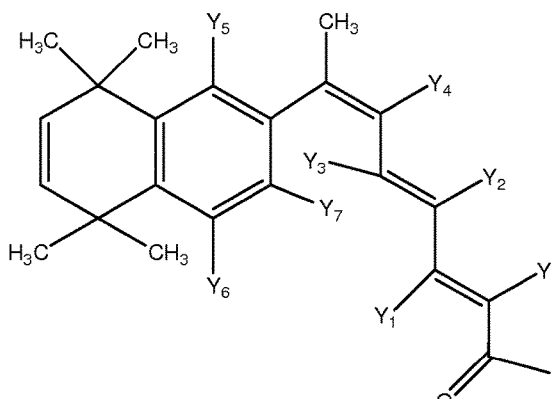
Figure 1:
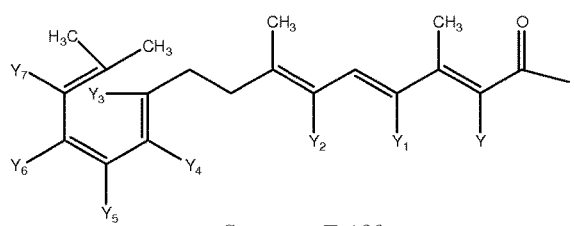
Figure 1:
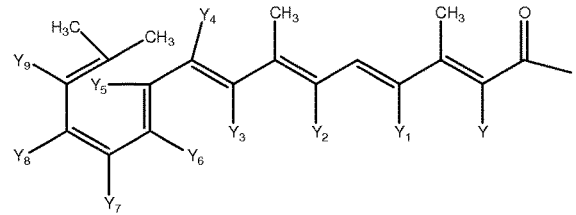
Figure 1:
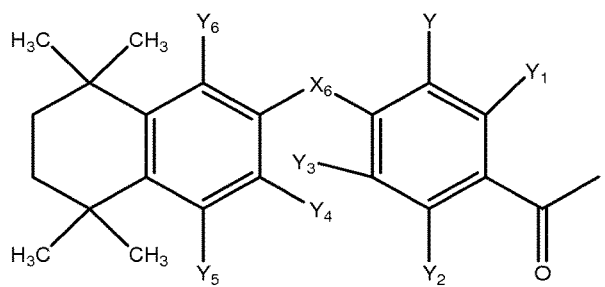
Figure 1:
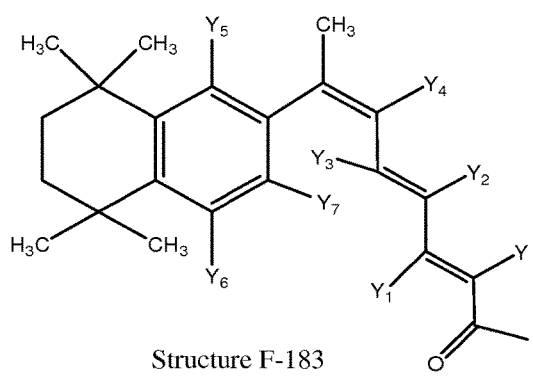
Figure 1:
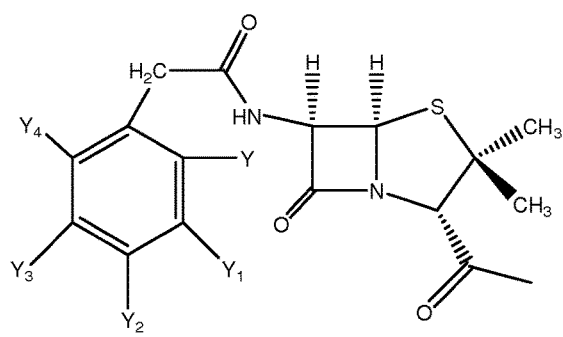
Figure 1:
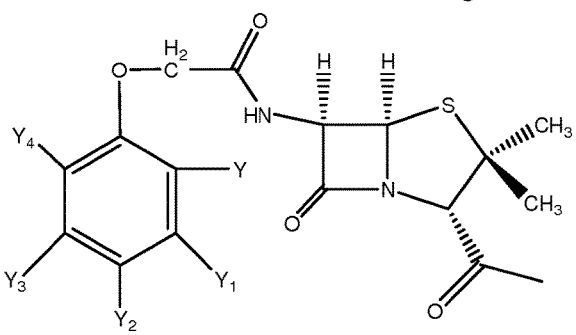
Figure 1:
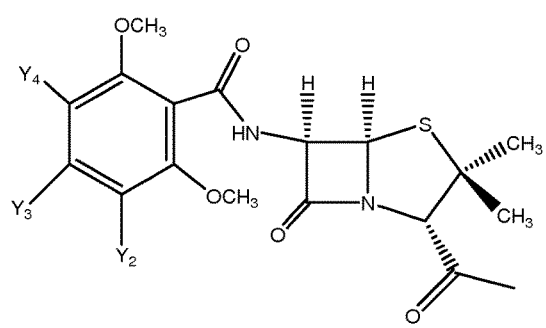
Figure 1:
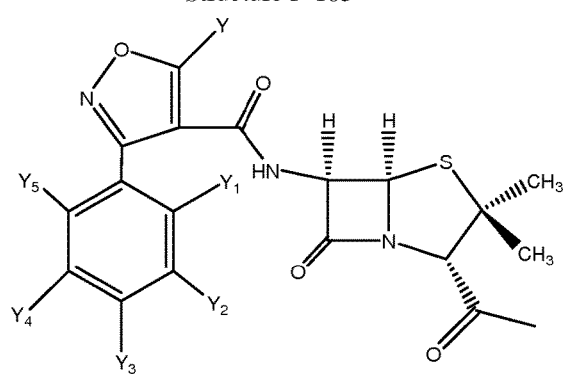
Figure 1:
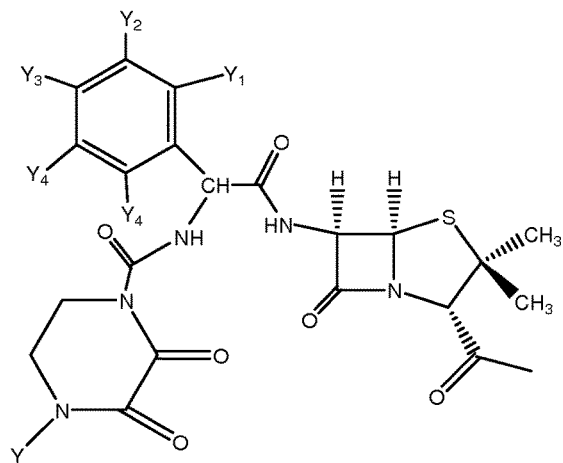
Figure 1:
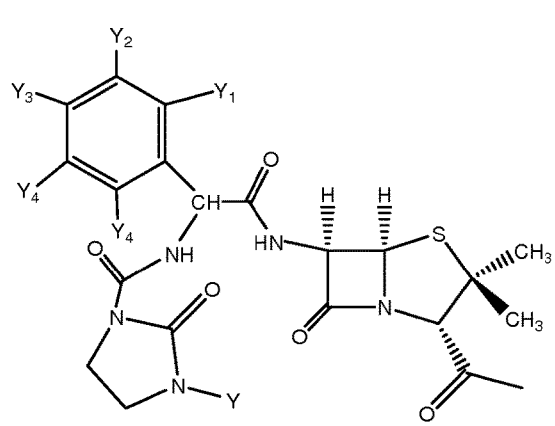
Figure 1:
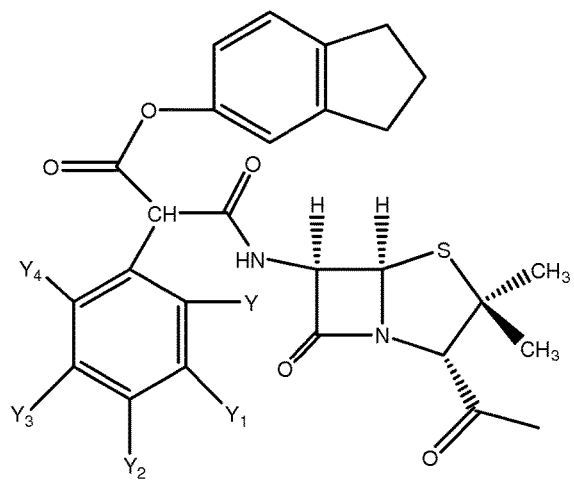
Figure 1:
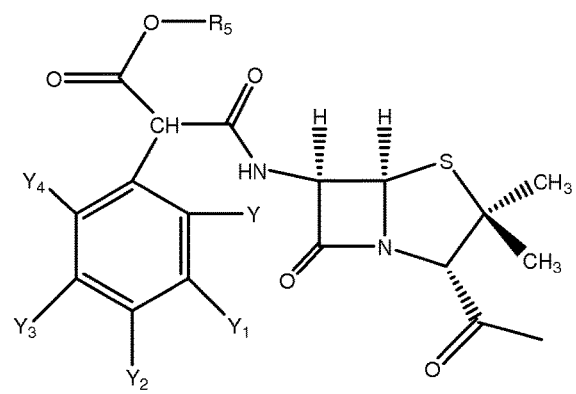
Figure 1:
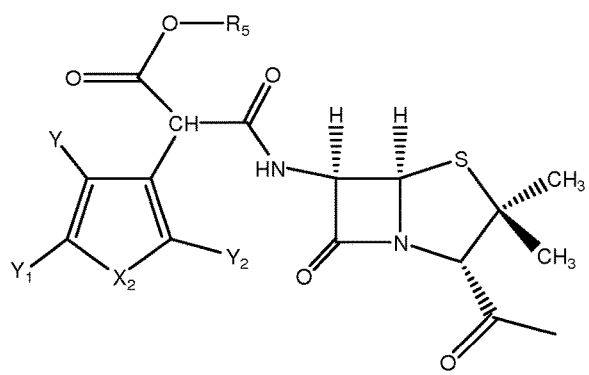
Figure 1:
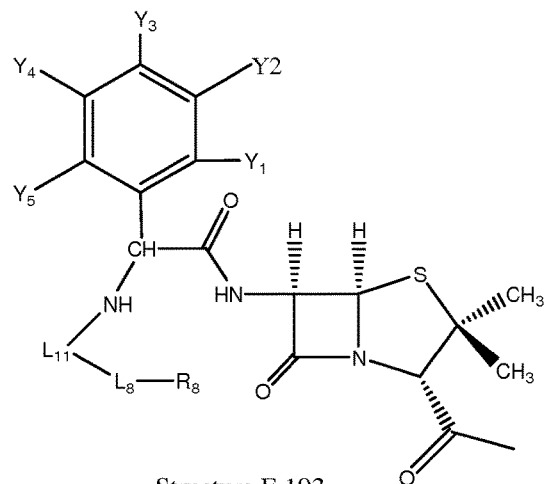
Figure 1:
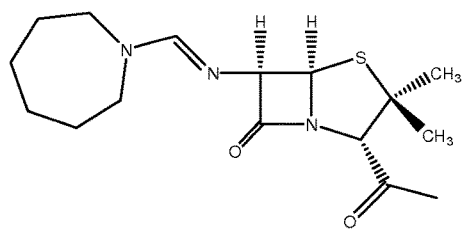
Figure 1:
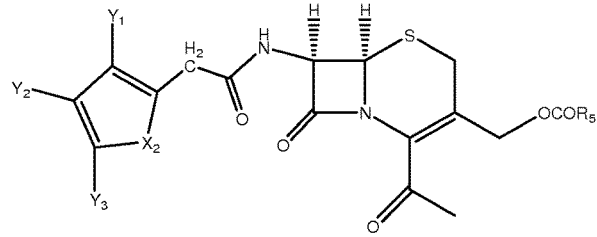
Figure 1:
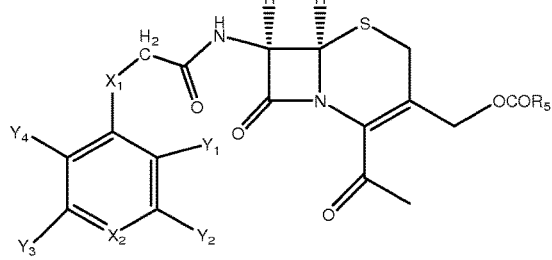
Figure 1:
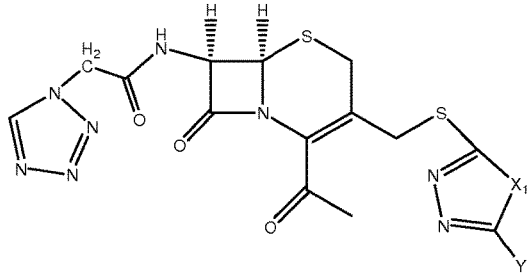
Figure 1:
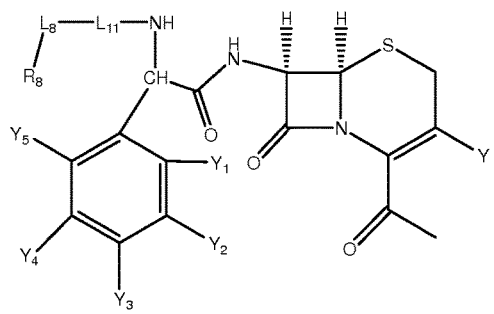
Figure 1:
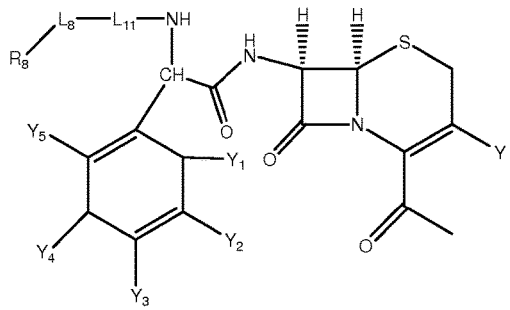
Figure 1:
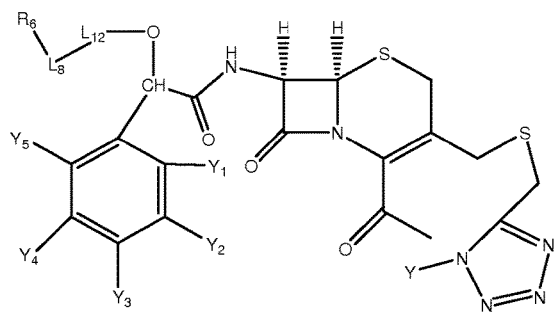
Figure 1:
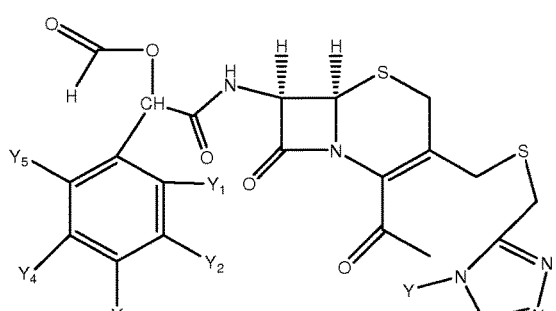
Figure 1:
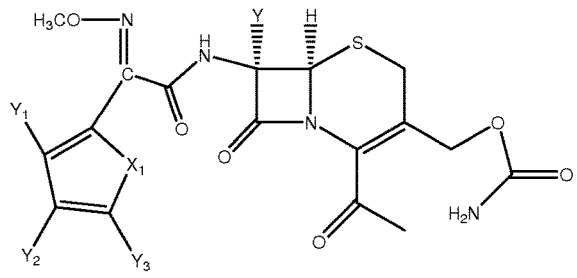
Figure 1:
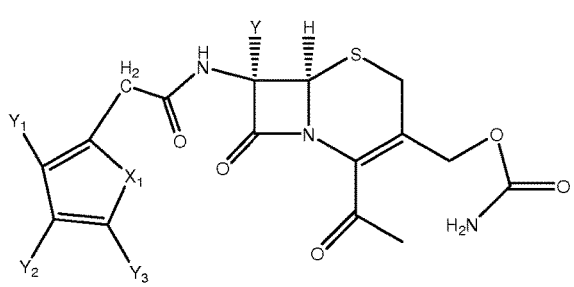
Figure 1:
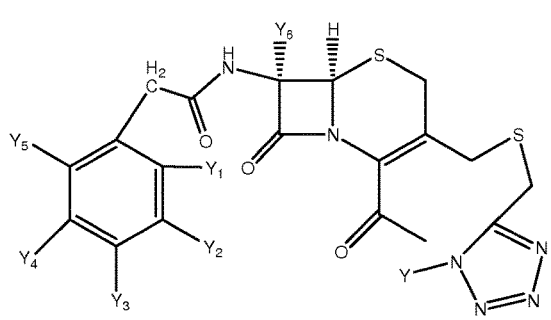
Figure 1:
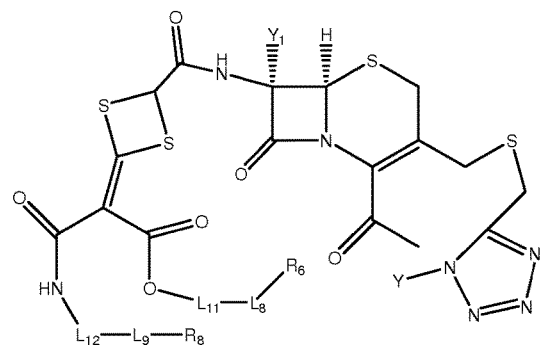
Figure 1:
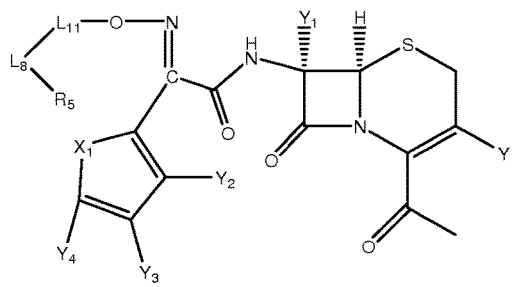
Figure 1:
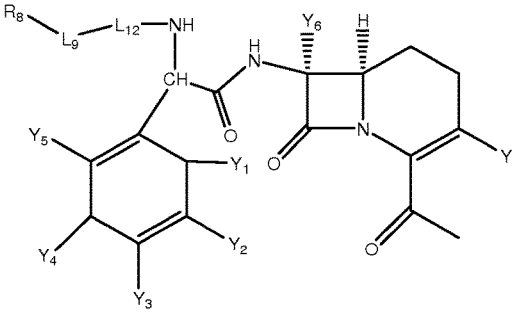
Figure 1:
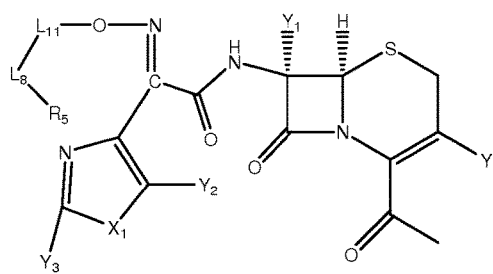
Figure 1:
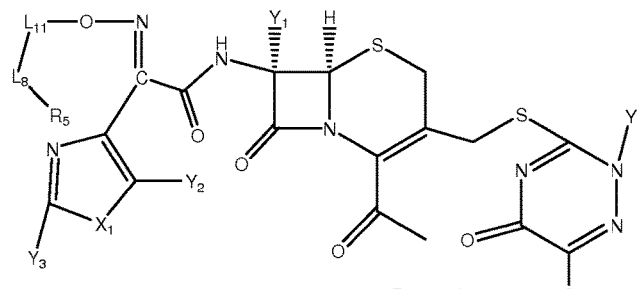
Figure 1:
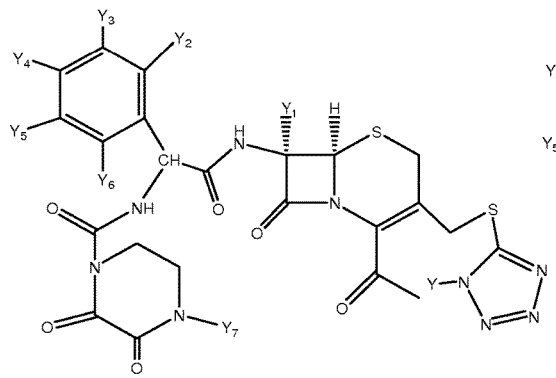
Figure 1:
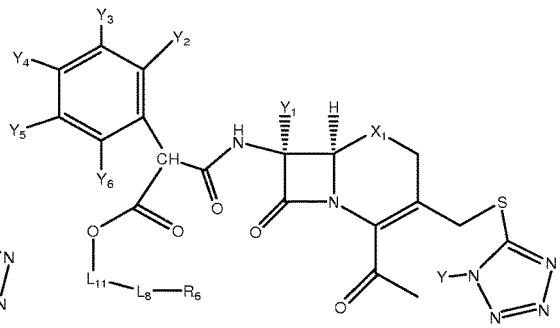
Figure 1:
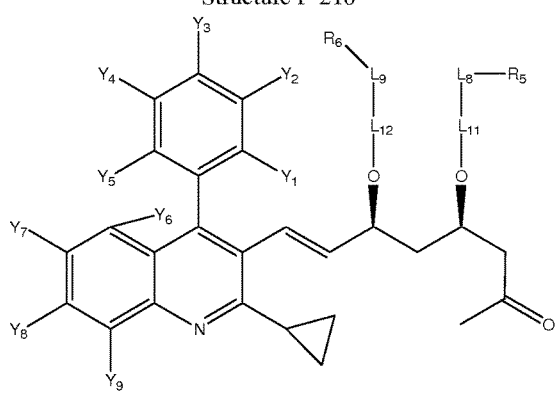
Figure 1:
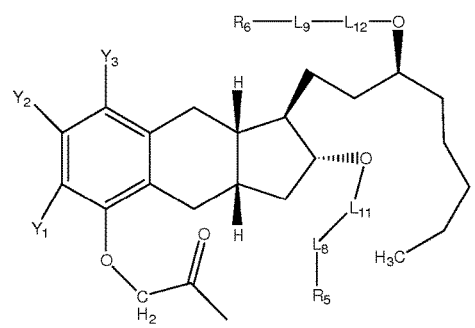
Figure 1:
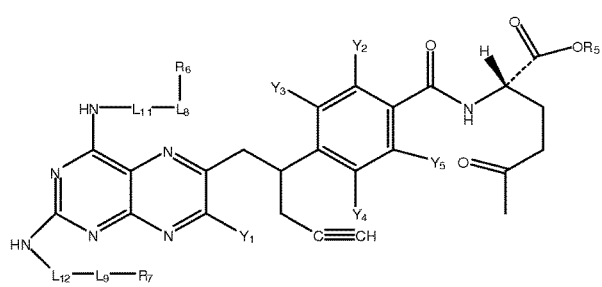
Figure 1:
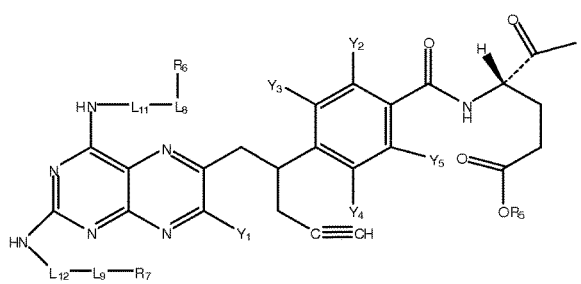
Figure 1:
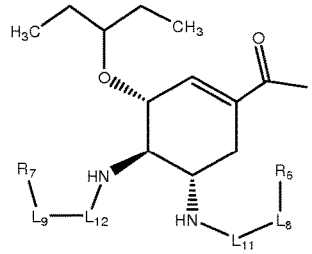
Figure 1:
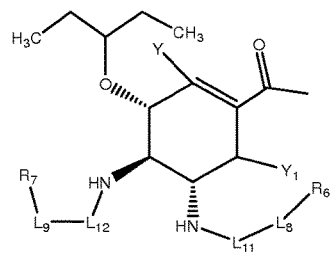
Figure 1:
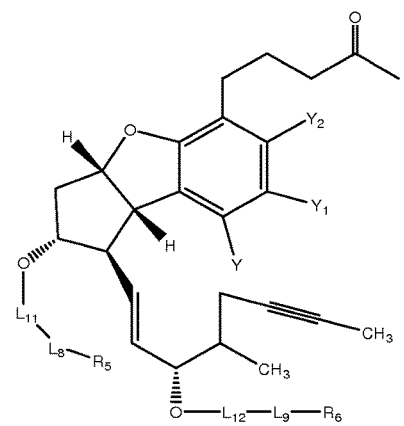
Figure 1:
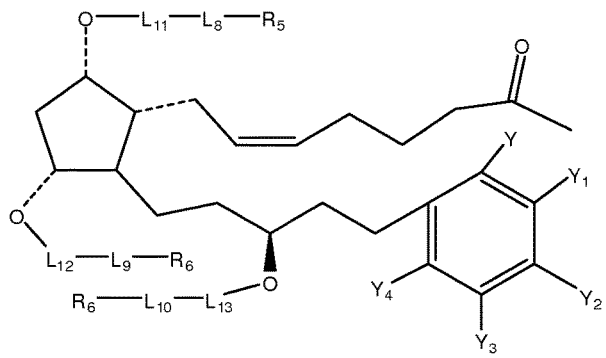

I. Structures of High Penetration Composition (HPC) of a Parent Drug

HPCs capable of penetrating across one or more biological barriers have been previously disclosed in the following disclosures which are incorporated herein by reference in their entireties: international application numbers: PCT/IB2006/052732, PCT/IB2006/052318, PCT/IB2006/052461, PCT/IB2006/052815, PCT/IB2006/052563, PCT/IB2006/052575, PCT/IB2006/053091, PCT/IB2006/053090, PCT/IB2006/053594, PCT/IB2006/052549, PCT/IB2006/053619 PCT/IB2006/054170, PCT/IB2006/054724, PCT/IB2006/053741, PCT/IB2007/050122, PCT/IB2007/050322, PCT/IB2007/052090.

One aspect of the present disclosure is directed to a high penetration composition (HPC). The term "high penetration composition" or "HPC" as used herein refers to a composition comprising a functional unit covalently linked to a transportational unit through a linker. The term "high penetration composition of a parent drug" or "HPC of a parent drug" or "a parent drug HPC" as used herein refers to a HPC wherein a functional unit of the HPC comprises a moiety of a parent drug or a parent drug-related compound. The term "parent drug-related compound" as used here in refers to a compound comprises a moiety of a parent drug, or a metabolite/mimic/analog of the parent drug, or a compound that can metabolized into the parent drug or a metabolite/mimic/analog of the parent drug. In certain embodiments, a parent drug of a HPC comprises at least a functional group such as carboxyl, hydroxyl, thiol, amino, phosphate/phosphonate, carbonyl, or guanidino group. In certain embodiments, a parent drug or a parent drug-related compound comprises more than one functional group. In certain embodiments, a parent drug of a HPC is a non-steroidal anti-inflammatory agent (NSAIA), and the HPC is a NSAIA HPC. In certain embodiments, a parent drug of a HPC is a peptide, and the HPC is a peptide HPC. In certain embodiments, a parent drug of a HPC is a mustard, and the HPC is a mustard HPC. In certain embodiments, a parent drug of a HPC is a beta-lactam antibiotics, and the HPC is a beta-lactam antibiotics HPC. In certain embodiments, a parent drug of a HPC is glibornuide, and the HPC is a glibornuide HPC. In certain embodiments, a parent drug of a HPC is a steroid, such as progesterone, desogestrel and ethinylestradiol, and the HPC is a steroid HPC, such as a progesterone HPC, a desogestrel HPC and a ethinylestradiol HPC. In certain embodiments, a parent drug of a HPC is atenolol, and the HPC is an atenolol HPC.

A functional unit of a HPC of a parent drug has the following properties: 1) that the parent drug, a parent drug-related compound or the HPC can be delivered into a biological subject and/or the transportation of the parent drug/a parent drug-related compound across a biological barrier is desired, 2) that the HPC is capable of penetrating or crossing one or more biological barriers, and 3) the HPC is capable of, but may or may not necessarily, being cleaved so as to turn the functional unit into the parent drug or a parent drug-related compound.

In certain embodiments, a functional unit may be hydrophilic, lipophilic, or amphiphilic (hydrophilic and lipophilic). The lipophilic moiety of the function unit may be inherent or achieved by converting its hydrophilic moieties to lipophilic moieties. For example, a lipophilic moiety of a functional unit is produced by converting one or more hydrophilic groups of the functional unit to lipophilic groups via traditional organic synthesis. Examples of the hydrophilic groups include, without limitation, carboxyl, hydroxyl, thiol, amino, phosphate/phosphonate, carbonyl, and guanidino group. The lipophilic moieties produced via the modification of these hydrophilic groups include, without limitation, ethers, thioethers, esters, thioesters, carbonates, carbamates, amides, phosphates and oximes comprising a lipophilic structure such as alkyl, alkyloxyl, alkenyl, perfluoroalkyl, alkyl halide, alkynyl, aryl, or heteroary group.

In certain embodiments, a parent drug of a HPC has a carboxyl group or a phosphate/phosphonate group. Examples of parent drugs that have a carboxyl group include, without limitation, Methallenestril, Aminosalicylic acid, Methallenestril, Aminosalicylic acid, Baclofen, Carbidopa, Levodopa, Aminobenzoic acid, Bumetanide, Captopril [1-[(2S)-3-mercapto-2-methylpropionyl]-L-proline], Cilastatin[(Z)-7-[[(R)-2-amino-2-carboxyethyl]thio]-2-[(S)-2,2-dimethylcyclo-propanecarboxamido]-2-heptenoic acid], Levothyroxine [D-3,5,3',5'-tetraiodothyronine], Amphotericin B, Etretinate, Eflornithine, 10-undecenoic acid, Cinoxacin, Clorazepate, Ciprofloxacin[1-cyclopropyl-6-fluoro-1,4-dihydro-4-oxo-7-(1-piperazinyl)-3-quinolinecarboxylic acid], Cromolyn, Dehydrocholic acid, Enalapril [(S)-1-[N-(1-carboxy-3-phenylpropyl)-L-alanyl]-L-proline], Enoxacin, Ethacrynic acid, Furosemide, Gemfibrozil, Oleic acid, 2-[4-(4-chlorobenzoyl)-phenoxy]-2-methyl-propionic acid (Fenofibric acid), 7-[(1S,3R,7S,8S,8aR)-1-(2S)-2-methyl-butyryloxy-3,7-dimethyl-1,2,3,7,8,8a-hexahydronaphthalen-1-yl][(3R,5R)-3,4-dihydroxyheptanoic acid, Gabapentin, Fosinopril, Pravastatin, Argatroban, Theophyllineacetic acid, lopanoic acid, Liothyronine, Iothalamate, Lodoxamide [N, N'-(2-chloro-5-cyano-m-phenylene)dioxamic acid], Probenecid, Lisinopril [(S)-1-[N-(1-carboxy-3-phenylpropyl)-L-lysyl]-L-proline], Methotrexate, Acetylaminopropane sulfonate, Nedocromil, Thiosalicylic acid, Quinapril, Ramipril, Norfloxacin, Ioxaglate, Sulfasalazine, Pravastatin, Valproic acid, Olmesartan, Ambrisentan (Letairis), Darusentan, Nonanedioic acid (Azelaic Acid), Ursodiol, Ofloxacin, TAK-044 {cyclo[D-Aspartyl-3-[(4-phenylpiperazin-1-yl) carbonyl]-L-alanyl-L-aspartyl-D-2-(2-thienyl)glycyl-L-leucyl-D-tryptophyl[}, BQ123 {cyclo[D-Trp-D-Asp-Pro-D-Val-Leu]}, Atorvastatin (Lipitor), Fluticasone furoate, Lubiprostone (Amitiza), Pregabalin (Lyrica), Pemetrexed (Alimta), Treprostinil, Rosuvastatin (Crestor), Methyldopa, Valsartan, Telmisartan, (E)-5-[[-4-(2-carboxyethyl)aminocarbonyl]phenyl]azo]-2-hydroxybenzoic acid, Eprosartan, Eprosartan, Fluvastatin (Lescol), (E)-5-[[-4-(2-carboxyethyl)aminocarbonyl]phenyl]azo]-2-hydroxybenzoic acid, Asn-Ala-Pro-Val-Ser-Ile-Pro-Gln, 2-Naphthaleneacetic acid, Suprofen, 3-(2-thienylcarbonyl)-benzeneacetic acid, Ibuprofen, Flurbiprofen, Aspirin, Carprofen, Pranoprofen, Alminoprofen, Benoxaprofen, Indoprofen, Hexaprofen, 10,11-Dihydro-10-oxo-dibenzo[b,f]thiepin-2-carboxylic acid, [4-(2-Oxocyclo-pentyl)-methyl]benzoic acid, [5-phenyl-(2-thienyl)]-carboxylic acid, (3-Phenoxyphenyl)acetic acid, 4-(4-Chlorophenyl)-2-phenyl-5-thiazoleacetic acid, 4-(2,5-dihydropyrrol-1-yl)-benzeneacetic acid, 4,5-Diphenyl-2-oxazole-propionic acid, [4-2-Oxocyclopentyl)-methyl]benzeneacetic acid, 10.11-Dihydro-10-oxo-dibenzo[b,f]thiepin-2-acetic acid, 5-Cyclohexyl-2,3-dihydro-1H-indene-1-carboxylic acid, 5-Phenyl-2-furanpropionic acid, gamma-Oxo-(1,1'-biphenyl)-4-butanoic acid, 5-Benzoyl-2,3-dihydro-1H-pyrrolizine carboxylic acid, Phenylmethylene-1H-indene-3-acetic acid, 1-Benzoyl-5-methoxy-2-methyl-1H-indole-3-acetic acid, 4-Benzoyl-1H-pyrrole-2-acetic acid, 1,3,4,9-Tetrahydropyrano-[3,4-b]indole-1-acetic acid, 3-Phenylamino-benzeneacetic acid, 2-Phenylamino-benzeneacetic acid, 3-(4-Chlorophenyl)-1-phenyl-1H-pyrazole-4-acetic acid, 4-(2-propenyloxy)benzene-acetic acid, 2-Phenyl-5-thiazole-acetic acid, 4-(6-Methoxy-2-naphthalene-2-propionic acid, Acetylsalicylic acid, 3-Phenylbenzoic acid, Salicylsalicylic acid, [(1-Benzyl-1H-indazol-3-yl)oxy] acetic acid, Salicylsalicylsalicylic acid, Sulfasalazine, 2-Phenylaminopyridine-3-carboxylic acid, Promacta(eltrombopag), Montelukast, Treanda (bendamustine), Prostaglandin $E_2$, Prostaglandin $F_2$alpha, Carboprost (15-methyl $PGF_2$alpha), Prostaglandin $D_2$, Prostaglandin $E_1$ (Alprostadil), Prostaglandin $F_{1alpha}$, (Z)-7-[(1R,2R,3R,5S)-3,5-dihydroxy-2-[(E,3S)-3-hydroxy-5-phenyl-1-pentenyl]cyclopentyl]-5-heptenoic acid, (E)-7-[(1R,2R,3R,5S)-3,5-dihydroxy-2-[(3R)-3-hydroxy-5-phenylpentyl]-cyclopentyl]-5-heptenoic acid, Prostaglandin $G_{l2}$ (prostacyclin), (Z)-7-[(1R,2R,3R,5S)-3,5-dihydroxy-2-[(E,3R)-3-hydroxy-4-[3-(trifluoromethyl)phenoxy]but-1-enyl] cyclopentyl]-5-heptenoic acid, (E)-7-[(1R,2R,3R,5S)-3,5-dihydroxy-2-(-3-oxodecyl)cyclopentyl]-5-heptenoic acid, Misoprostol, Gemeprost, 7-[3-Hydroxy-2-3(3-hydroxy-4-phenoxy-1-butenyl)-5-oxocyclopentyl]-5-heptenoic acid, Fenprostalene, Prostaglandin $A_1$, Prostaglandin $A_2$, Prostaglandin $B_1$, Prostaglandin $A_2$, Retinoic acid, Bexarotene, 9-cis-retinoic acid (alitretinoin), Retinoid analogs, 13-cis-Retinoic acid (isotretinoin), Bexarotene analogs, Bexarotene analogs, Benzylpenicillin, Phenoxymethylpenicillin, Methicillin, Oxacillin, Piperacillin, Mezlocillin, Carbenicillin, Ticarcillin, Ampicillin, Mecillinam, Cephalothin, Cephapirin, Cefazolin, Cefadroxil, Cephradine, Cefonicid, Cefamandole, Cefuroxime, Cefoxitin, Ceforanide, Cefotetan, Cefuroxime, Loracarbef, Cefotaxime, Ceftriaxone, Cefoperazone, Moxalactam, LIVALO (pitavastatin), Tyvaso (Treprostinil), Folotyn(Pralatrexate), TAMIFLU (oseltamivir), beraprost.

In certain embodiments, a parent drug of a HPC having a following Structure P-F1:

 (Structure P-F1)

Including stereoisomers and salts thereof.

As used herein, the term "$F_1$" or "F1" comprises a structure selected from the group consisting of Structure F-1, Structure F-2, Structure F-3, Structure F-4, Structure F-5, Structure F-6, Structure F-7, Structure F-8, Structure F-9, Structure F-10, Structure F-11, Structure F-12, Structure F-13, Structure F-14, Structure F-15, Structure F-16, Structure F-17, Structure F-18, Structure F-19, Structure F-20, Structure F-21, Structure F-22, Structure F-23, Structure F-24, Structure F-25, Structure F-26, Structure F-27, Structure F-28, Structure F-29, Structure F-30, Structure F-31, Structure F-32, Structure F-33, Structure F-34, Structure F-35, Structure F-36, Structure F-37, Structure F-38, Structure F-39, Structure F-40, Structure F-41, Structure F-42, Structure F-43, Structure F-44, Structure F-45, Structure F-46, Structure F-47, Structure F-48, Structure F-49, Structure F-50, Structure F-51, Structure F-52, Structure F-53, Structure F-54, Structure F-55, Structure F-56, Structure F-57, Structure F-58, Structure F-59, Structure F-60, Structure F-61, Structure F-62, Structure F-63, Structure F-64, Structure F-65, Structure F-66, Structure F-67, Structure F-68, Structure F-69, Structure F-70, Structure F-71, Structure F-72, Structure F-73, Structure F-74, Structure F-75, Structure F-76, Structure F-77, Structure F-78, Structure F-79, Structure F-80, Structure F-81, Structure F-82, Structure F-83, Structure F-84, Structure F-85, Structure F-86, Structure F-87, Structure F-88, Structure F-89, Structure F-90, Structure F-91, Structure F-92, Structure F-93, Structure F-94, Structure F-95, Structure F-96, Structure F-97, Structure F-98, Structure F-99, Structure F-100, Structure F-101, Structure F-102, Structure F-103, Structure F-104, Structure F-105, Structure F-106, Structure F-107, Structure F-108, Structure F-109, Structure F-110, Structure F-111, Structure F-112, Structure F-113, Structure F-114, Structure F-115, Structure F-116, Structure F-117, Structure F-118, Structure F-119, Structure F-120, Structure F-121, Structure F-122, Structure F-123, Structure F-124, Structure F-125, Structure F-126, Structure F-127, Structure F-128, Structure F-129, Structure F-130, Structure F-131, Structure F-132, Structure F-133, Structure F-134, Structure F-135, Structure F-136, Structure F-137, Structure F-138, Structure F-139, Structure F-140, Structure F-141, Structure F-142, Structure F-143, Structure F-144, Structure F-145, Structure F-146, Structure F-147, Structure F-148, Structure F-149, Structure F-150, Structure F-151, Structure F-152, Structure F-153, Structure F-154, Structure F-155, Structure F-156, Structure F-157, Structure F-158, Structure F-159, Structure F-160, Structure F-161, Structure F-162, Structure F-163, Structure F-164, Structure F-165, Structure F-166, Structure F-167, Structure F-168, Structure F-169, Structure F-170, Structure F-171, Structure F-172, Structure F-173, Structure F-174, Structure F-175, Structure F-176, Structure F-177, Structure F-178, Structure F-179, Structure F-180, Structure F-181, Structure F-182, Structure F-183, Structure F-184, Structure F-185, Structure F-186, Structure F-187, Structure F-188, Structure F-189, Structure F-190, Structure F-191, Structure F-192, Structure F-193, Structure F-194, Structure F-195, Structure F-196, Structure F-197, Structure F-198, Structure F-199, Structure F-200, Structure F-201, Structure F-202, Structure F-203, Structure F-204, Structure F-205, Structure F-206, Structure F-207, Structure F-208, Structure F-209, Structure F-210, Structure F-211, Structure F-212, Structure F-213, Structure F-214, Structure F-215, Structure F-216, Structure F-217, Structure F-218, Structure F-219 (FIG. 1), Including stereoisomers and salts thereof.

As used herein, unless otherwise specified:

each Y and $Y_1$-$Y_{14}$ is independently selected from the group consisting of H, Cl, F, Br, I, CN, $R_{10}$, $CH_3C\equiv C$, $CR_6\equiv C$, $P(O)OR_6$, $CF_3$, $CF_3O$, $CH_3$, $CF_3CF_2$, $R_5$, $R_6$, $R_7$, $R_8$, $CF_3CF_2O$, $CH_3CH_2$, $CH_3CH_2CH_2$, $(CH_3)_2CH$, $(CH_3)_2CHCH_2$, $CH_3CH_2CH(CH_3)$, $(CH_3)_3C$, $C_4H_9$, $C_5H_{11}$, $CH_3CO$, $CH_3CH_2CO$, $R_5CO$, $CH_3C(=O)$, $CH_3CH_2OC(=O)$, $R_5OC(=O)$, $R_6C(=NOR_5)$, $R_6C(=NR_5)$, $CH_3COO$, $R_5COO$, $R_5COOCH_2$, $R_6NHCOOCH_2$, $CH_3COS$, $CH_3O$, $R_5O$, HO, $R_{10}O$, $CF_3CH_2SCH_2$, $CHCl_2$, $CH_2COOR_6$, $CH_3S$, $R_5S$, HS, $R_{10}S$, $CH_3OCH_2CH_2$, $R_5OCH_2$, $R_{10}OCH_2CH_2$, $R_5O(C=O)$, $C_2H_5OCONH$, $CH_2NHR_8$, $CH_3OCONH$, $CH_3SO_2$, $CH_3SO$, $R_5SO_2$, $R_5SO$, $NH_2SO_2$, $C_6H_5CH_2$, $NH_2$, $NHR_{10}$, cyclobutyl, cyclopropyl, 4-chlorophenyl, 4-fluorophenyl, $CH_2=CH$, $CH_2=CHCH_2$, $CH_3CH=CH$, $NHR_5SO_2$, $N(R_5)_2SO_2$, $R_5OCH_2CH_2CH_2$, and $NO_2$;

each X, $X_1$-$X_6$ is independently selected from the group consisting of H, $CH_3$, $R_5$, $CH_2$, $CHR_6$, S, O, $NR_6$, CO, CH, $CR_6$, $P(O)OR_6$, N, $CH_2=C$, $CH=CH$, $C\equiv C$, CONH, CSNH, COO, OCO, COS, $COCH_2$, and $CH_2CO$;

each $R_1$ and $R_2$, is independently selected from the group consisting of nothing, H, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NR_6$, or any other pharmaceutically acceptable groups;

each $R_3$, $R_4$, $R_5$, $R_6$, $R_7$, $R_8$ and $R_9$ is independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, $P(O)OL_7$, $CH=CH$, $C\equiv C$, $CHL_7$, $CL_5L_7$, aryl, heteroaryl, or cyclic groups;

each R, $R_{11}$-$R_{16}$ is independently selected from the group consisting of nothing, H, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NR_S$, or any other pharmaceutically acceptable groups;

$L_1$ is selected from the group consisting of nothing, O, S, $-N(L_3)-$, $-N(L_3)-CH_2-O-$, $-N(L_3)-CH_2-N(L_5)-$, $-O-CH_2-O-$, $-O-CH(L_3)-O-$, and $-S-CH(L_3)-O-$;

each $L_2$, $L_8$, $L_9$, and $L_{10}$ is independently selected from the group consisting of nothing, $-O-$, $-S-$, $-N(L_3)-$, $-O-N(L_3)-$, $-N(L_3)-O-$, $-N(L_3)-N(L_5)-$, $-N(L_3)-CH_2-O-$, $-N(L_3)-CH_2-N(L_5)-$, $-O-CH_2-O-$, $-O-CH(L_3)-O-$, $-S-CH(L_3)-O-$, $-O-L_3-$, $-S-L_3-$, $-N(L_3)-L_5-$, and $L_3$;

$L_4$ is selected from the group consisting of nothing, C=O, C=S,

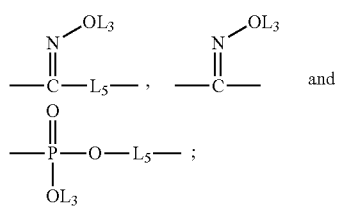

each $L_{11}$, $L_{12}$, and $L_{13}$ is independently selected from the group consisting of nothing, $-C(=O)-$, $-C(=S)-$, $-C(=N(L_3))-$,

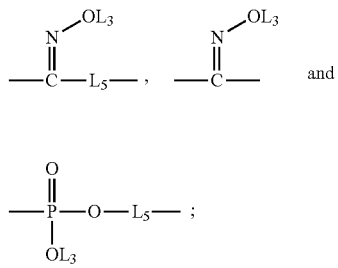

for each $L_1$, $L_2$, $L_4$, $L_8$, $L_9$, $L_{10}$, $L_{11}$, $L_{12}$, and $L_{13}$, each $L_3$ and $L_6$ is independently selected from the group consisting of nothing, H, $CH_2COOL_6$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NL_3$, or any other pharmaceutically acceptable groups;

$L_6$ is independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, $P(O)OL_7$, $CH=CH$, $C\equiv C$, $CHL_7$, $CL_5L_7$, aryl, heteroaryl, or cyclic groups;

$L_7$ is independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, $P(O)OL_6$, $CH=CH$, $C\equiv C$, $CHL_6$, $CL_6L_5$, aryl, heteroaryl, or cyclic groups;

each $R_{10}$, $R_{20}$, $R_{21}$, $R_{22}$, $R_{23}$, $R_{24}$, $R_{25}$, $R_{26}$, $R_{27}$, $R_{28}$ and $R_{29}$ is independently selected from the group consisting of nothing, H, $R_1$, $R_2$, $R_3$, $R_4$, $R_5$, $R_6$, $R_7$, $R_8$, $R_6CO$, $R_6NHC(=O)$, $R_6OC(=O)$, $R_6C(=NOR_5)$, $R_6C(=NR_5)$, $R_6C(=S)$, $CNR_6$, and $R_6OC(=O)(CH_2)_nC(=O)$, $R_6(O=)CO(CH_2)_nC(=O)$;

each m and n is independently selected from the group consisting of 0 and integer, for example, m or n=0, 1, 2, 3, 4, 5, 6, 7, 8, 9, 10, 11, 12, 13, 14, 15, 16, 17, 18, 19, 20, . . . ;

W is selected from the group consisting of NH, NR$_5$, O, S; CH$_2$, and NH;

Z is H,

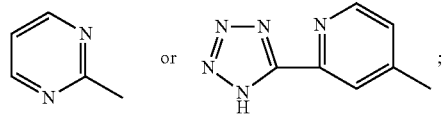

each -AA- and -AA$_1$-represents one or more natural or non-natural amino acid residues or a related residue wherein one or more hydrophilic groups such as carboxyl, hydroxyl, thiol, amino, phosphate/phosphonate, carbonyl, or guanidino group is/are converted to a lipophilic group as described in paragraph 0045, example of a -AA-include, without limitation, a structure comprising one of the following structures:

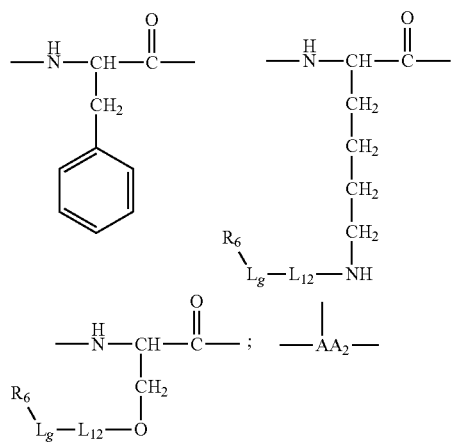

represents amino acid residues comprising a carboxyl group side chain, examples include, without limitation, the following structures:

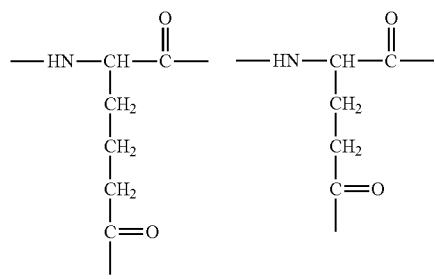

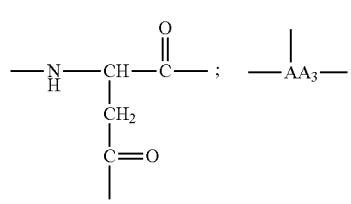

is an amino acid residue having a hydroxyl, amino, guanidine, or thiol group side chain, examples include, without limitation, the following structures:

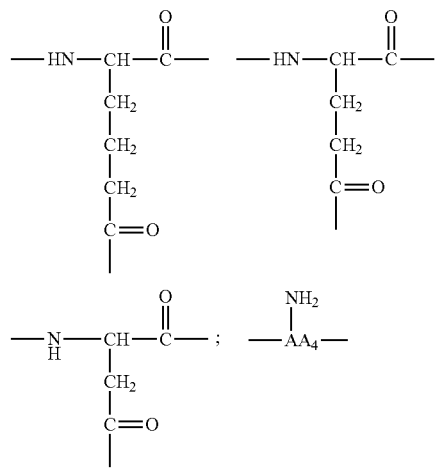

is an amino acid group comprising an amino group side chain, examples include, without limitation, one of the following structures:

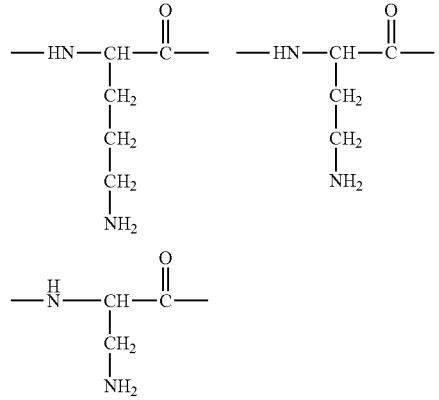

each Bx- and By- is independently selected from the group consisting of DNA bases and RNA bases wherein any hydrophilic groups can be converted to a lipophilic group as described in paragraph 0045, examples of DNA bases and RNA bases include, without limitation, Adenine, Guanine, Cytosine, Thymine, Uracil and related compounds having the following structures:

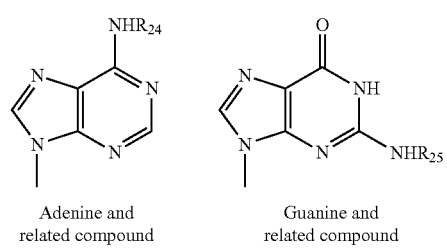

Adenine and related compound

Guanine and related compound

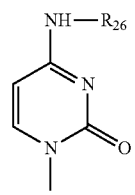 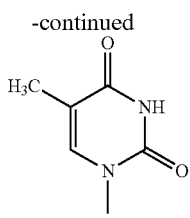 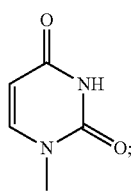

Cytosine and related compound    Thymine and related compound    Uracil and related compound each —$B_1$— or —B— independently represents Adenine, Guanine, or Cytosine residues having the following structures:

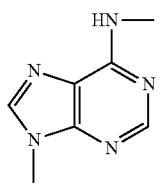 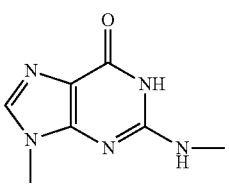

Adenine and related compound    Guanine and related compound

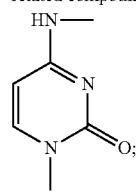

Cytosine and related compound the term "HA" or "AH" is an acid. In certain embodiments, an acid is a pharmaceutically acceptable acid.

In certain embodiments, a parent drug of a HPC comprises a functional group such as amino group, hydroxyl group, phenol group, thiol group or guanidino group. Examples of a parent drug comprising an amino group, hydroxyl group, phenol group, thiol group or guanidine group include, without limitation, Acetohydroxamic acid, Acyclovir 12-amino-1,9-dihydro-9-[(2-hydroxyethoxy)-methyl]-6H-purin-6-one), Allopurinol, Adenosine (6-amino-9-beta-D-ribofuranosyl-9-H-purine), Prednisolone, Prednisone, Triamcinolone acetonide, Cortisol(hydrocortisone), Adenosine (6-amino-9-beta-D-ribofuranosyl-9-H-purine), Cortisone, Estradiol, Estrone, Estratriol, 16-hydroxyestrone, Equilin, Equilenin, Dienestrol, Hexestrol, Diethylstilbestrol, Benzestrol, 4-Hydroxyandrostenedione, ICI 164384, Aminoglutethimide, ICI 182780, 7-Aminophenylthioandrost-4-ene-3,17-dione, Megestrol, Chlormadinone, Norgestrel, Lynestrenol, Methandrostenolone, Mifepristone, Onapristone, Danazol, Methenolone, Stanozolol, Amikacin (D-Streptamine), 9-Aminoacridine, Aminoacridine, Atovaquone, Baclofen, Calcifediol, Calcitriol, Phenylpropanolamine, Captopril [1-[(2S)-3-mercapto-2-methylpropionyl]-L-proline], Butabarbital, Carbamazepine, Carbidopa, Theophylline, Levodopa, Pseudoephedrine, Chloramphenicol, Chloroxine, Clioquinol, Chloroxylenol, Chlorphenesin carbamate, Chlorthalidone, Phenylpropanolamine, Clonidine [2-(2,6-dichlorophenylamino)-2-imidazoline], Cladribine, Phenylpropanolamine, Clonazepam, Cytarabine [4-amino-1-beta-D-arabinofuranosyl-2-(1H)-pyrimidinone], Danazol, Dexpanthenol, Guaifenesin, Daunorubicin, Doxorubicin, Idarubicin, Dextrothyroxine [D-3,5,3',5'-tetraiodothyronine], Didanosine, Dezocine, Dopamine, Dihydrotachysterol, Dicumarol, Dronabinol, Dyphylline, Enoxacin, Enalapril [(S)-1-[N-(1-carboxy-3-phenylpropyl)-L-alanyl]-L-proline], Dienestrol, Calcipotriene [(5Z,7E,22E, 24S)-24-cyclopropyl-9,10-secochola-5,7,10(19),22-tetrane-1alpha, 3beta,24-triol], Ergocalciferol[9,10-secoergsta-5,7, 10(19),22-tetraen-3-ol, (3beta,5Z,7E,22E)], Levonorgestrel, norgestrel, Norethindrone, Procarbazine, Famciclovir, Felodipine, Norgestimate, Floxuridine, idoxuridine, Etoposide, Monobenzone, Fludarabine phosphate, Dihydrotachysterol, Finasteride, Fluconazole, Fludarabine, Fluorouracil, Flucytosine, Ethchlorvynol, Fluorometholone, Halobetasol, Mometasone, Fluvoxamine, Flurandrenolide, Ganciclovir, Fluticasone, Desogestrel, Ethinyl estradiol, Ethinyl estradiol, Mestranol, Desoximetasone, Dexamethasone, Gentamicin, Hydroxyprogesterone, Medroxyprogesterone, Indapamide, Levodopa, Methyldopa, Hydralazine, Hydrochlorothiazide, Hydroflumethiazide, Iodoquinol, Kanamycin, Lovastatin, Masoprocol, Lorazepam, Oxazepam, Medrysone, Mephobarbital, Metolazone, Metaxalone, Methocarbamol, Methyclothiazide, Metronidazole, Mercaptopurine, Methimazole, Methotrexate, Milrinone, Nandrolone, Naphazoline, Mexiletine, Nitrofurantoin, Niclosamide, Nifedipine, Nimodipine, Norepinephrine, Novobiocin, Omeprazole, Oxandrolone, Pemoline, Pentamidine, Oxymetholone, Omeprazole, Oxandrolone, Nordihydroguaiaretic acid, Zafirlukast, Banzel (rufinamide), Phenacemide, Phenelzine, Phenazopyridine, Phenobarbital, Sulfisoxazole, Phentolamine, Phenyloin, Podofilox, Procarbazine, Polythiazide, Trichlormethiazide, Primidone, Probucol, Propofol, Propylthiouracil, Procarbazine, Procarbazine, Sulfadoxine, Quinethazone, Propylthiouracil, Ribavirin, Streptozocin,Rimexolone, Simvastatin, Staticin, Stanozolol, Sulfamethizole, Sulfamethoxazole, Sulfisoxazole, Sulfanilamide, Sulfadiazine, Sulfasalazine, Temazepam, Terazosin, Tacrine, Thiabendazole, Thiopental, Tolazoline, Thioguanine, Olmesartan Medoxomil [(5-methyl-2-oxo-1,3-dioxol-4-yl)methyl5-(1-hydroxy-1-methyl-ethyl)-2-propyl-3-[[4-[2-(2H-tetrazol-5-yl)-phenyl]-phenyl]methyl]-3H-imidazole-4-carboxylate], Teniposide, Torsemide, Triamterene, Trifluridine, Trimethoprim, Trimetrexate, Uracil mustard, Tropicamide, Vidarabine, Warfarin, Zalcitabine, Zidovudine, Fluticasone furoate, Ro 46-2005, Bosentan, Clazosentan, Tezosentan, Isentress 1N-[(4-Fluorophenyl)methyl]-1,6-dihydro-5-hydroxy-1-methyl-2-[1-methyl-1-[[(5-methyl-1,3,4-oxadiazol-2-yl)carbonyl]amino]ethyl]-6-oxo-4-pyrimidinecarboxamide}, Aliskiren (2S,4S,5S,7R)-5-amino-N-(2-carbamoyl-2-methyl-propyl)-4-hydroxy-7-{[4-methoxy-3-(3-methoxypropoxy)-phenyl]methyl}-8-methyl-2-propan-2-yl-nonanamide, Efavirenz, Dextroamphetamine, Finasteride, Armodafinil, Eraxis(Anidulafungin), Prezista (Darunavir), Tipranavir, Amprenavir, Brecanavir, Telbivudine (Tyzeka), Lenalidomide, Thalidomide, Entecavir, Conivaptan, Sorafenib (Nexavar), Entecavir (Baraclude), Azacitidine (Vidaza), Pemetrexed (Alimta), Ramelteon, Ezetimibe, Clofarabine (Clolar), Nelarabine (Arrnon), Erlotinib (Tarceva), Tadalafil (Clalis), Amprenavir, Atazanavir (Reyataz), Ezetimibe, Acetaminophen, Glibornuride, Etravirine, Abacavir (Ziagen), N-[1-[(2R,3R,4S,5R)-3,4-dihydroxy-5-methyloxolan-2-yl]-5-fluoro-2-oxopyrimidin-4-yl] amine, Tenofovir, voriconazole, Hydrochlorothiazide, Zoledronic acid, Melatonin, 3-aminopropane-1-sulfonic acid, Fulvestrant, Voriconazole, Resveratrol, Lovastatin, Tenofovir disoproxil, Tenofovir, Simvastatin, Pentyl N-[1-[(2R,3R,4S,5R)-3,4-dihydroxy-5-methyloxolan-2-yl]-5- fluoro-2-oxopyrimidin-4-yl]carbamate (Capecitabine), Ergocalciferol (Vitamin $D_2$), Cholecalciferol (Vitamin $D_3$), 1,25-dihydroxycholecalciferol, Lamivudine, Doxercalciferol(1a-hydroxyvitamin $D_2$), Dihydrotachysterol (Vitamin $D_4$), Lopinavir, 3-[4-(4-chlorophenyl)cyclohexyl]-4-hydroxynaphthalene-1,2-dione, Cidofovir, Ritonavir, Entacapone, Tadalafil (Clalis), Finasteride, Zileuton, Melatonin, TAMIFLU (oseltamivir), Paricalcitol, Metronidazole, Diflunisal, Aspirin, Oxicams, Januvia (Sitagliptin), Emtricitabine (5-fluoro-1-(2R,5S)-[2-(hydroxymethyl)-1,3-oxathiolan-5-yl]cytosine, Propofol, Vitamin A analogs, Afinitor [everolimus, (1R,9S,12S,15R,16E,18R,19R,21R,23S,24E, 26E,28E,30S,32S,35R)-1,18-dihydroxy-12-{(1R)-2-[(1S, 3R,4R)-4-(2-hydroxyethoxy)-3-methoxycyclohexyl]-1-methylethyl}-19,30-dimethoxy-15,17,21,23,29,35-hexamethyl-11,36-dioxa-4-aza-tricyclo[30.3.1.04,9] hexatriaconta-16,24, 26,28-tetraene-2,3,10,14,20-pentaone], Curcumin, Aptivus (Tipranavir), Intelence (Etravirine), Adcirca (tadalafil), Samsca (Tolvaptan), Peptides, DNAs, RNAs, Adenine, Guanine, Cytosine, Thymine, and Uracil.

In certain embodiments, a parent drug of a HPC having the following Structure P-F2:

F2-H    (Structure P-F2)

Including stereoisomers and salts thereof.

Figure 2:
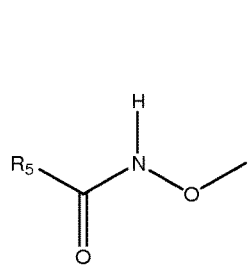
FIG. 2: Exemplary structures of functional unit F2.
Figure 2:
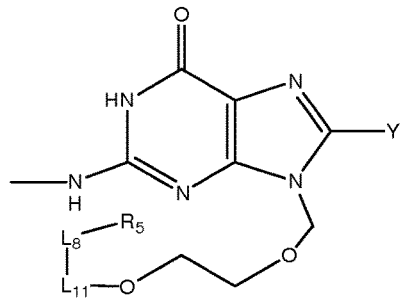
Figure 2:
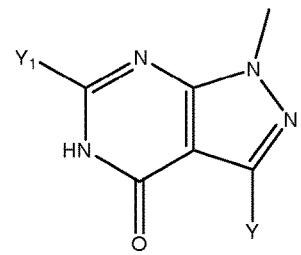
Figure 2:
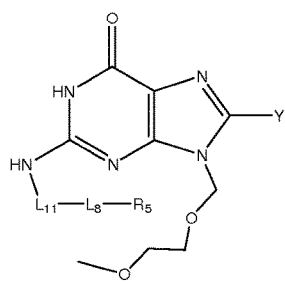
Figure 2:
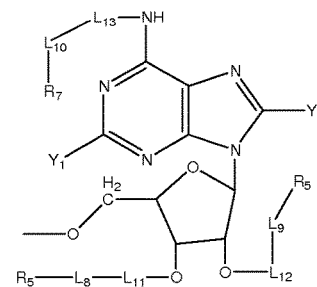
Figure 2:
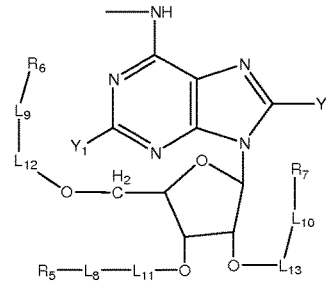
Figure 2:
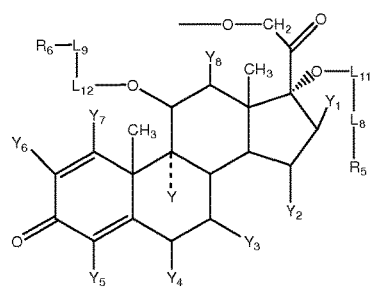
Figure 2:
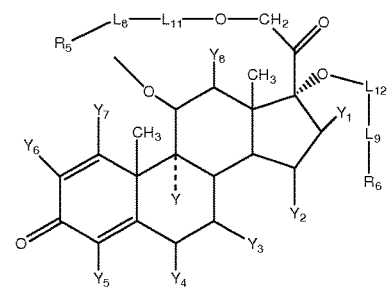
Figure 2:
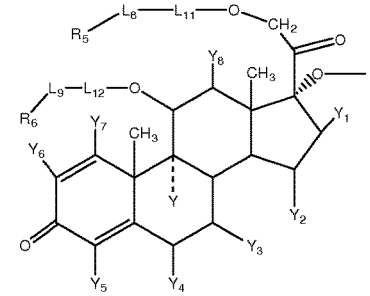
Figure 2:
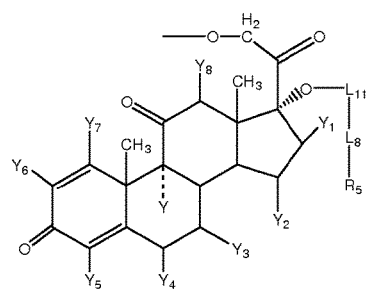
Figure 2:
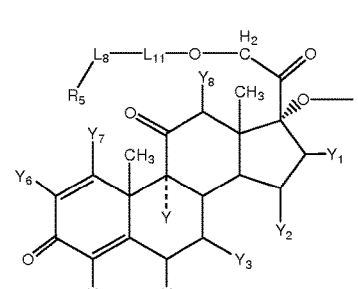
Figure 2:
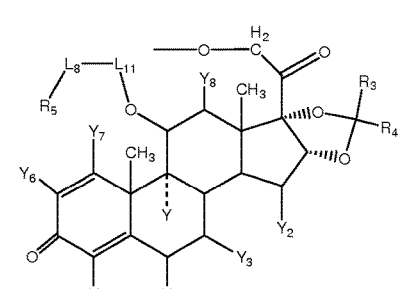
Figure 2:
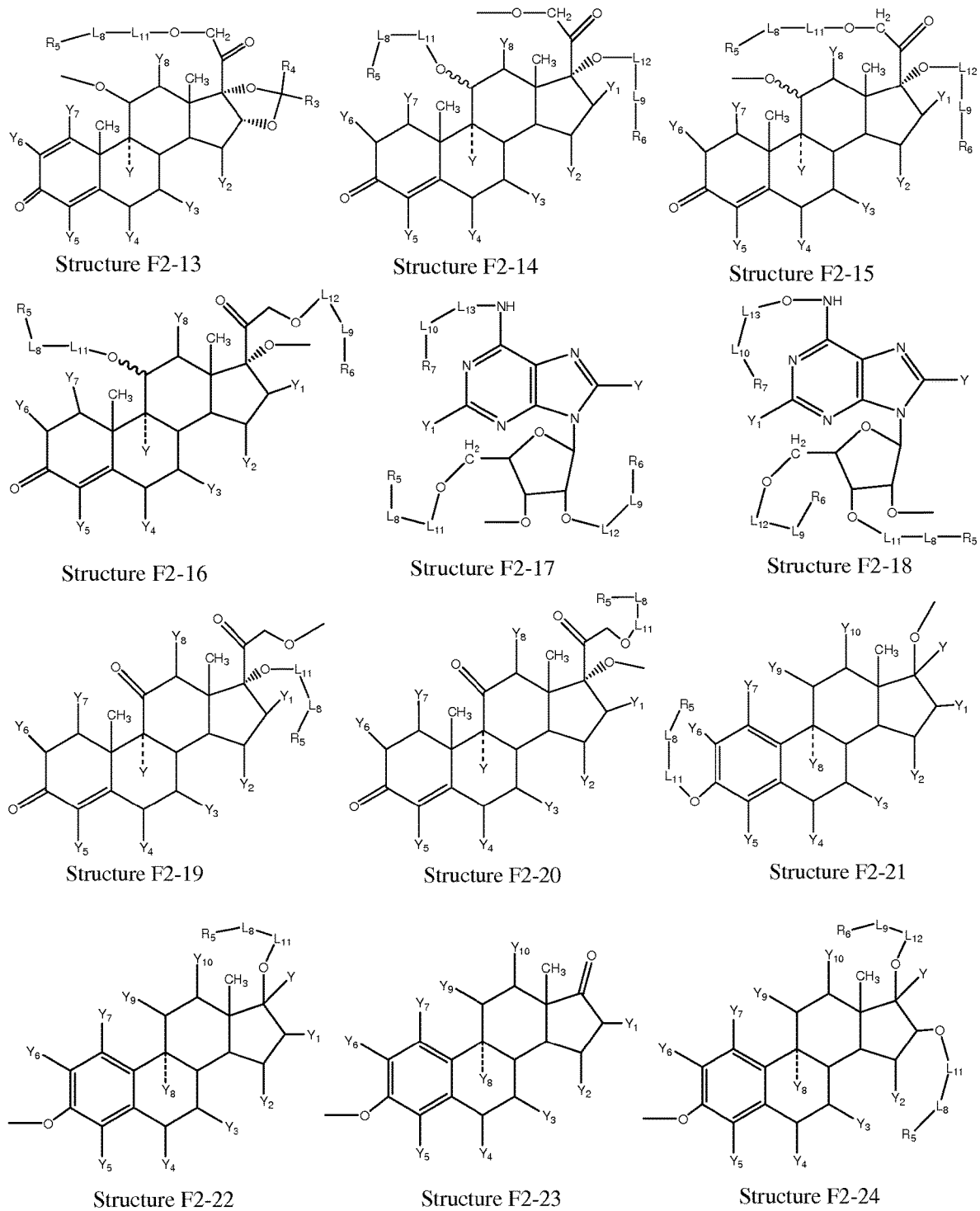
Figure 2:
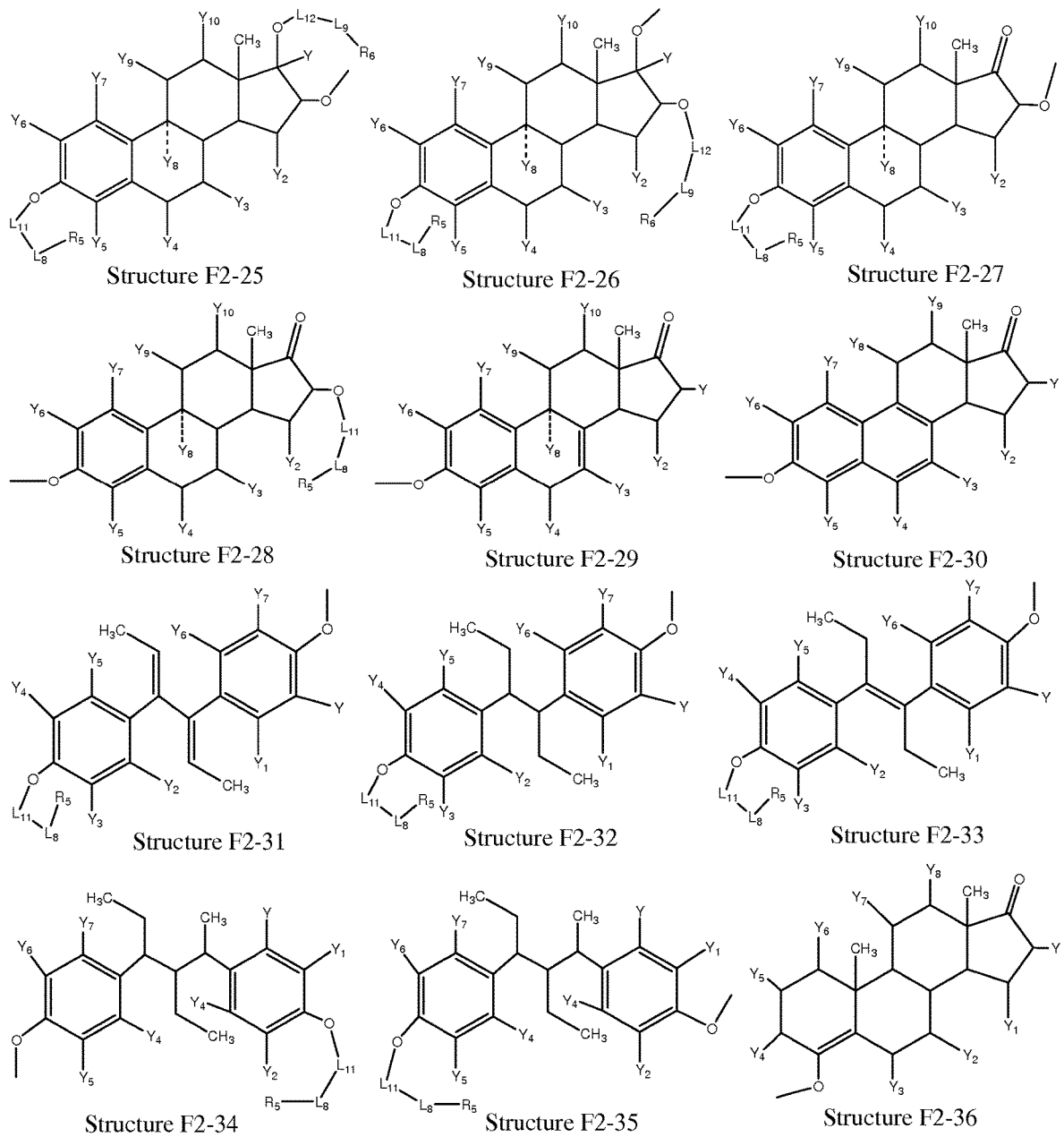
Figure 2:
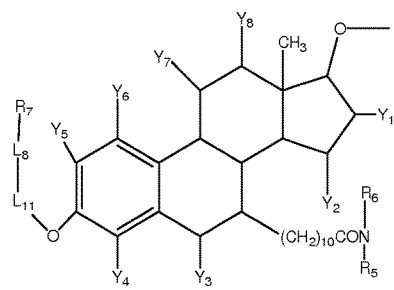
Figure 2:
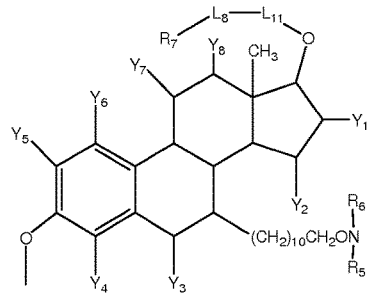
Figure 2:
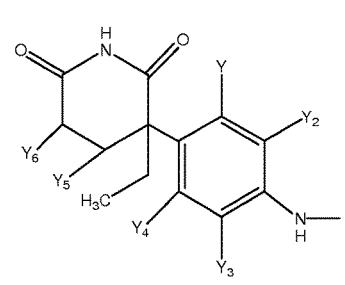
Figure 2:
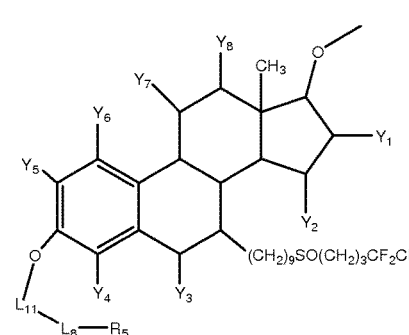
Figure 2:
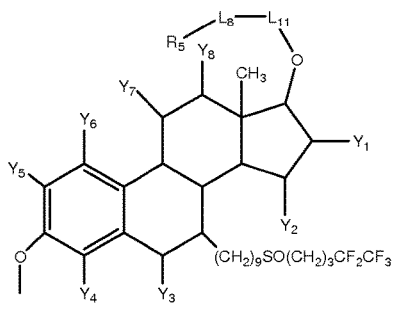
Figure 2:
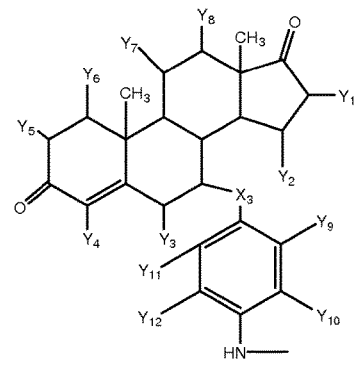
Figure 2:
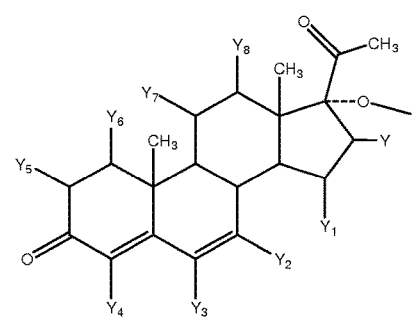
Figure 2:
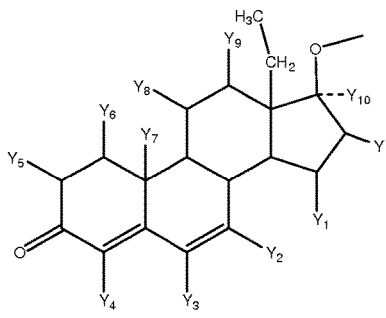
Figure 2:
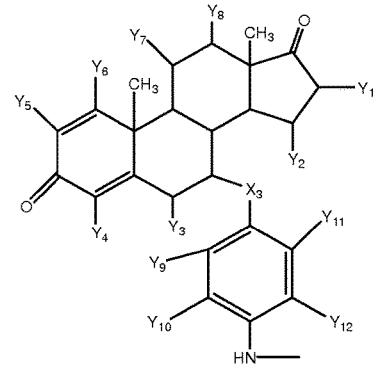
Figure 2:
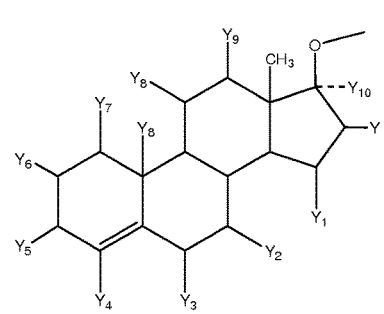
Figure 2:
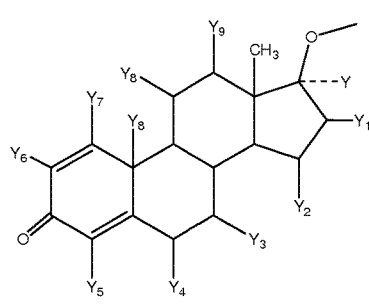
Figure 2:
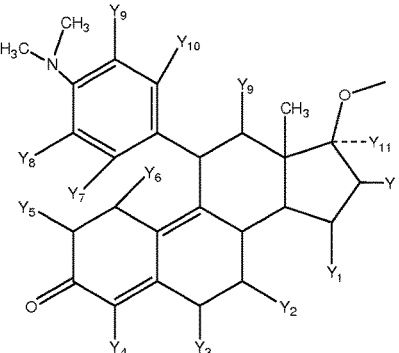
Figure 2:
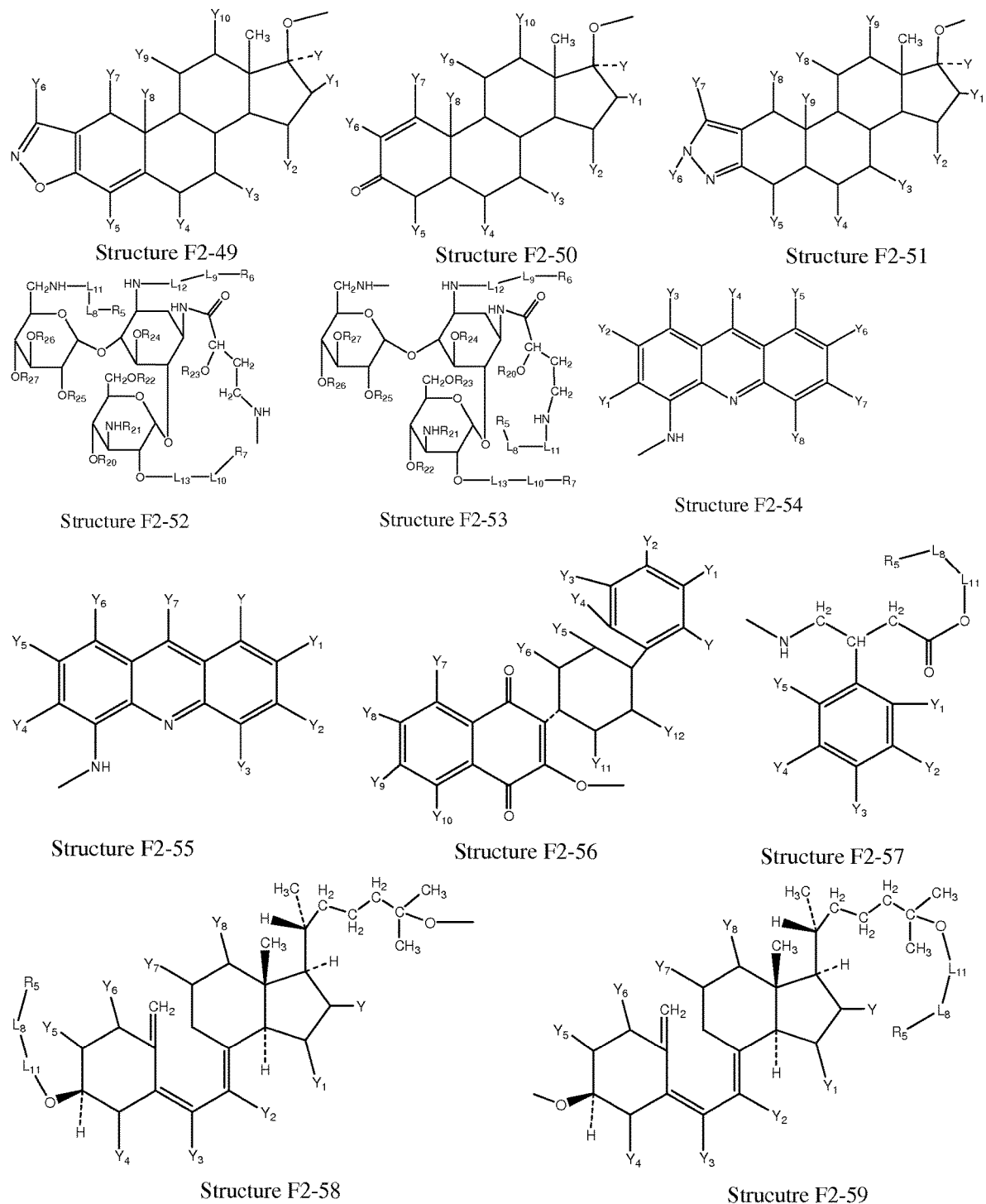
Figure 2:
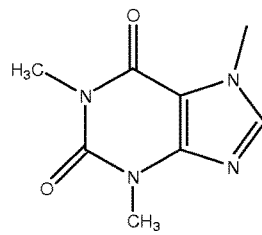
Figure 2:
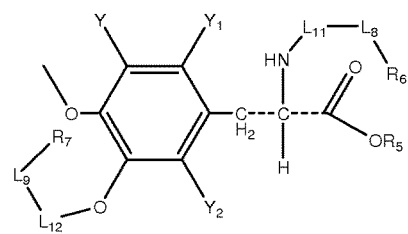
Figure 2:
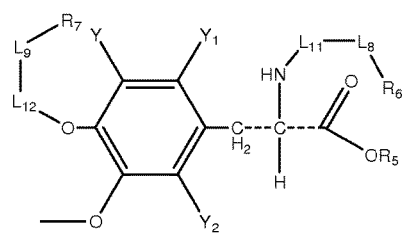
Figure 2:
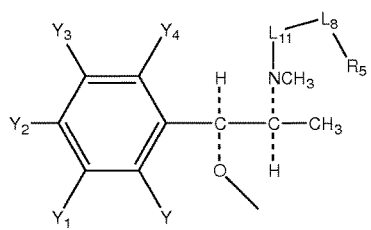
Figure 2:
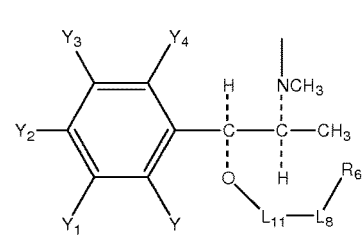
Figure 2:
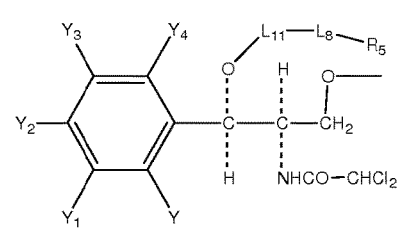
Figure 2:
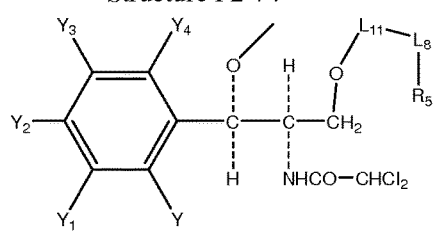
Figure 2:
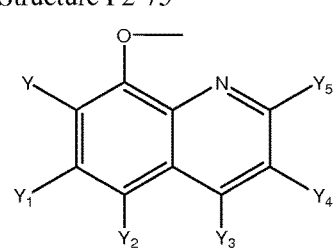
Figure 2:
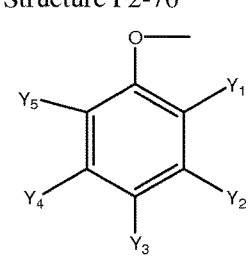
Figure 2:
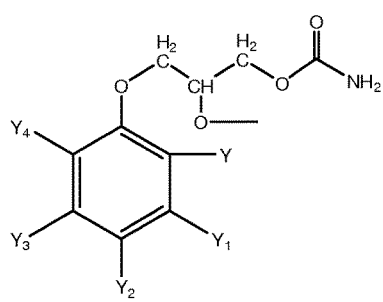
Figure 2:
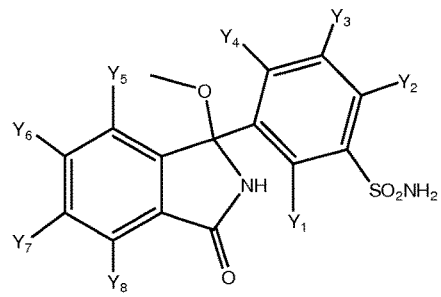
Figure 2:
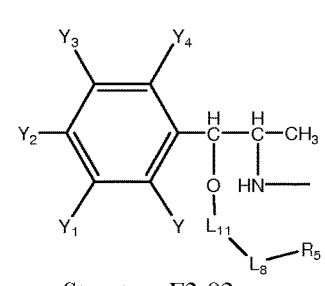
Figure 2:
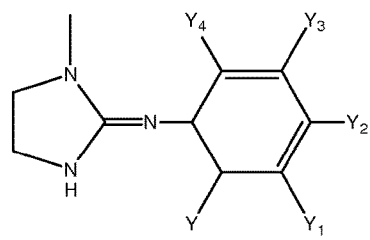
Figure 2:
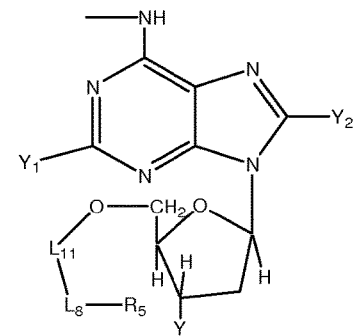
Figure 2:
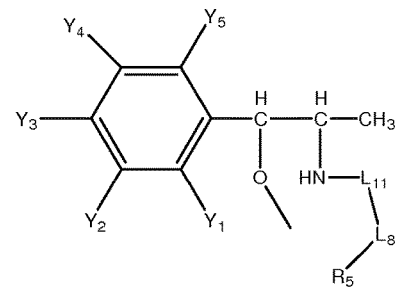
Figure 2:
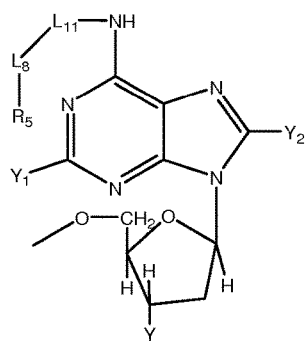
Figure 2:
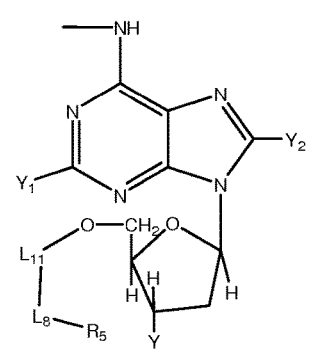
Figure 2:
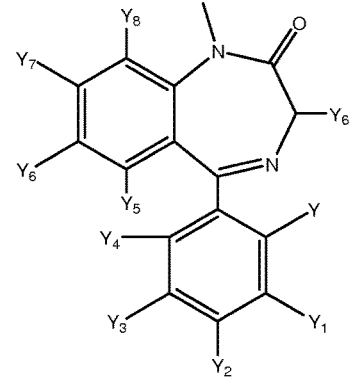
Figure 2:
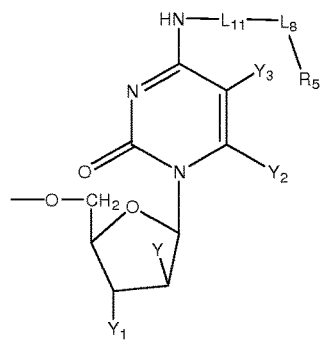
Figure 2:
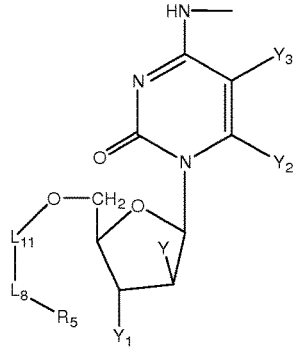
Figure 2:
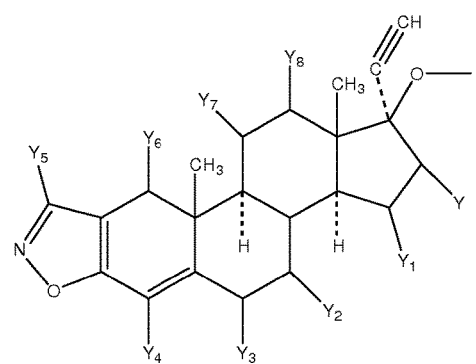
Figure 2:
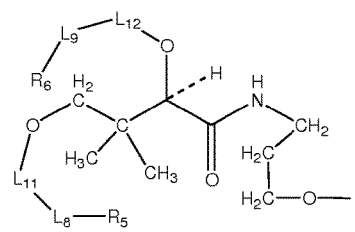
Figure 2:
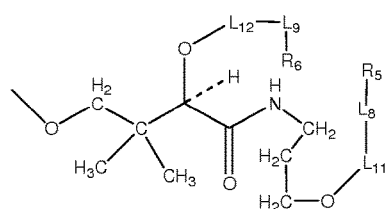
Figure 2:
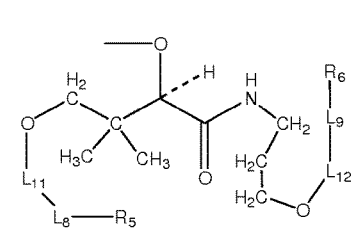
Figure 2:
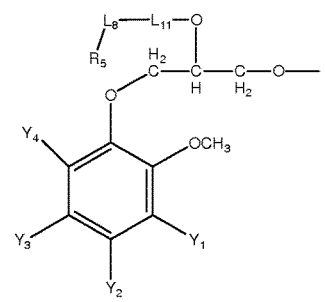
Figure 2:
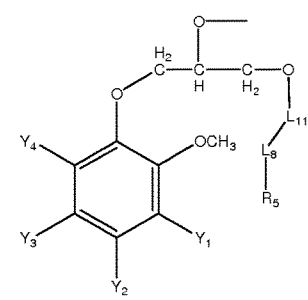
Figure 2:
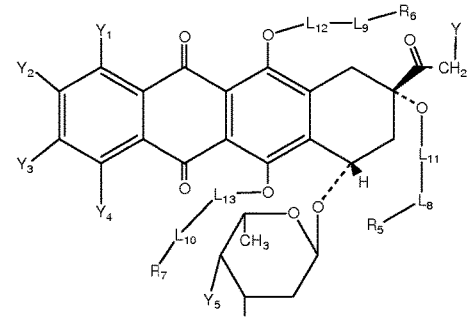
Figure 2:
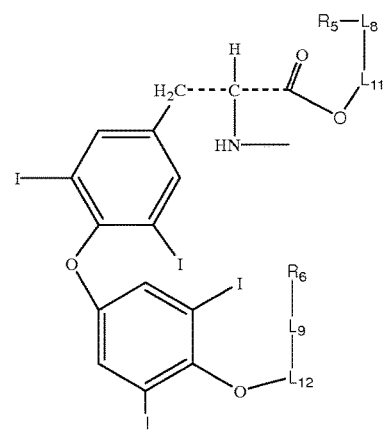
Figure 2:
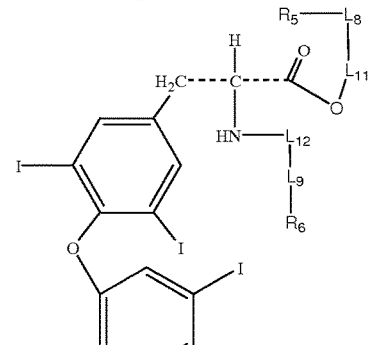
Figure 2:
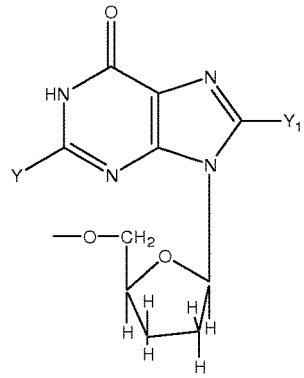
Figure 2:
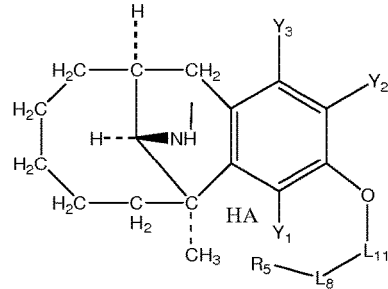
Figure 2:
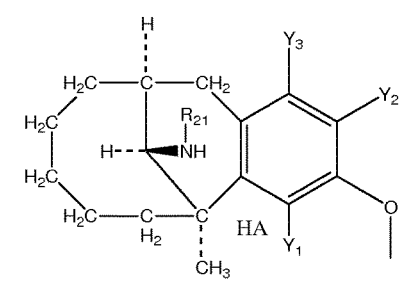
Figure 2:
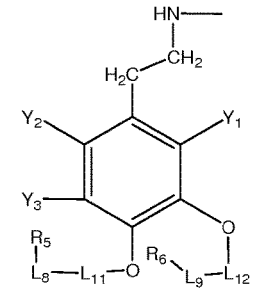
Figure 2:
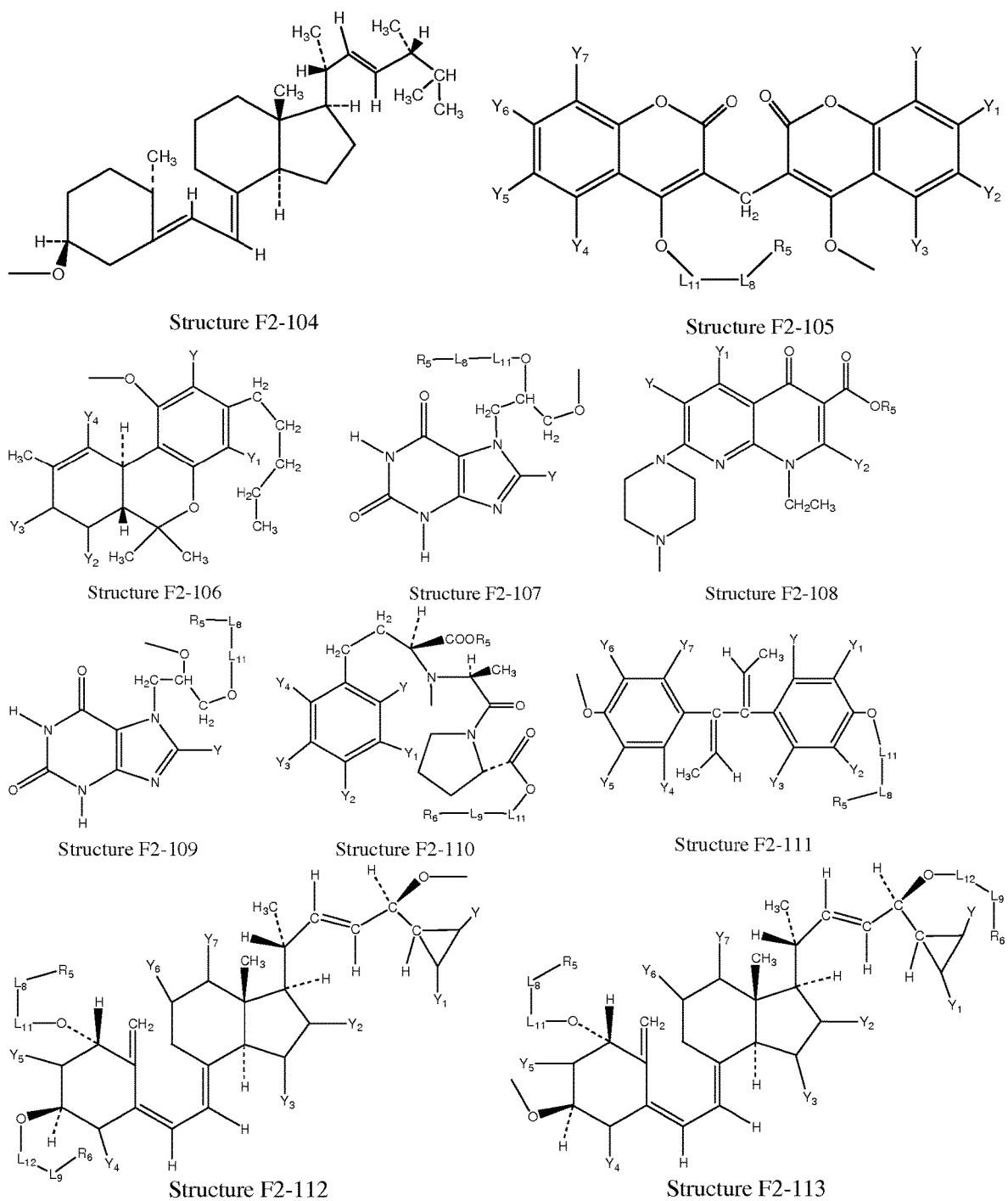
Figure 2:
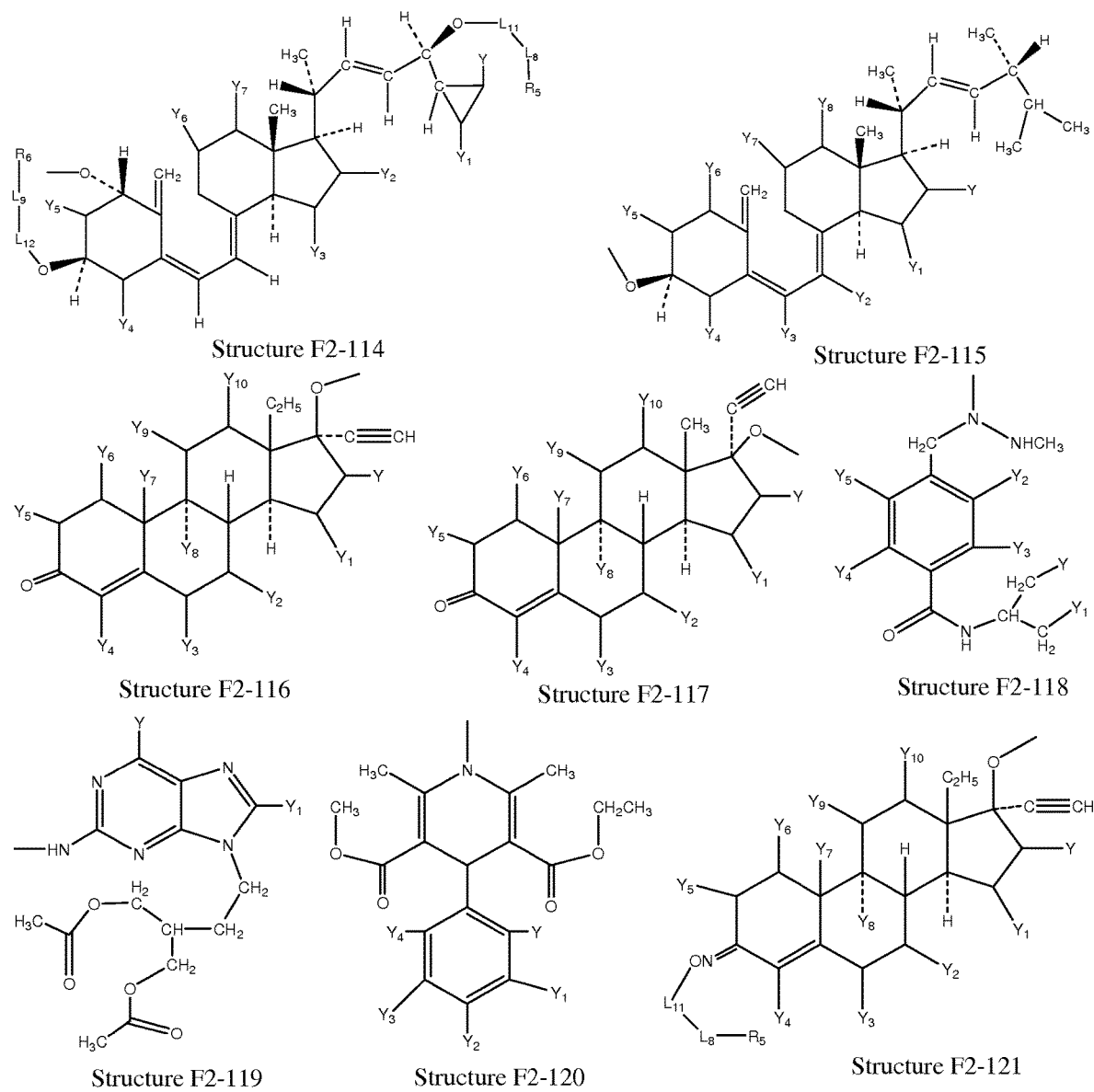
Figure 2:
Figure 2:
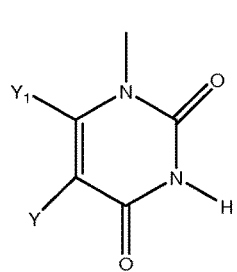
Figure 2:
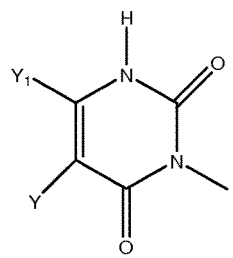
Figure 2:
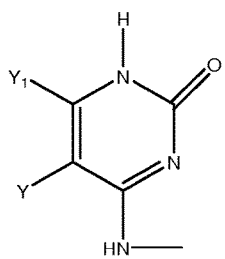
Figure 2:
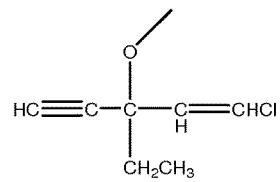
Figure 2:
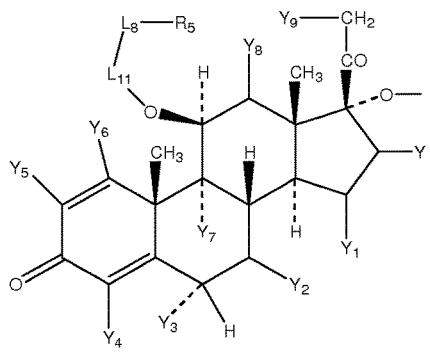
Figure 2:
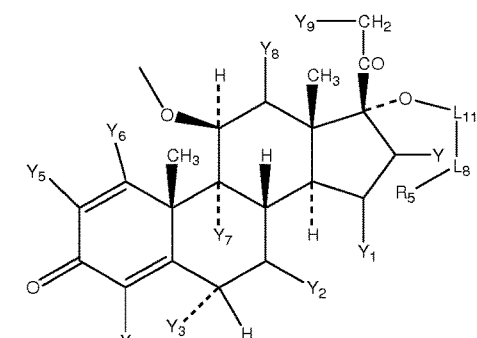
Figure 2:
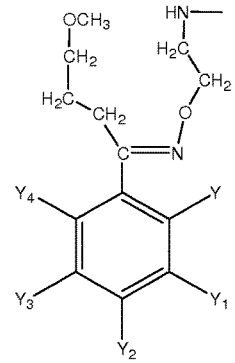
Figure 2:
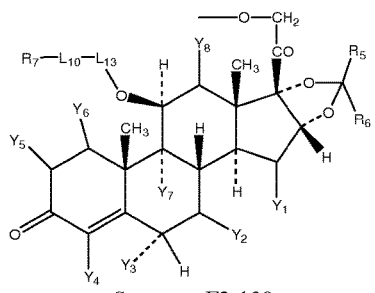
Figure 2:
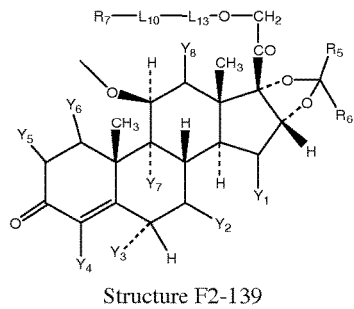
Figure 2:
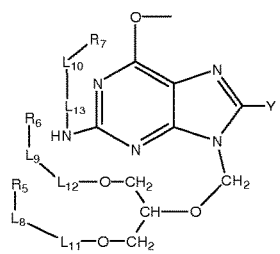
Figure 2:
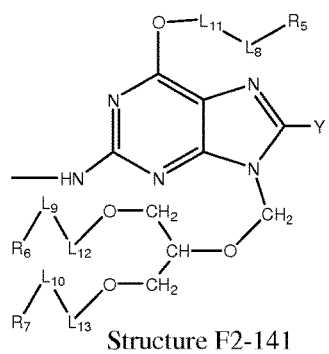
Figure 2:
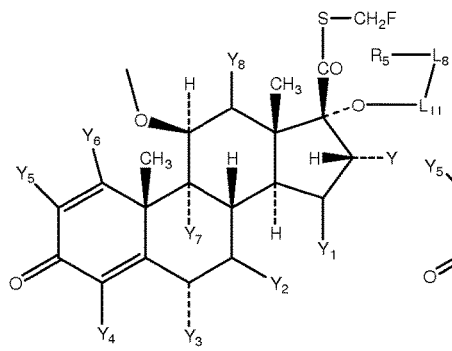
Figure 2:
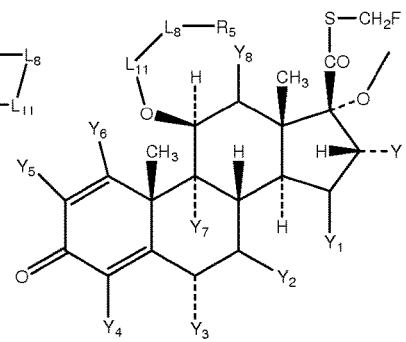
Figure 2:
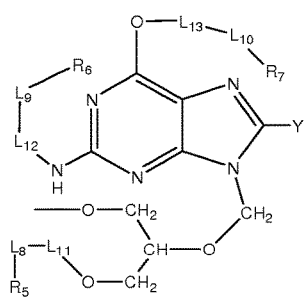
Figure 2:
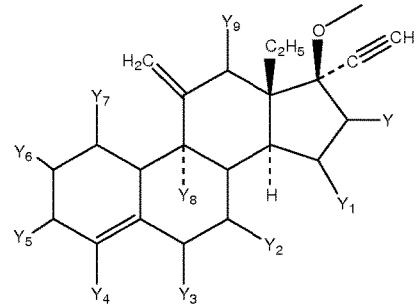
Figure 2:
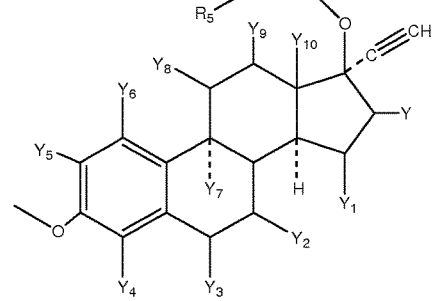
Figure 2:
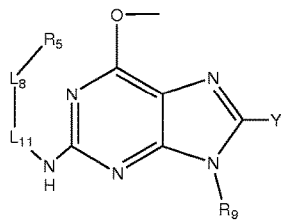
Figure 2:
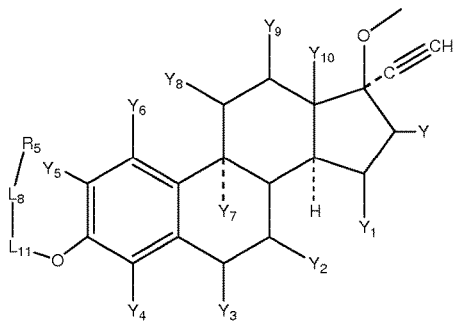
Figure 2:
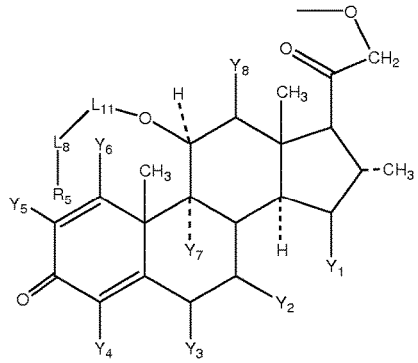
Figure 2:
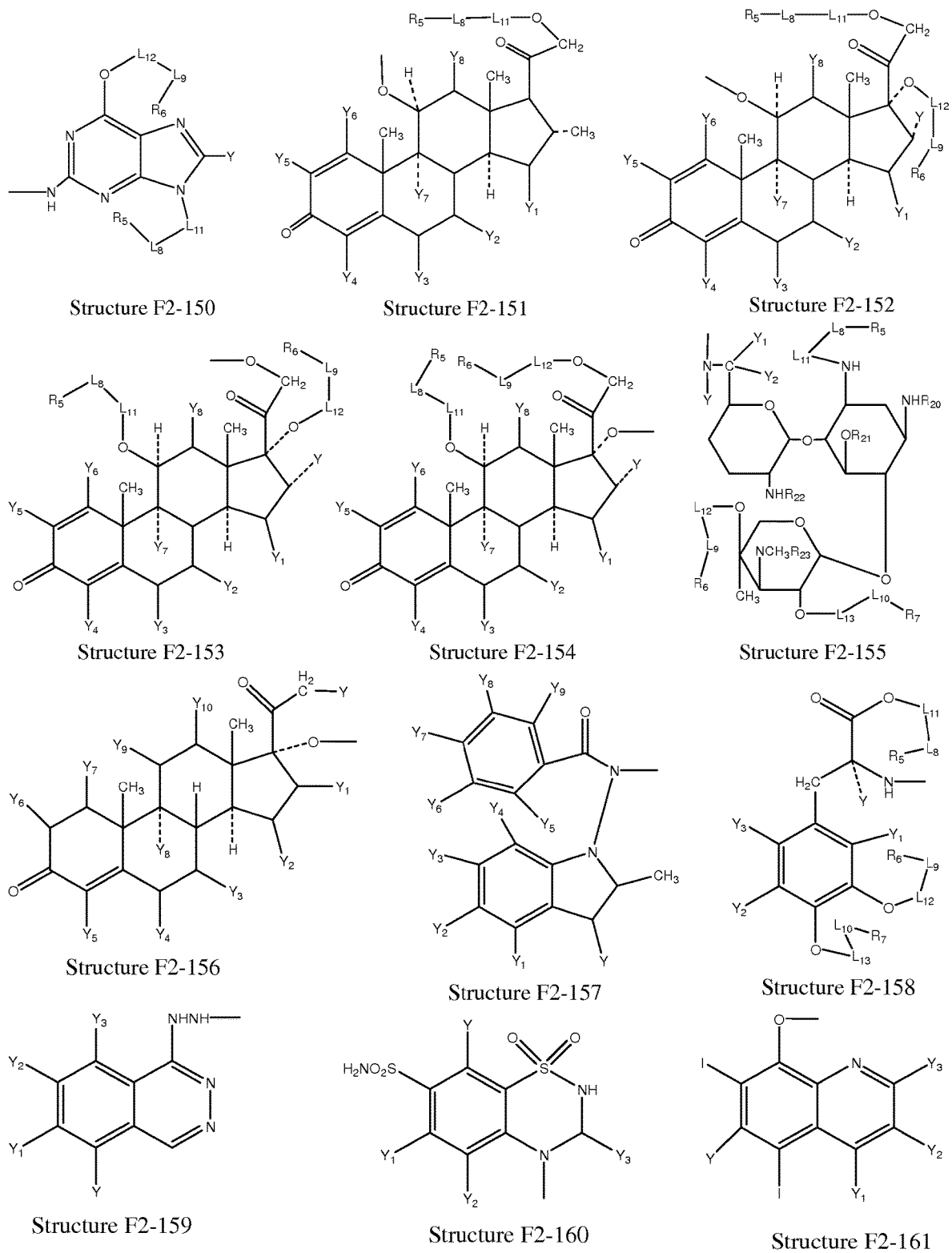
Figure 2:
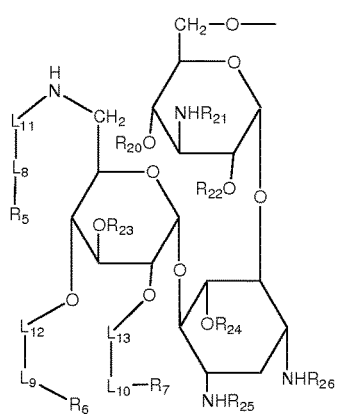
Figure 2:
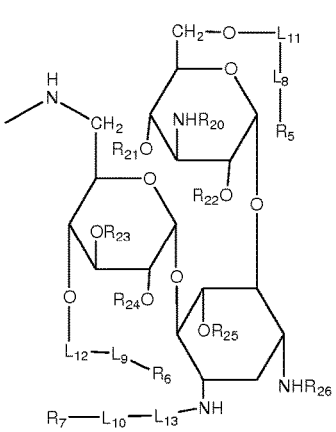
Figure 2:
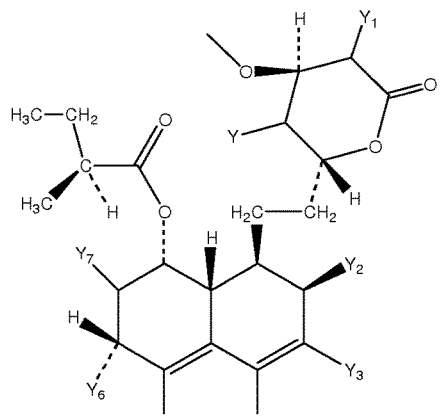
Figure 2:
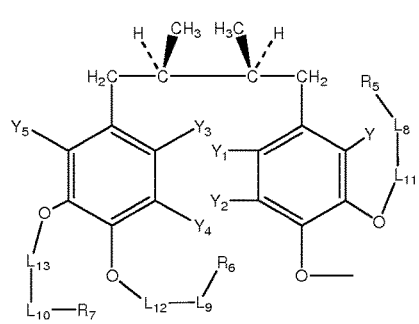
Figure 2:
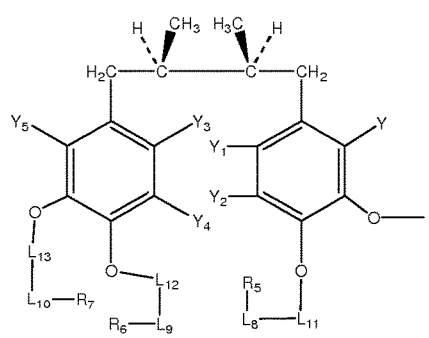
Figure 2:
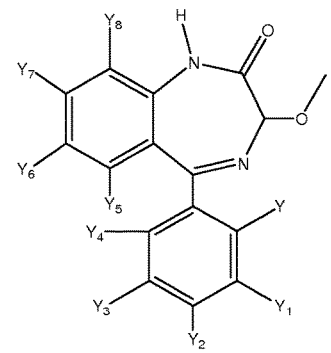
Figure 2:
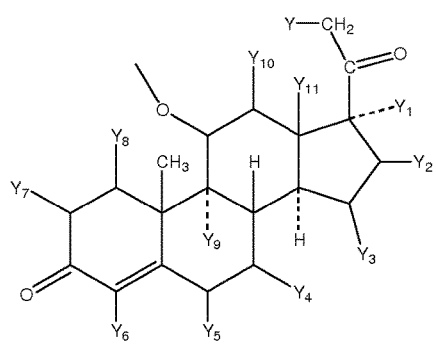
Figure 2:
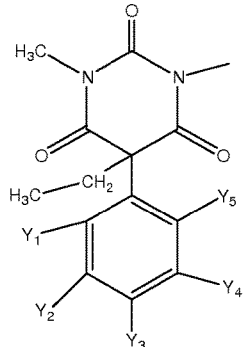
Figure 2:
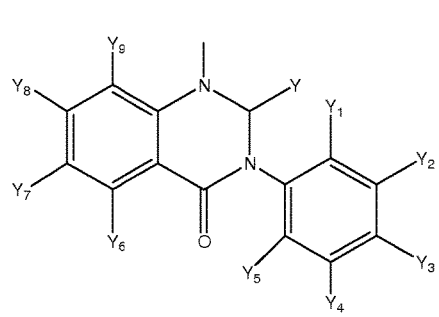
Figure 2:
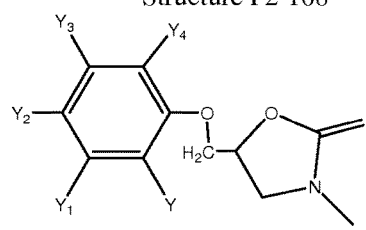
Figure 2:
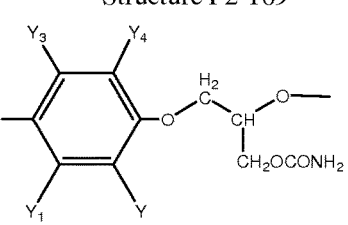
Figure 2:
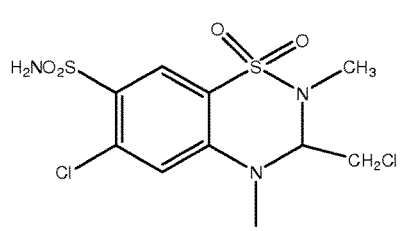
Figure 2:
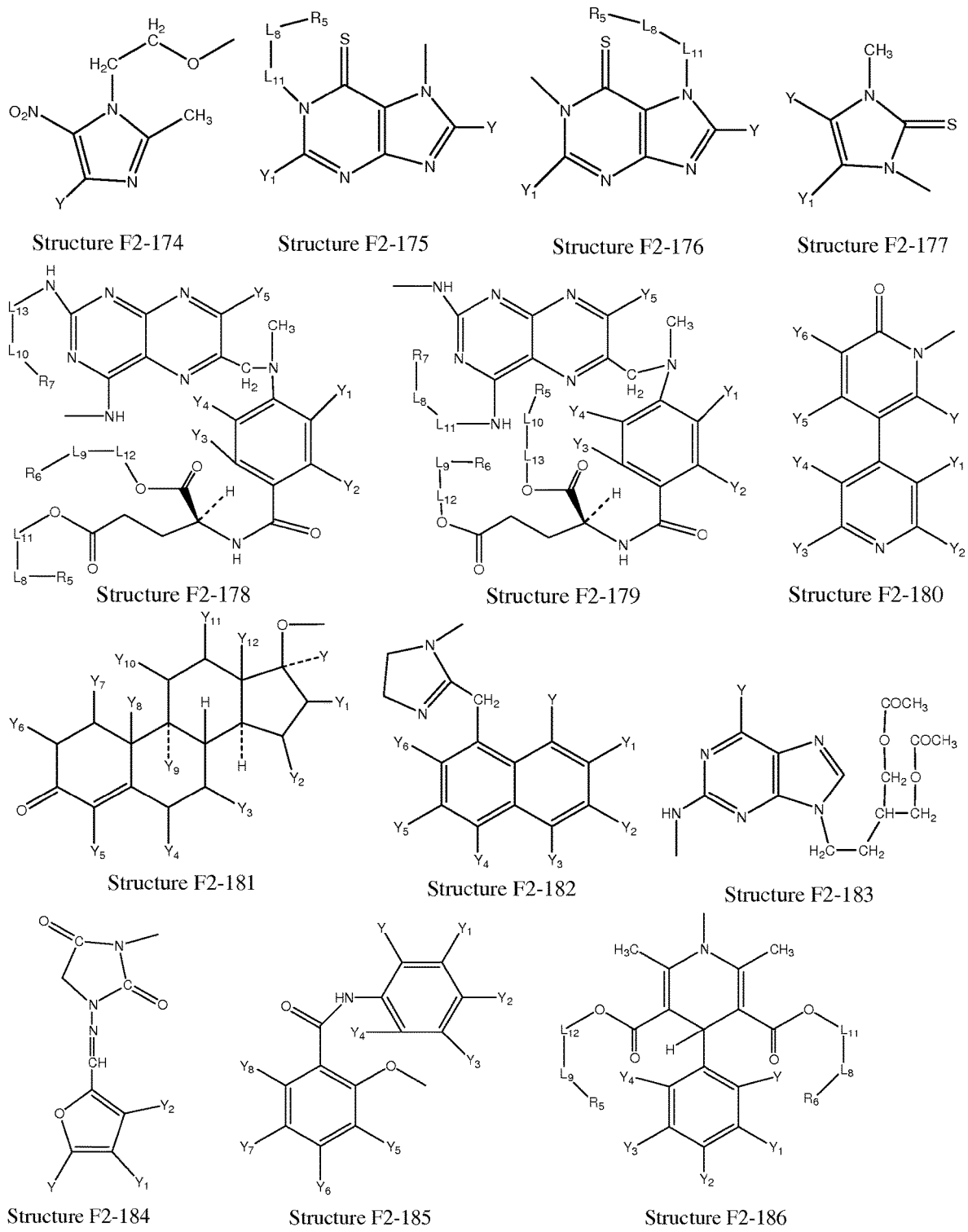
Figure 2:
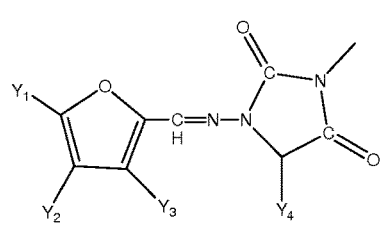
Figure 2:
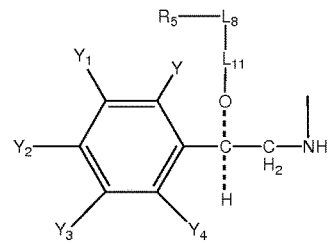
Figure 2:
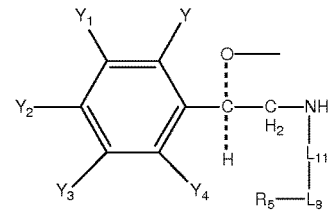
Figure 2:
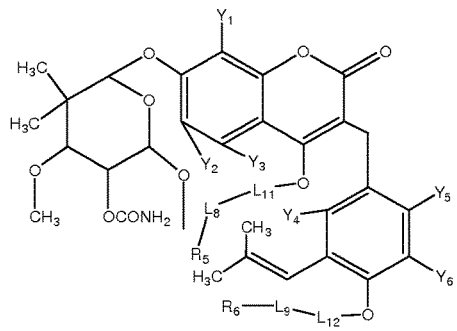
Figure 2:
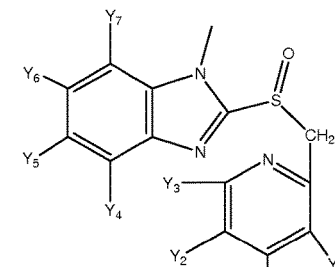
Figure 2:
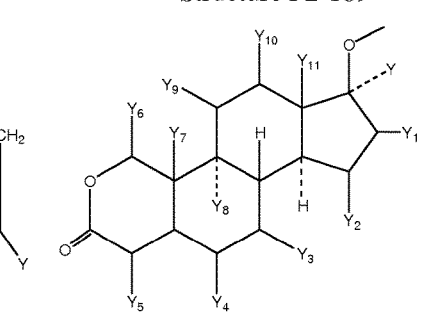
Figure 2:
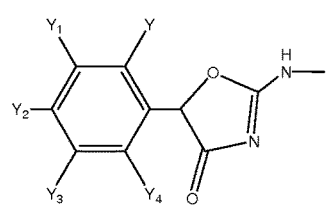
Figure 2:
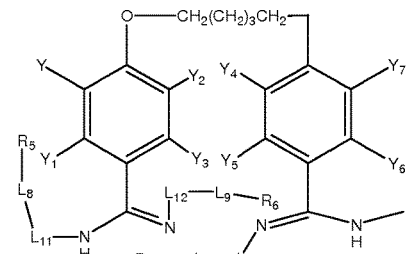
Figure 2:
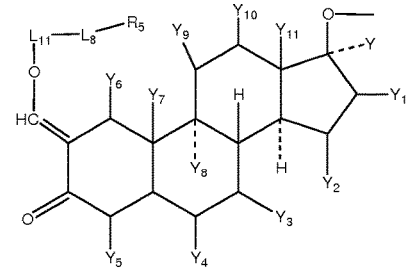
Figure 2:
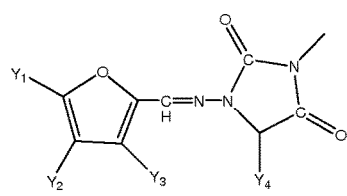
Figure 2:
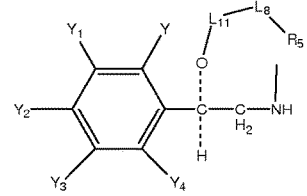
Figure 2:
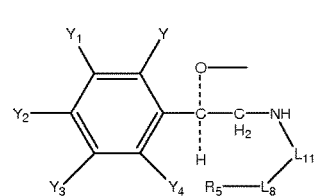
Figure 2:
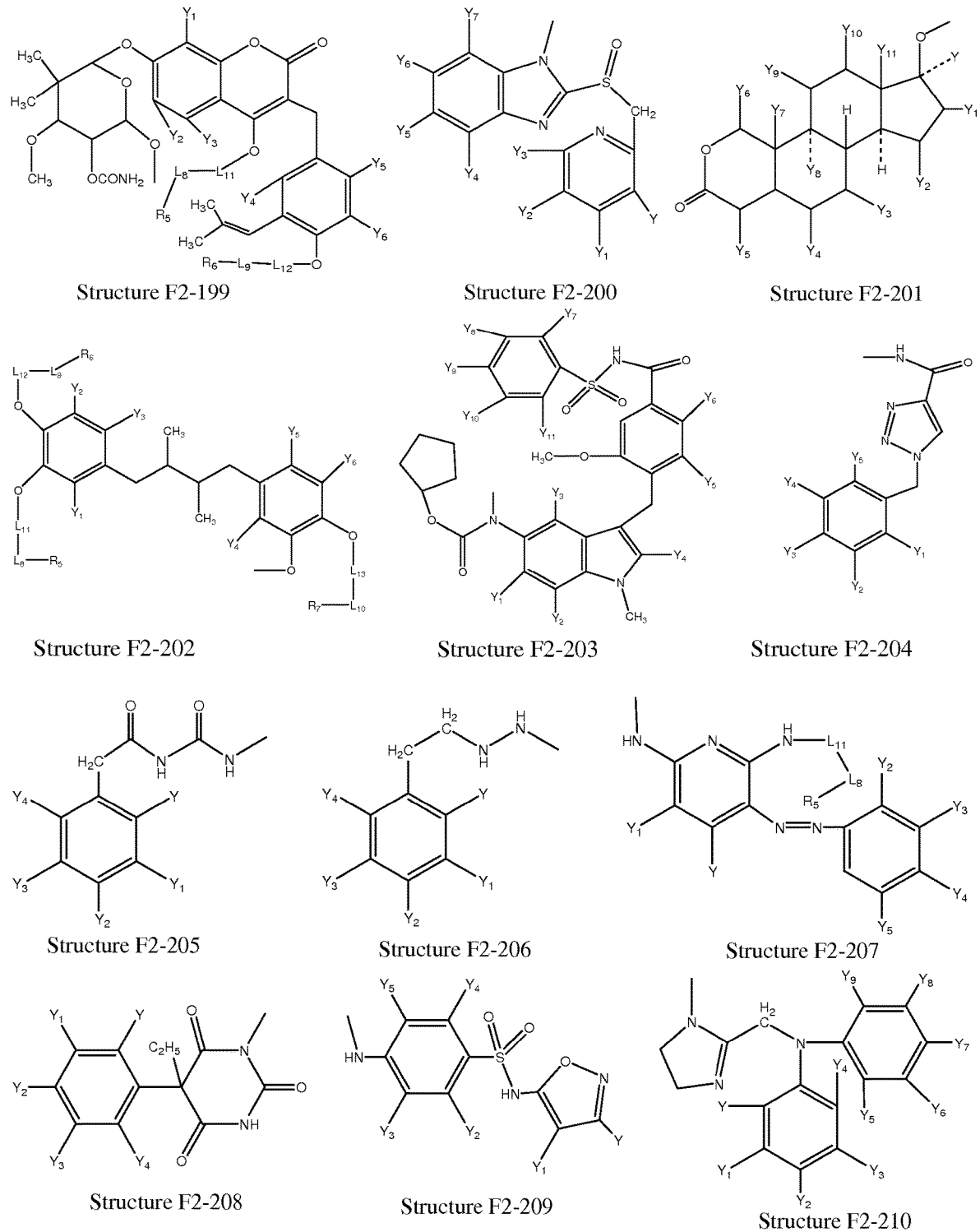
Figure 2:
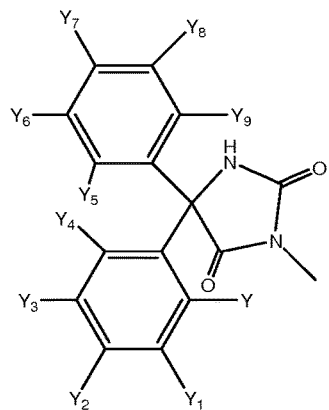
Figure 2:
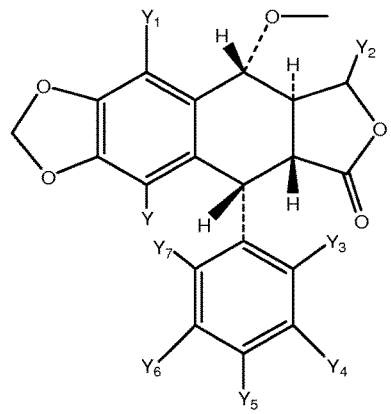
Figure 2:
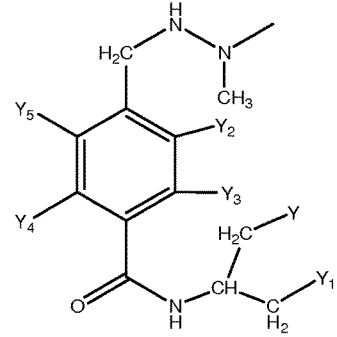
Figure 2:
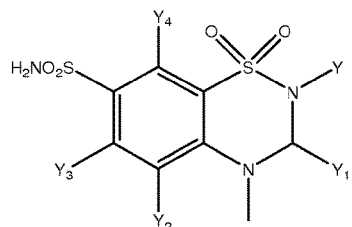
Figure 2:
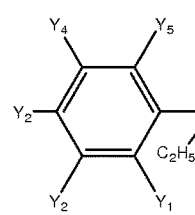
Figure 2:
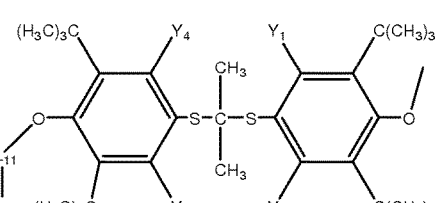
Figure 2:
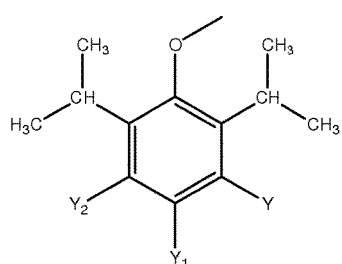
Figure 2:
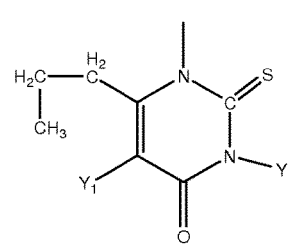
Figure 2:
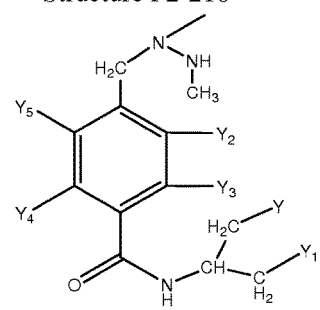
Figure 2:
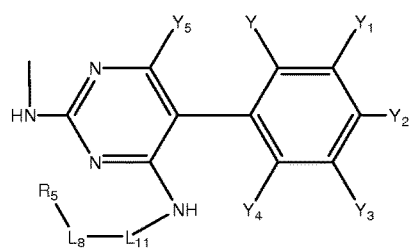
Figure 2:
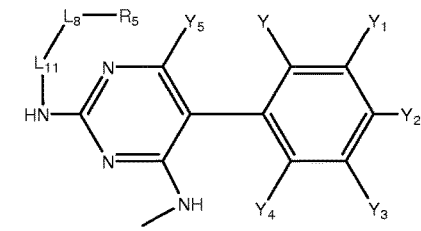
Figure 2:
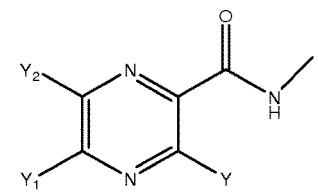
Figure 2:
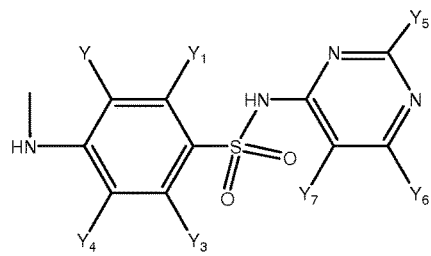
Figure 2:
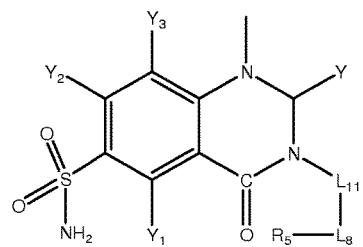
Figure 2:
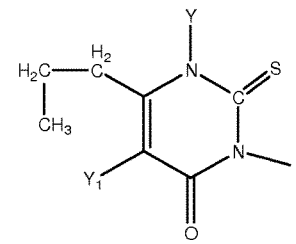
Figure 2:
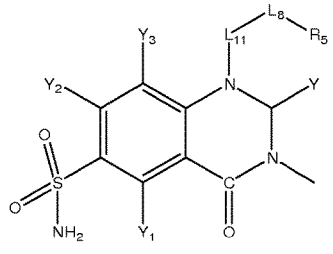
Figure 2:
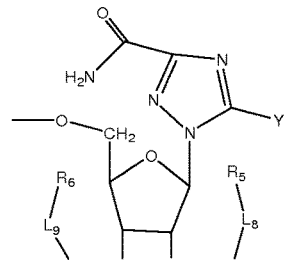
Figure 2:
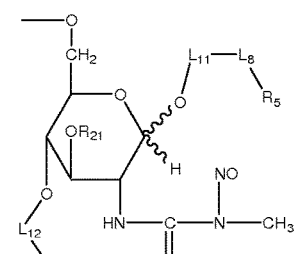
Figure 2:
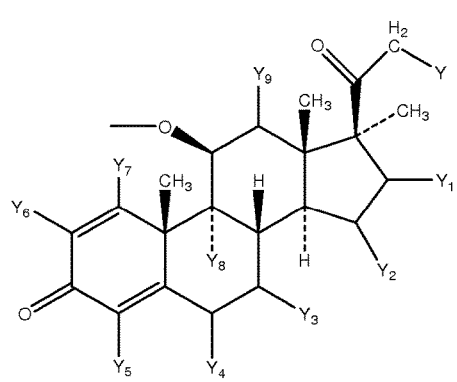
Figure 2:
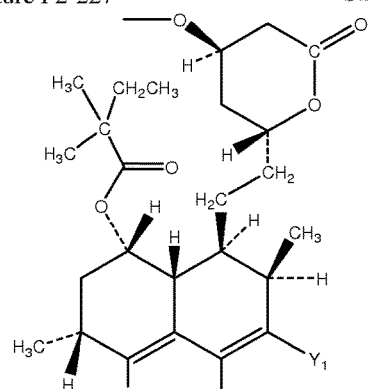
Figure 2:
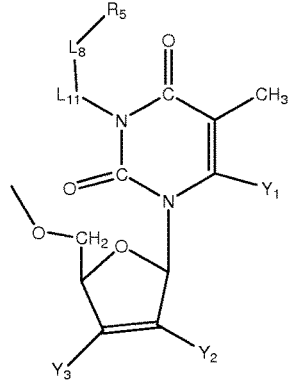
Figure 2:
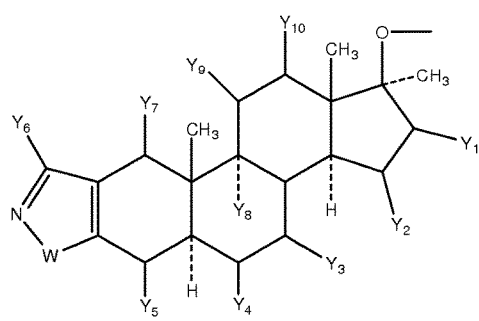
Figure 2:
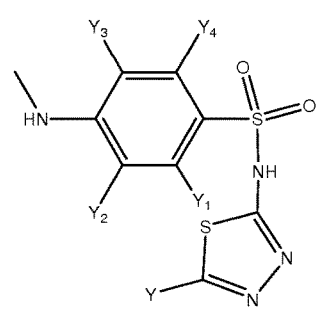
Figure 2:
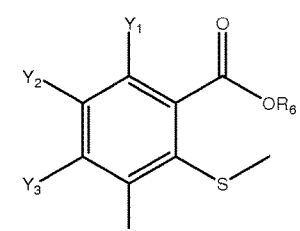
Figure 2:
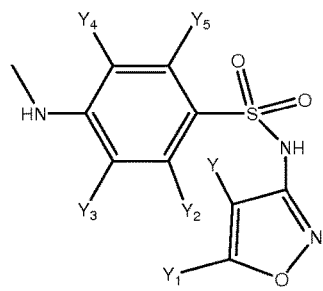
Figure 2:
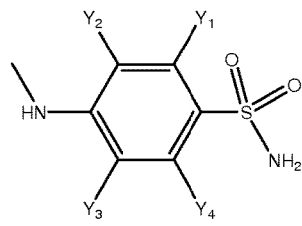
Figure 2:
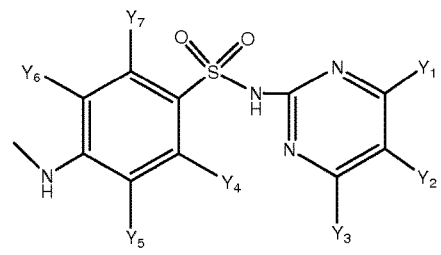
Figure 2:
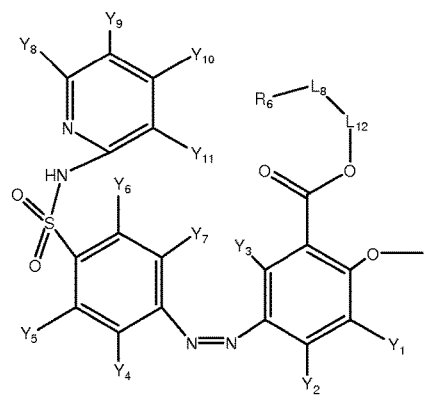
Figure 2:
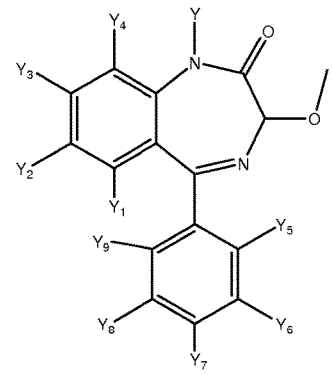
Figure 2:
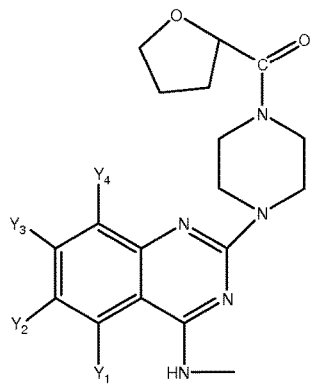
Figure 2:
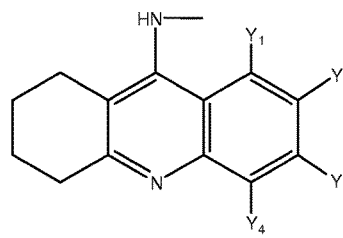
Figure 2:
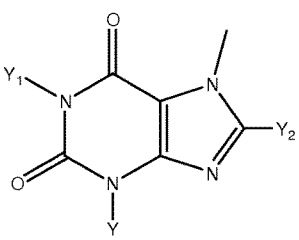
Figure 2:
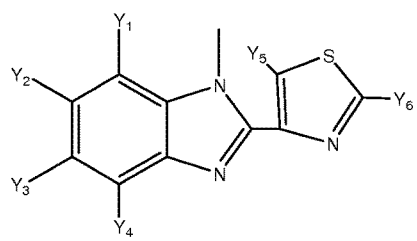
Figure 2:
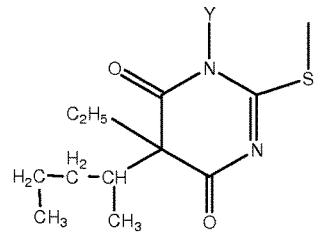
Figure 2:
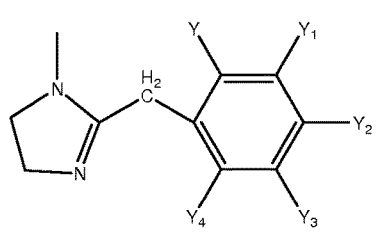
Figure 2:
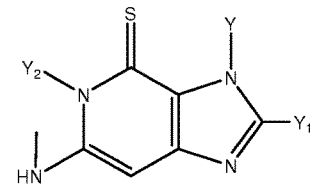
Figure 2:
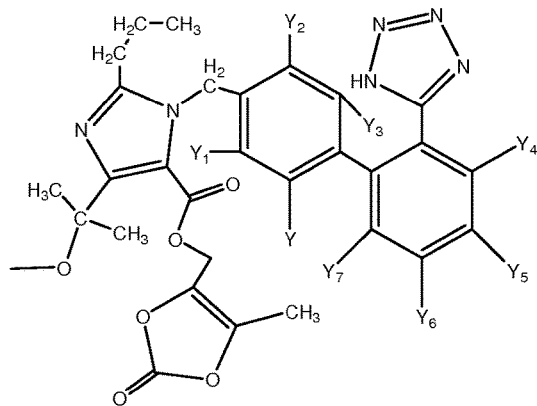
Figure 2:
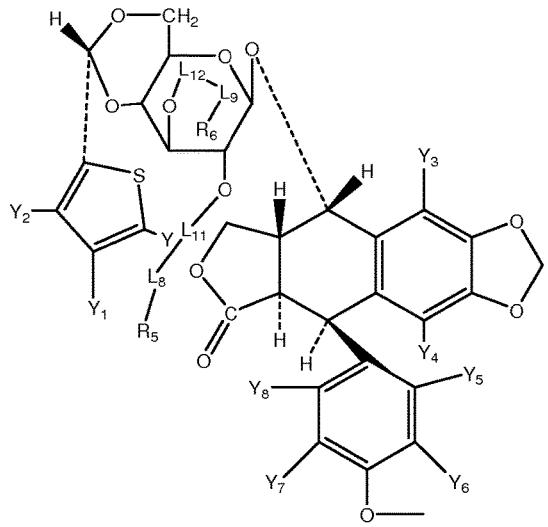
Figure 2:
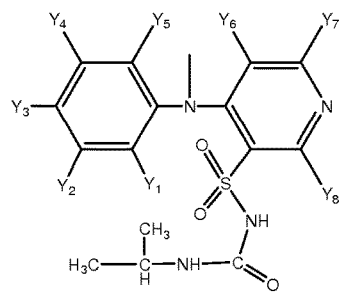
Figure 2:
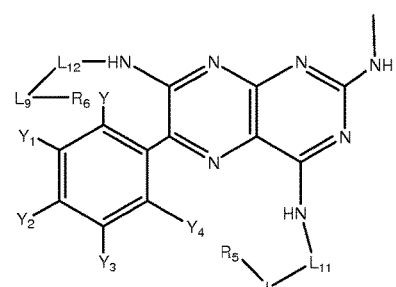
Figure 2:
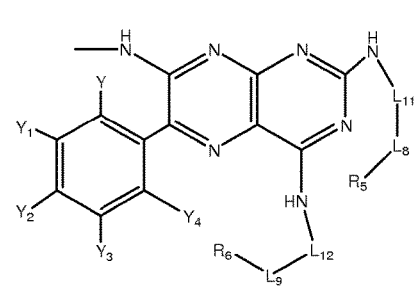
Figure 2:
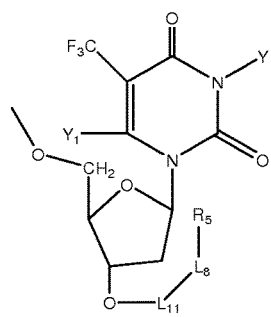
Figure 2:
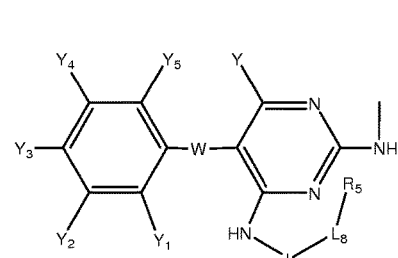
Figure 2:
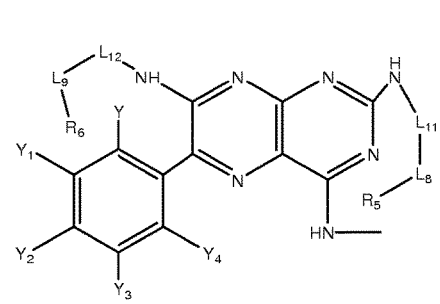
Figure 2:
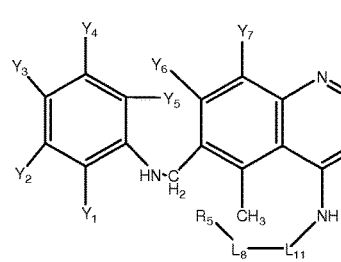
Figure 2:
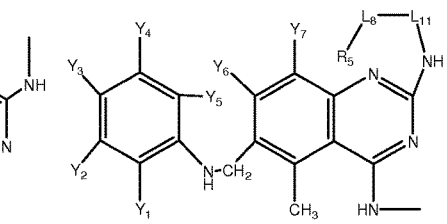
Figure 2:
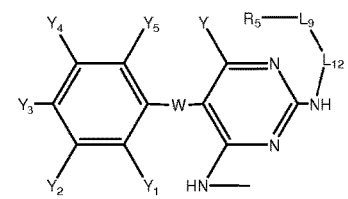
Figure 2:
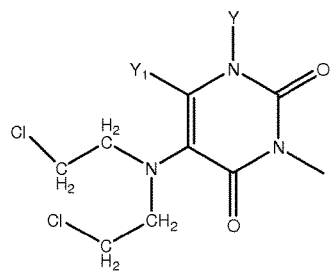
Figure 2:
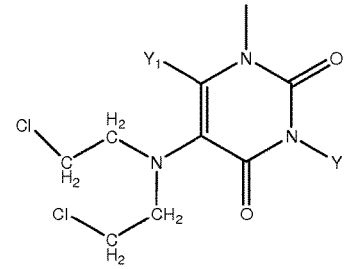
Figure 2:
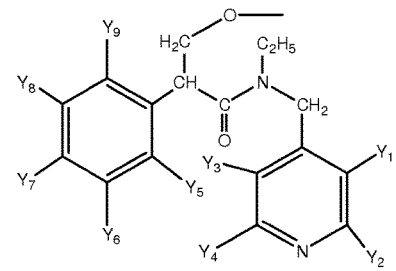
Figure 2:
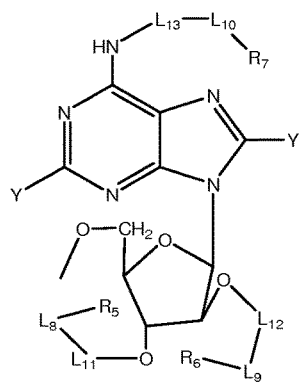
Figure 2:
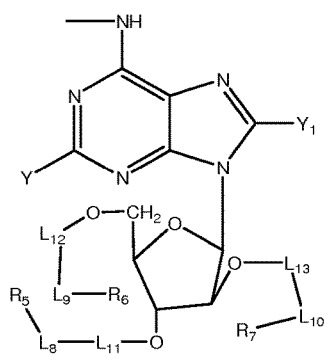
Figure 2:
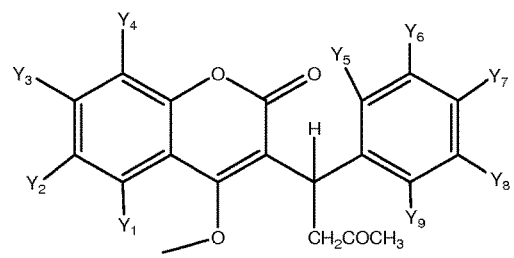
Figure 2:
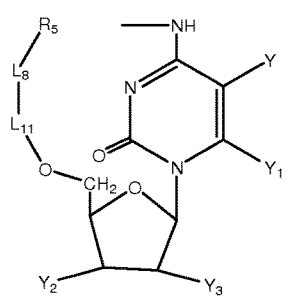
Figure 2:
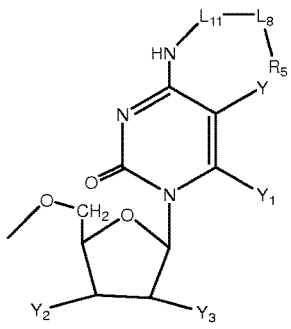
Figure 2:
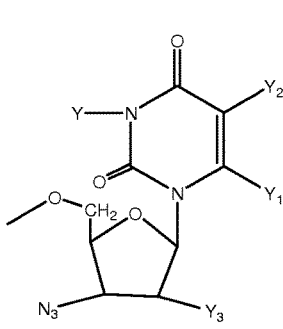
Figure 2:
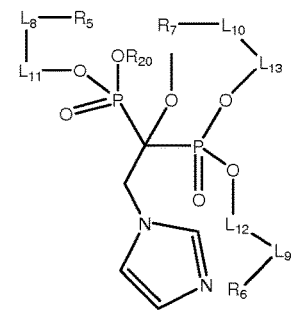
Figure 2:
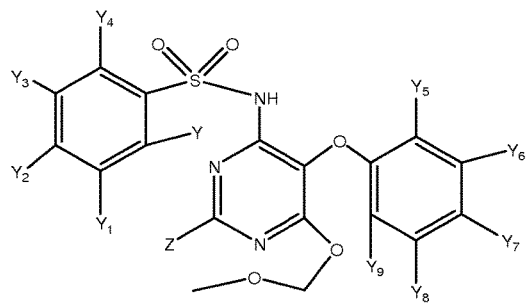
Figure 2:
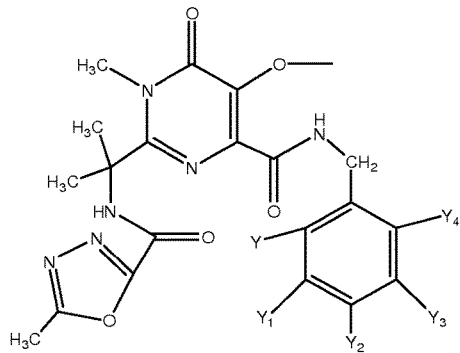
Figure 2:
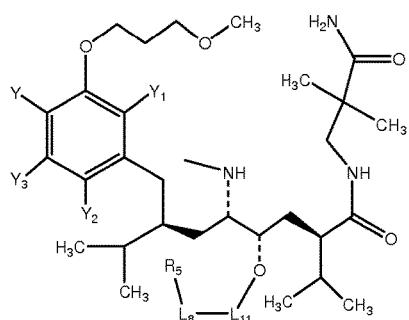
Figure 2:
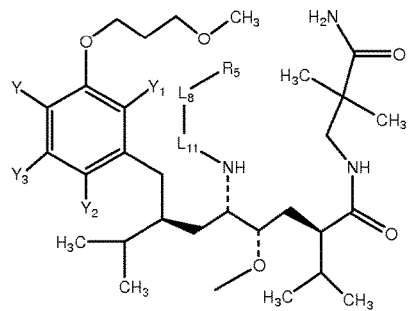
Figure 2:
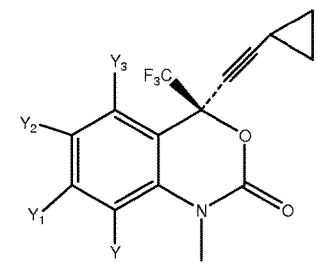
Figure 2:
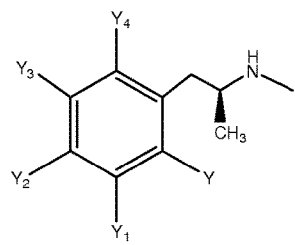
Figure 2:
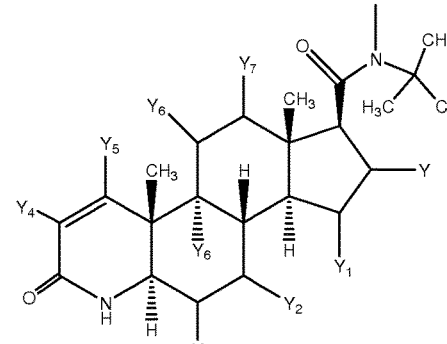
Figure 2:
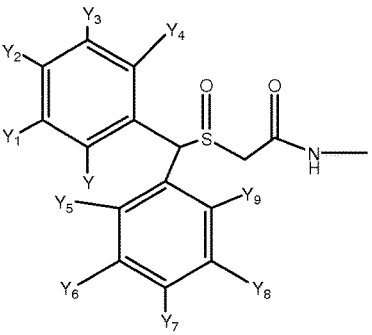
Figure 2:
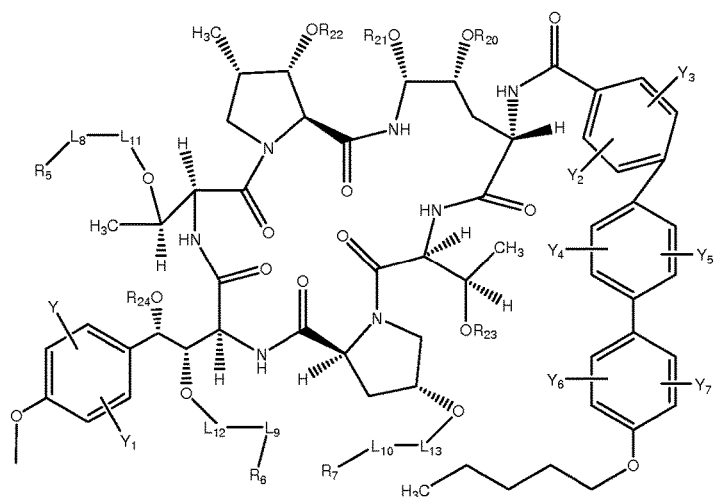
Figure 2:
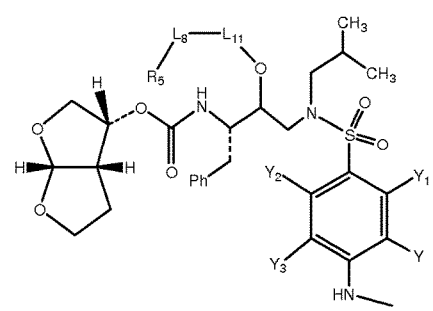
Figure 2:
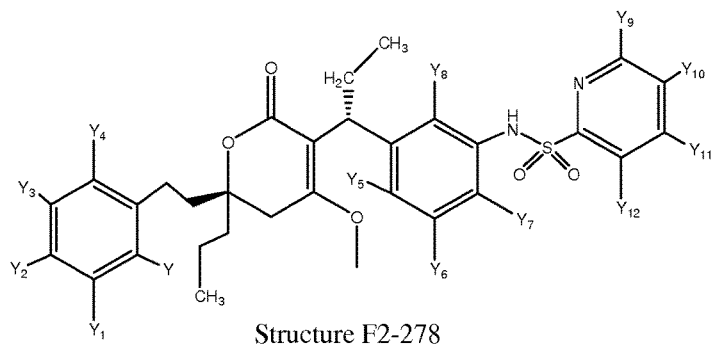
Figure 2:
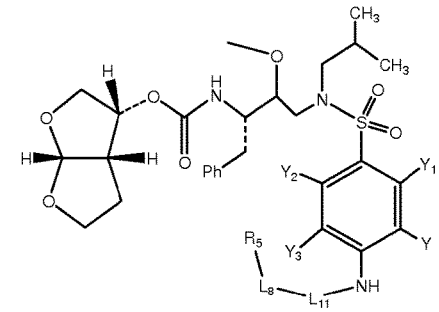
Figure 2:
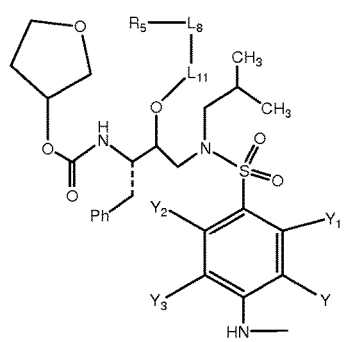
Figure 2:
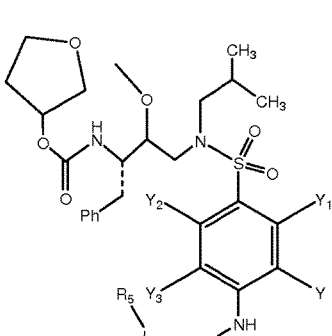
Figure 2:
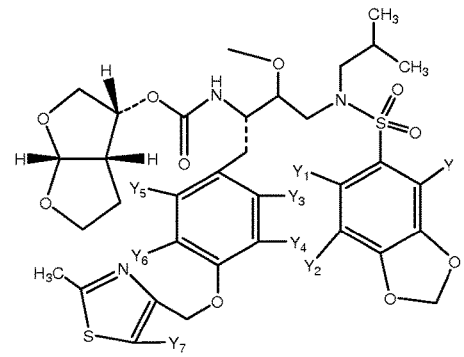
Figure 2:
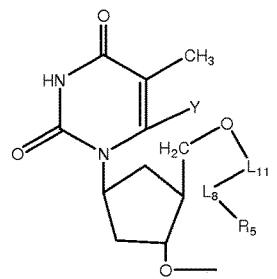
Figure 2:
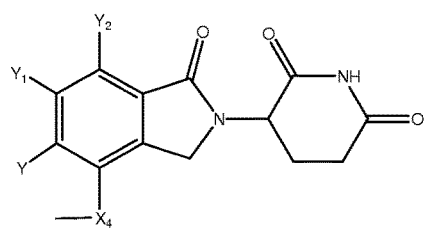
Figure 2:
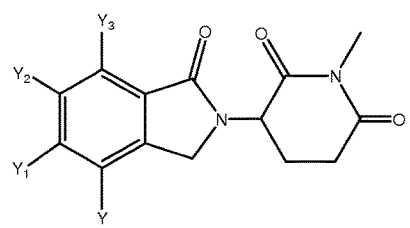
Figure 2:
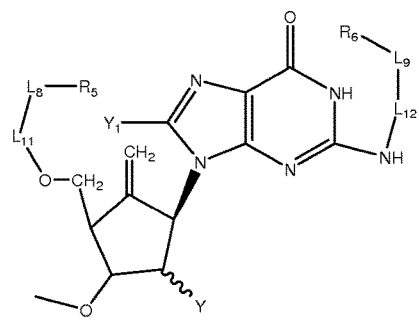
Figure 2:
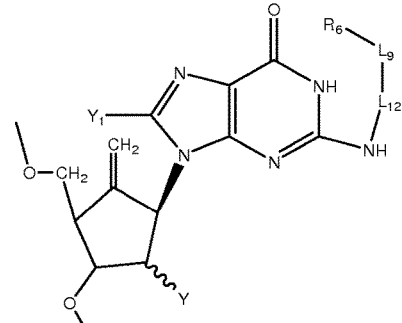
Figure 2:
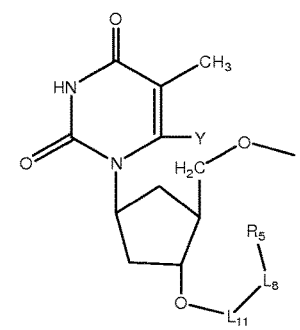
Figure 2:
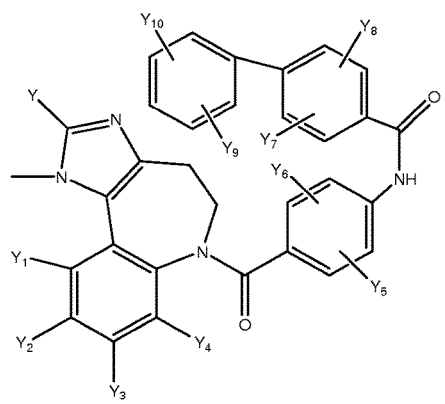
Figure 2:
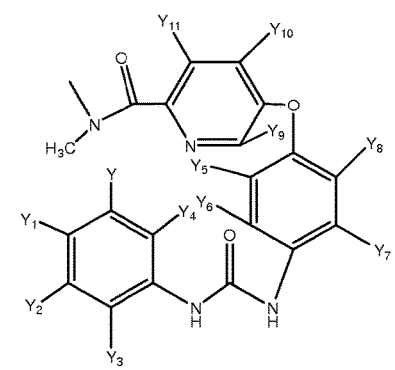
Figure 2:
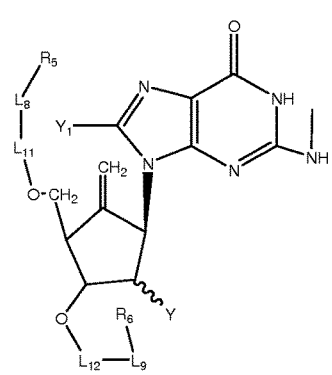
Figure 2:
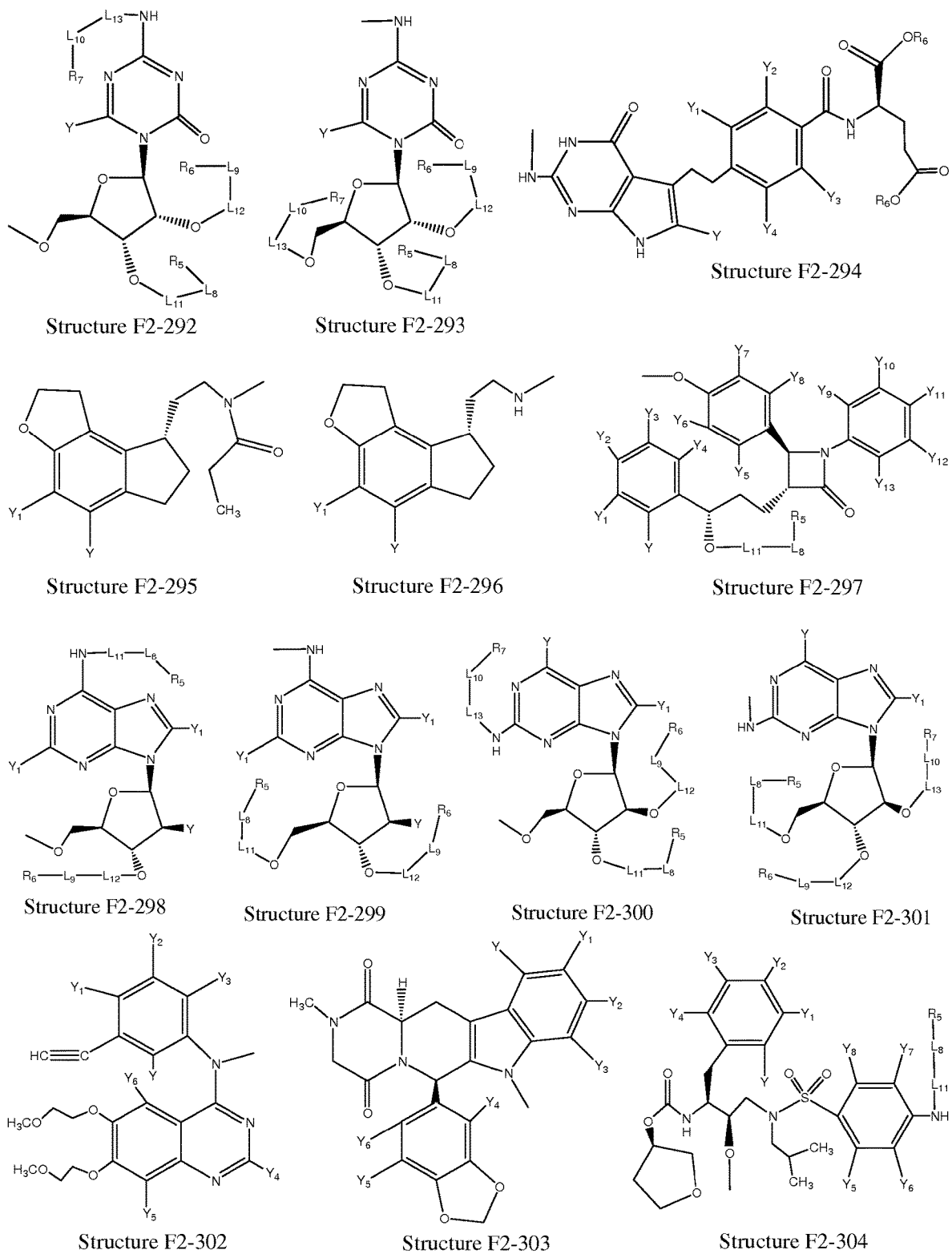
Figure 2:
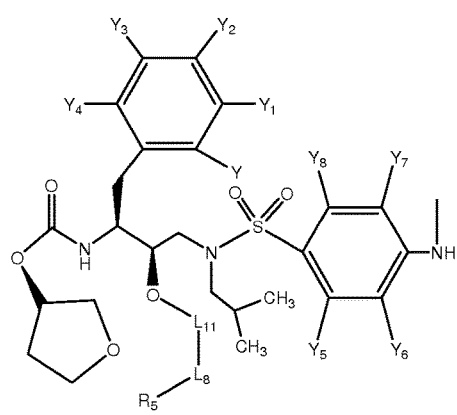
Figure 2:
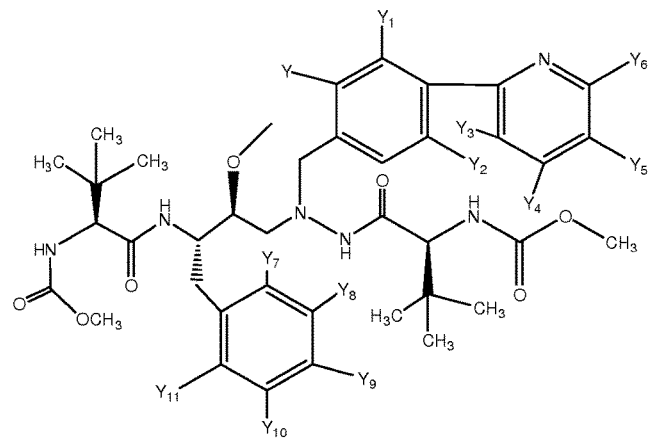
Figure 2:
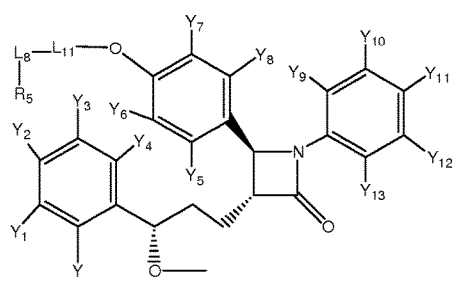
Figure 2:
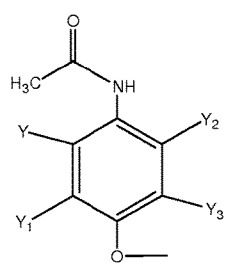
Figure 2:
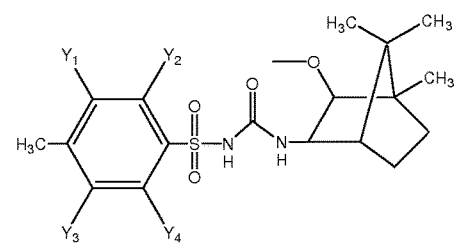
Figure 2:
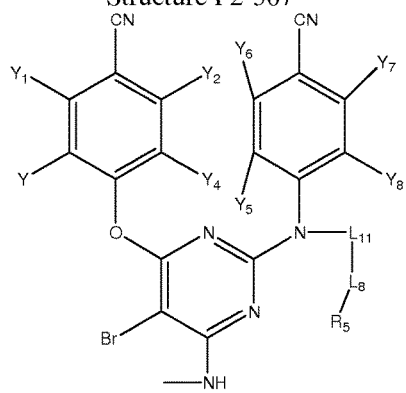
Figure 2:
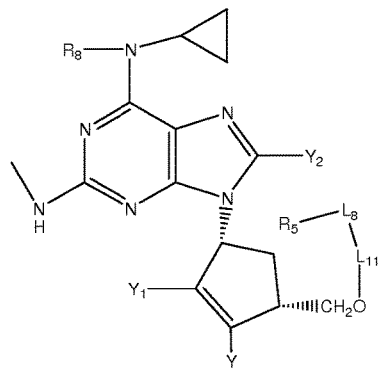
Figure 2:
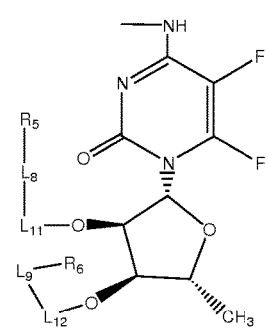
Figure 2:
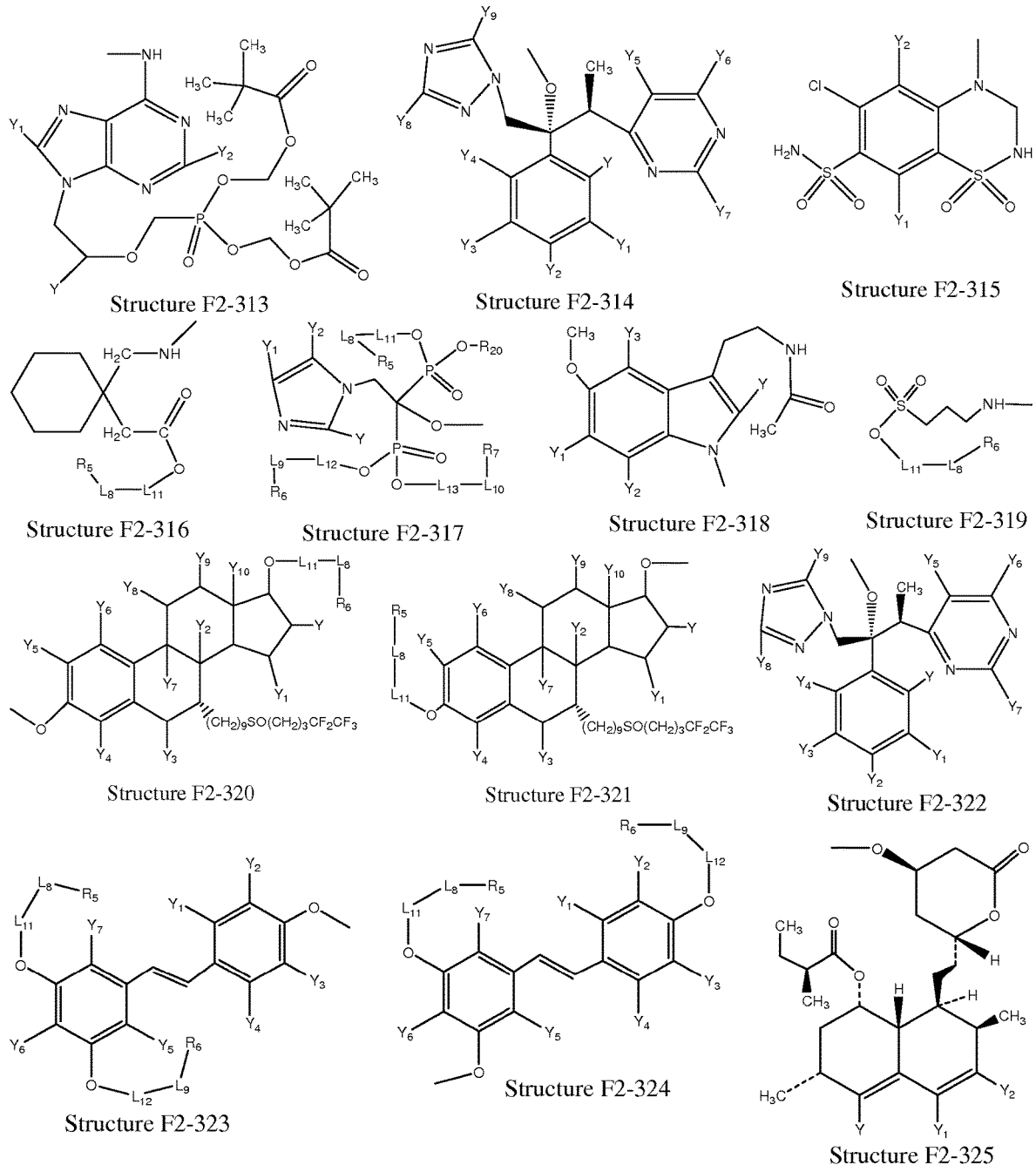
Figure 2:
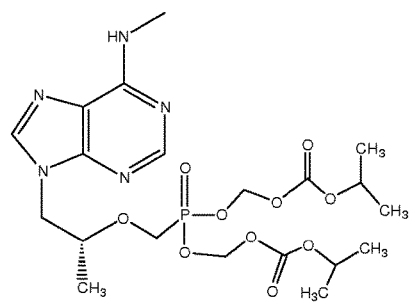
Figure 2:
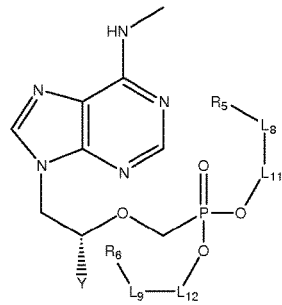
Figure 2:
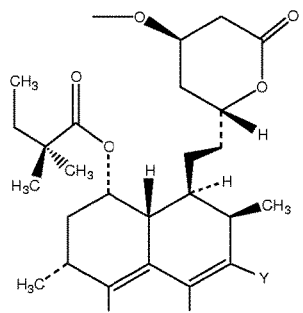
Figure 2:
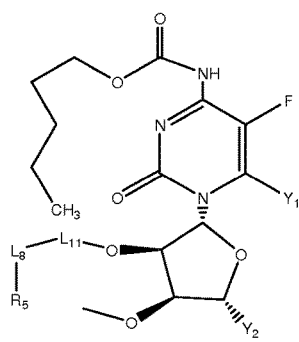
Figure 2:
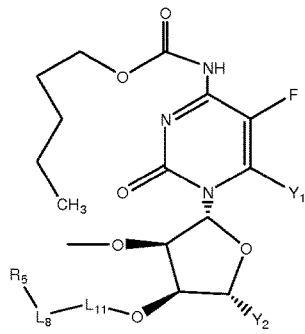
Figure 2:
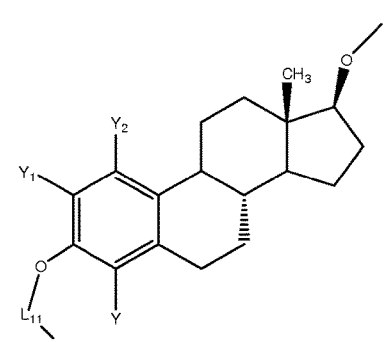
Figure 2:
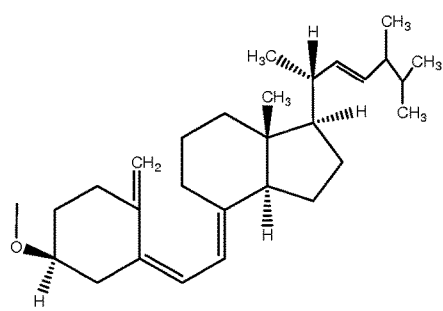
Figure 2:
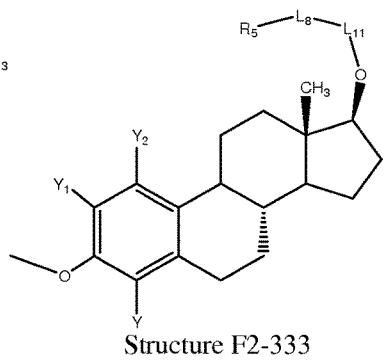
Figure 2:
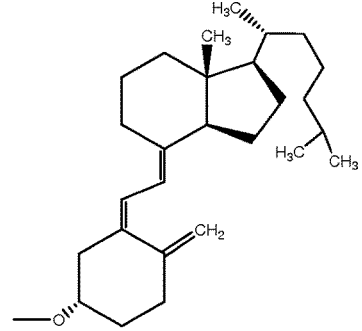
Figure 2:
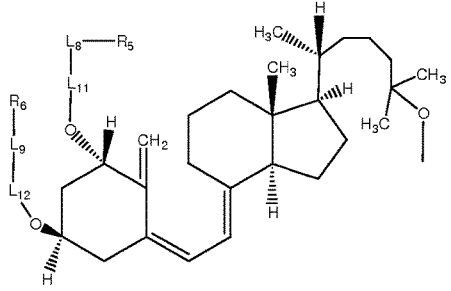
Figure 2:
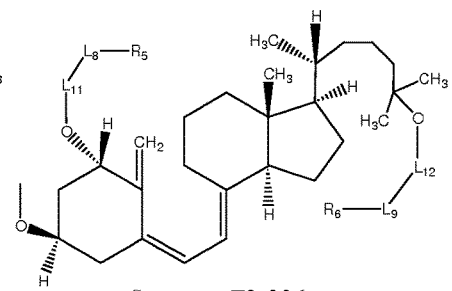
Figure 2:
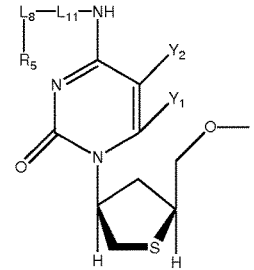
Figure 2:
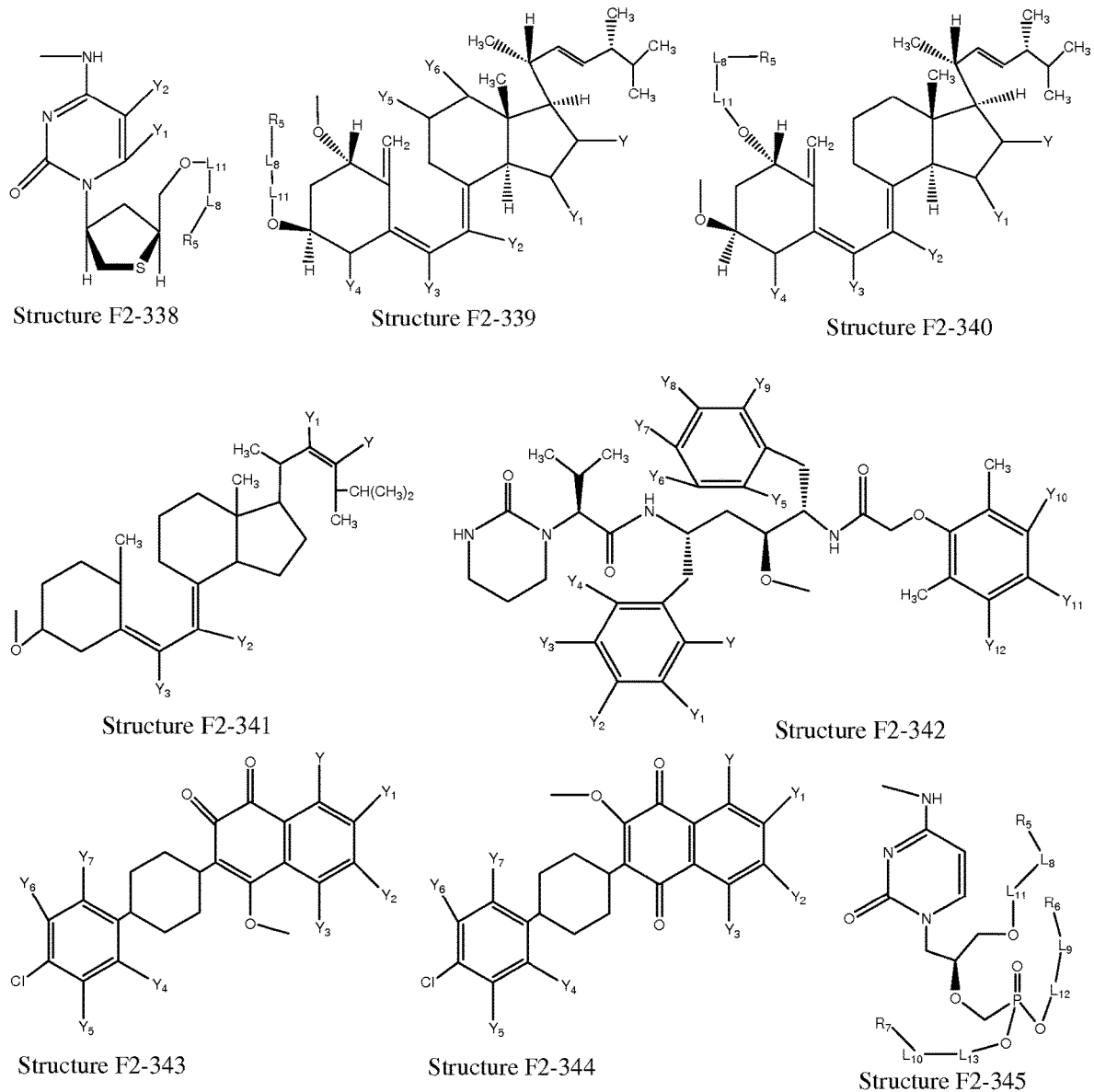
Figure 2:
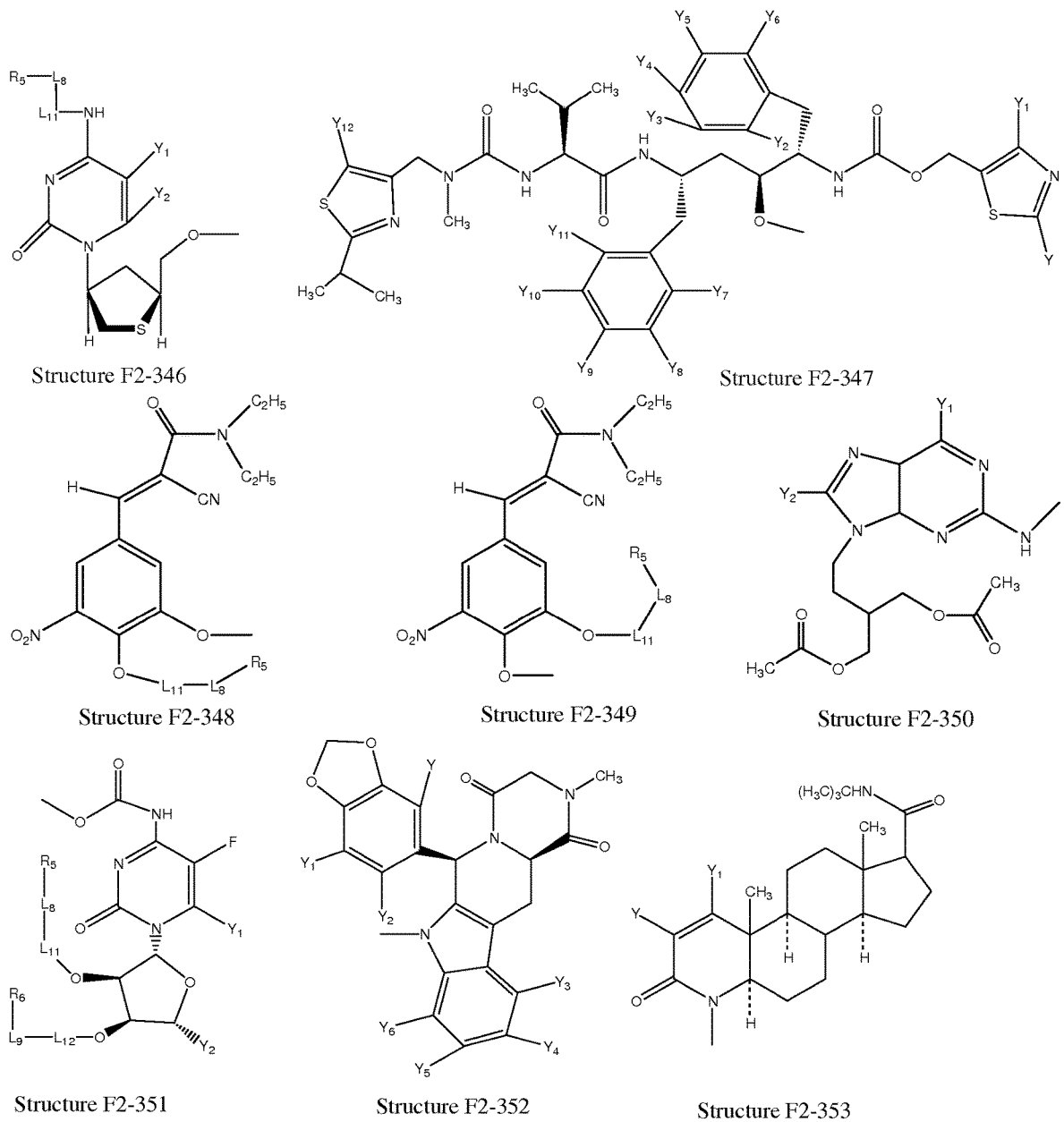
Figure 2:
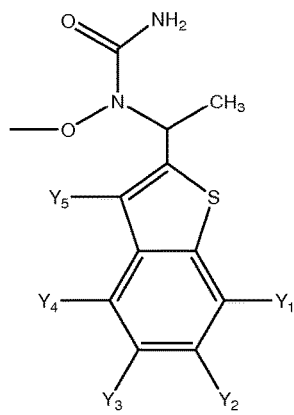
Figure 2:
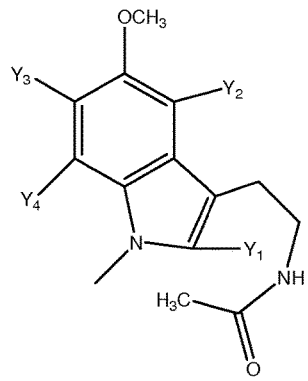
Figure 2:
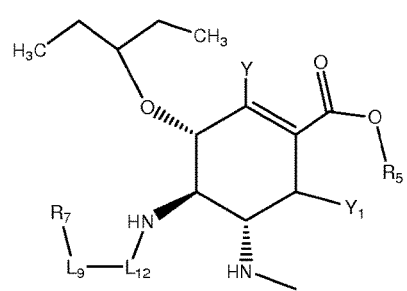
Figure 2:
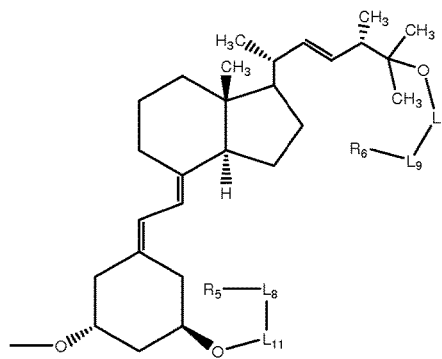
Figure 2:
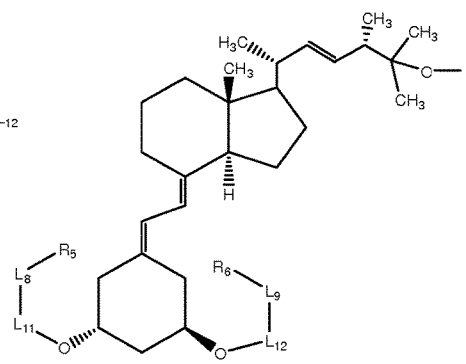
Figure 2:
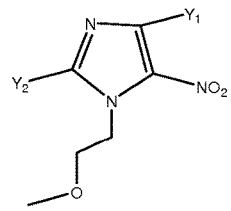
Figure 2:
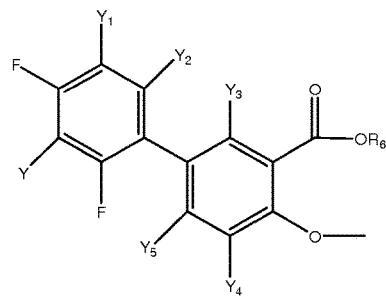
Figure 2:
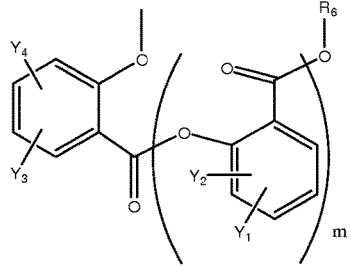
Figure 2:
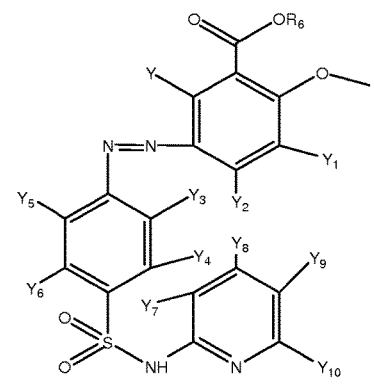
Figure 2:
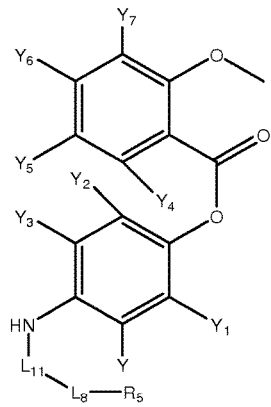
Figure 2:
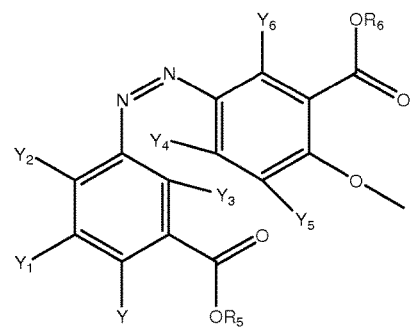
Figure 2:
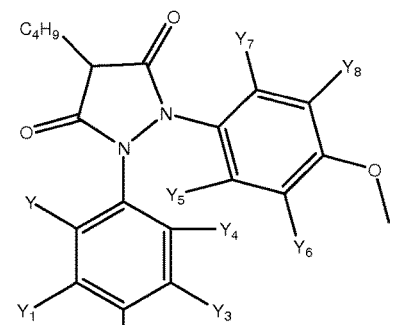
Figure 2:
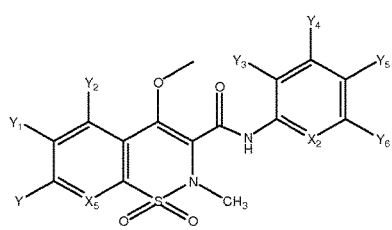
Figure 2:
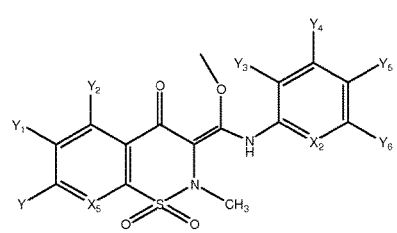
Figure 2:
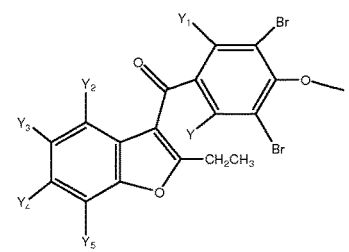
Figure 2:
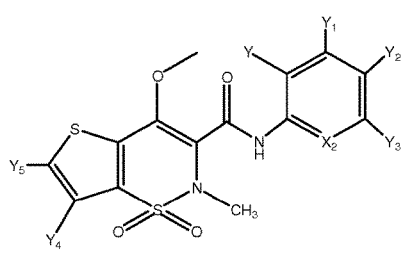
Figure 2:
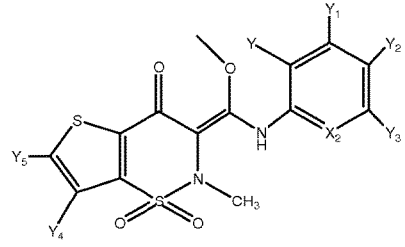
Figure 2:
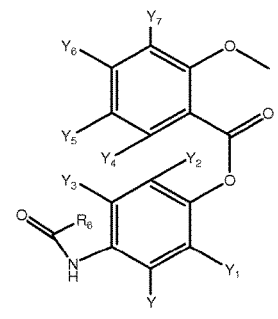
Figure 2:
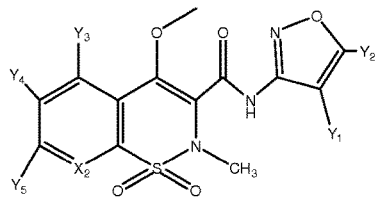
Figure 2:
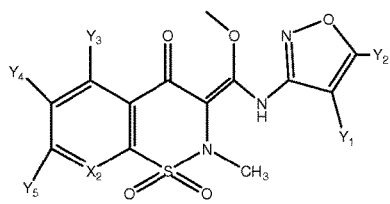
Figure 2:
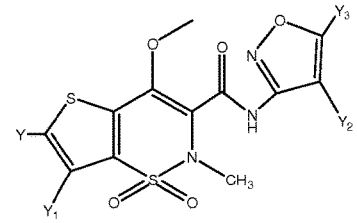
Figure 2:
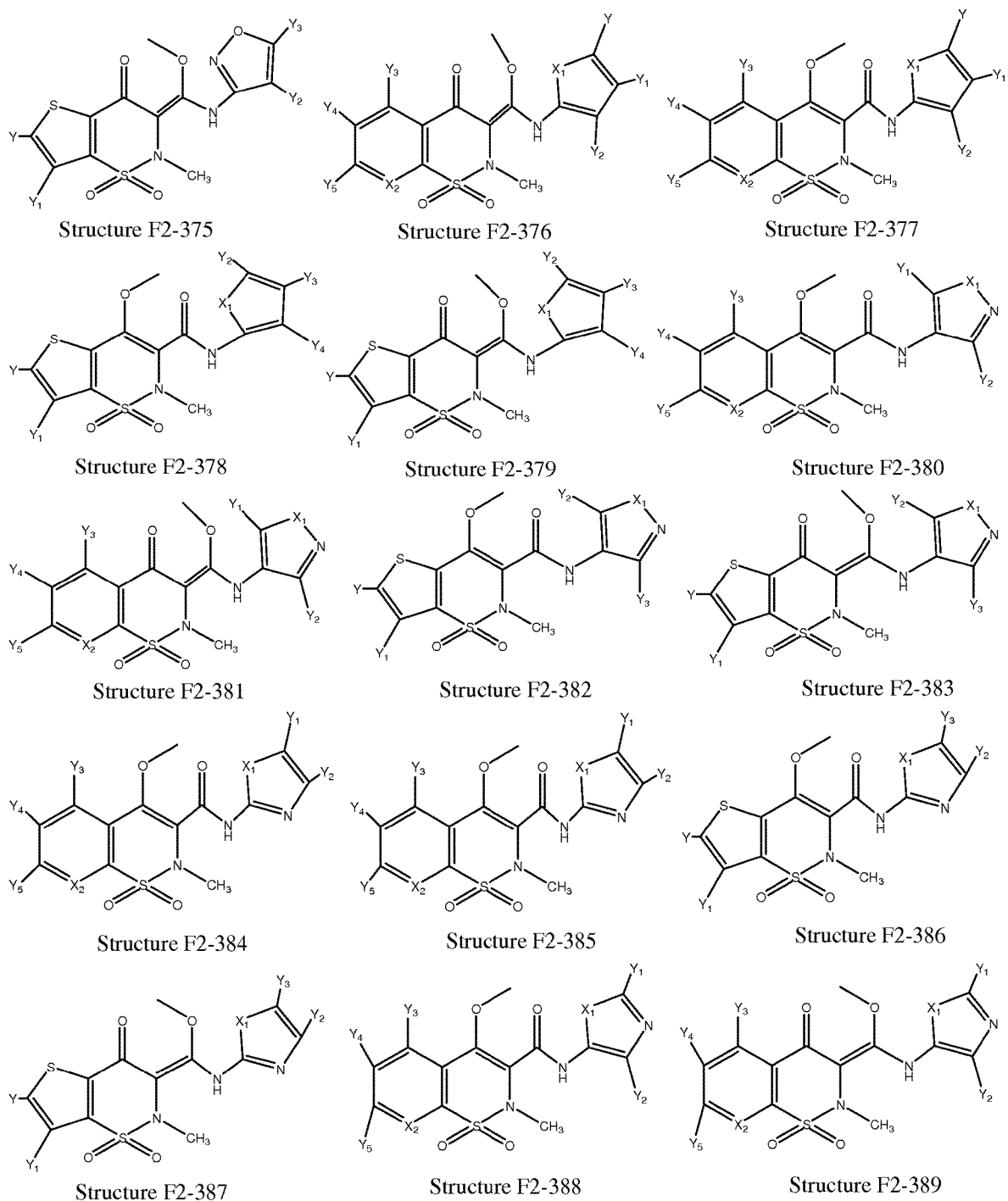
Figure 2:
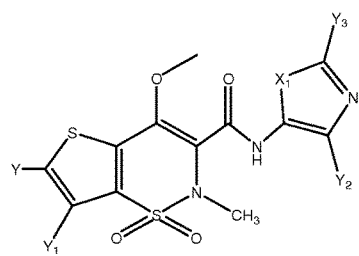
Figure 2:
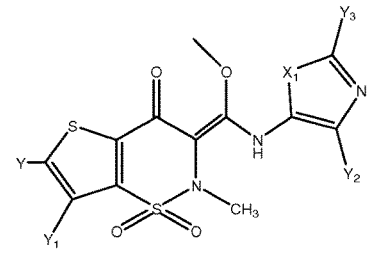
Figure 2:
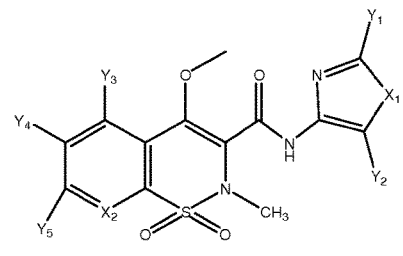
Figure 2:
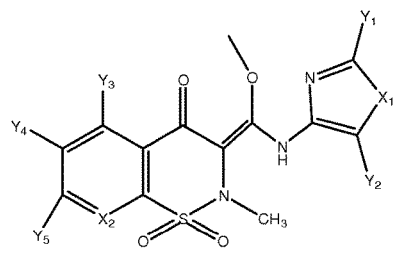
Figure 2:
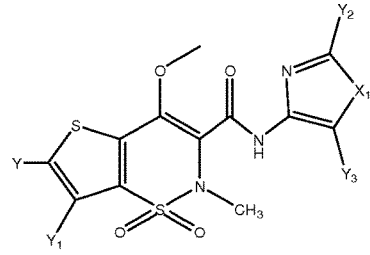
Figure 2:
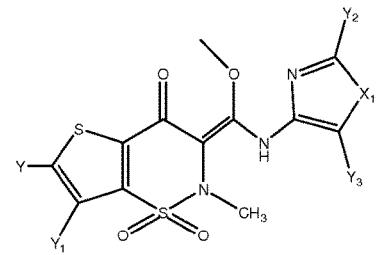
Figure 2:
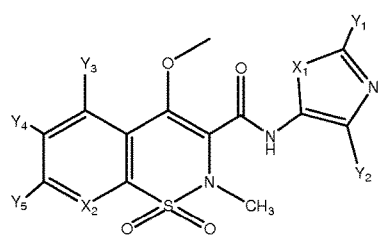
Figure 2:
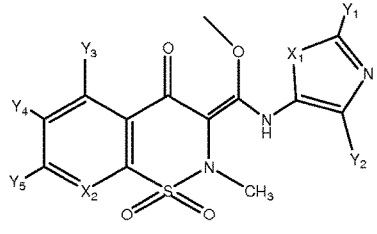
Figure 2:
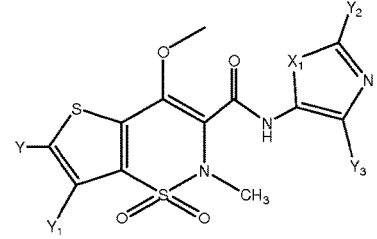
Figure 2:
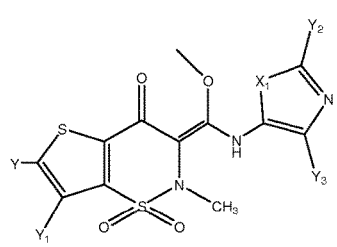
Figure 2:
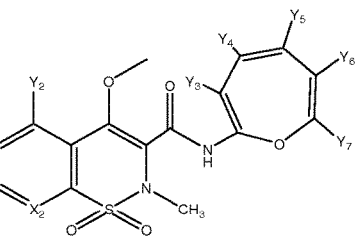
Figure 2:
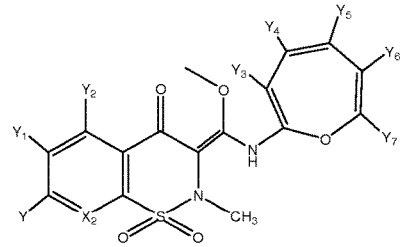
Figure 2:
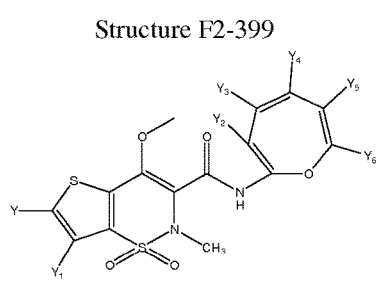
Figure 2:
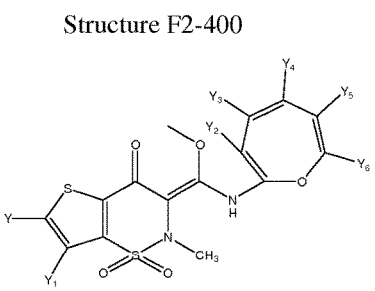
Figure 2:
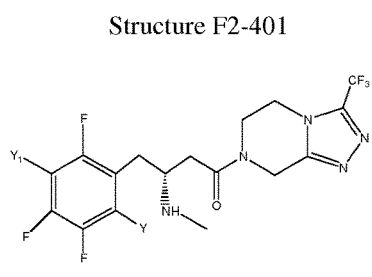
Figure 2:
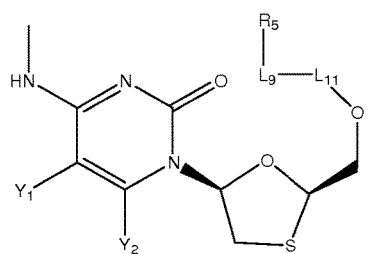
Figure 2:
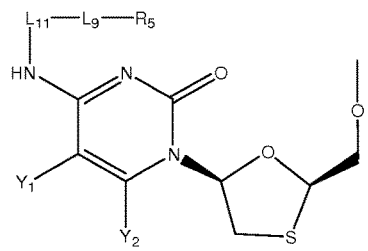
Figure 2:
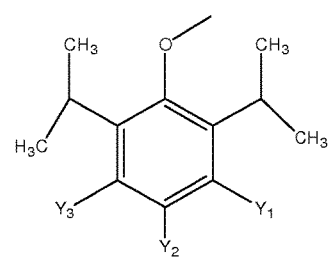
Figure 2:
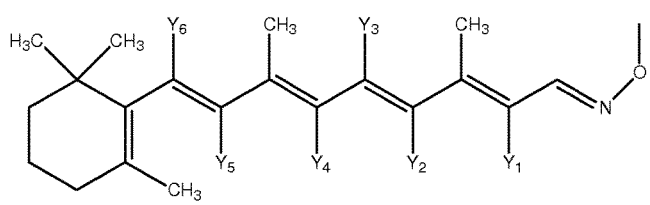
Figure 2:
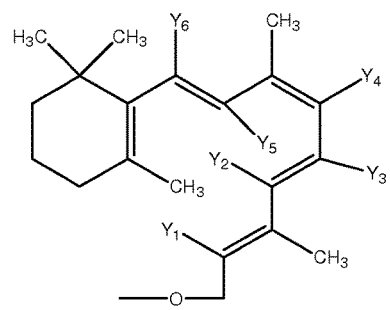
Figure 2:
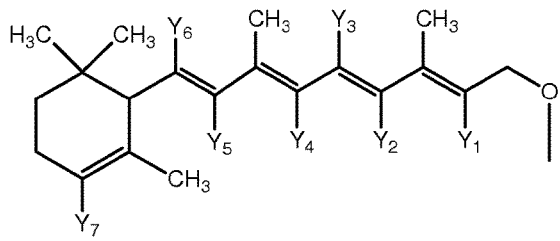
Figure 2:
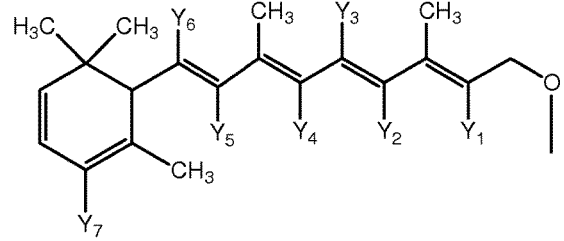
Figure 2:
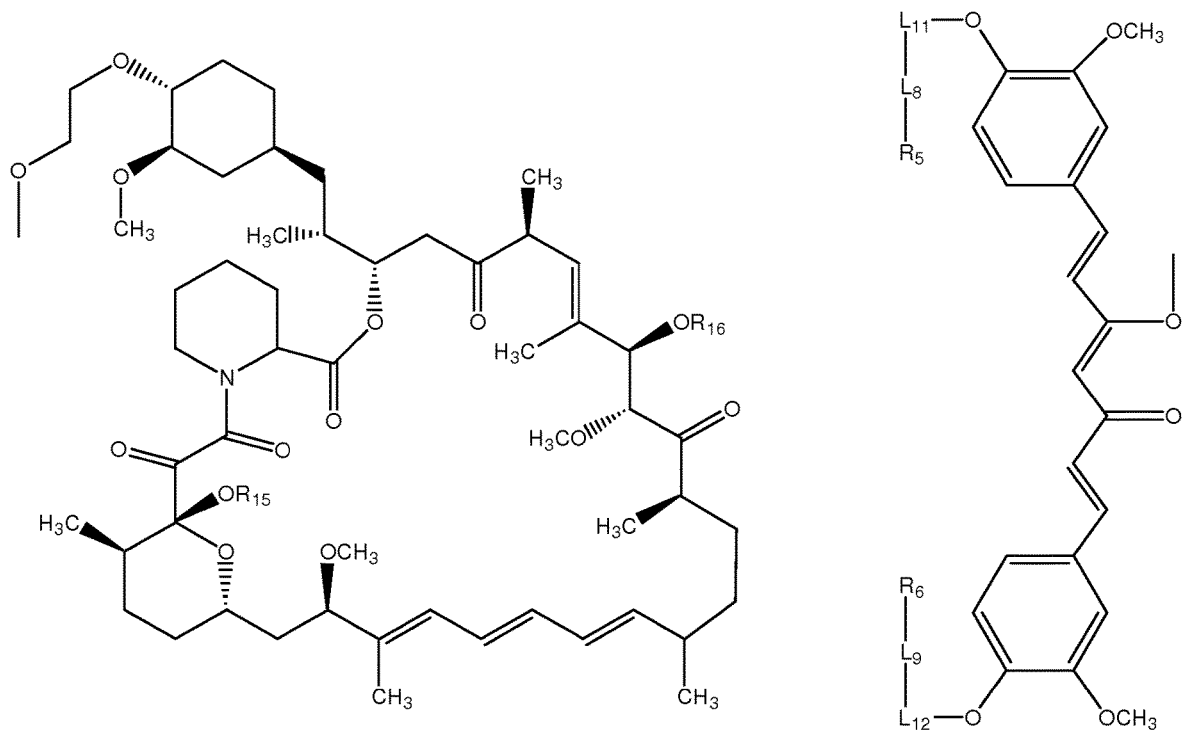
Figure 2:
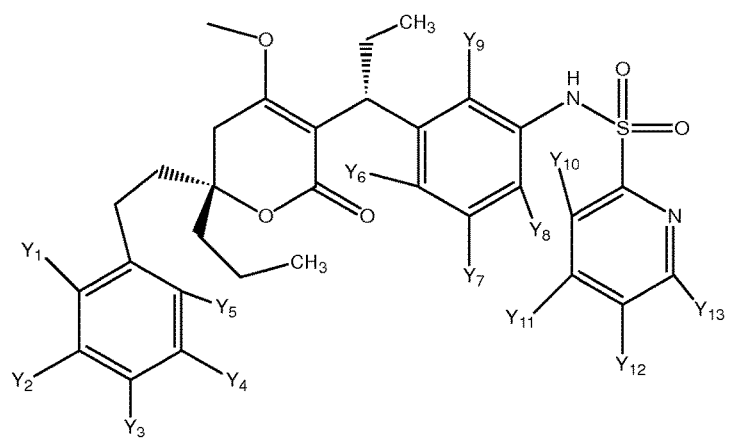
Figure 2:
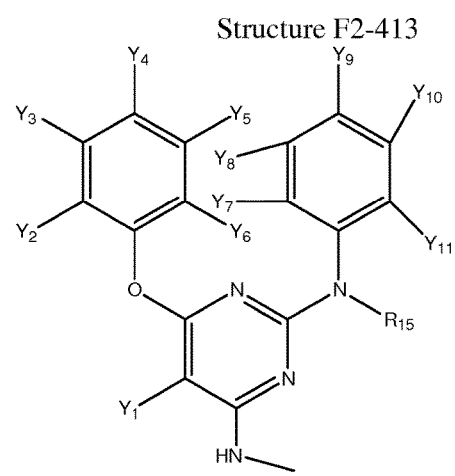
Figure 2:
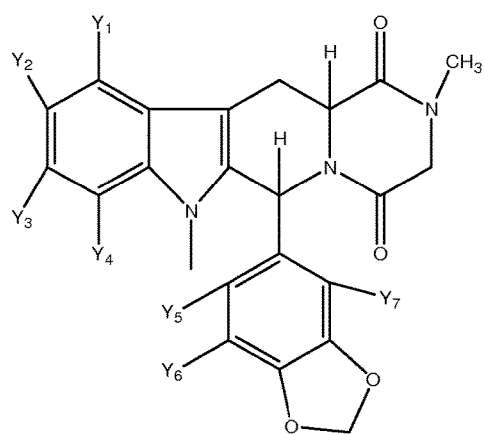
Figure 2:
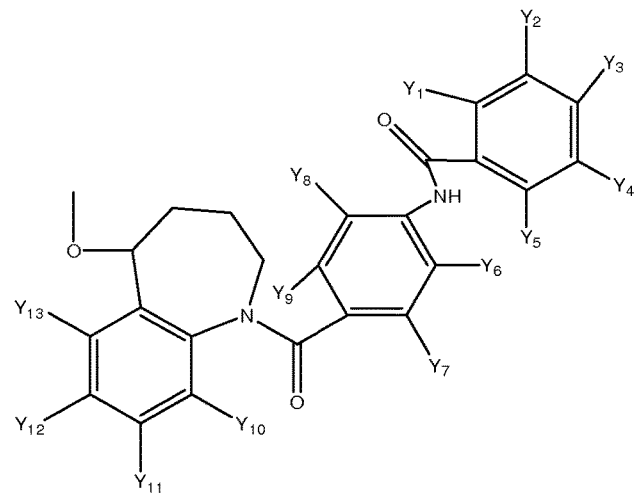
Figure 2:
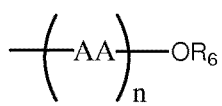
Figure 2:
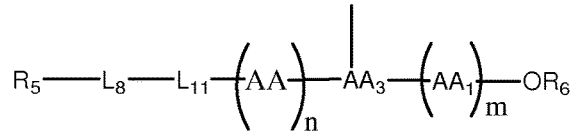
Figure 2:
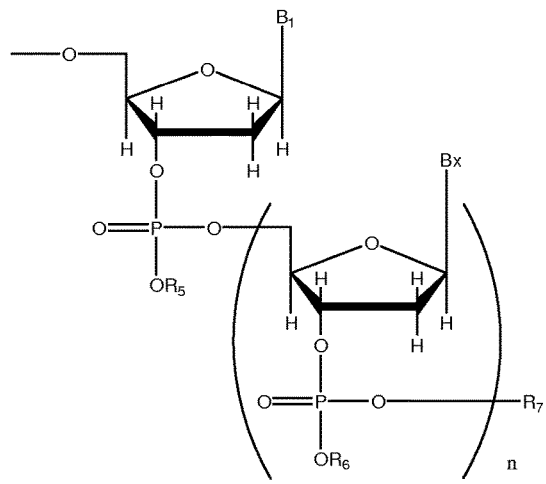
Figure 2:
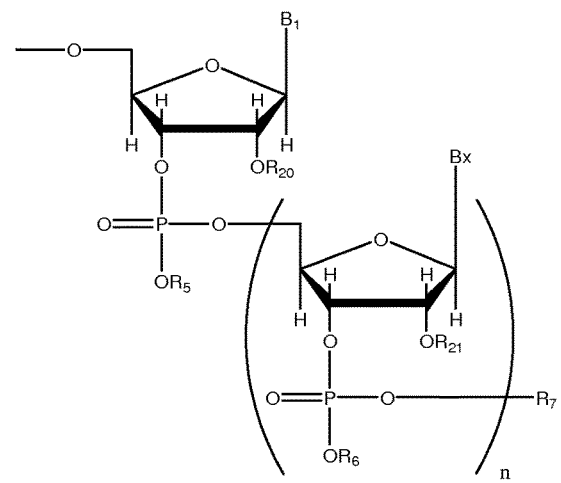
Figure 2:
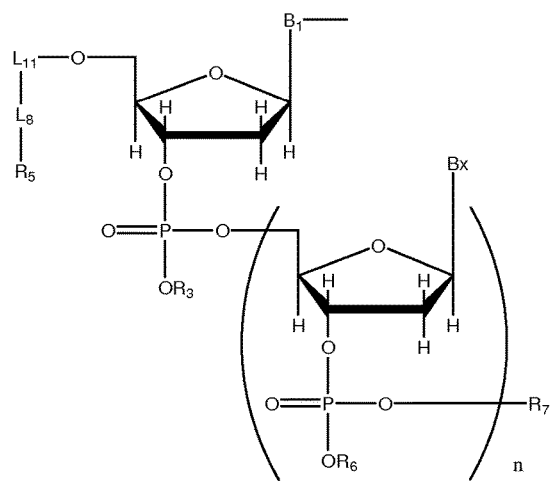
Figure 2:
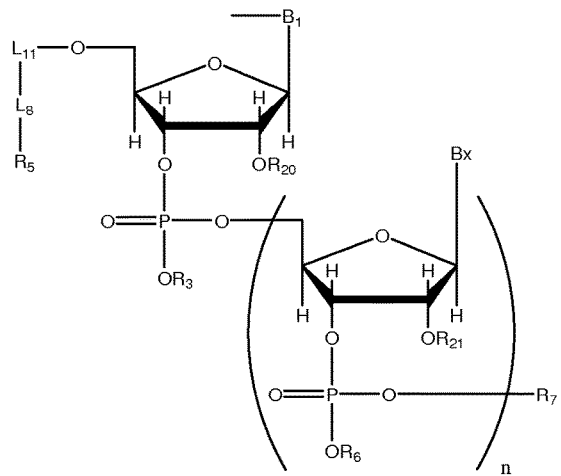
Figure 2:
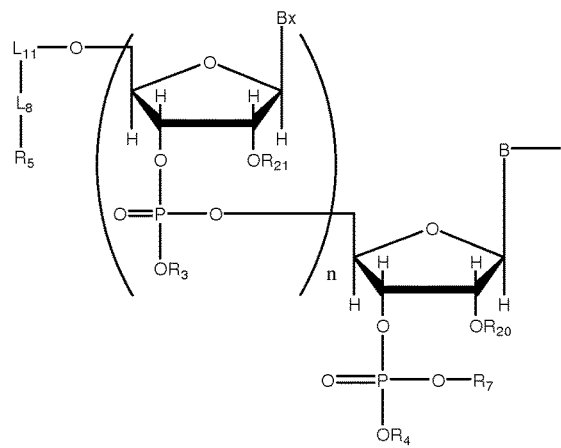
Figure 2:
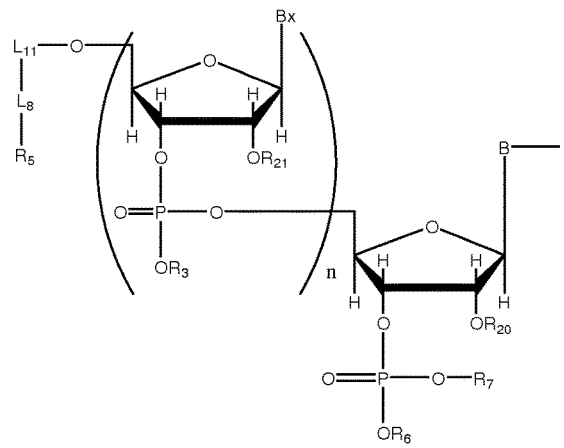
Figure 2:
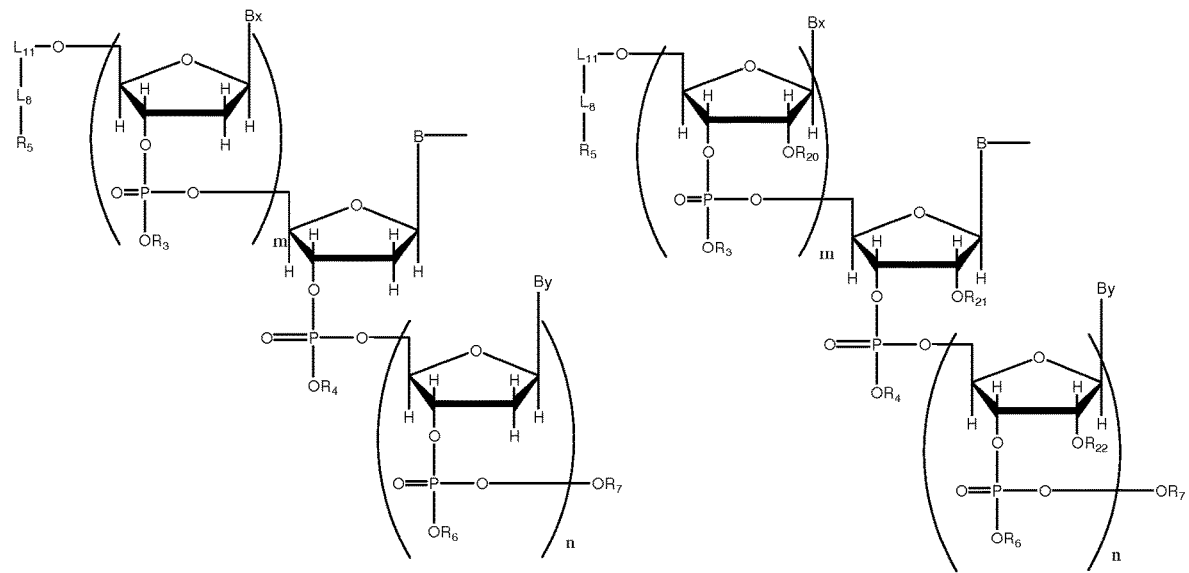
Figure 2:
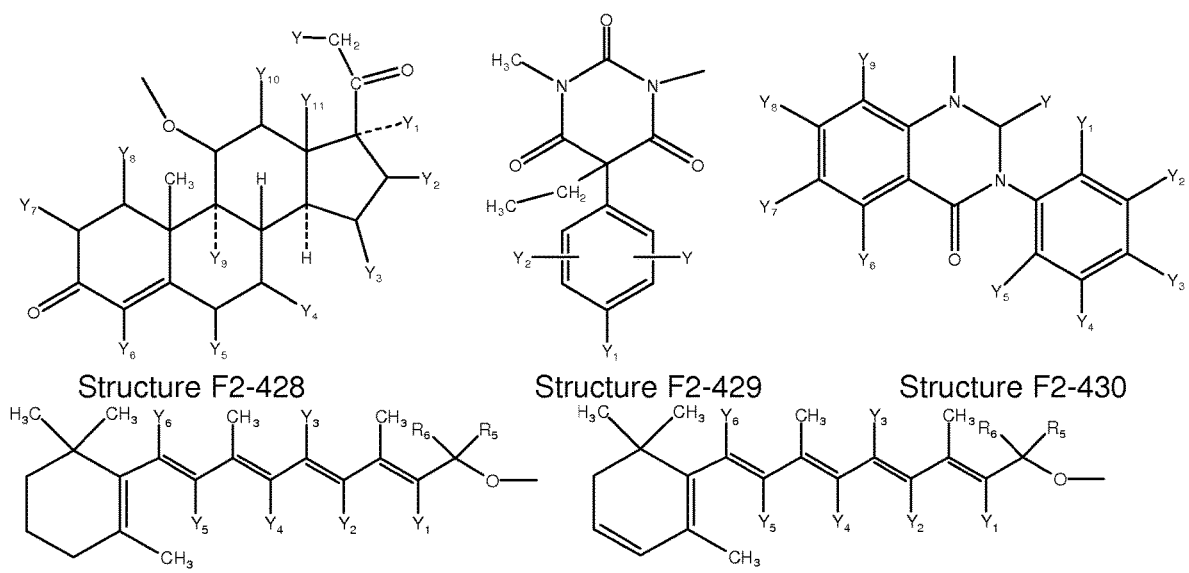
Figure 2:
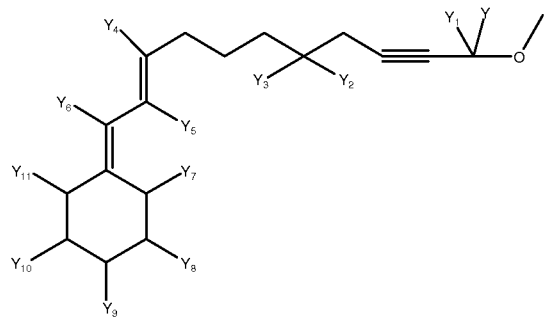
Figure 2:
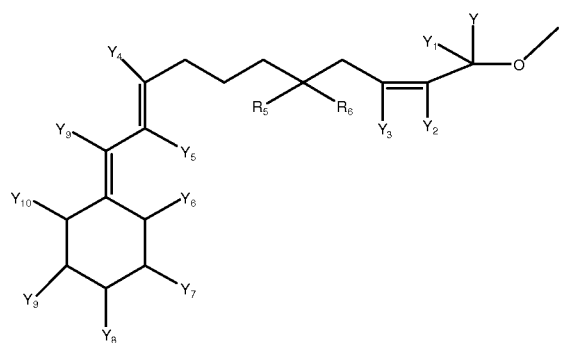
Figure 2:
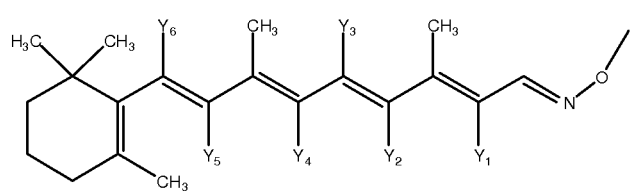
Figure 2:
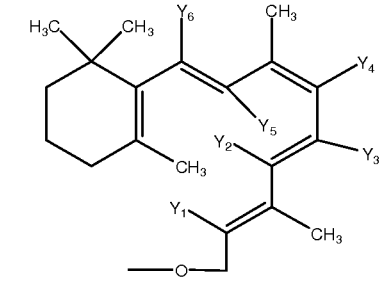
Figure 2:
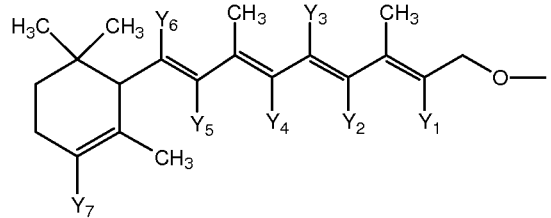
Figure 2:
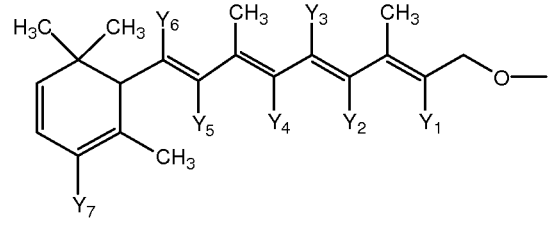
Figure 3A:
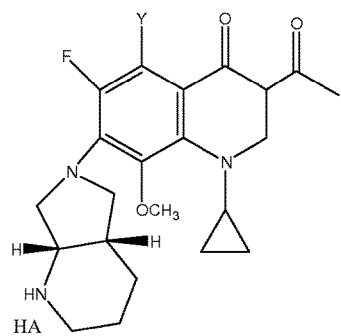
FIG. 3: Exemplary structures of functional unit F3.
Figure 3A:
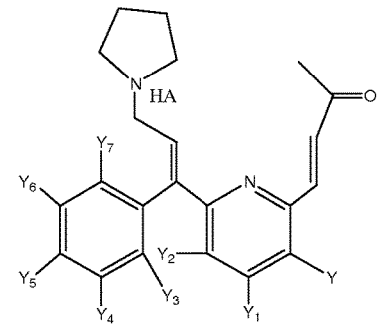
Figure 3A:
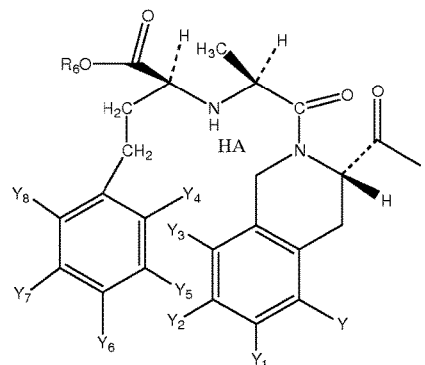
Figure 3A:
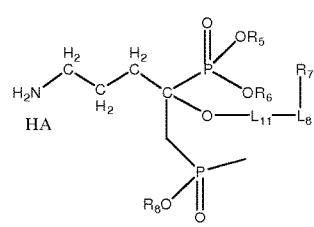
Figure 3A:
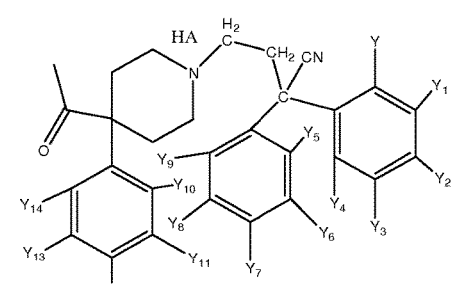
Figure 3A:
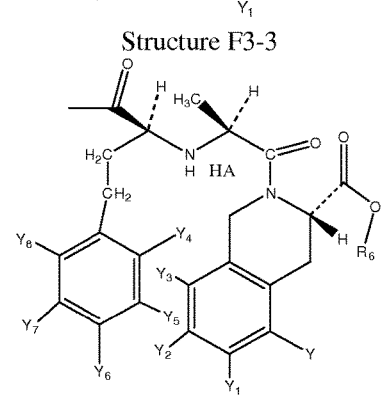
Figure 3A:
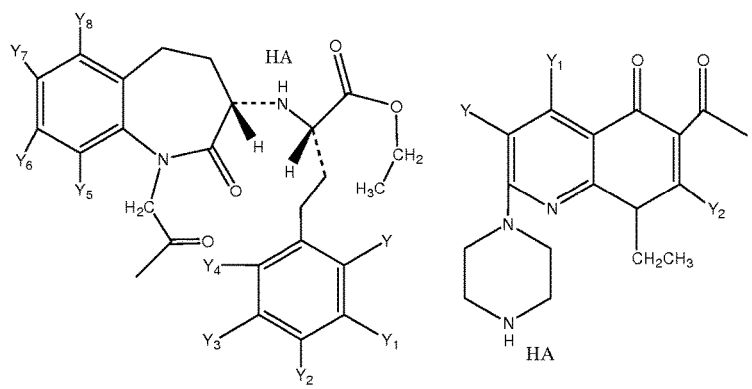
Figure 3A:
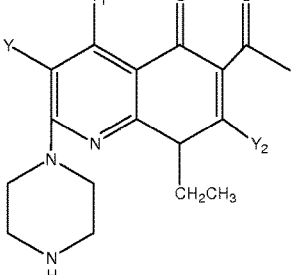
Figure 3A:
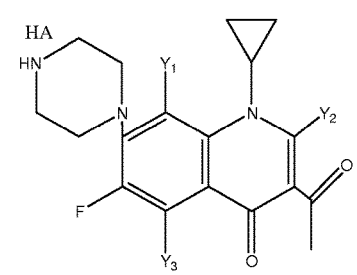
Figure 3B:
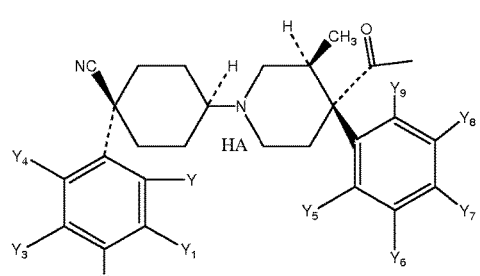
Figure 3B:
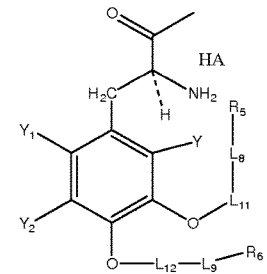
Figure 3B:
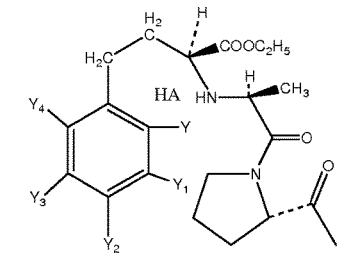
Figure 3B:
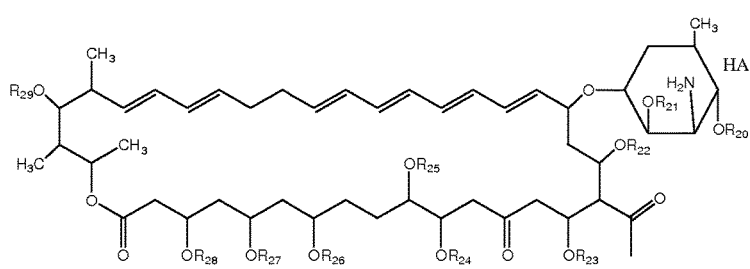
Figure 3B:
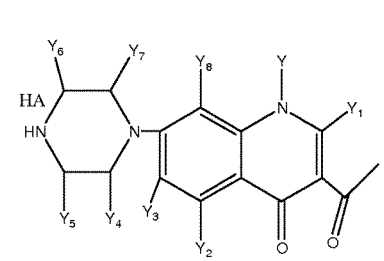
Figure 3B:
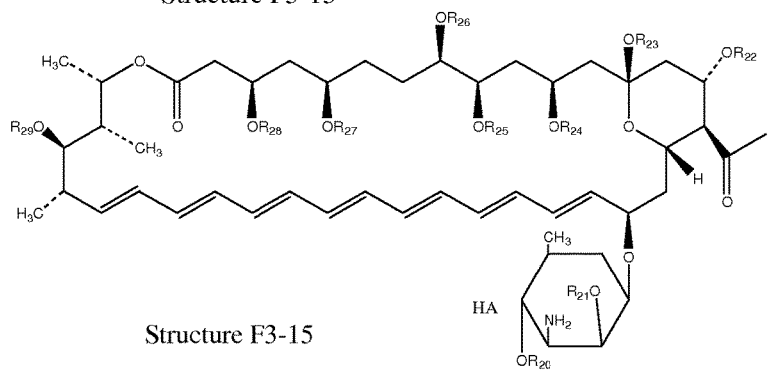
Figure 3B:
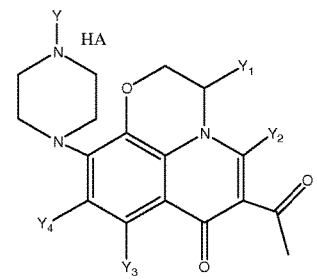
Figure 3B:
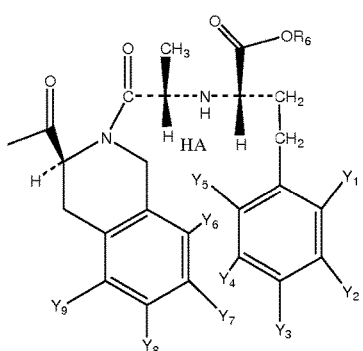
Figure 3B:
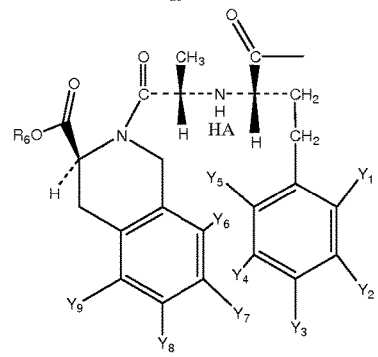
Figure 3B:
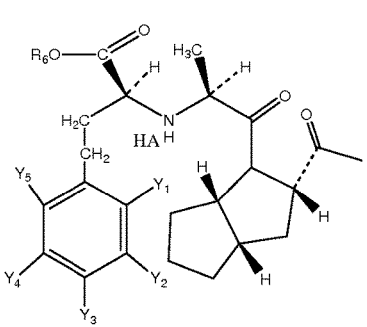
Figure 3C:
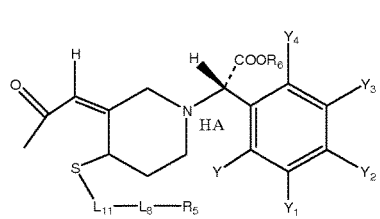
Figure 3C:
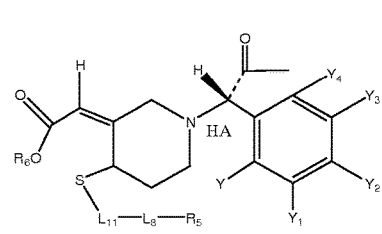
Figure 3C:
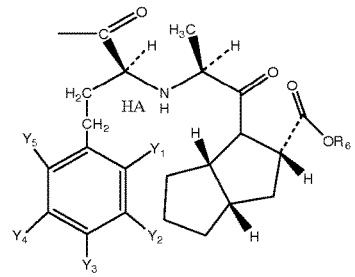
Figure 3C:
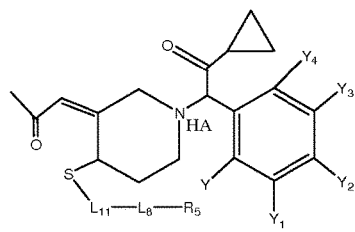
Figure 3C:
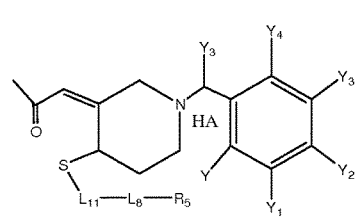
Figure 3C:
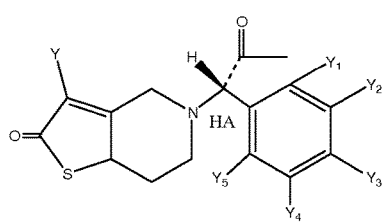
Figure 3C:
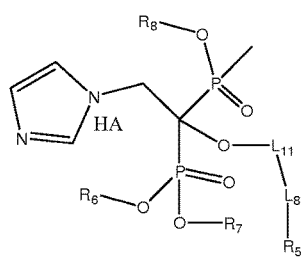
Figure 3C:
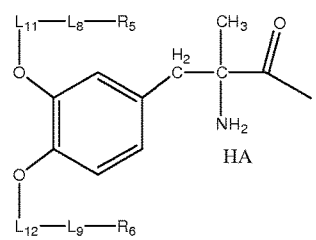
Figure 3C:
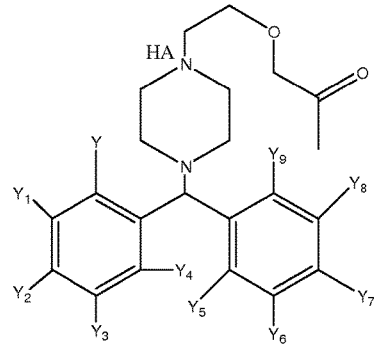
Figure 3C:
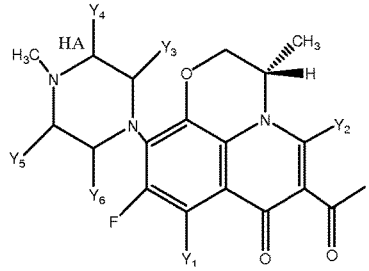
Figure 3C:
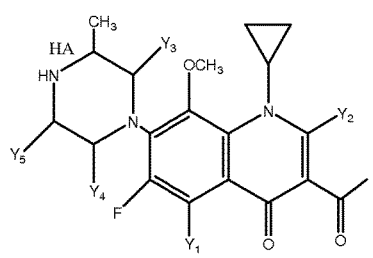
Figure 3C:
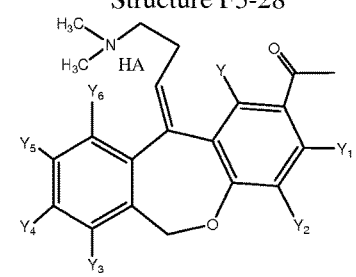
Figure 3D:
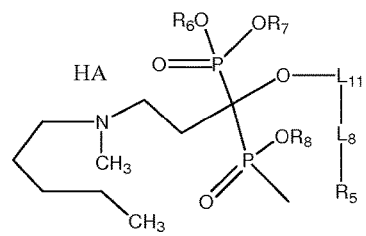
Figure 3D:
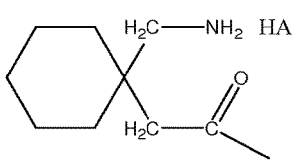
Figure 3D:
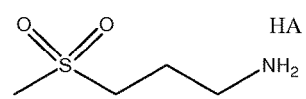
Figure 3D:
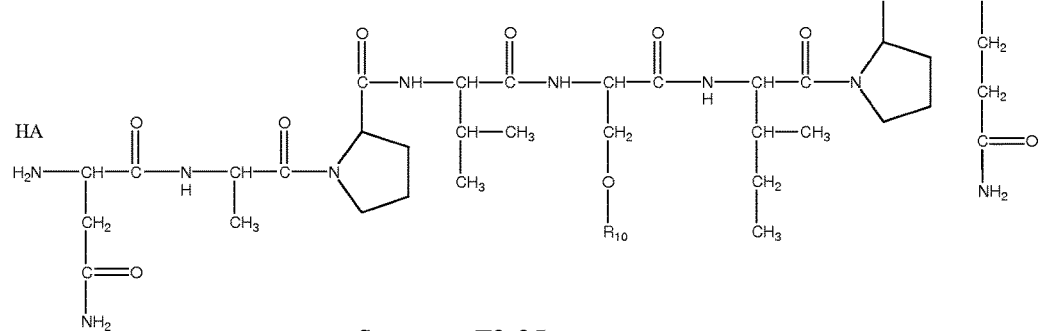
Figure 3D:
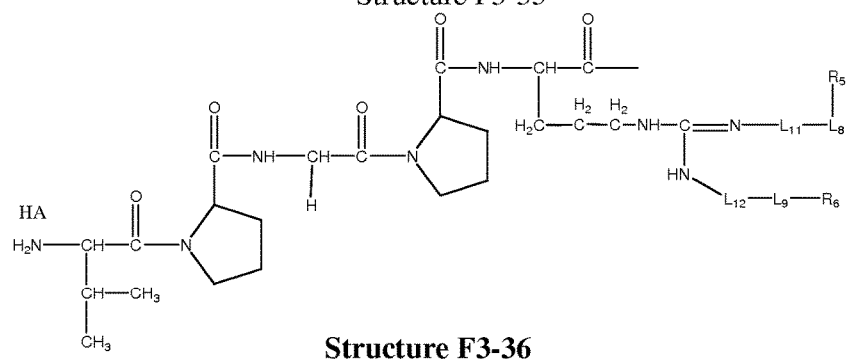
Figure 3D:
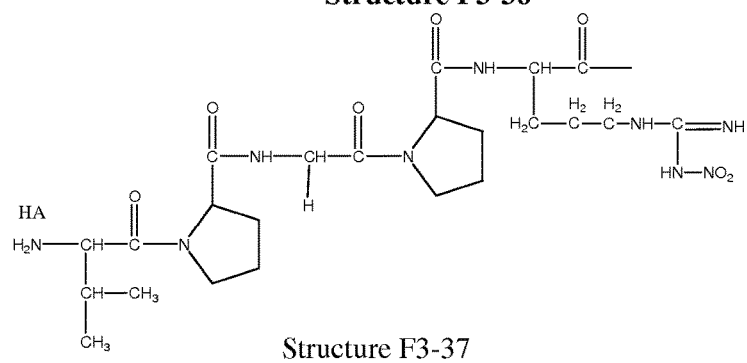
Figure 3E:
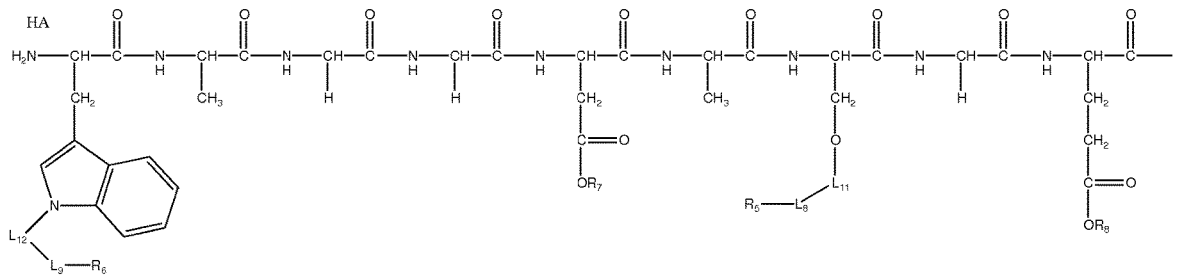
Figure 3E:
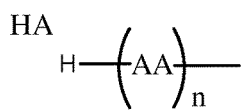
Figure 3E:
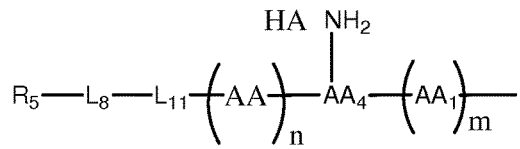
Figure 3E:
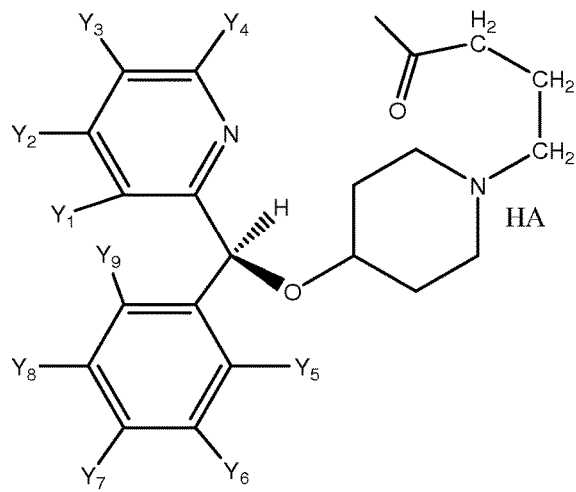
Figure 3E:
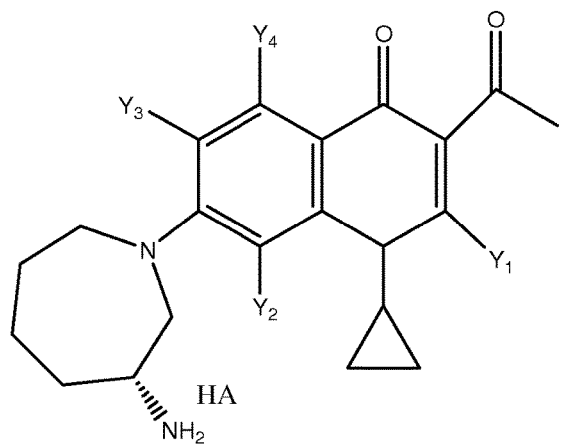
Figure 3F:
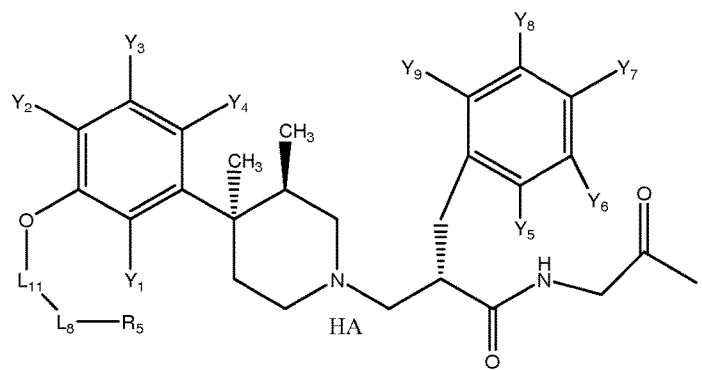
Figure 3F:
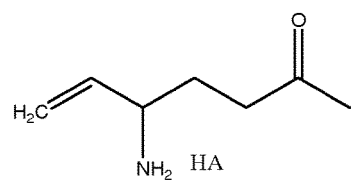

As used herein, the term "F2" or "$F_2$" is a structure selected from the group consisting of Structure F2-1, Structure F2-2, Structure F2-3, Structure F2-4, Structure F2-5, Structure F2-6, Structure F2-7, Structure F2-8, Structure F2-9, Structure F2-10, Structure F2-11, Structure F2-12, Structure F2-13, Structure F2-14, Structure F2-15, Structure F2-16, Structure F2-17, Structure F2-18, Structure F2-19, Structure F2-20, Structure F2-21, Structure F2-22, Structure F2-23, Structure F2-24, Structure F2-25, Structure F2-26, Structure F2-27, Structure F2-28, Structure F2-29, Structure F2-30, Structure F2-31, Structure F2-32, Structure F2-33, Structure F2-34, Structure F2-35, Structure F2-36, Structure F2-37, Structure F2-38, Structure F2-39, Structure F2-40, Structure F2-41, Structure F2-42, Structure F2-43, Structure F2-44, Structure F2-45, Structure F2-46, Structure F2-47, Structure F2-48, Structure F2-49, Structure F2-50, Structure F2-51, Structure F2-52, Structure F2-53, Structure F2-54, Structure F2-55, Structure F2-56, Structure F2-57, Structure F2-58, Structure F2-59, Structure F2-60, Structure F2-61, Structure F2-62, Structure F2-63, Structure F2-64, Structure F2-65, Structure F2-66, Structure F2-67, Structure F2-68, Structure F2-69, Structure F2-70, Structure F2-71, Structure F2-72, Structure F2-73, Structure F2-74, Structure F2-75, Structure F2-76, Structure F2-77, Structure F2-78, Structure F2-79, Structure F2-80, Structure F2-81, Structure F2-82, Structure F2-83, Structure F2-84, Structure F2-85, Structure F2-86, Structure F2-87, Structure F2-88, Structure F2-89, Structure F2-90, Structure F2-91, Structure F2-92, Structure F2-93, Structure F2-94, Structure F2-95, Structure F2-96, Structure F2-97, Structure F2-98, Structure F2-99, Structure F2-100, Structure F2-101, Structure F2-102, Structure F2-103, Structure F2-104, Structure F2-105, Structure F2-106, Structure F2-107, Structure F2-108, Structure F2-109, Structure F2-110, Structure F2-111, Structure F2-112, Structure F2-113, Structure F2-114, Structure F2-115, Structure F2-116, Structure F2-117, Structure F2-118, Structure F2-119, Structure F2-120, Structure F2-121, Structure F2-122, Structure F2-123, Structure F2-124, Structure F2-125, Structure F2-126, Structure F2-127, Structure F2-128, Structure F2-129, Structure F2-130, Structure F2-131, Structure F2-132, Structure F2-133, Structure F2-134, Structure F2-135, Structure F2-136, Structure F2-137, Structure F2-138, Structure F2-139, Structure F2-140, Structure F2-141, Structure F2-142, Structure F2-143, Structure F2-144, Structure F2-145, Structure F2-146, Structure F2-147, Structure F2-148, Structure F2-149, Structure F2-150, Structure F2-151, Structure F2-152, Structure F2-153, Structure F2-154, Structure F2-155, Structure F2-156, Structure F2-157, Structure F2-158, Structure F2-159, Structure F2-160, Structure F2-161, Structure F2-162, Structure F2-163, Structure F2-164, Structure F2-165, Structure F2-166, Structure F2-167, Structure F2-168, Structure F2-169, Structure F2-170, Structure F2-171, Structure F2-172, Structure F2-173, Structure F2-174, Structure F2-175, Structure F2-176, Structure F2-177, Structure F2-178, Structure F2-179, Structure F2-180, Structure F2-181, Structure F2-182, Structure F2-183, Structure F2-184, Structure F2-185, Structure F2-186, Structure F2-187, Structure F2-188, Structure F2-189, Structure F2-190, Structure F2-191, Structure F2-192, Structure F2-193, Structure F2-194, Structure F2-195, Structure F2-196, Structure F2-197, Structure F2-198, Structure F2-199, Structure F2-200, Structure F2-201, Structure F2-202, Structure F2-203, Structure F2-204, Structure F2-205, Structure F2-206, Structure F2-207, Structure F2-208, Structure F2-209, Structure F2-210, Structure F2-211, Structure F2-212, Structure F2-213, Structure F2-214, Structure F2-215, Structure F2-216, Structure F2-217, Structure F2-218, Structure F2-219, Structure F2-220, Structure F2-221, Structure F2-222, Structure F2-223, Structure F2-224, Structure F2-225, Structure F2-226, Structure F2-227, Structure F2-228, Structure F2-229, Structure F2-230, Structure F2-231, Structure F2-232, Structure F2-233, Structure F2-234, Structure F2-235, Structure F2-236, Structure F2-237, Structure F2-238, Structure F2-239, Structure F2-240, Structure F2-241, Structure F2-242, Structure F2-243, Structure F2-244, Structure F2-245, Structure F2-246, Structure F2-247, Structure F2-248, Structure F2-249, Structure F2-250, Structure F2-251, Structure F2-252, Structure F2-253, Structure F2-254, Structure F2-255, Structure F2-256, Structure F2-257, Structure F2-258, Structure F2-259, Structure F2-260, Structure F2-261, Structure F2-262, Structure F2-263, Structure F2-264, Structure F2-265, Structure F2-266, Structure F2-267, Structure F2-268, Structure F2-269, Structure F2-270, Structure F2-271, Structure F2-272, Structure F2-273, Structure F2-274, Structure F2-275, Structure F2-276, Structure F2-277, Structure F2-278, Structure F2-279, Structure F2-280, Structure F2-281, Structure F2-282, Structure F2-283, Structure F2-284, Structure F2-285, Structure F2-286, Structure F2-287, Structure F2-288, Structure F2-289, Structure F2-290, Structure F2-291, Structure F2-292, Structure F2-293, Structure F2-294, Structure F2-295, Structure F2-296, Structure F2-297, Structure F2-298, Structure F2-299, Structure F2-300, Structure F2-301, Structure F2-302, Structure F2-303, Structure F2-304, Structure F2-305, Structure F2-306, Structure F2-307, Structure F2-308, Structure F2-309, Structure F2-310, Structure F2-311, Structure F2-312, Structure F2-313, Structure F2-314, Structure F2-315, Structure F2-316, Structure F2-317, Structure F2-318, Structure F2-319, Structure F2-320, Structure F2-321, Structure F2-322, Structure F2-323, Structure F2-324, Structure F2-325, Structure F2-326, Structure F2-327, Structure F2-328, Structure F2-329, Structure F2-330, Structure F2-331, Structure F2-332, Structure F2-333, Structure F2-334, Structure F2-335, Structure F2-336, Structure F2-337, Structure F2-338, Structure F2-339, Structure F2-340, Structure F2-341, Structure F2-342, Structure F2-343, Structure F2-344, Structure F2-345, Structure F2-346, Structure F2-347, Structure F2-348, Structure F2-349, Structure F2-350, Structure F2-351, Structure F2-352, Structure F2-353, Structure F2-354, Structure F2-355, Structure F2-356, Structure F2-357, Structure F2-358, Structure F2-359, Structure F2-360, Structure F2-361, Structure F2-362, Structure F2-363, Structure F2-364, Structure F2-365, Structure F2-366, Structure F2-367, Structure F2-368, Structure F2-369, Structure F2-370, Structure F2-371, Structure F2-372, Structure F2-373, Structure F2-374, Structure F2-375, Structure F2-376, Structure F2-377, Structure F2-378, Structure F2-379, Structure F2-380, Structure F2-381, Structure F2-382, Structure F2-383, Structure F2-384, Structure F2-385, Structure F2-386, Structure F2-387, Structure F2-388, Structure F2-389, Structure F2-390, Structure F2-391, Structure F2-392, Structure F2-393, Structure F2-394, Structure F2-395, Structure F2-396, Structure F2-397, Structure F2-398, Structure F2-399, Structure F2-400, Structure F2-401, Structure F2-402, Structure F2-403, Structure F2-404, Structure F2-405, Structure F2-406, Structure F2-407, Structure F2-408, Structure F2-409, Structure F2-410, Structure F2-411, Structure F2-412, Structure F2-413, Structure F2-414, Structure F2-415, Structure F2-416, Structure F2-417, Structure F2-418, Structure F2-419, Structure F2-420, Structure F2-421, Structure F2-422, Structure F2-423, Structure F2-424, Structure F2-425, Structure F2-426, Structure F2-427, F2-428, Structure F2-429, Structure F2-430, Structure F2-431, Structure F2-432, Structure F2-433, Structure F2-434, Structure F2-435, Structure F2-436, Structure F2-437, and Structure F2-438 (FIG. 2), Including stereoisomers and salts thereof.

In certain embodiments, a parent drug of a HPC comprises both an amino group, and further comprises a carboxylic or phosphate/phosphonate group. Examples of a parent drug of a HPC comprising both amino group and carboxyl/phosphate/phosphonate group include, without limitation, Moxifloxacin, Acrivastine, Moexipril, (4-Amino-1-hydroxy-butylidene)bisphosphonic acid, Benzepril [3-[[1-(ethoxy-carbonyl)-3-phenyl-(1S)-propyl]amino]-2,3,4,5-tetrahydro-2-oxo-1H-1-(3S)-benzazepine-1-acetic acid], Enoxacin, Ciprofloxacin [1-cyclopropyl-6-fluoro-1,4-dihydro-4-oxo-7-(1-piperazinyl)-3-quinoline-carboxylic acid], Levocabastine, Levodopa, Enalapril [(S)-1-[N-(1-carboxy-3-phenylpropyl)-L-alanyl]-L-proline], Nystatin, Lomefloxacin, Norfloxacin, Amphotericin B, Ofloxacin, Quinapril, Ramipril, (2-{1-[2-(chlorophenyl)-2-methoxy-2-oxoethyl]-4-sulfanyl-3-piperidinylidene}-acetic acid}, R-138727, 2-Oxo-clopidogrel, Zoledronic acid, Methyldopa, levocetirizine (Xyzal), Cetirizine (Zyrtec), Levofloxacin, Gatifloxacin, Olopatadine, Ibandronate (Boniva), Gabapentin, 3-aminopropane-1-sulfonic acid, peptides, amino acids, H-Asn-Ala-Pro-Val-Ser-Ile-Pro-Gln-OH, H-Val-Pro-Gly-Pro-Arg-OH, H-Val-Pro-Gly-Pro-Arg(NO2)-OH, H-Trp-Ala-Gly-Gly-Asp(OBz)-Ala-Ser(Ac)-Gly-Glu(OEt)-OH, Bepreve (bepotastine besilate), Besivance (besifloxacin), Entereg {alvimopan, [[2(S)-[[4(R)-(3-hydroxyphenyl)-3(R),4-dimethyl-1-piperidinyl]methyl]-1-oxo-3-phenylpropyl]amino]acetic acid dehydrate, and Sabril (vigabatrin).

In certain embodiments, a parent drug of a HPC comprises following Structure P-F3:

$$F3\text{-}OH \qquad \text{(Structure P-F3)}$$

including stereoisomers and salts thereof.

As used herein, the term "F3" or "F$_3$" is a structure selected from the group consisting of Structure F3-1, Structure F3-2, Structure F3-3, Structure F3-4, Structure F3-5, Structure F3-6, Structure F3-7, Structure F3-8, Structure F3-9, Structure F3-10, Structure F3-11, Structure F3-12, Structure F3-13, Structure F3-14, Structure F3-15, Structure F3-16, Structure F3-17, Structure F3-18, Structure F3-19, Structure F3-20, Structure F3-21, Structure F3-22, Structure F3-23, Structure F3-24, Structure F3-25, Structure F3-26, Structure F3-27, Structure F3-28, Structure F3-29, Structure F3-30, Structure F3-31, Structure F3-32, Structure F3-33, Structure F3-34, Structure F3-35, Structure F3-36, Structure F3-37, Structure F3-38, Structure F3-39, Structure F3-40, Structure F3-41, Structure F3-42, Structure F3-43, and Structure F3-44 (FIG. 3), including stereoisomers and salts thereof.

In certain embodiments, a parent drug of a HPC comprises a carbonyl group. Example of a parent drug comprising a carbonyl group include, without limitation, Vitamin A aldehyde, Androstenedione, Progesterone, 1-Methylandrosta-1,4-diene-3,17-dione, 106-Propynylest-4-ene-3,17-dione, 6-Methyleneandrost-4-ene-3,17-dione, 7a-Aminophenylthioandrost-4-ene-3,17-dione, and 7a-Aminophenylthioandrost-1,4-diene-3,17-dione.

In certain embodiments, a parent drug of a HPC having the following Structure P-F4:

$$F4\text{=}O \qquad \text{(Structure P-F4)}$$

including stereoisomers and salts thereof.

Figure 4:
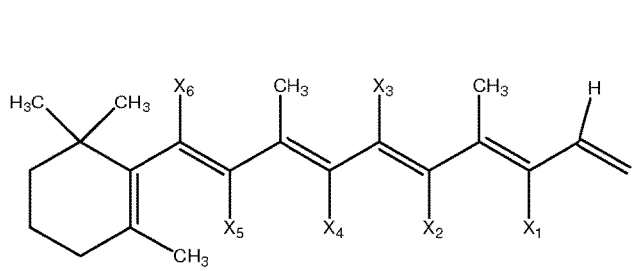
FIG. 4: Exemplary structures of functional unit F4.
Figure 4:
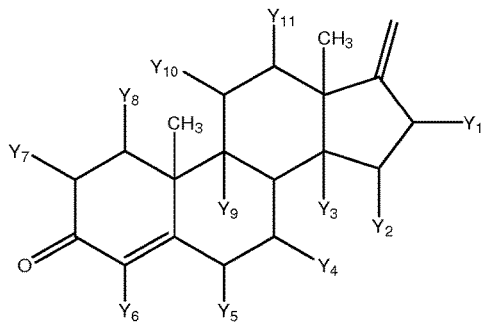
Figure 4:
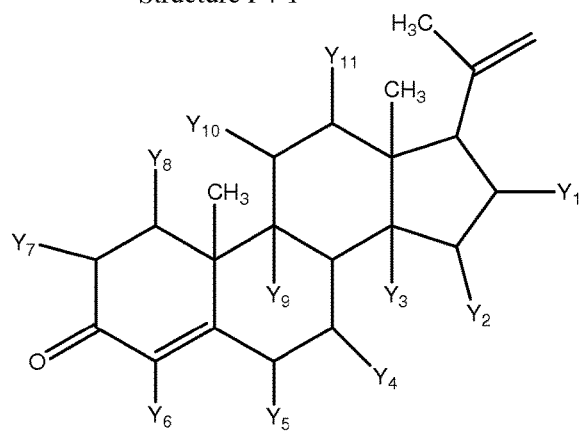
Figure 4:
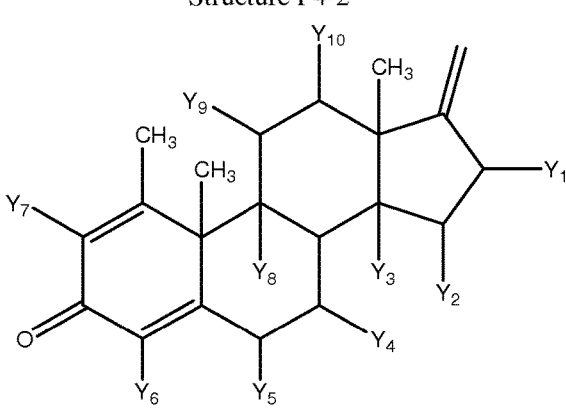
Figure 4:
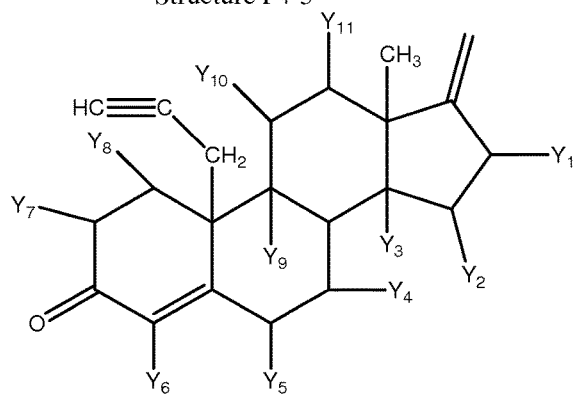
Figure 4:
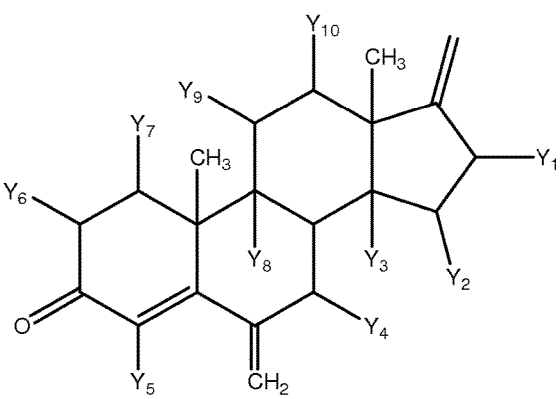
Figure 4:
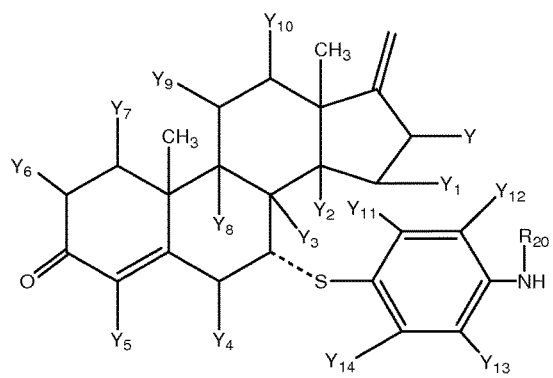
Figure 4:
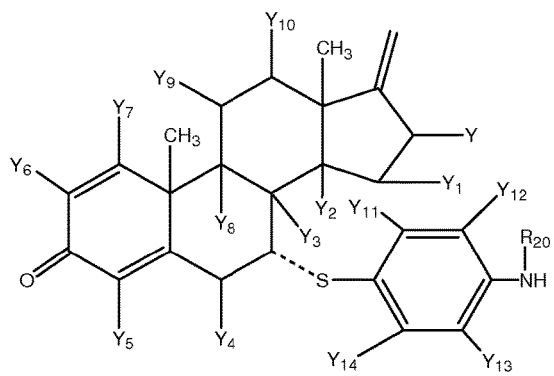
Figure 4:
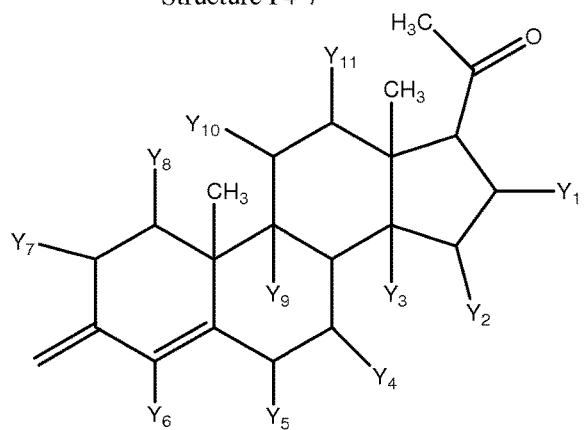
Figure 4:
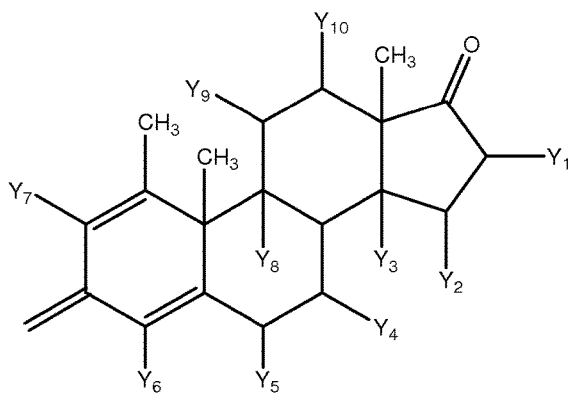
Figure 4:
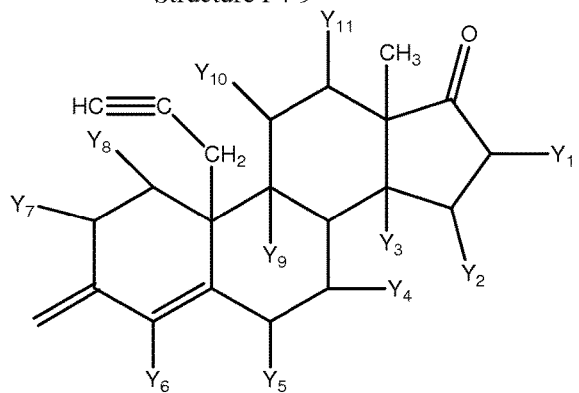
Figure 4:
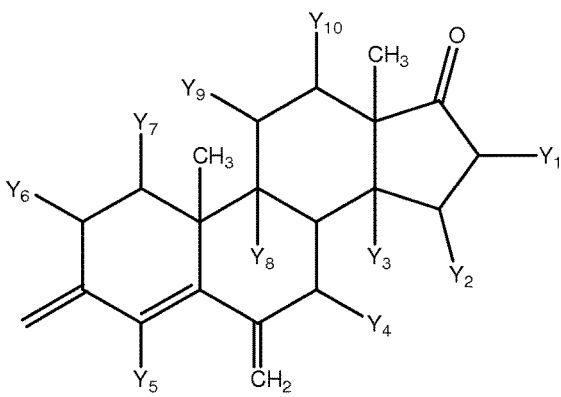
Figure 4:
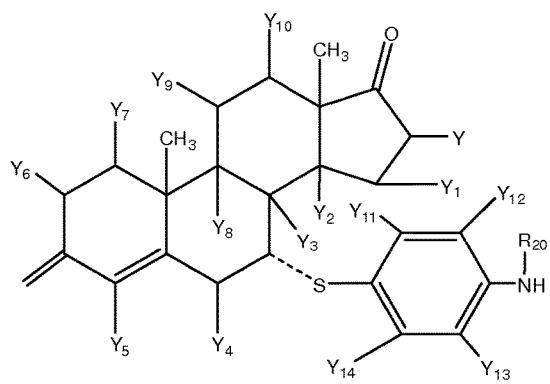
Figure 4:
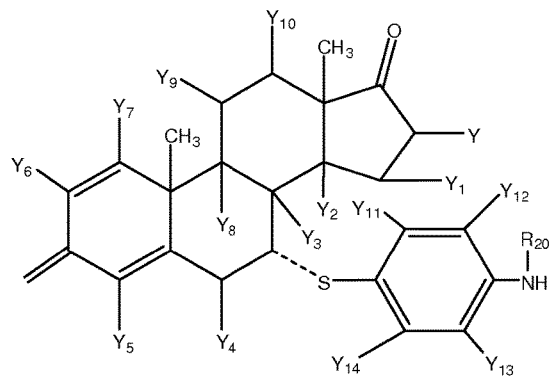
Figure 4:
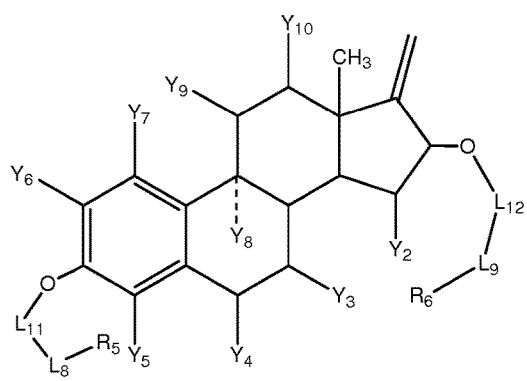
Figure 4:
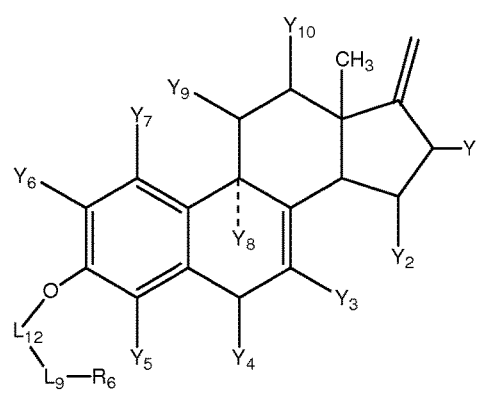
Figure 4:
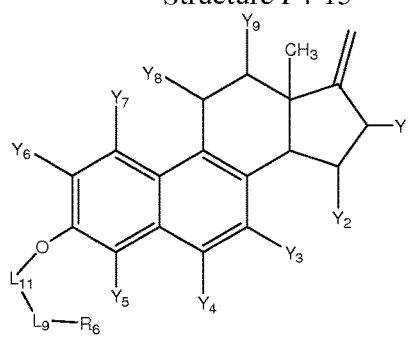
Figure 4:
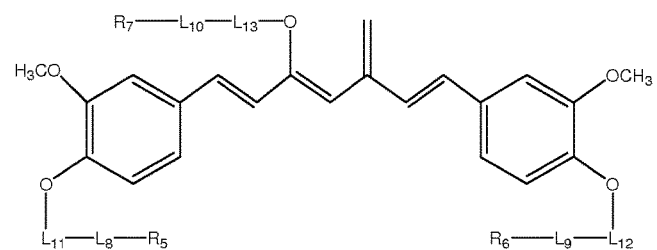
Figure 5A:
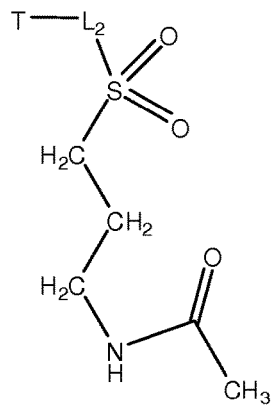
FIG. 5: Exemplary structures of HPC having functional units of F1, F2, and F4.
Figure 5A:
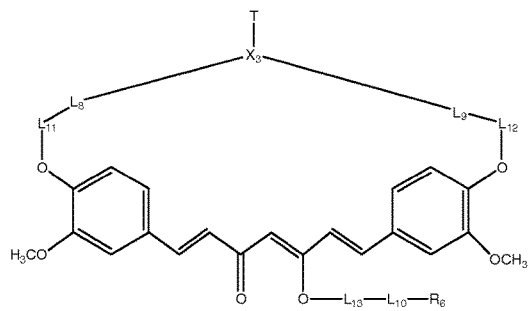
Figure 5A:
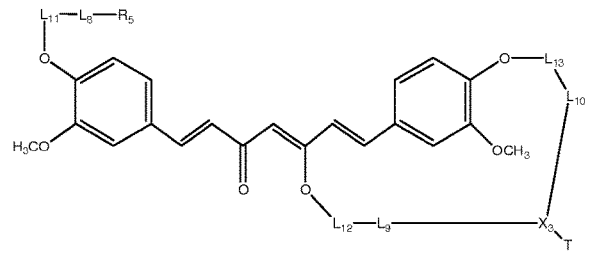
Figure 5A:
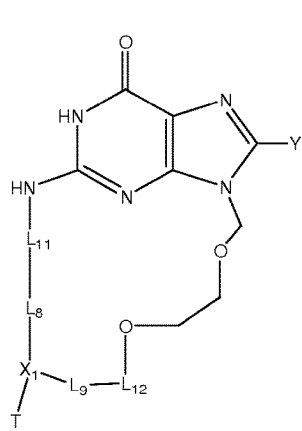
Figure 5A:
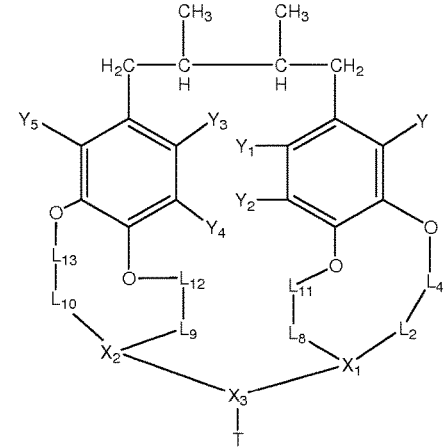
Figure 5A:
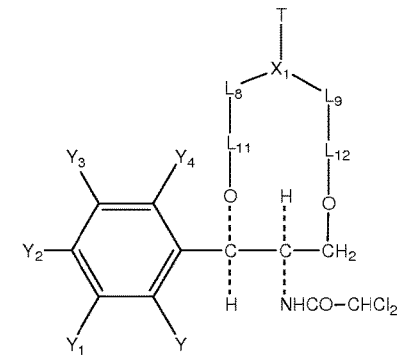
Figure 5B:
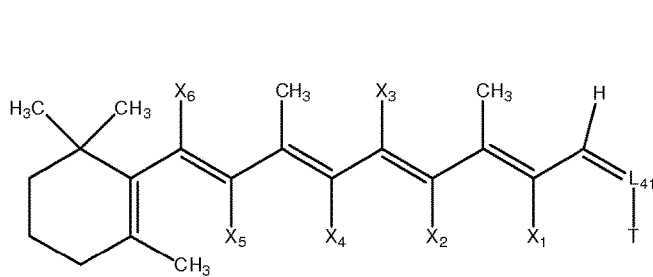
Figure 5B:
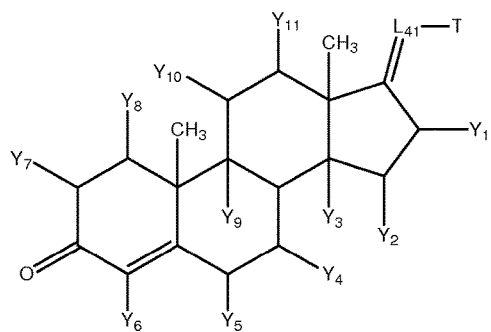
Figure 5B:
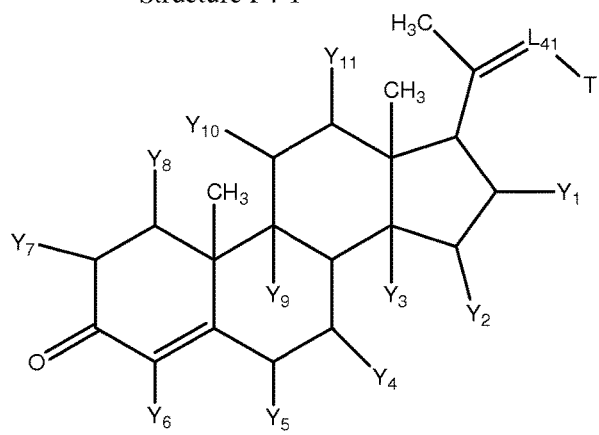
Figure 5B:
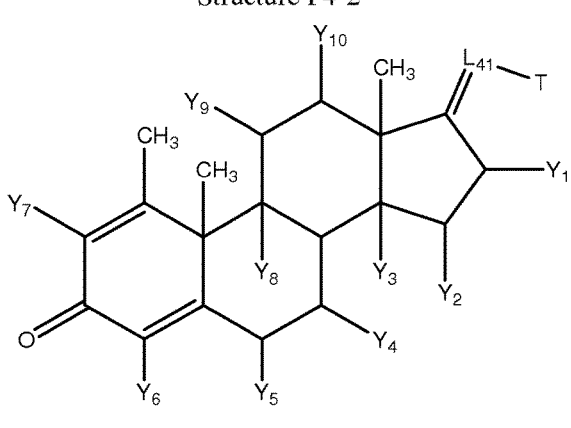
Figure 5B:
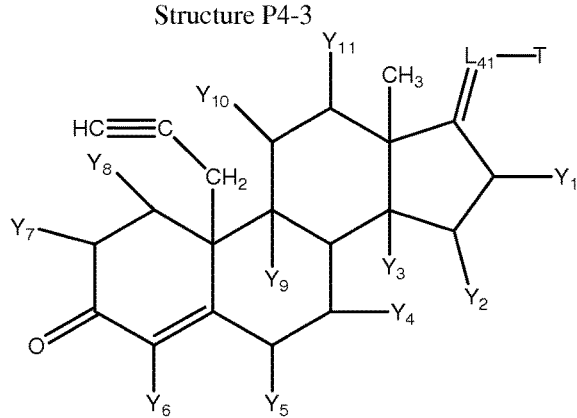
Figure 5B:
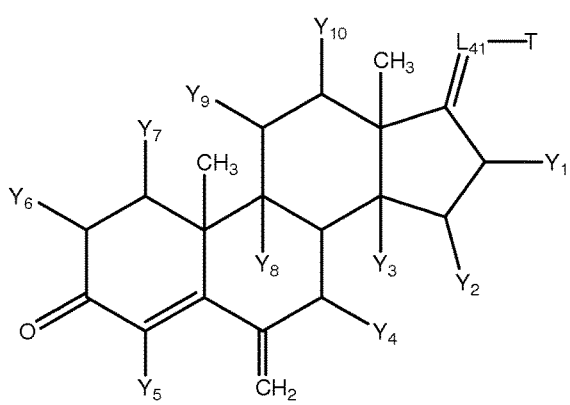
Figure 5C:
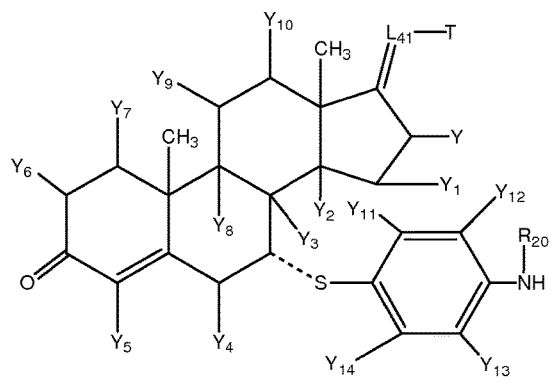
Figure 5C:
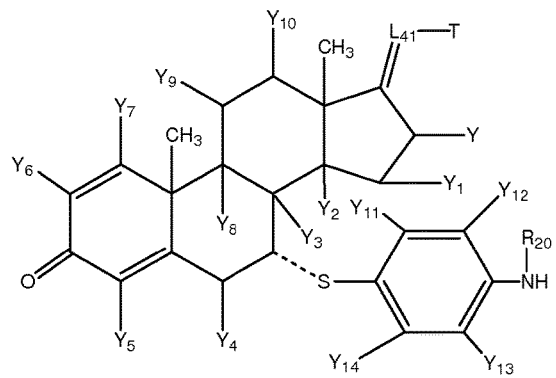
Figure 5C:
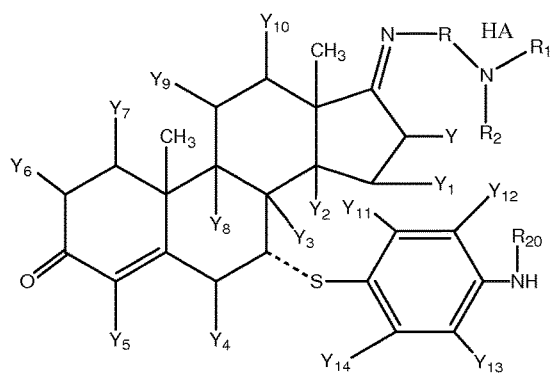
Figure 5C:
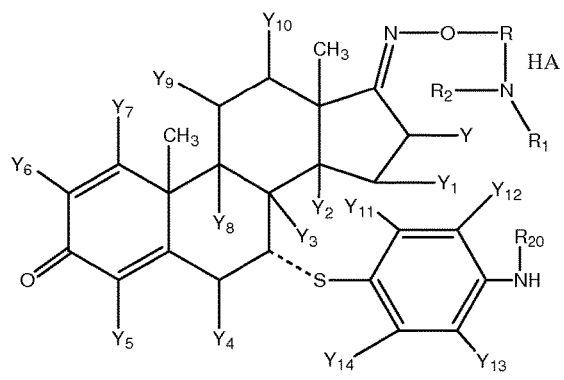
Figure 5C:
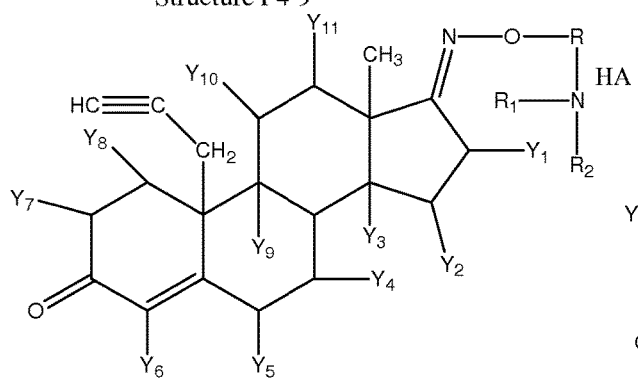
Figure 5C:
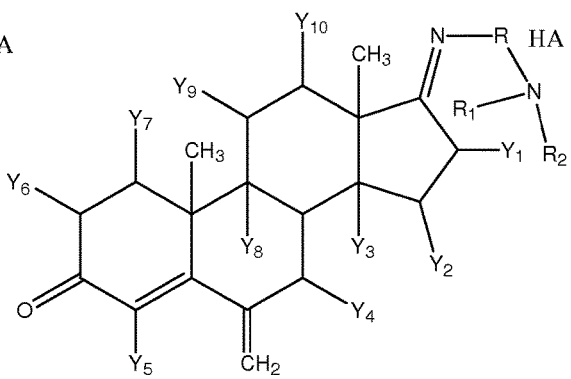
Figure 5D:
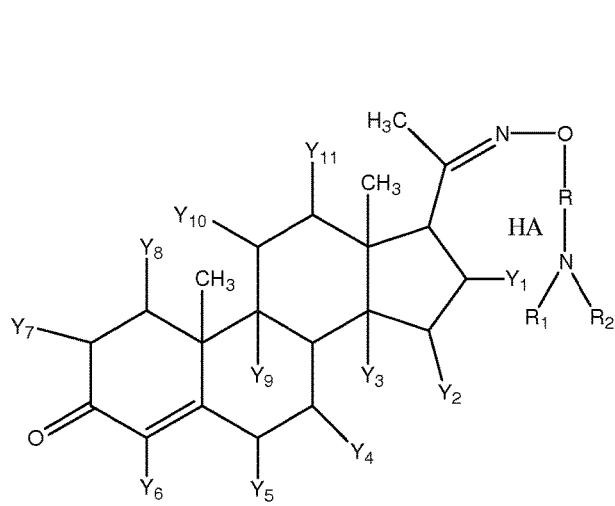
Figure 5D:
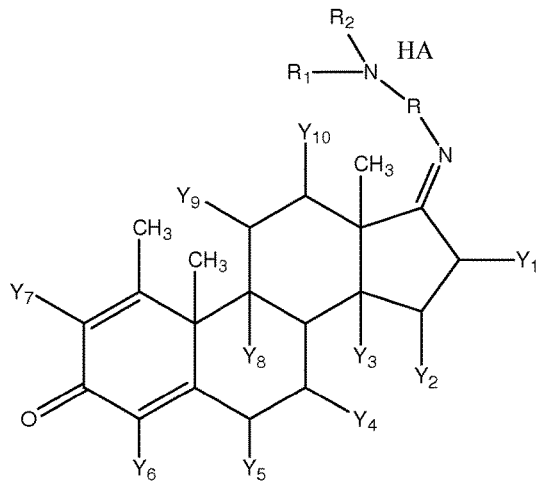
Figure 5D:
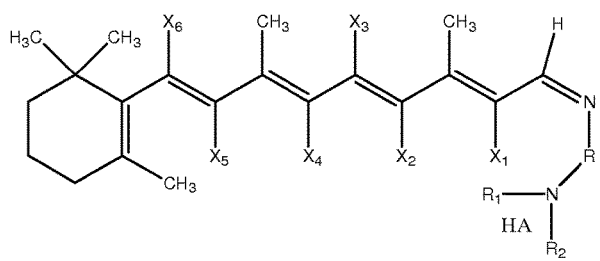
Figure 5D:
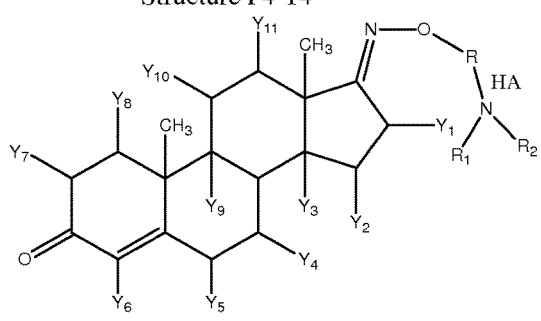
Figure 5D:
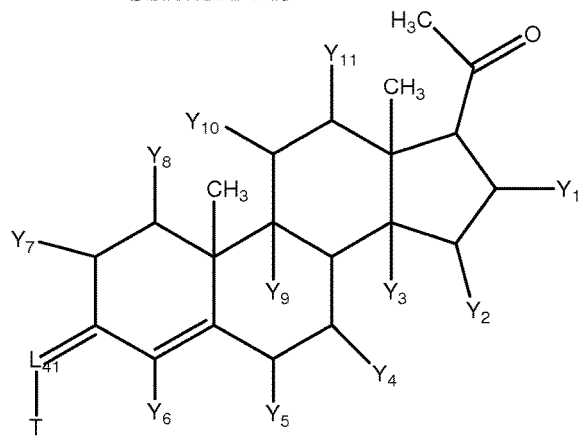
Figure 5D:
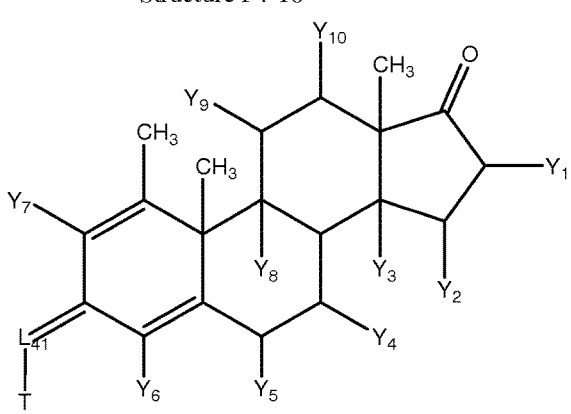
Figure 5E:
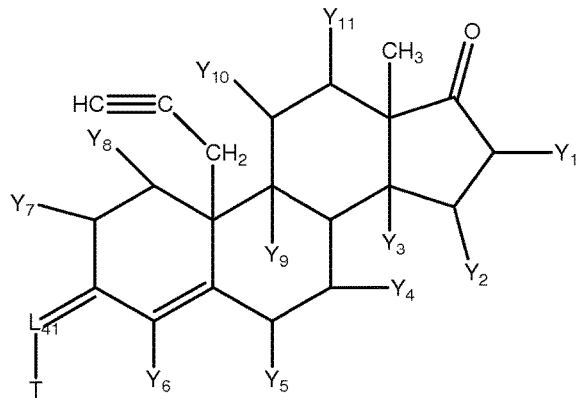
Figure 5E:
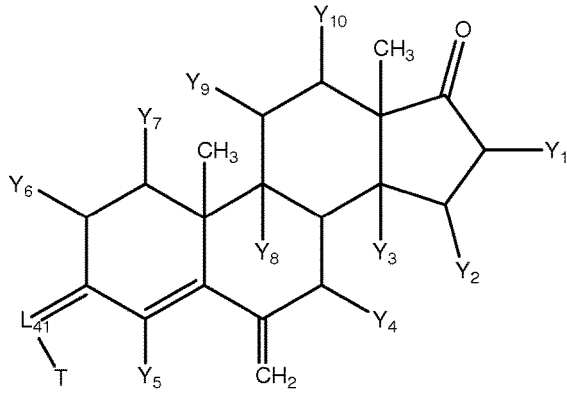
Figure 5E:
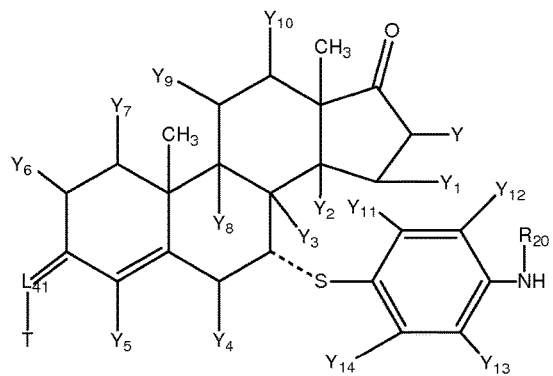
Figure 5E:
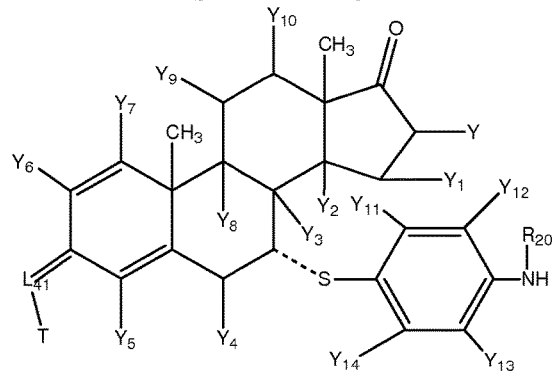
Figure 5E:
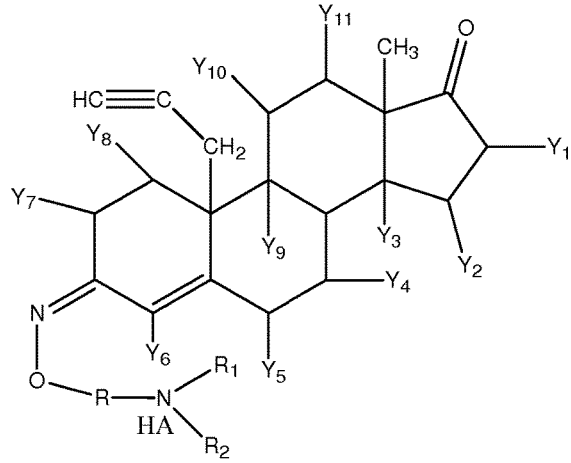
Figure 5E:
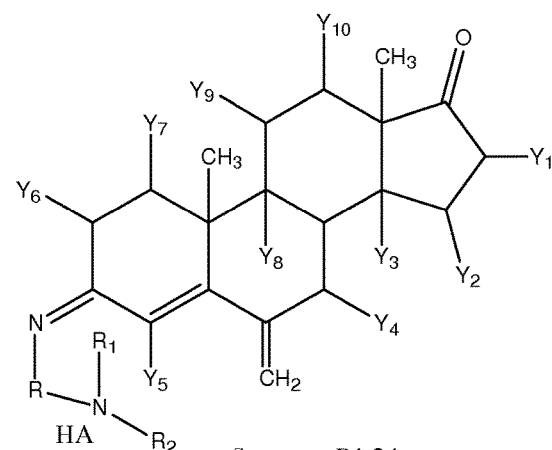
Figure 5F:
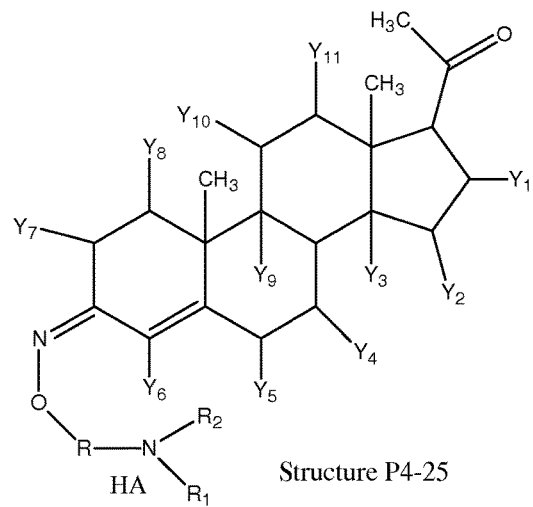
Figure 5F:
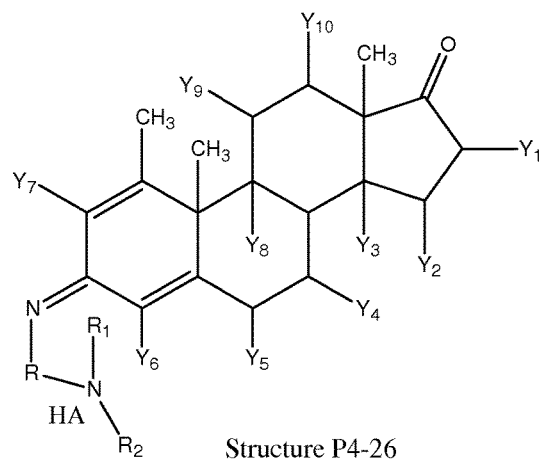
Figure 5F:
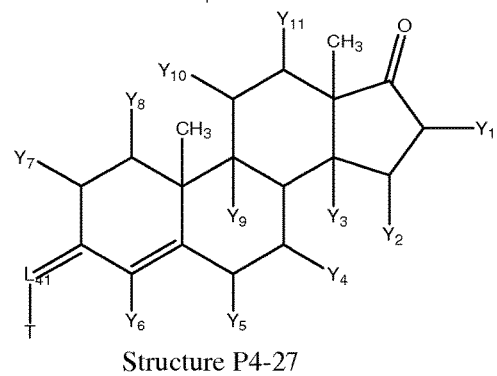
Figure 5F:
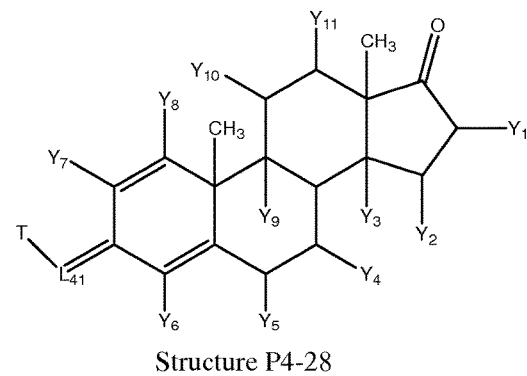
Figure 5F:
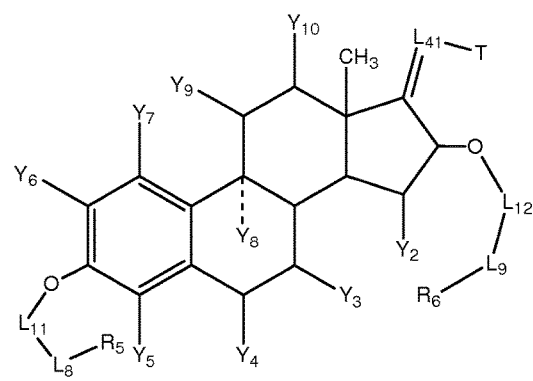
Figure 5F:
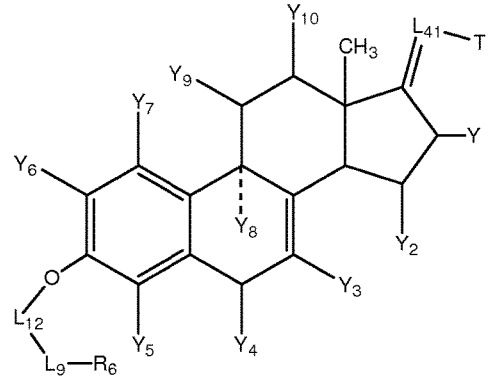

As used herein, the term "F4" or "F$_4$" is a structure selected from the group consisting of Structure F4-1, Structure F4-2, Structure F4-3, Structure F4-4, Structure F4-5, Structure F4-6, Structure F4-7, Structure F4-8, Structure F4-9, Structure F4-10, Structure F4-11, Structure F4-12, Structure F4-13, Structure F4-14, Structure F4-15, Structure F4-16, Structure F4-17, and Structure F4-18 (FIG. 4), Including stereoisomers and salts thereof.

The term "non-steroidal anti-inflammatory agent" or "NSAIA" is well known in the art and is a non-steroidal agent used to treat inflammation related conditions. NSAIA has anti-inflammatory effect, and some examples of NSAIA also have analgesic and/or antipyretic effects. Examples of NSAIA include, but are not limited to, acetylsalicylic acid (aspirin), 5-(2,4-difluorophenyl) salicylic acid (diflunisal), salicylsalicylic acid (salsalate), salicylic acid, N-Acetyl-p-aminophenol (acetaminophen), 2-(ρ-isobutylphenyl) propionic acid (ibuprofen), 2-(3-benzoylphenyl) propionic acid (ketoprofen), 2-(3-phenoxyphenyl) propionic acid (fenoprofen), 2-(6-methoxy-2-naphthyl) propionic acid (naproxen), α-methyl-4-(2-thienylcarbonyl)benzeneacetic acid (suprofen), α-methyl-(p-chlorobenzoyl)-5-methoxy-2-methylindole 3-acetic acid, 2-(2-fluoro-4-biphenylyl)propionic acid (flurbiprofen), 6-chloro-α-methyl-9H-carbazole-2-acetic acid (carprofen), α-methyl-5H-[1]benzopyrano[2,3-b]pyridine-7-acetic acid (pranoprofen), 2-(4-chlorophenyl)-α-methyl-5-benzoxazoleacetic acid (benoxaprofen), α-methyl-4-[(2-methyl-2-propenyl)amino]benzeneacetic acid (alminoprofen), 5-benzoyl-α-methyl-2-thiopheneacetic acid (tiaprofenic acid), 3-chloro-4-(2,5-dihydro-1H-pyrrol-1-yl)-α-methyl benzeneacetic acid (pirprofen), 2-(10,11-dihydro-10-oxodibenzo(b,f)thiepin-2-yl)propionic acid (zaltoprofen), 2-(8-methyl-10,11-dihydro-11-oxodibenz(b,f) oxepin-2-yl)propionic acid (bermoprofen), 2-[4-(2-oxocyclopentyl-methyl)phenyl]propionic acid (loxoprofen), 4-(1,3-dihydro-1-oxo-2H-isoindol-2-yl)-α-methylbenzeneacetic acid (indoprofen), α,3-dichloro-4-cyclohexylbenzeneacetic acid (fenclorac), 2-aryl and heteroarylpropionic acids, 4,5-Diphenyl-2-oxazole propionic acid (oxaprozin), 3-(4-biphenylylcarbonyl)propionic acid (fenbufen), 5-(4-chlorophenyl)-beta-hydroxy-2-furanpropionic acid (orpanoxin), 3-aryl and heteroarylpropionic acids, 5-benzoyl-2,3-dihydro-1H-pyrrolizine-1-carboxylic acid (ketorolac), 6-chloro-5-cyclohexyl-2,3-dihydro-1H-indene-1-carboxylic acid (clidanac), 1-Methyl-5-(4-methylbenzoyl)-1H-pyrrole-2-acetic acid (tolmetin), 5-(4-Chlorobenzoyl)-1,4-dimethyl-1H-pyrrole-2-acetic acid (zomepirac), 1,8-diethyl-1,3,4,9-tetrahydropyrano-[3,4-b]indole-1-acetic acid (etodolac), 2-amino-3-benzoylbenzeneacetic acid (amfenac), 2-amino-3-(4-bromo-benzoyl)benzeneacetic acid (bromofenac), 3-chloro-4-(2-propenyloxy)benzeneacetic acid (alclofenac), 2-(2,4-dichlorophenoxy)benzeneacetic acid (fenclofenac), 1-(4-chlorobenzoyl-5-methoxy-2-methyl-1H-indole-3-acetic acid carboxymethyl ester (acemetacin), 4-(4-chlorophenyl)-2-phenyl-5-thiazoleacetic acid (fentiazac), 1-(p-chlorobenzoyl)-5-methoxy-2-methylindole 3-acetic acid (indomethacin), (Z)-5-fluoro-2-methyl-1-[(4-methylsulfinyl)phenylmethylene]-1H-indene-3-acetic acid (sulindac), 3-(4-chlorophenyl)-1-phenyl-1H-pyrazole-4-acetic acid (lonazolac), [(1-benzyl-1H-indazol-3-yl)oxy]acetic acid (bendazac), 6-methoxyl-2-naphthalene-2-acetic acid (6MNA), 2[(2,6-dichlorophenyl)amino]benzene acetic acid (diclofenac), 2-[(2,3-Dimethylphenyl)amino]benzoic acid (mefenamic acid), 2-[(2,6-dichloro-3-methylphenyl)amino]benzoic acid (meclofenamic acid), 2-[[(3-trifluoromethyl)phenyl]amino]benzoic acid (flufenamic acid), 2-[[3-(trifluoromethyl)phenyl]amino]-3-pyridinecarboxylic acid (niflumic acid), 2-[[2-methyl-3-(trifluoromethyl)phenyl]amino]-3-pyridinecarboxylic acid (flunixin), 4-hydroxy-2-methyl-N-2-pyridinyl-2H,1,2-benzothiazine-3-carboxamide 1,1-dioxide (piroxicam), sudoxiam, 6-chloro-4-hydroxy-2-methyl-N-2-pyridinyl-2H-thieno[2,3-e]-1,2-thiazine-3-carboxamide 1,1-dioxide (lornoxicam), 4-hydroxy-2-methyl-N-2-pyridinyl-2H-thieno[2,3-e]-1,2-thiazine-3-carboxamide 1,1-dioxide (tenoxicam), ethyl 1-[2-methyl-1,1-dioxo-3-(pyridin-2-ylcarbamoyl)benzo[e]thiazin-4-yl]oxyethyl carbonate (ampiroxicam), 8-chloro-(4-hydroxyl-4-pyridine-2-ylamino-methylidene)-3-methyl-2,2-dioxo-2$\lambda^{6,}$ 7-dithia-3-azabicyclo[4,3,0]nona-8,10-dien-5-one (lomoxicam), 4-hydroxy-2-methyl-N-[5-Methyl-3-isoxolyl-2H-1,2-benzothiazine-3-carboxamide 1,1-dioxide] (isoxicam), cinnoxicam and N-(2-thiazolyl)-4-hydroxy-2-methyl-2H,1,2-benzothiazine-3-arboxamide 1,1-dioxide (meloxicam).

In certain embodiments, a functional unit of a NSAIA HPC comprises a moiety having a structure selected from the group consisting of Structure F-2, Structure F-82 to Structure F-125, and Structure F2-360 to Structure F2-403.

As used herein, a prostaglandin or "a prostaglandin analog" is a compound comprising a five-member ring and a fatty acid group, wherein the five-member ring may be part of a multiple ring structure. Examples of prostaglandins and prostaglandin analogs include, but are not limited to, $PGA_1$, $PGA_2$, $PGA_3$, $PGB_1$, $PGB_2$, $PGB_3$, $PGD_1$, $PGD_2$, $PGD_3$, $PGE_1$, $PGE_2$, $PGE_3$, $PGF_{1\alpha}$, $PGF_{1\beta}$, $PGF_{2\alpha}$, $PGF_{2\beta}$, $PGF_{3\alpha}$, $PGG_2$, $PGH_1$, $PGH_2$, $PGI_2$ (prostacyclin), $PGI_3$, $PGJ_2$, $PGK_1$, $PGK_2$, carboprost, prostalene, misoprostol, gemeprost, sulprostone, fluprostenol cloprostenol, bimatoprost {(Z)-7-[(1R,2R,3R,5S)-3,5-Dihydroxy-2-[1E,3S]-3-hydroxy-5-phenyl-1-pentenyl]cyclopentyl}-5-N-ethylheptenamide}, latanoprost (13,14-dihydro-17-phenyl-18,19,20-trinor $PGF_{2\alpha}$ isopropyl ester), travoprost {(Z)-7-[(1R,2R,3R,5S)-3,5-dihydroxy-2-[(1E,3R)-3-hydroxy-4-[(α,α,α-trifluoro-m-tolyl)oxy]-1-butenyl]cyclopentyl]-5-heptenoate}, and unoprostone (13,14-dihydro-15-keto-20-ethyl Prostaglandin $F_{2\alpha}$).

In certain embodiments, a functional unit of a prostaglandin HPC comprises a moiety having a structure selected fro the group consisting of Structure F-132 to Structure F-151

Mustards are well known in the art and are used in connection with various conditions. Examples of mustards include, but are not limited to, nitrogen mustards, nitrobenzyl mustards, phosphoramide mustard, isophosphoramide mustards and aldophosphamide.

In certain embodiments, a functional unit of a HPC of a mustard and mustard-related compound comprises a moiety having a structure selected from the group consisting of Structure F-MA and Structure F-MB:

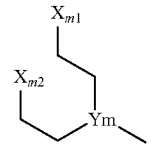

Structure F-MA

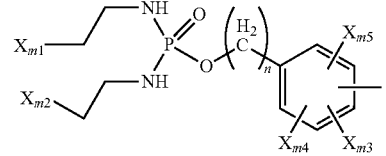

Structure F-MB including stereoisomers and salts thereof, wherein:

is selected from the group consisting of Structure Ym-a, Structure Ym-b, Structure Ym-c, Structure Ym-d, and Structure Ym-e:

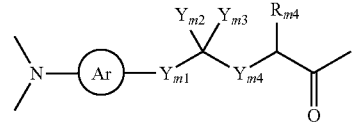

Structure Ym-a

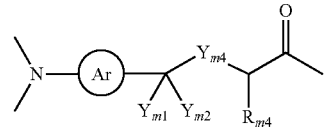

Structure Ym-b

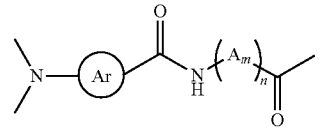

Structure Ym-c

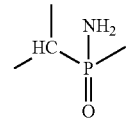

Structure Ym-d

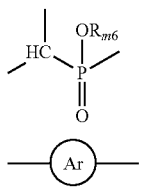

Structure Ym-e is selected from the group consisting of substituted and unsubstituted aryl, Structure Ar-ma, Structure Ar-mb, Structure Ar-mc, Structure Ar-md, Structure Ar-me, Structure Ar-mf, Structure Ar-mg, Structure Ar-mh and Structure Ar-mi:

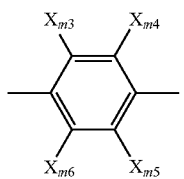

Structure Ar-ma

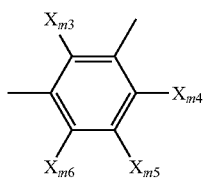

Structure Ar-mb

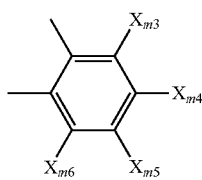

Structure Ar-mc

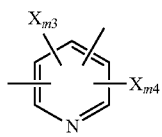

Structure Ar-md

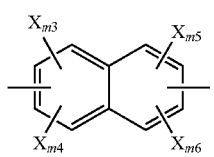

Structure Ar-me

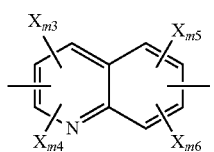

Structure Ar-mf

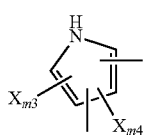

Structure Ar-mg

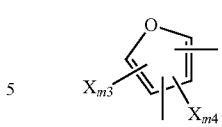

Structure Ar-mh

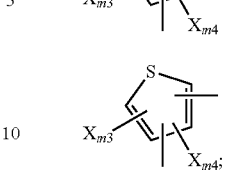

Structure Ar-mi each $X_{m1}$ and $X_{m2}$ is independently selected from the group consisting of Cl, Br, F, I, and $OSO_2R_{m4}$;

each $R_{m4}$ and $R_{m6}$ is independently selected from the group consisting of substituted and unsubstituted alkyl, substituted and unsubstituted alkoxyl, substituted and unsubstituted perfluoroalkyl, substituted and unsubstituted alkyl halide, substituted and unsubstituted aryl, and substituted and unsubstituted heteroaryl groups;

each $X_{m3}$-$X_{m7}$ is independently selected from the group consisting of $NHCOR_{m4}$, $OR_{m4}$, $SR_{m4}$, $NHR_{m4}$, $OCOR_{m4}$, $R_{m4}$, substituted and unsubstituted alkoxyl, substituted and unsubstituted alkylthio, substituted and unsubstituted alkylamino, substituted and unsubstituted alkyl halide, H, F, Cl, Br, I, $NO_2$, CN, $CF_3$, $NHCOCH_3$, $OCH_3$, $SCH_3$, $NH_2$, $NHCH_3$, $OCOCH_3$, $OCOC_2H_5$, $OC_2H_5$, $OC_3H_7$, $CH_3$, $C_2H_5$, and $C_3H_7$;

n is an integer;

$Y_{mi}$ is selected from the group consisting of $CH_2$, O, S, and NH;

$Y_{m2}$ and $Y_{m3}$ are either independently selected from the group consisting of $NHCOR_{m4}$, H, OH, $NHCOCH_3$, $NHCOC_2H_5$, Cl, F, Br, and I, or taken together is =O;

$Y_{m4}$ is selected from the group consisting of $R_{m4}$, $CH_2$, $(CH_2)_n$, O, S, and NH;

$A_m$ is selected from the group consisting of α-amino acids, β-amino acids, and amino acids residues;

any $CH_2$ groups may be replaced with O, S, or NH; and when a bond is not linked with any atom of an aryl or heteroaryl ring, the bond can be put into any position of the ring.

Peptides and amino acids are well known in the art and are used in connection with various conditions. As used herein, a peptide means a compound formed by connecting more than one amino acid via amide bonds. Examples of peptides include, but are not limited to, peptide hormones (e.g. hyrotropin-releasing hormone, tuftsin (Thr-Lys-Pro-Arg), met-enkephaline (Tyr-Gly-Gly-Phe-Met), oxytocin, angiotensin, gastrin, somatostatin, dynorphin, endothelin, secretin, calcitonin, and insulin), enterostatins (e.g. Val-Pro-Asp-Pro-Arg (VPDPR), Val-Pro-Gly-Pro-Arg (VPGPR), and Ala-Pro-Gly-Pro-Arg (APGPR)), Melanocortin II (cyclo(1, 6)-Ac-Nle-Asp-His-Phe-Arg-Trp-Lys-OH), opioid peptides (e.g. Met-enkephalin (H-Tyr-Gly-Gly-Phe-Met-OH), Leu-enkephalin (H-Tyr-Gly-Gly-Phe-Leu-OH), H-Tyr-D-Ala-Gly-N-Me-Phe-Met(O)—OL, and H-Tyr-D-Ala-Gly-Phe-Leu-OH), antimicrobial peptides (e.g. tachyplesins, histatin peptides and the derivatives), calcium binding peptides, competence stimulating peptides, peptide vaccines, and peptide mimics (e.g. α-helix mimics and β-sheet mimics).

In certain embodiments, a functional unit of a peptide HPC comprises a moiety having a structure selected from the group consisting of Structure F-79 to Structure F-81, Structure F2-418, Structure F2-419, Structure F3-35 to Structure F3-40 as defined supra.

RNA, DNA, nucleosides and nucleotides are well known in the art and are used in connection with various conditions. As used herein, a RNA or DNA means a compound formed by connecting more than one nucleotides via covalent bonds.

In certain embodiments, a functional unit of a RNA HPC or a DNA HPC comprises a moiety having a structure selected from the group consisting of Structure F2-420 to Structure F2-427.

As used herein, a beta-lactam antibiotics refers to a compound that comprises a beta-lactam nucleus. Examples of beta-lactam antibiotics include, but are not limited to, penicillin derivatives, cephalosporins, penems, monobactams, carbapenems, beta-lactamase inhibitors and combinations thereof. Examples of penicillin derivatives include, but are not limited to, aminopenicillins (e.g. amoxicillin, ampicillin, and epicillin); carboxypenicillins (e.g. carbenicillin, ticarcillin, and temocillin); ureidopenicillins (e.g. azlocillin, piperacillin and mezlocillin); mecillinam, sulbenicillin, benzathine penicillin, penicillin G (benzylpenicillin), penicillin V (phenoxymethylpenicillin), penicillin O (allylmercaptomethylpenicillinic), procaine penicillin, oxacillin, methicillin, nafcillin, cloxacillin, dicloxacillin, flucloxacillin, pivampicillin, hetacillin, becampicillin, metampicillin, talampicillin, co-amoxiclav (amoxicillin plus clavulanic acid), and piperacillion. Examples of cephalosporins include, but are not limited to, cephalexin, cephalothin, cefazolin, cefaclor, cefuroxime, cefamandole, cefotetan, cefoxitin, ceforanide, ceftriaxone, cefotaxime, cefpodoxime proxetil, ceftazidime, cefepime, cefoperazone, ceftizoxime, cefixime and cefpirome. Examples of penems include, without limitation, faropenem. Examples of monobactams include, without limitation, aztreonam and tigemonam. Examples of carbapenems include, but are not limited to, biapenem, •doripenem, ertapenem, •imipenem, •meropenem, •and panipenem. Examples of beta-lactamase inhibitors include, but are not limited to, tazobactam ([2S-(2alpha,3beta,5alpha)]-3-Methyl-7-oxo-3-(1H-1,2,3-triazol-1-ylmethyl)-4-thia-1-azabicyclo[3.2.0]heptane-2-carboxylic acid 4,4-dioxide sodium salt), sulbactam (2S,5R)-3,3-dimethyl-7-oxo-4-thia-1-azabicyclo[3.2.0]heptane-2-carboxylic acid 4,4-dioxide sodium), and clavulanic acid ((2R,5R,Z)-3-(2-hydroxyethylidene)-7-oxo-4-oxa-1-azabicyclo[3.2.0]heptane-2-carboxylic acid). Other examples of antibiotics include, without limitation, [(N-benzyloxycarbonylamino)methyl]-phosphonic acid mono-(4-nitrophenyl) ester sodium salt, [(N-benzyloxycarbonylamino)methyl]-phosphonic acid mono-(3-pyridinyl) ester sodium salt, sulfanilamide (4-aminobenzenesulfonamide), sulfasalazine (6-oxo-3-(2-[4-(N-pyridin-2-ylsulfamoyl)phenyl]hydrazono)cyclohexa-1,4-dienecarboxylic acid), 1-cyclopropyl-6-fluoro-4-oxo-7-piperazin-1-yl-quinoline-3-carboxylic acid, nalidixic acid (1-ethyl-7-methyl-4-oxo-[1,8]naphthyridine-3-carboxylic acid), In certain embodiments, a functional unit of a beta-lactam antibiotics HPC comprises a moiety having a structure selected from the group consisting of Structure F-184 to Structure F-211.

In certain embodiments, a moiety of a parent drug or parent drug-related compound in a HPC can be further converted to a lipophilic moiety as described supra.

In certain embodiments, a transportational unit of a HPC comprises a protonatable amine group that is capable of facilitating the transportation or crossing of the HPC through one or more biological barriers (e.g., >about 10 times, >about 50 times, >about 100 times, >about 300 times, >about 500 times, >about 1,000 times, >about 10,000 times faster than the parent drug). In certain embodiments, a protonatable amine group is substantially protonated at the pH of one or more biological barriers the HPC penetrates. In certain embodiments, the amine group can be reversibly protonated and deprotonated. In certain embodiments, the transportational unit may or may not be cleaved from the functional unit after the penetration of HPC through one or more biological barriers.

In certain embodiments, a protonatable amine group is selected from the group consisting of substituted and unsubstituted primary amine groups, substituted and unsubstituted secondary amine groups, and substituted and unsubstituted tertiary amine groups.

Figure 7A:
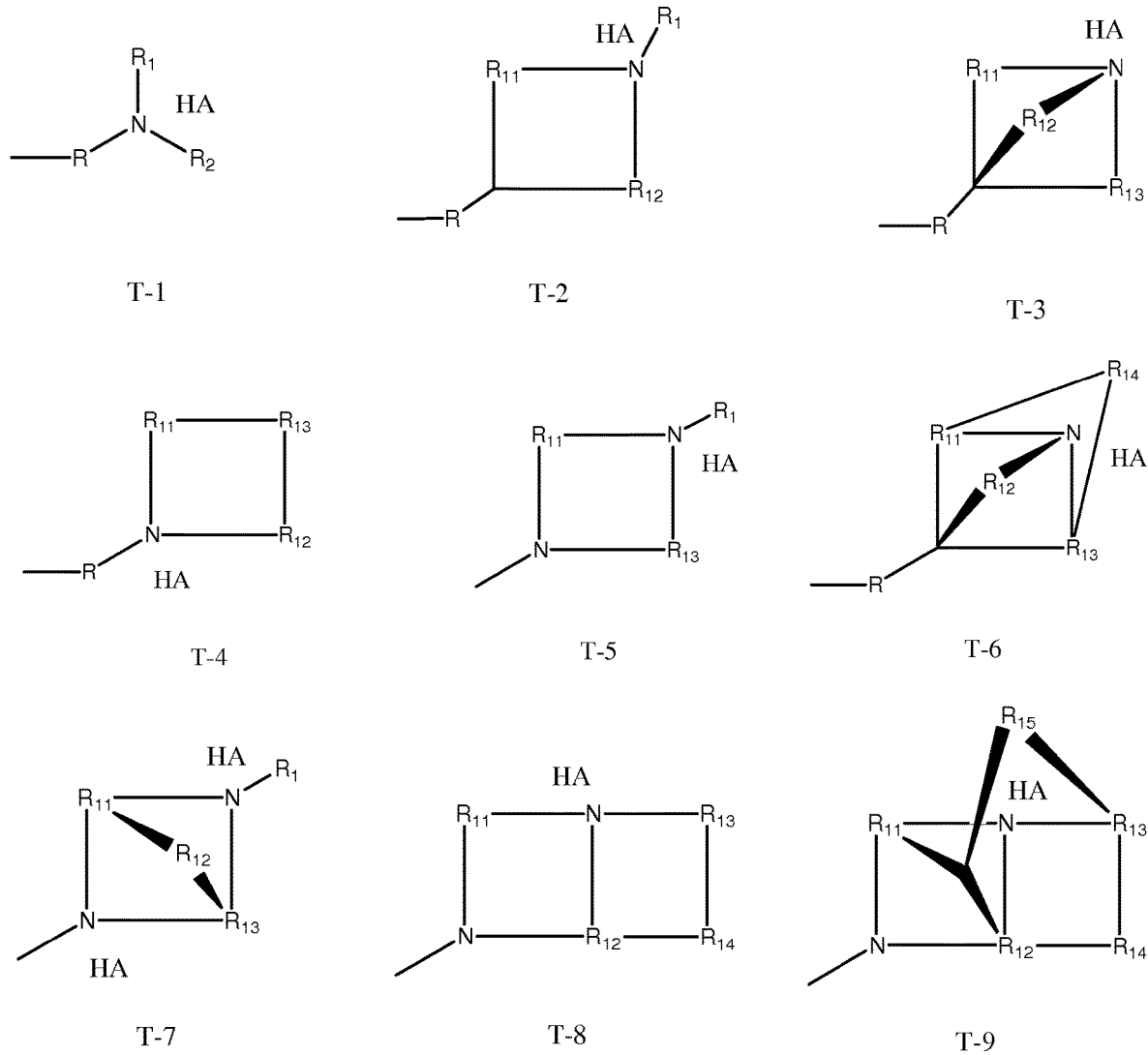
FIG. 7: Exemplary structures of transportational unit T.
Figure 7B:
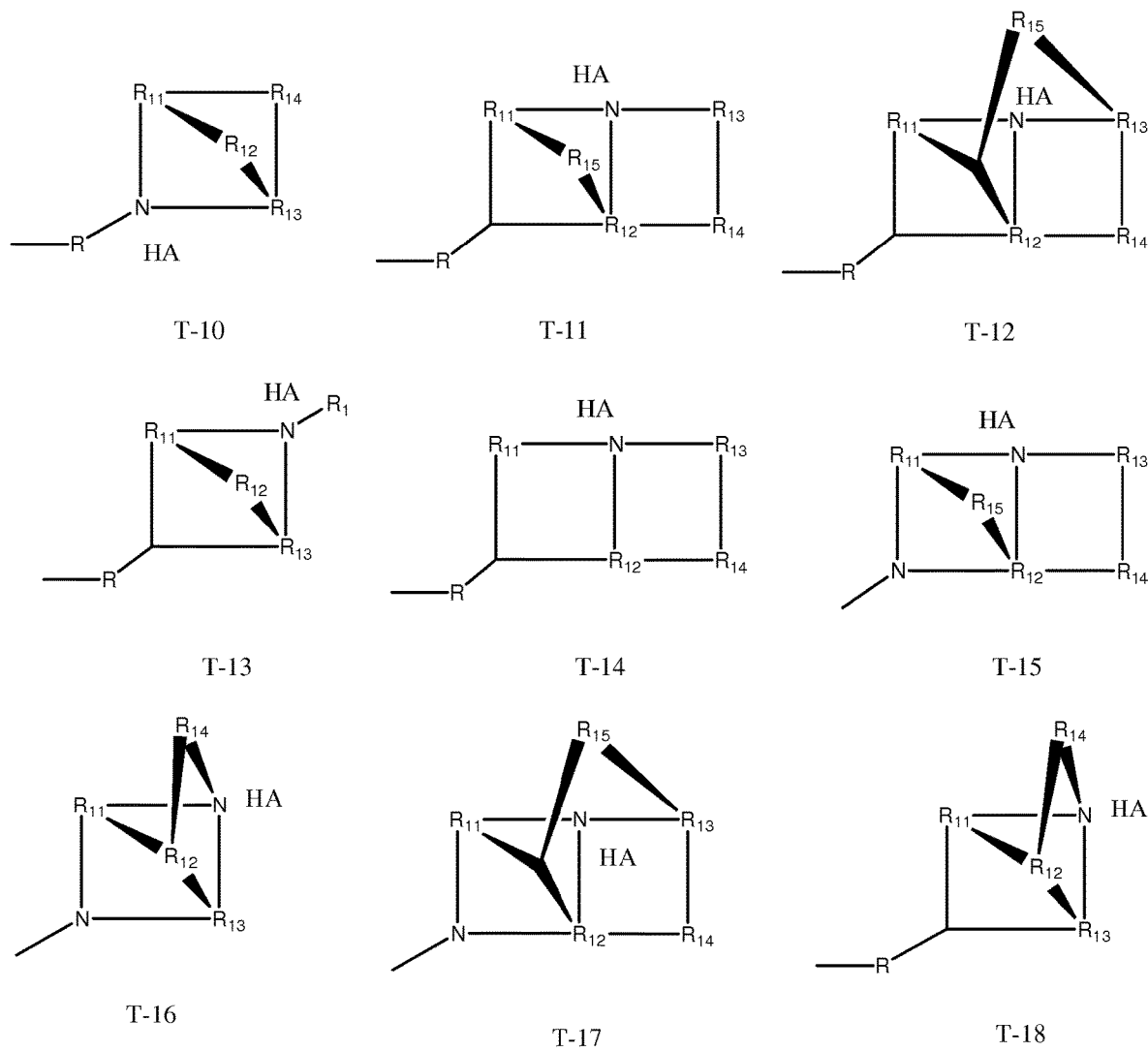

In certain embodiments, an amine group is selected from the group consisting of Structure T-1, Structure T-2, Structure T-3, Structure T-4, Structure T-5, Structure T-6, Structure T-7, Structure T-8, Structure T-9, Structure T-10, Structure T-11, Structure T-12, Structure T-13, Structure T-14, Structure T-15, Structure T-16, Structure T-17 and Structure T-18 as shown in FIG. 7, including stereoisomers and salts thereof.

In certain embodiments, a linker covalently linking a functional unit and a transportational unit of a HPC comprises a bond that is capable of being cleaved after the HPC penetrates across one or more biological barriers. The cleavable bond comprises, for example, a covalent bond, an ether, thioether, amide, ester, thioester, carbonate, carbamate, phosphate or oxime bond.

In certain embodiments, a HPC of a parent drug has the following general Structure L:

Structure L including stereoisomers and salts thereof, wherein:

T is a transportational unit of a HPC. For example, T is selected from the group consisting of Structure T-1, Structure T-2, Structure T-3, Structure T-4, Structure T-5, Structure T-6, Structure T-7, Structure T-8, Structure T-9, Structure T-10, Structure T-11, Structure T-12, Structure T-13, Structure T-14, Structure T-15, Structure T-16, Structure T-17 and Structure T-18; and $F_g$ is a functional unit of a HPC of a parent drug. Examples of $F_g$ include structures selected from the group consisting of F1, F2, F-MA and F-MB.

In certain embodiments, a HPC comprises the structure of Structure L, including stereoisomers and salts thereof, wherein $F_g$ is F1, and $L_1$ and $L_4$ are nothing.

In certain embodiments, a HPC comprises the structure of Structure L, including stereoisomers and salts thereof, wherein $F_g$ is F2, and $L_1$ is nothing.

In certain embodiments, a HPC comprises a structure of Structure L-3:

$$F3-L_2-R \hspace{2cm} \text{(Structure L-3)}$$

including stereoisomers and salts thereof.

In certain embodiments, a functional unit comprising a carbonyl group (e.g. ketone and aldehyde) is linked to a transportational unit through an imine bond, oxime bond, or hydrazon bond to form a HPC having the following Structure L-4:

Structure L-4 including stereoisomers and salts thereof, wherein:

$L_{41}$ is selected from the group consisting of nothing, N, N—O, N—N($L_3$), N—S, N—O—CH$_2$—O, N—S—CH$_2$—O, N-$L_3$, N—O-$L_3$, N—N($L_3$)-$L_5$, and $L_3$; and T is defined as in paragraph 0076.

In certain embodiments, a HPC is selected from the group consisting of Structure P-44, P2-428, Structure P2-429, Structure P2-430, Structure P2-431, Structure P2-432, Structure P-4-1, Structure P4-2, Structure P4-3, Structure P4-4, Structure P4-5, Structure P4-6, Structure P4-7, Structure P4-8, Structure P4-9, Structure P4-10, Structure P4-11, Structure P4-12, Structure P4-13, Structure P4-14, Structure P4-15, Structure P4-16, P4-17, Structure P4-18, Structure P4-19, Structure P4-20, Structure P4-21, Structure P4-22, Structure P4-23, Structure P4-24, Structure P4-25, and Structure P4-26, P4-27, Structure P4-28, Structure P4-29, Structure P4-30, Structure P4-31, and Structure P4-32 as shown in FIG. 5, including stereoisomers and salts thereof, wherein:

T is defined as in paragraph 0076; and $L_{41}$ is defined as in paragraph 0080.

In certain embodiments, a parent drug of HPC already comprises both a lipophilic portion and a primary, secondary or tertiary amine group that can be protonated and deprotonated at a pH of one or more biological barriers. Examples of parent drugs that comprise both a lipophilic portion and a primary, secondary or tertiary amine group include, without limitation, beta blockers (e.g. propranolol, atenolol, acebutolol, bisoprolol, esmolol, nadolol, pindolol, sotalol, salmeterol, timolol), local anesthetic (procaine, mepivacaine, chloroprocaine, etidocaine), antianxiety/antipsychotic agents (e.g. chlorpromazine, methotrimeprazine, triflupromazine, and trimeprazine), anti-schizophrenia (e.g. perphenazine, prochlorperazine, trifluoperazine), skeletal muscle relaxant (e.g. cyclobenzaprine), and platelet aggregation inhibitor (e.g. ticlopidine).

Figure 6:
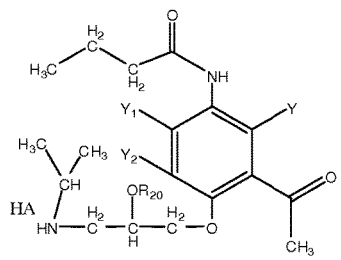
FIG. 6: Exemplary structures of HPC.
Figure 6:
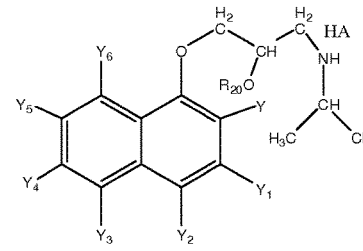
Figure 6:
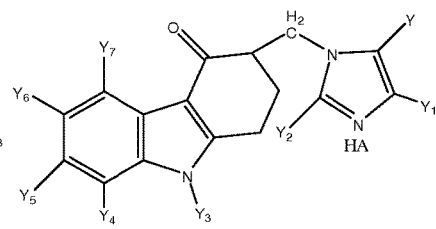
Figure 6:
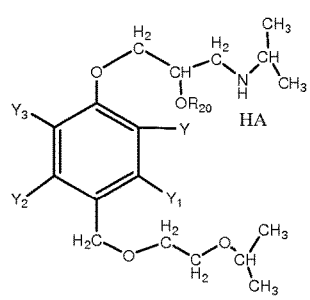
Figure 6:
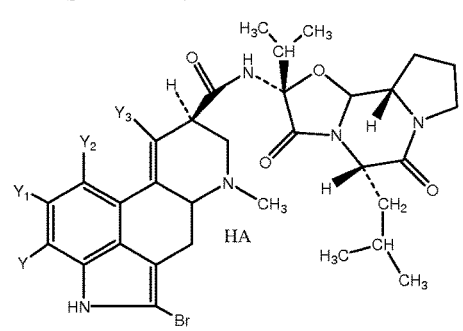
Figure 6:
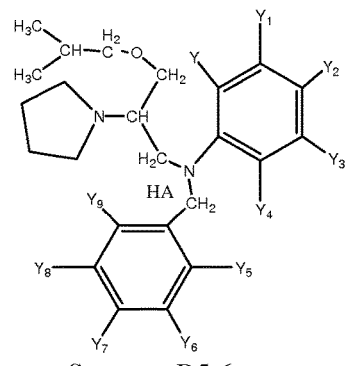
Figure 6:
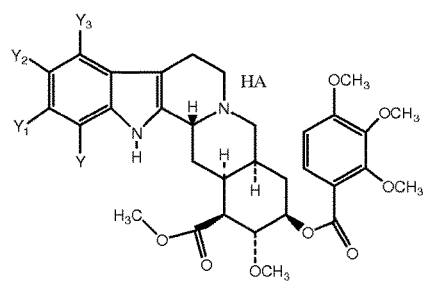
Figure 6:
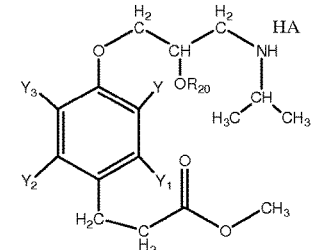
Figure 6:
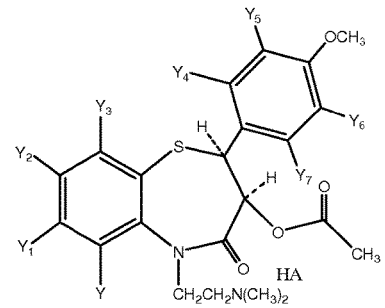
Figure 6:
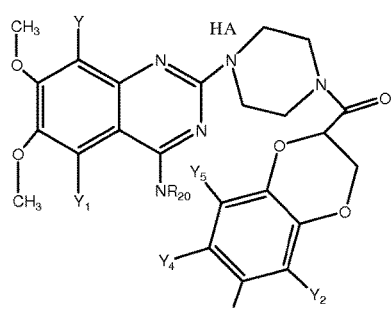
Figure 6:
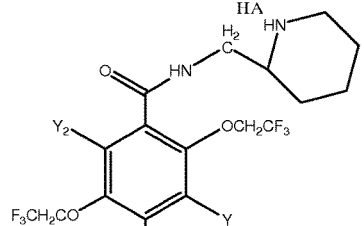
Figure 6:
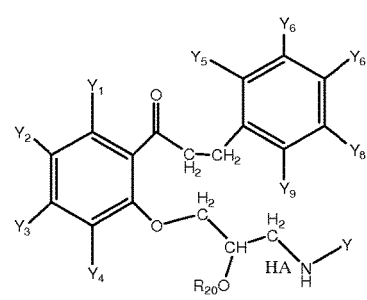
Figure 6:
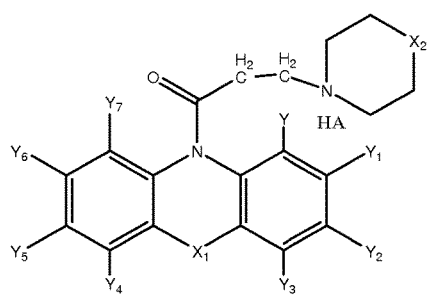
Figure 6:
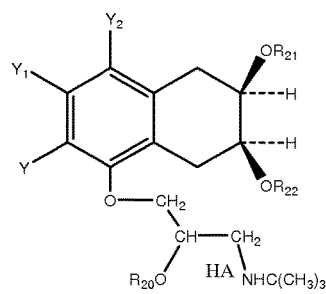
Figure 6:
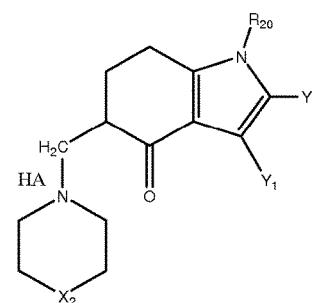
Figure 6:
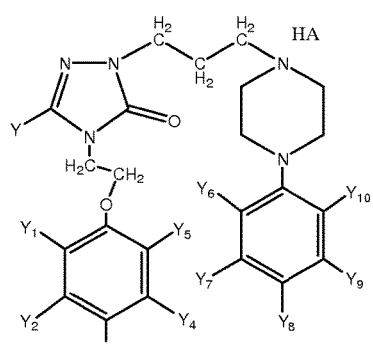
Figure 6:
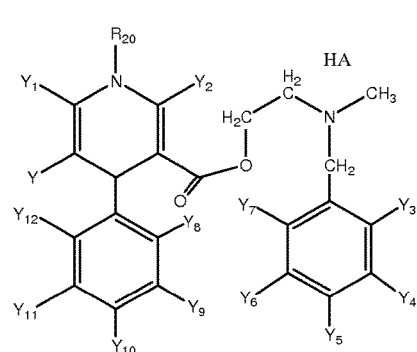
Figure 6:
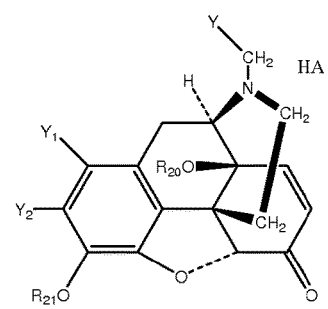
Figure 6:
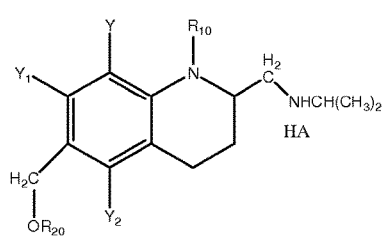
Figure 6:
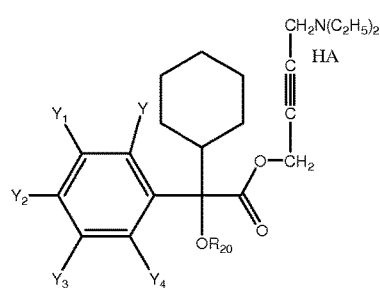
Figure 6:
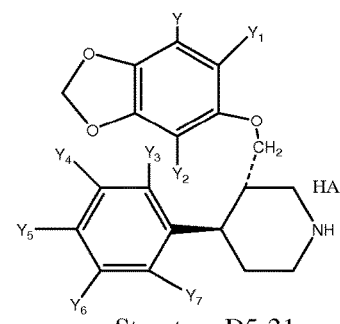
Figure 6:
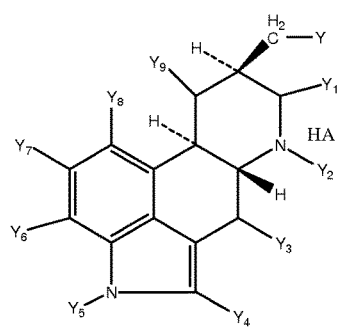
Figure 6:
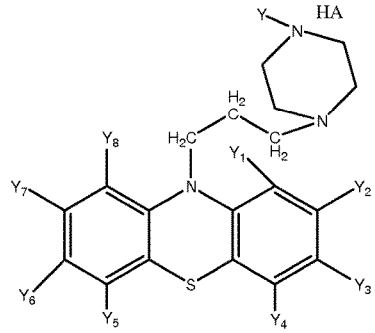
Figure 6:
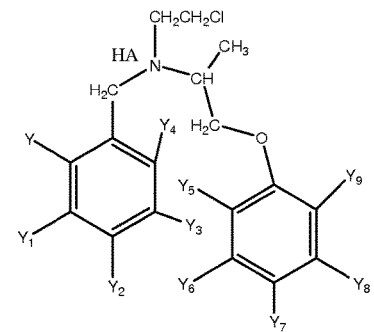
Figure 6:
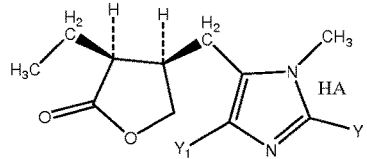
Figure 6:
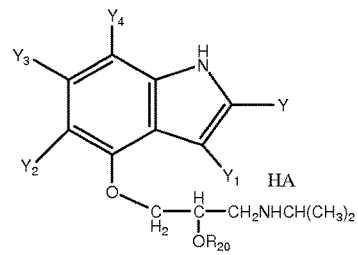
Figure 6:
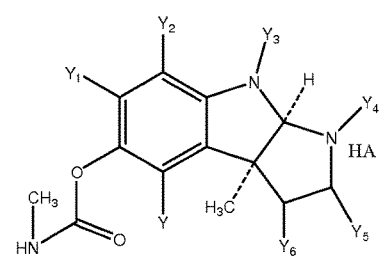
Figure 6:
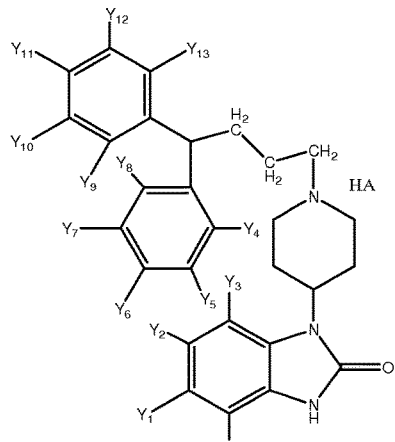
Figure 6:
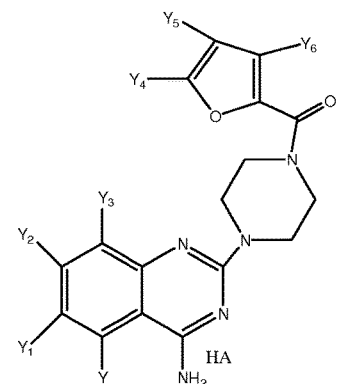
Figure 6:
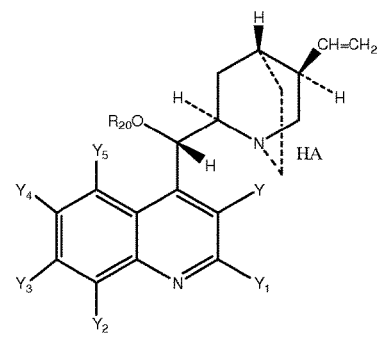
Figure 6:
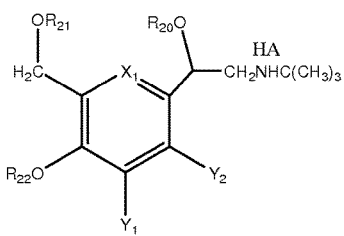
Figure 6:
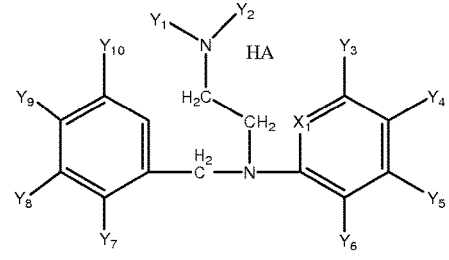
Figure 6:
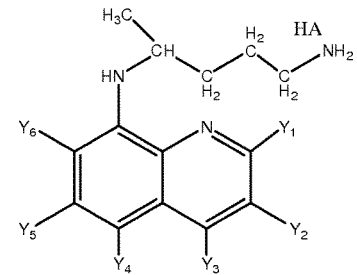
Figure 6:
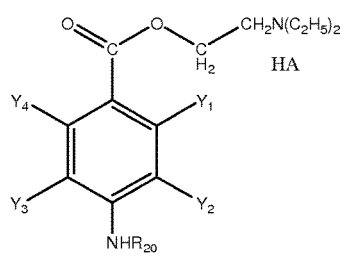
Figure 6:
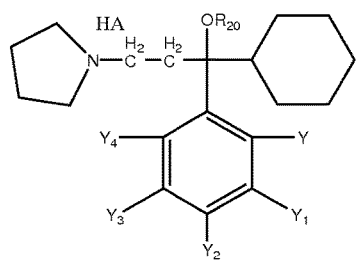
Figure 6:
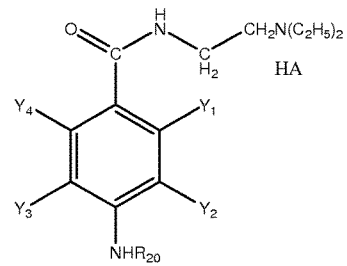
Figure 6:
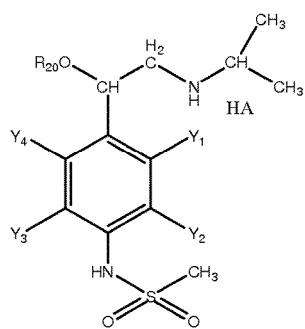
Figure 6:
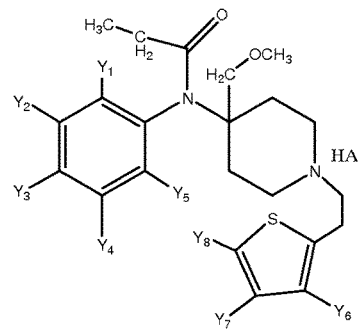
Figure 6:
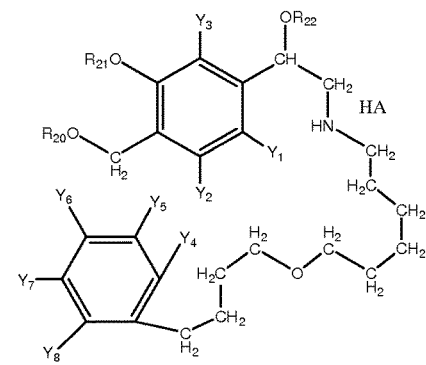
Figure 6:
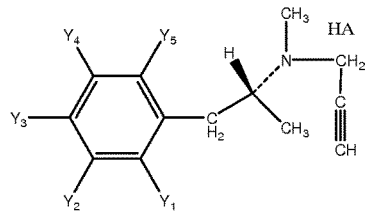
Figure 6:
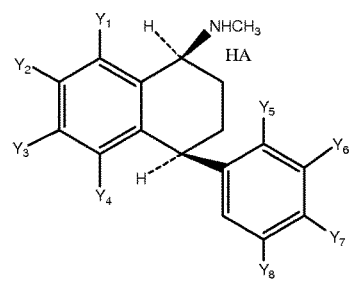
Figure 6:
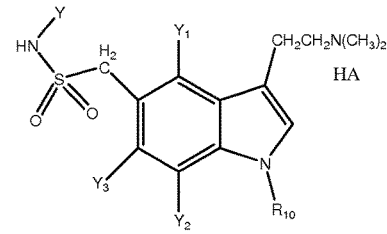
Figure 6:
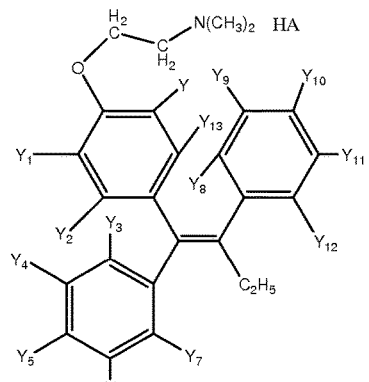
Figure 6:
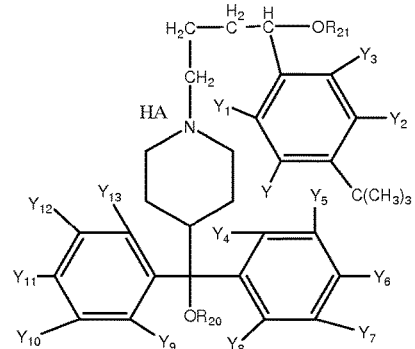
Figure 6:
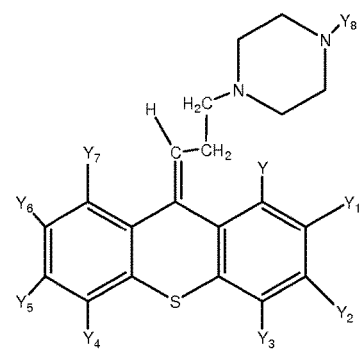
Figure 6:
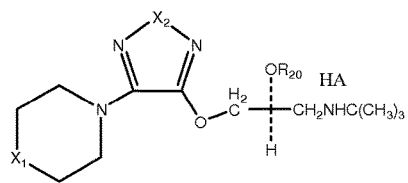
Figure 6:
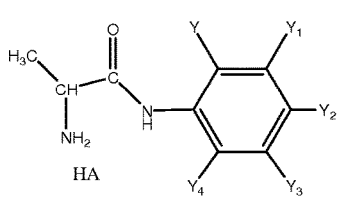
Figure 6:
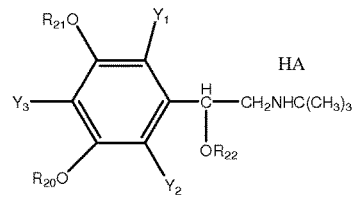
Figure 6:
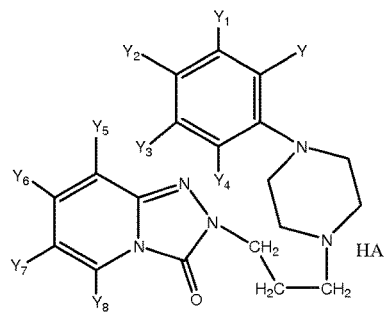
Figure 6:
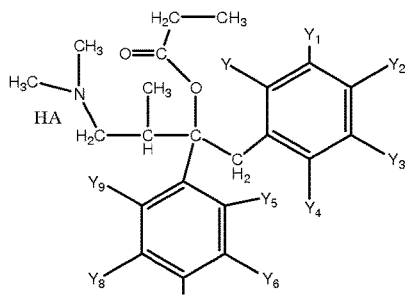
Figure 6:
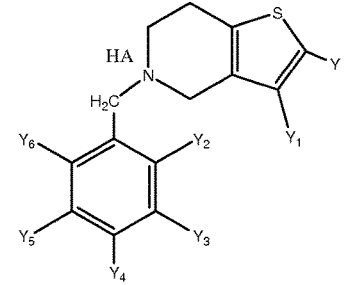
Figure 6:
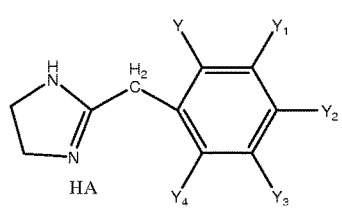
Figure 6:
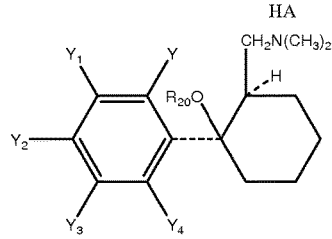
Figure 6:
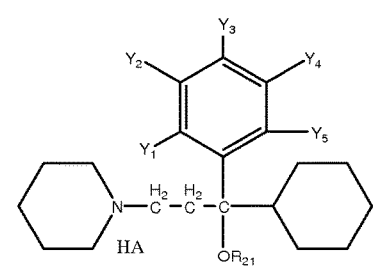
Figure 6:
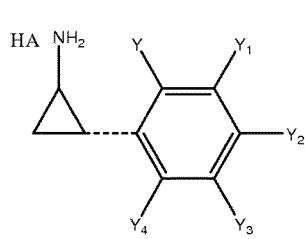
Figure 6:
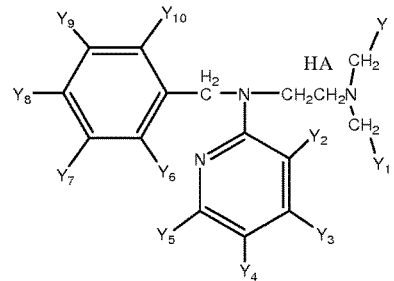
Figure 6:
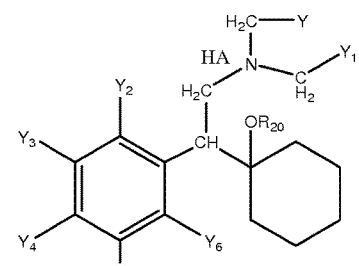
Figure 6:
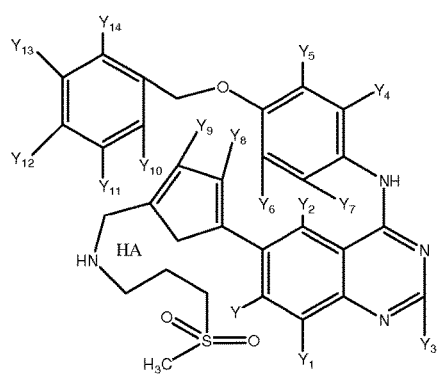
Figure 6:
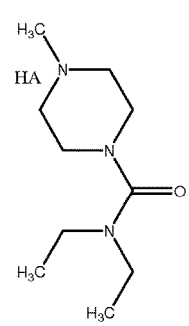
Figure 6:
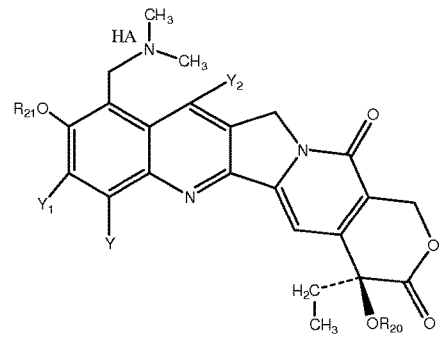
Figure 6:
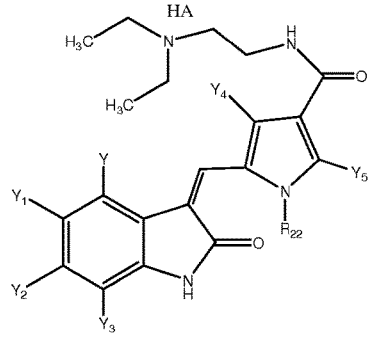
Figure 6:
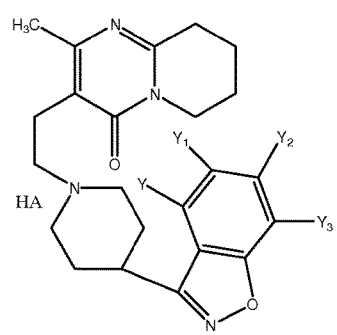
Figure 6:
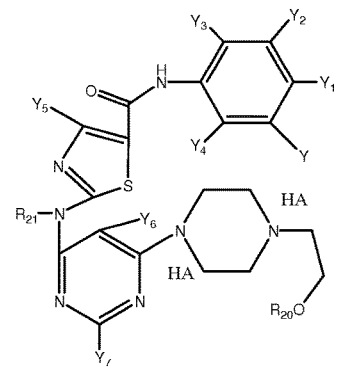
Figure 6:
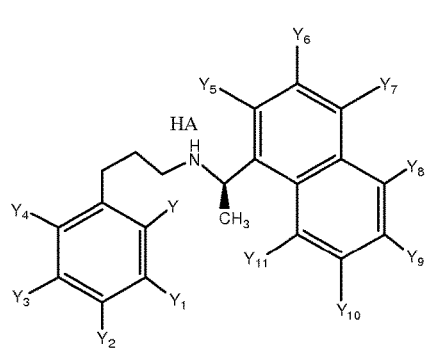
Figure 6:
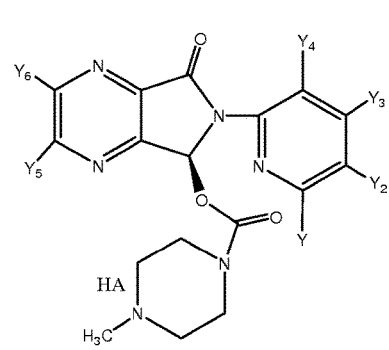
Figure 6:
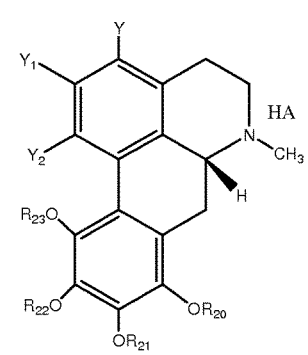
Figure 6:
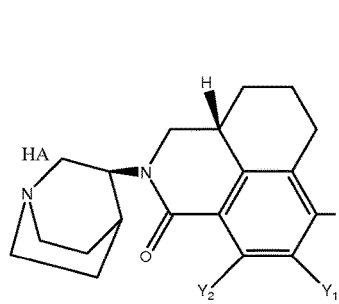
Figure 6:
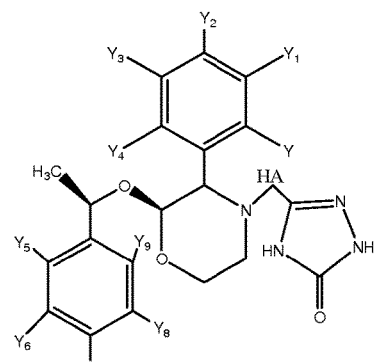
Figure 6:
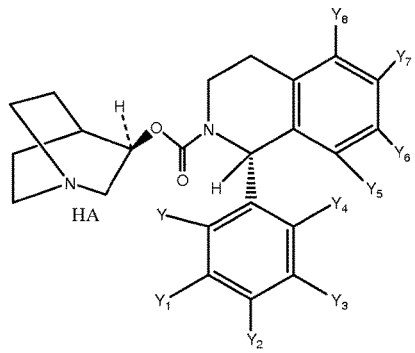
Figure 6:
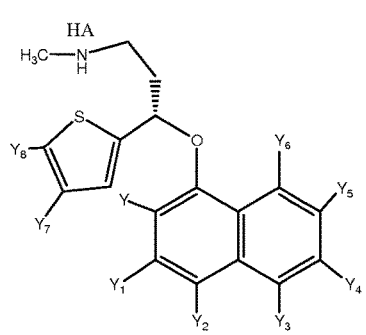
Figure 6:
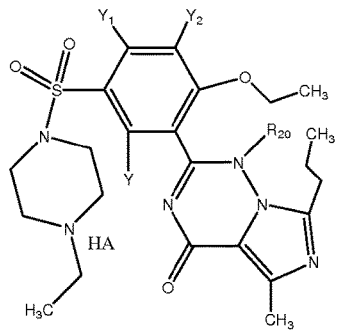
Figure 6:
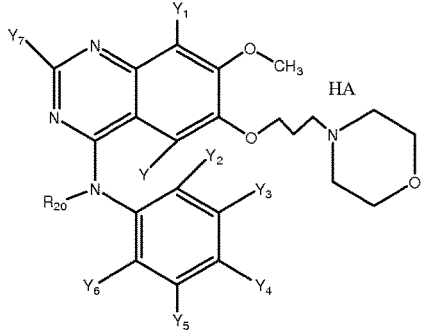
Figure 6:
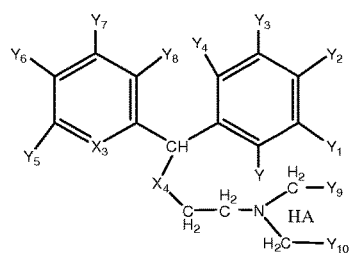
Figure 6:
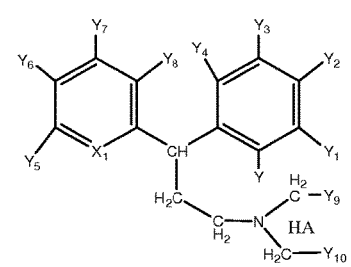
Figure 6:
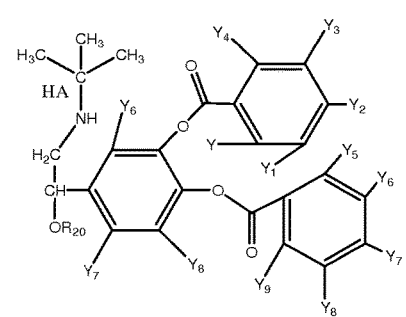
Figure 6:
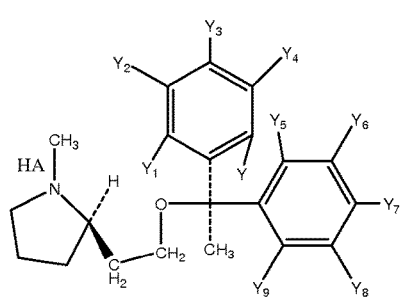
Figure 6:
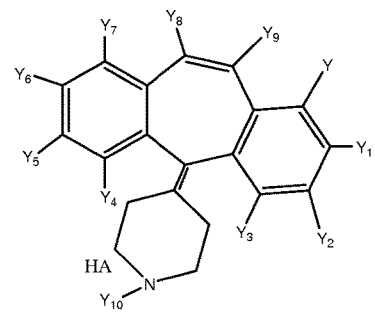
Figure 6:
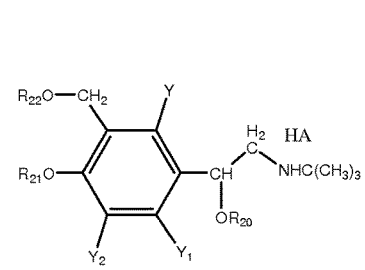
Figure 6:
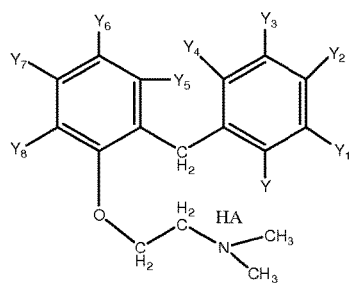
Figure 6:
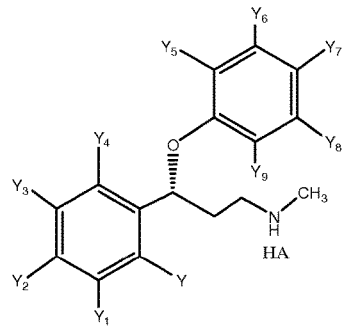
Figure 6:
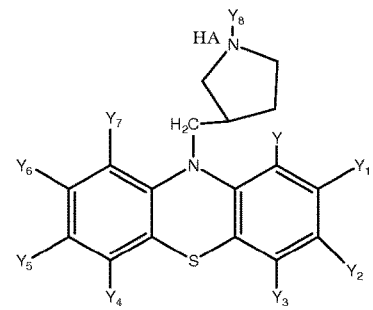
Figure 6:
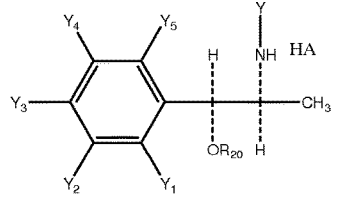
Figure 6:
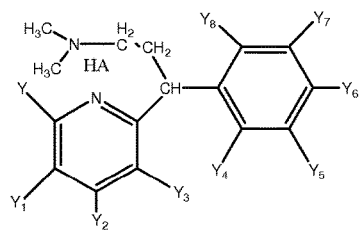
Figure 6:
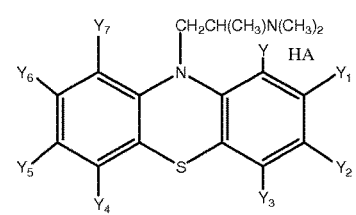
Figure 6:
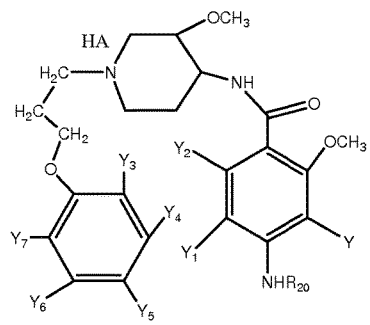
Figure 6:
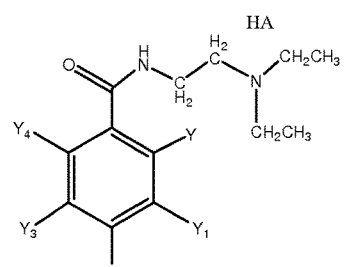
Figure 6:
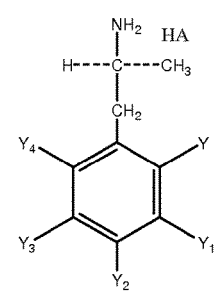
Figure 6:
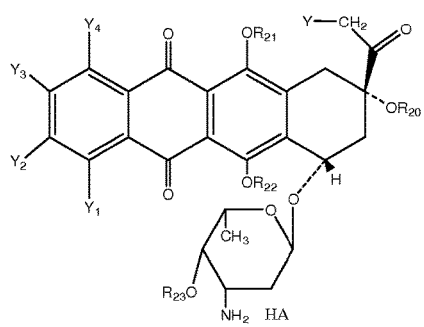
Figure 6:
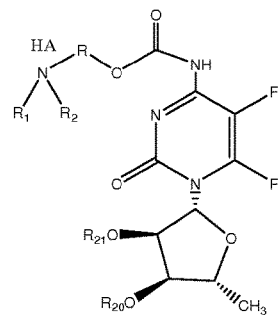
Figure 6:
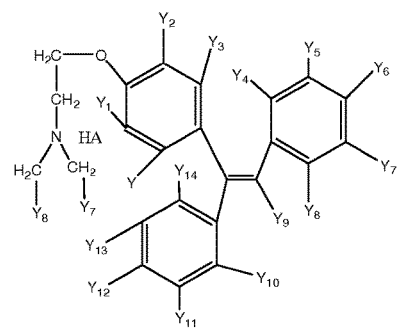
Figure 6:
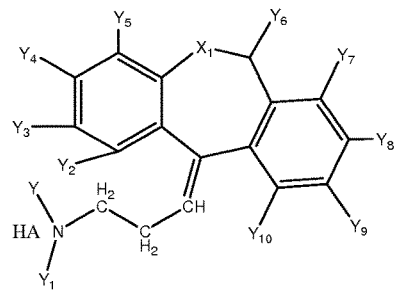
Figure 6:
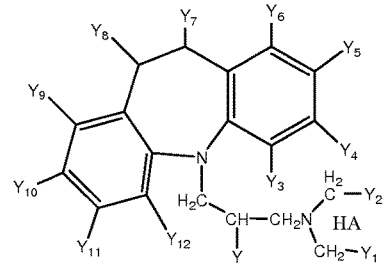
Figure 6:
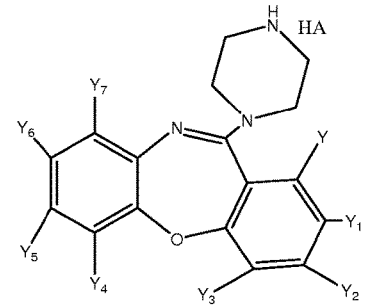
Figure 6:
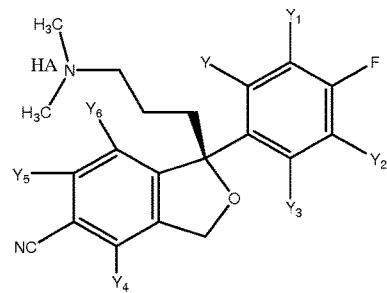
Figure 6:
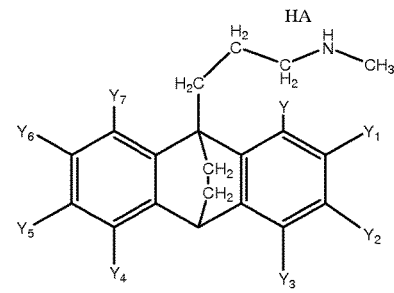
Figure 6:
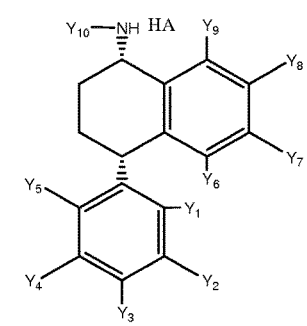
Figure 6:
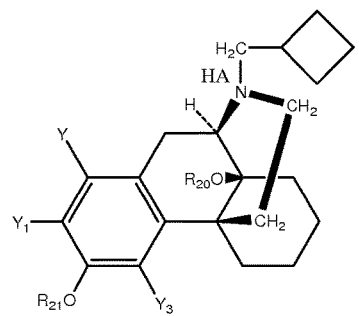
Figure 6:
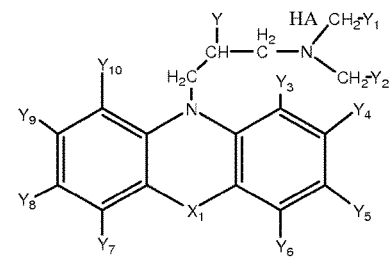
Figure 6:
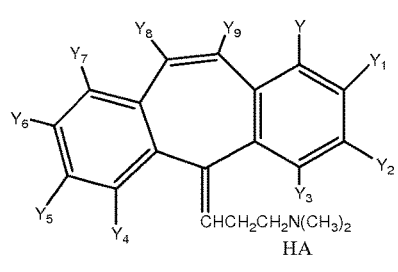
Figure 6:
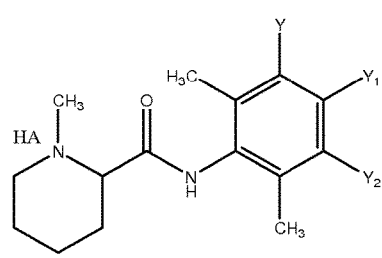
Figure 6:
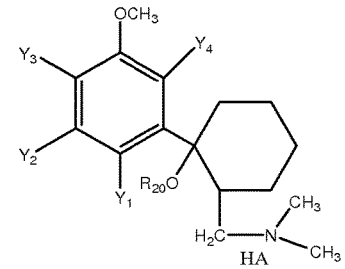
Figure 6:
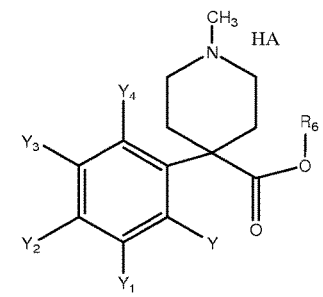
Figure 6:
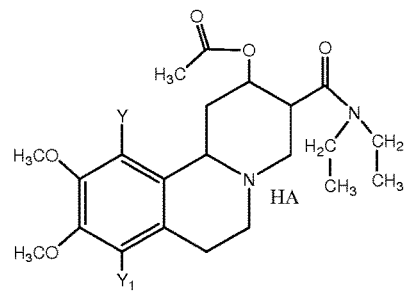
Figure 6:
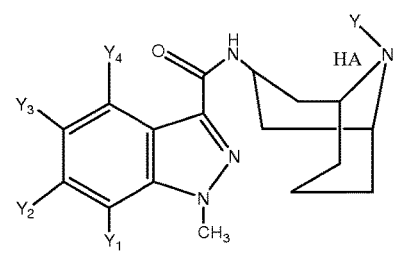
Figure 6:
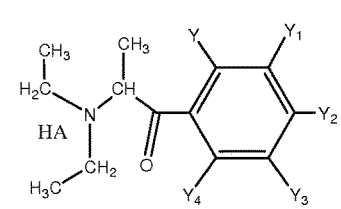
Figure 6:
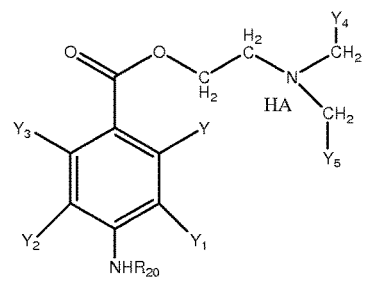
Figure 6:
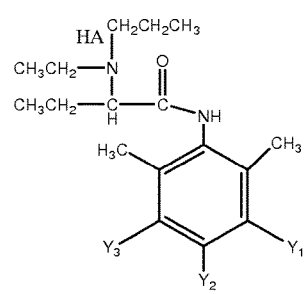
Figure 6:
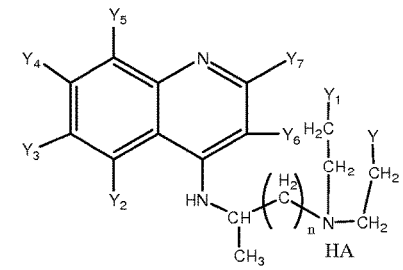
Figure 6:
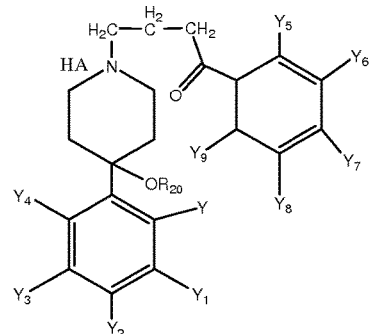
Figure 6:
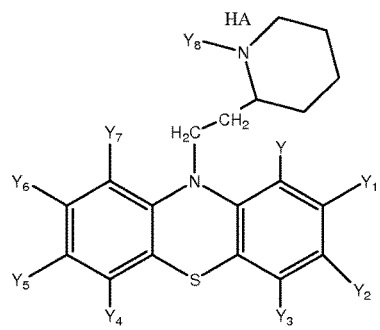
Figure 6:
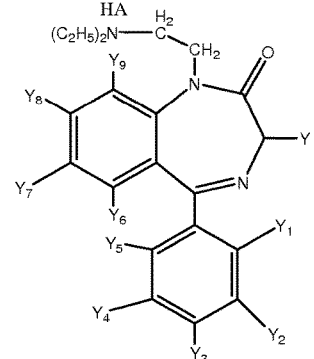
Figure 6:
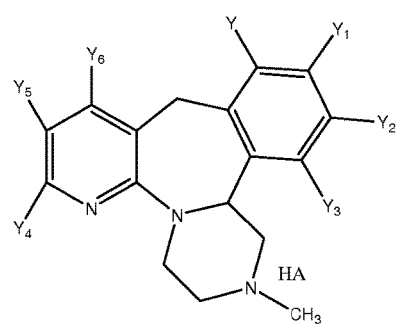
Figure 6:
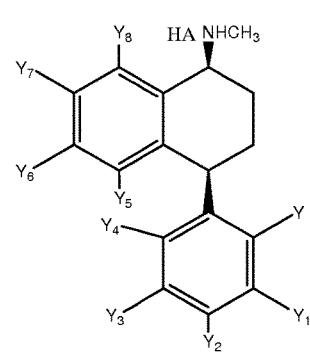
Figure 6:
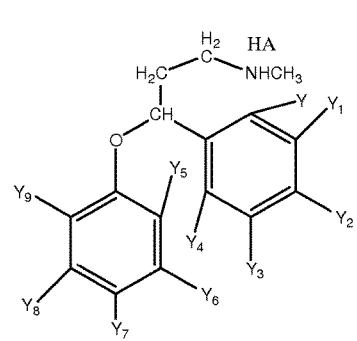
Figure 6:
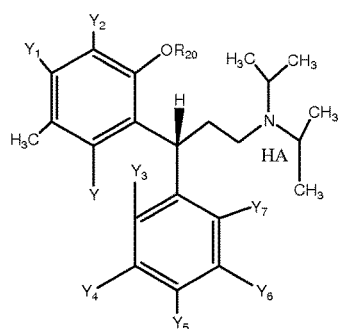
Figure 6:
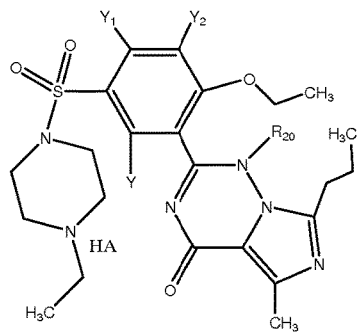
Figure 6:
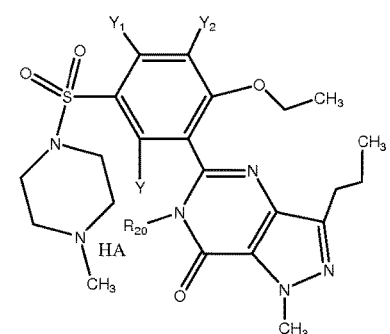
Figure 6:
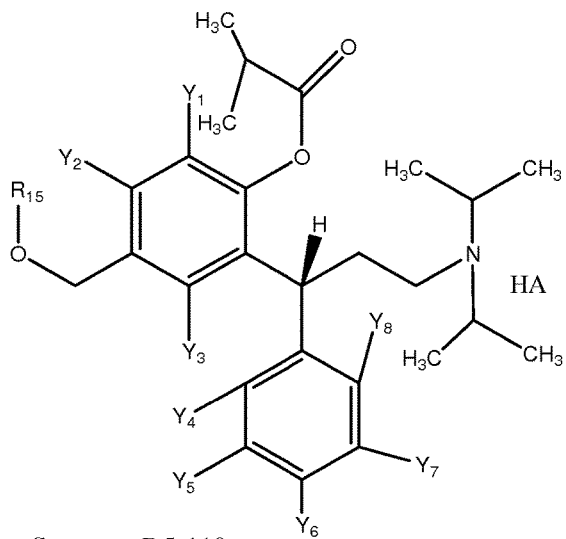
Figure 6:
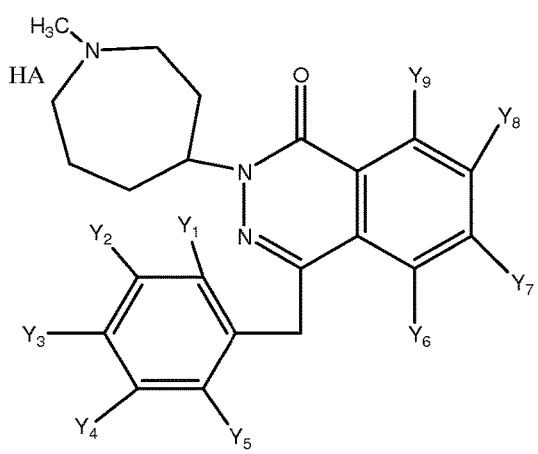
Figure 6:
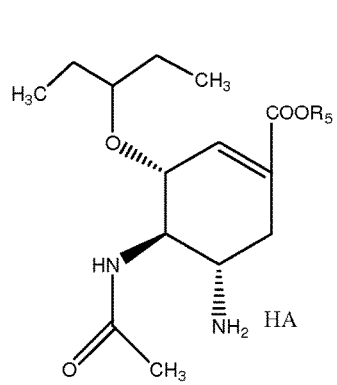
Figure 6:
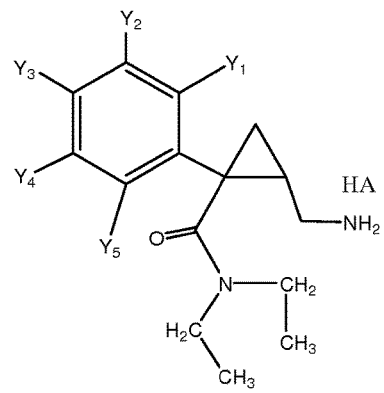
Figure 6:
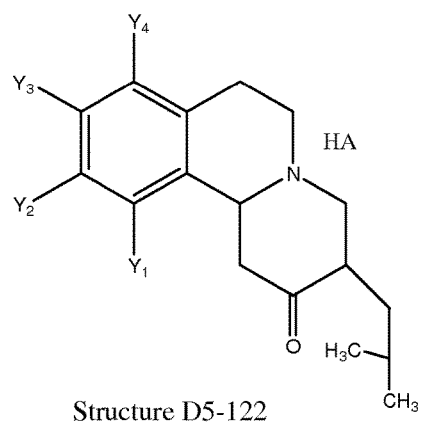
Figure 6:
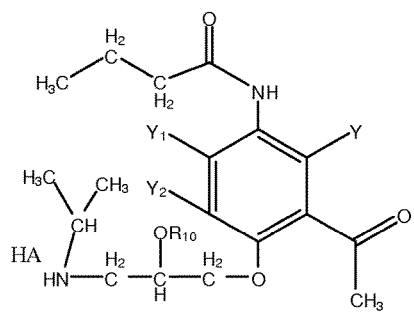
Figure 6:
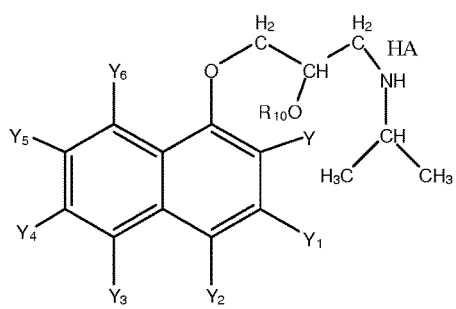
Figure 6:
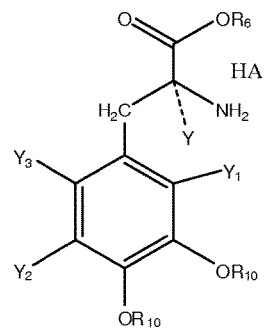
Figure 6:
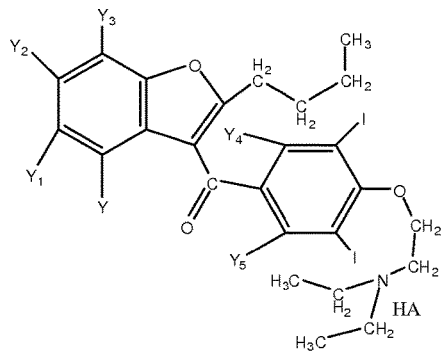
Figure 6:
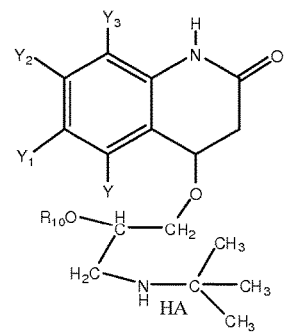
Figure 6:
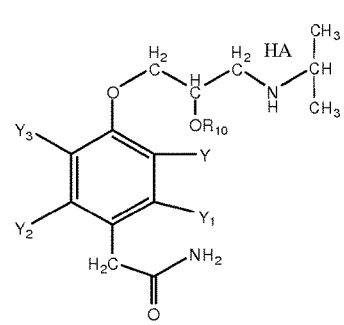
Figure 6:
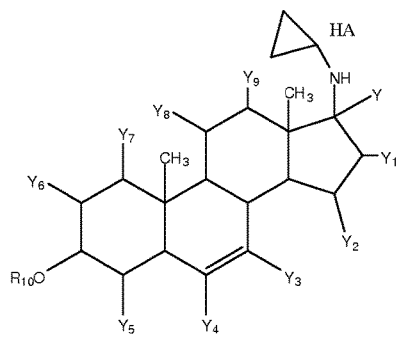
Figure 6:
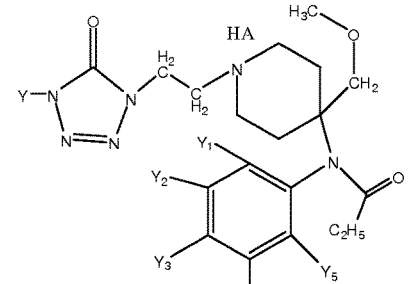
Figure 6:
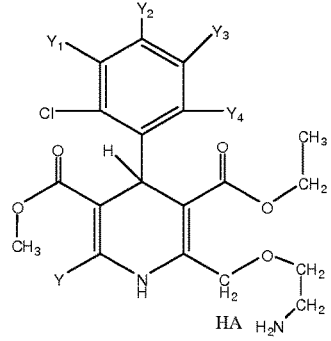
Figure 6:
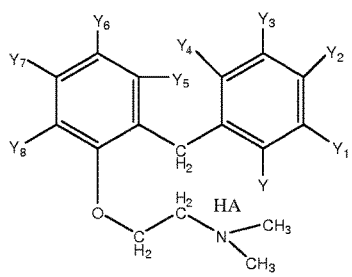
Figure 6:
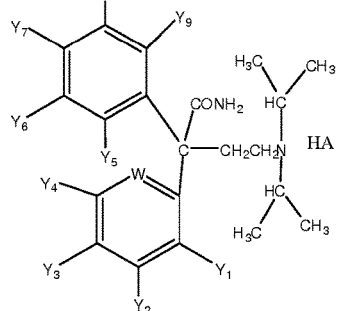
Figure 6:
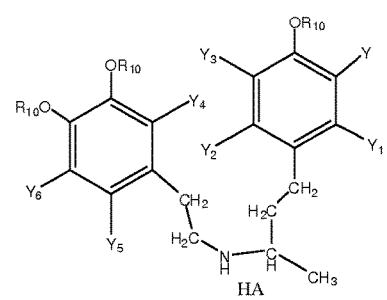
Figure 6:
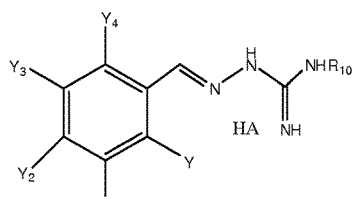
Figure 6:
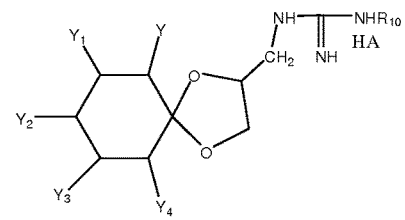
Figure 6:
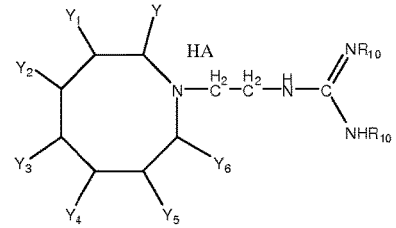
Figure 6:
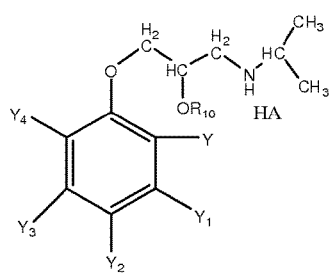
Figure 6:
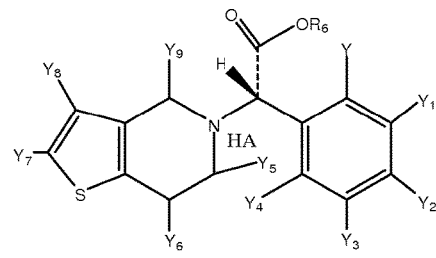
Figure 6:
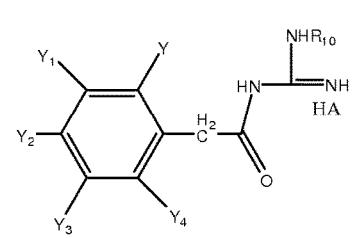
Figure 6:
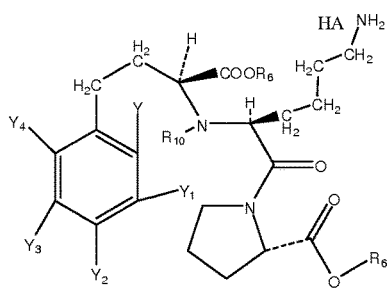
Figure 6:
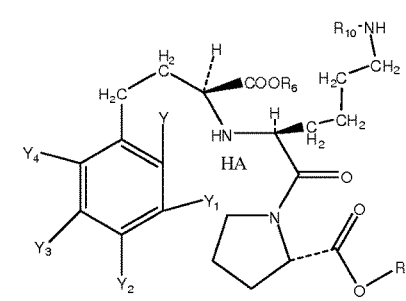
Figure 6:
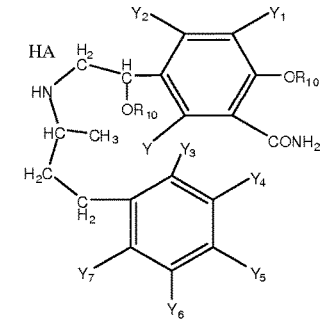
Figure 6:
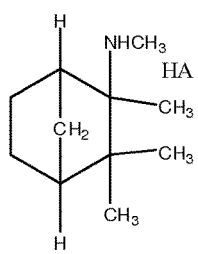
Figure 6:
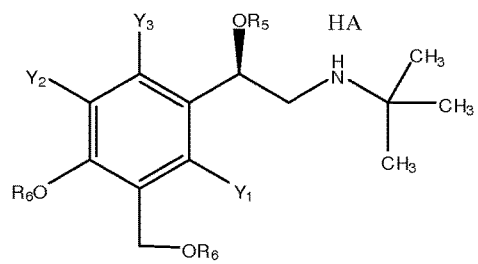
Figure 6:
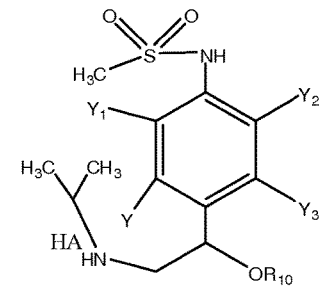
Figure 6:
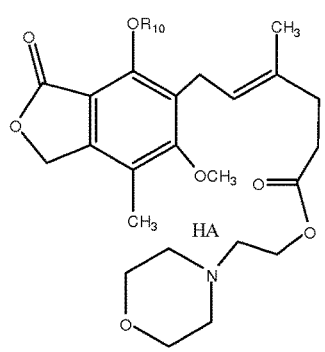
Figure 6:
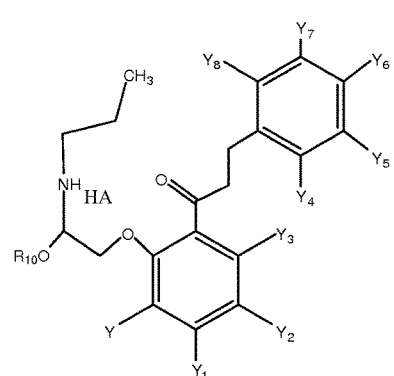
Figure 6:
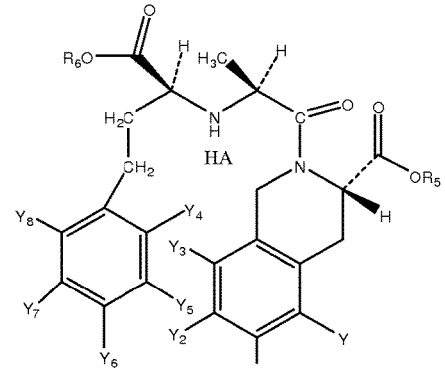
Figure 6:
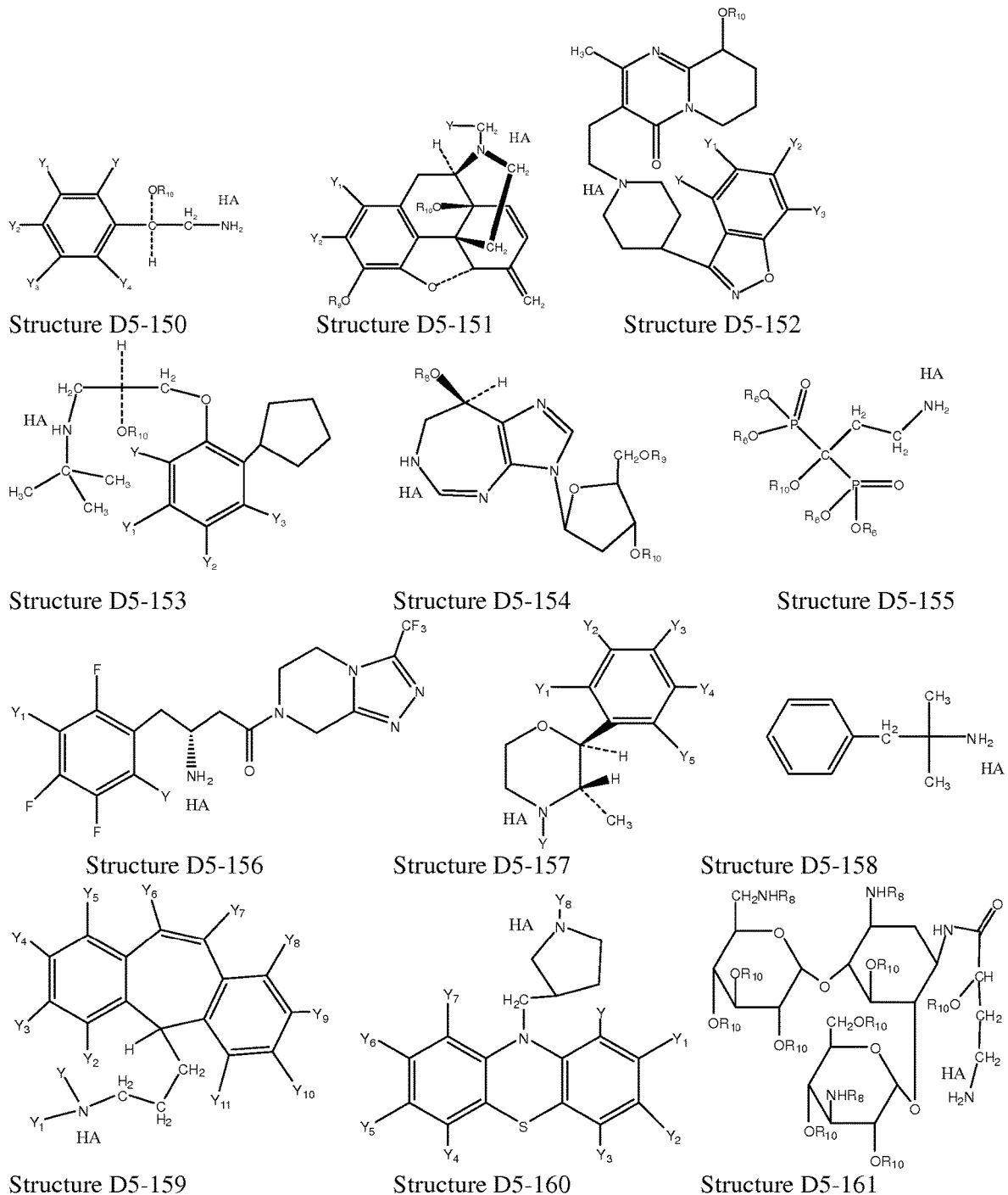
Figure 6:
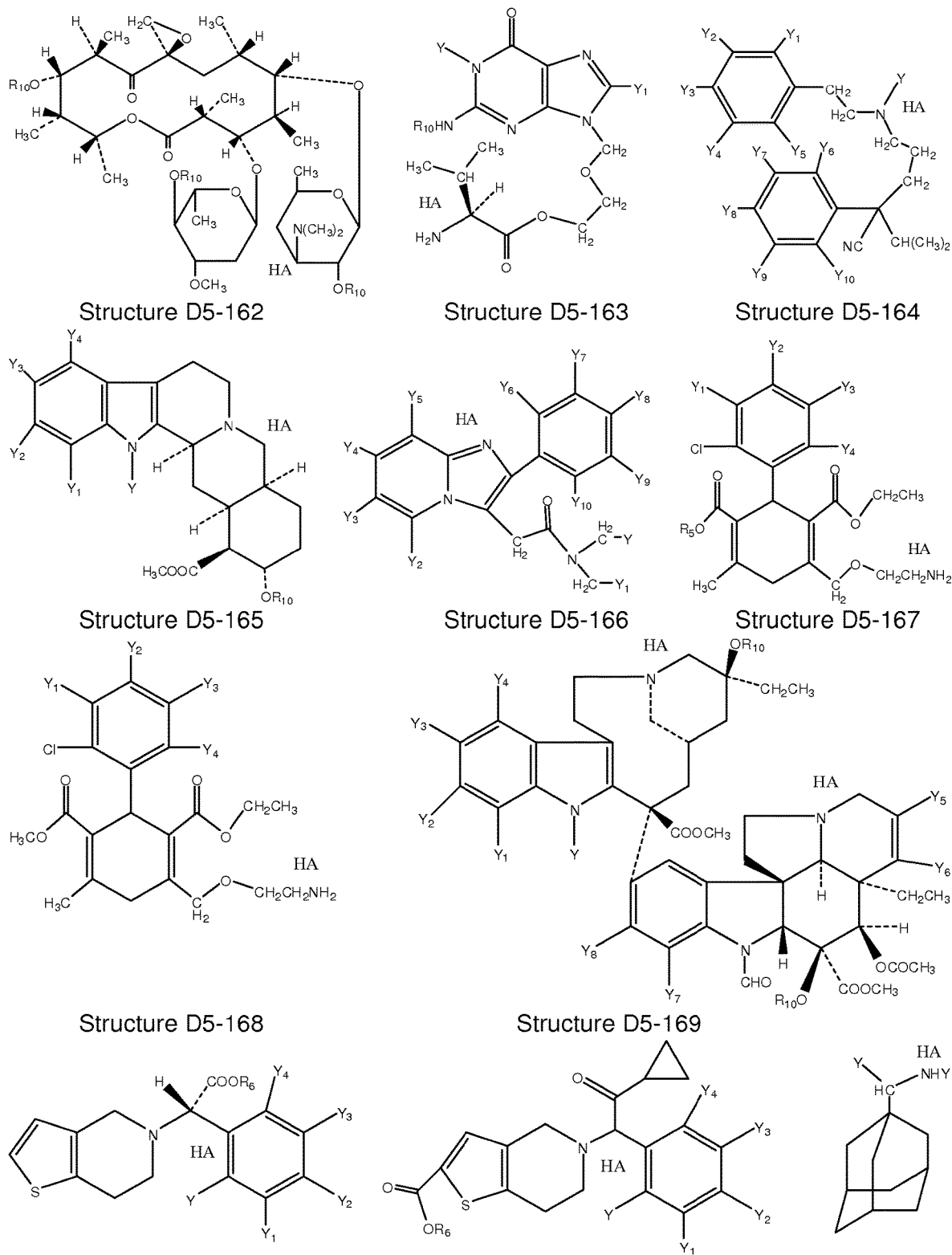
Figure 6:
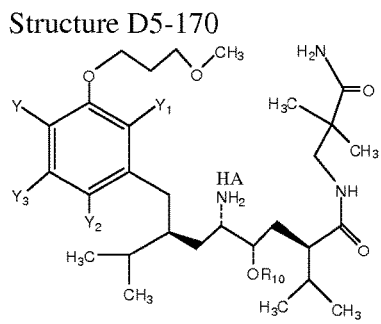
Figure 6:
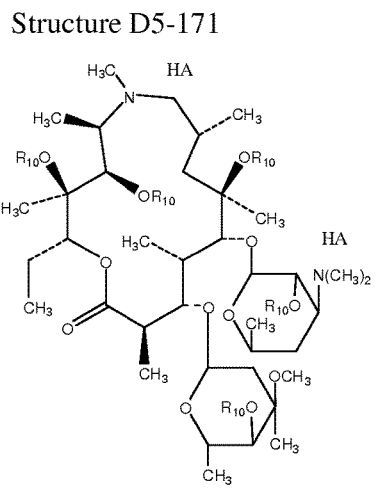
Figure 6:
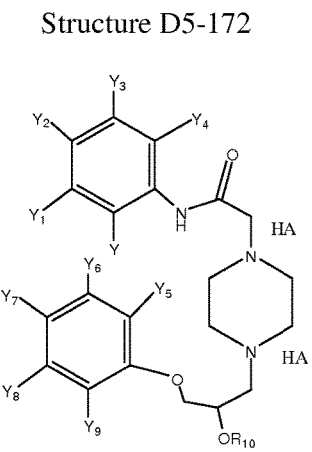
Figure 6:
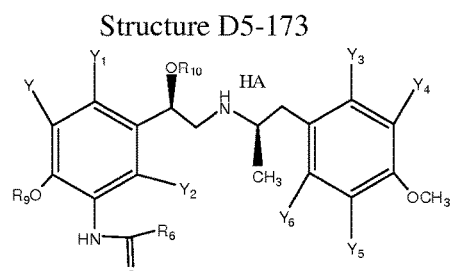
Figure 6:
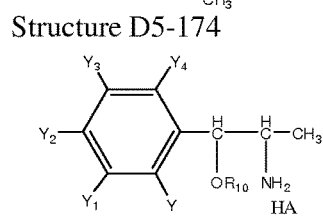
Figure 6:
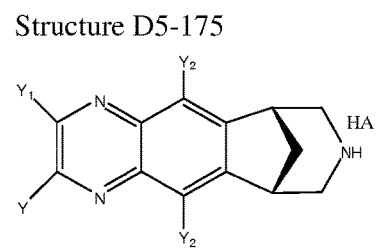
Figure 6:
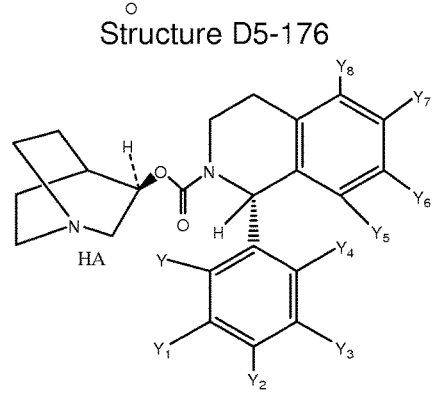
Figure 6:
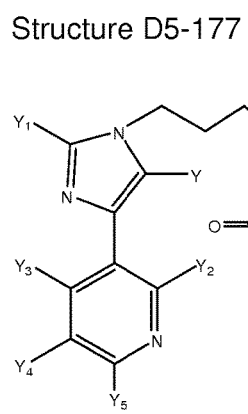
Figure 6:
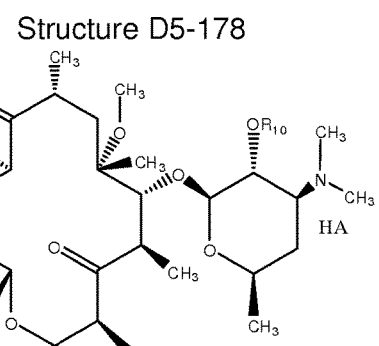
Figure 6:
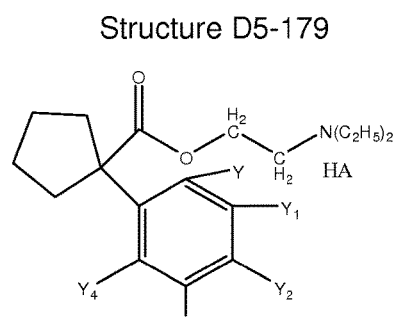
Figure 6:
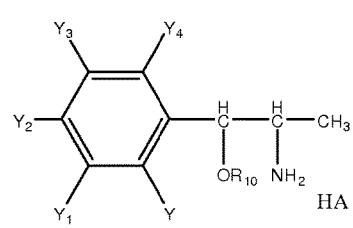
Figure 6:
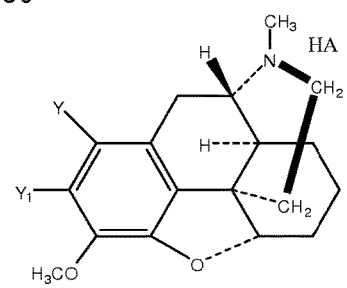
Figure 6:
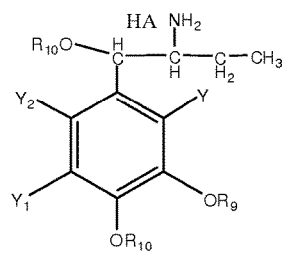
Figure 6:
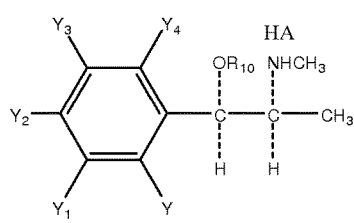
Figure 6:
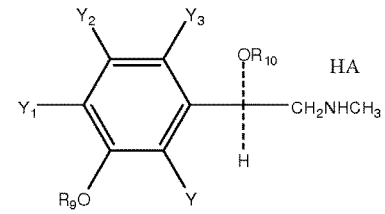
Figure 6:
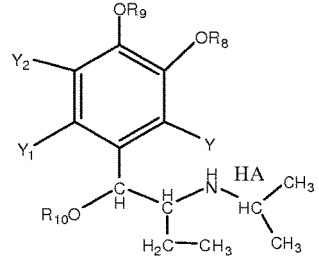
Figure 6:
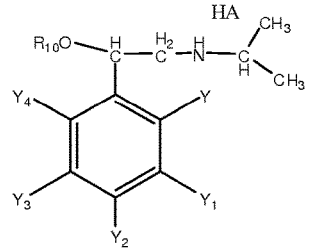
Figure 6:
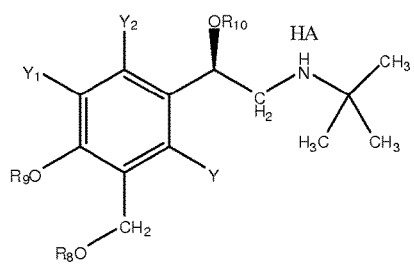
Figure 6:
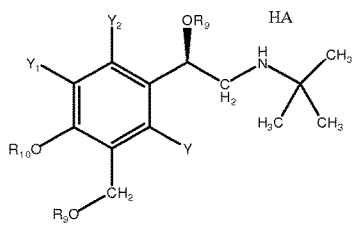
Figure 6:
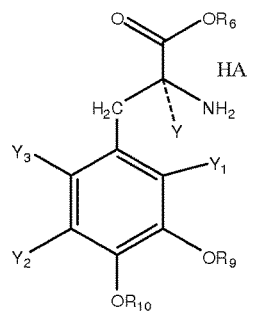
Figure 6:
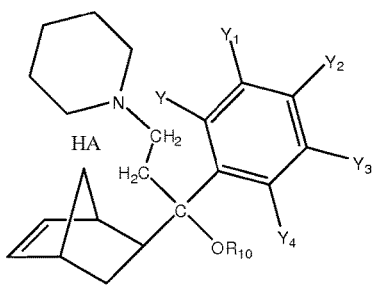
Figure 6:
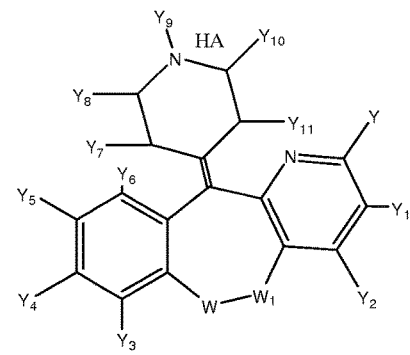
Figure 6:
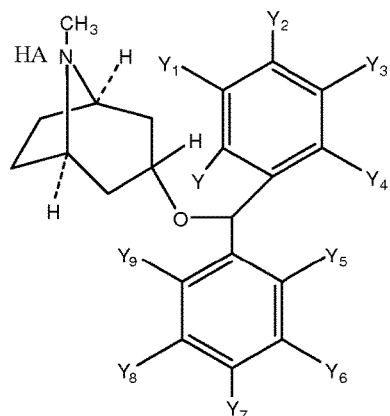
Figure 6:
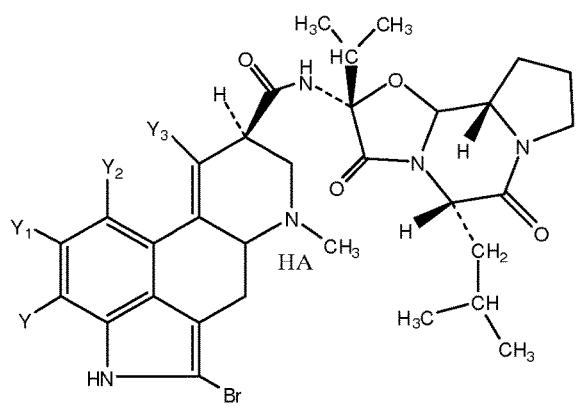
Figure 6:
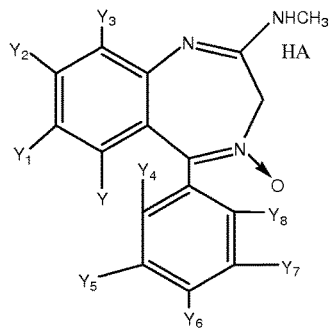
Figure 6:
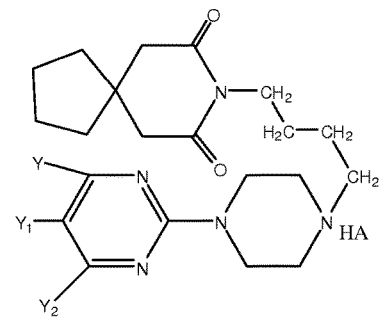
Figure 6:
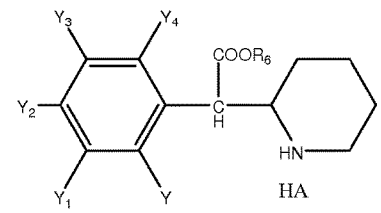
Figure 6:
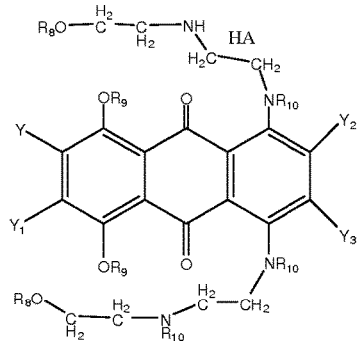
Figure 6:
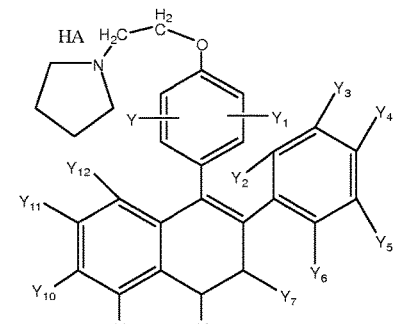
Figure 6:
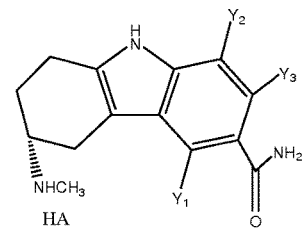
Figure 6:
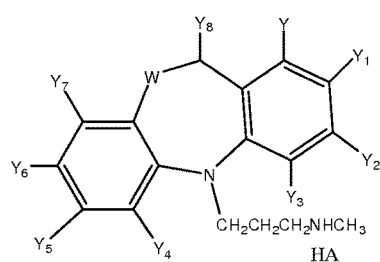
Figure 6:
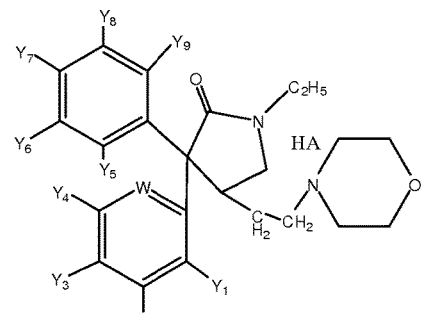
Figure 6:
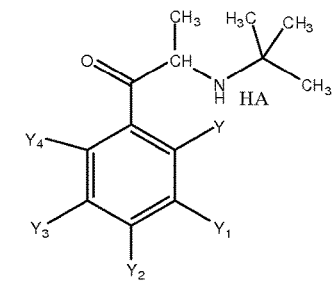
Figure 6:
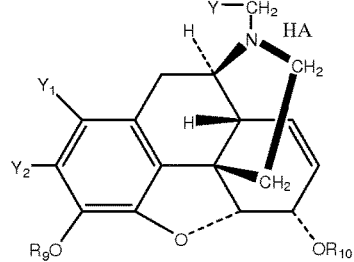
Figure 6:
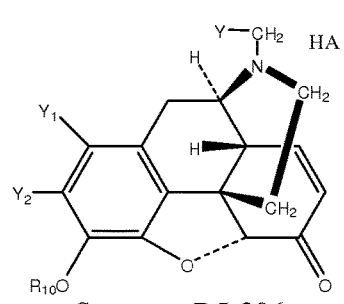
Figure 6:
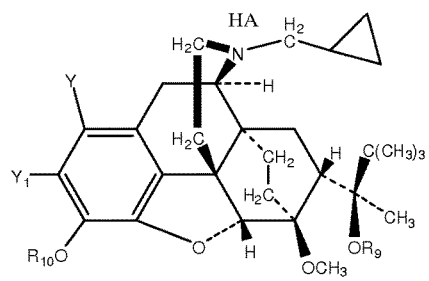
Figure 6:
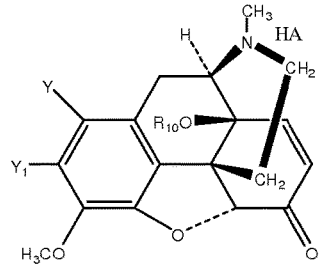
Figure 6:
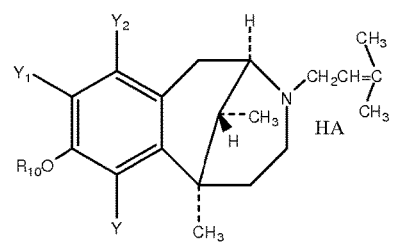
Figure 6:
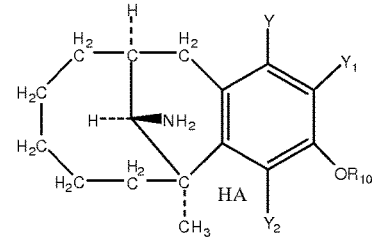
Figure 6:
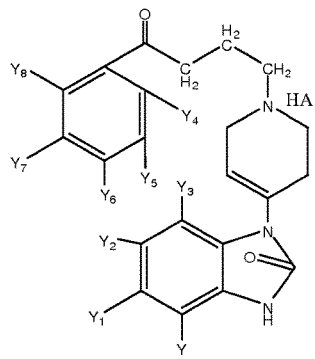
Figure 6:
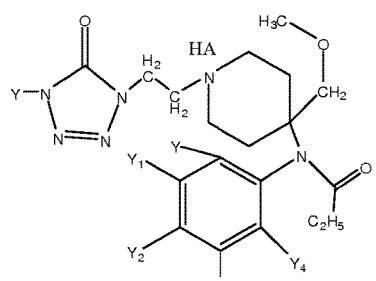
Figure 6:
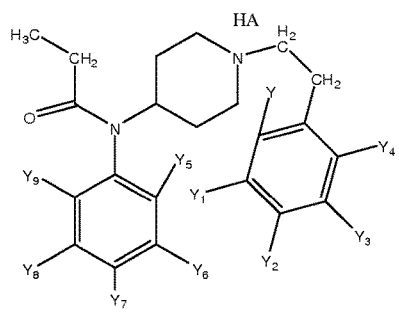
Figure 6:
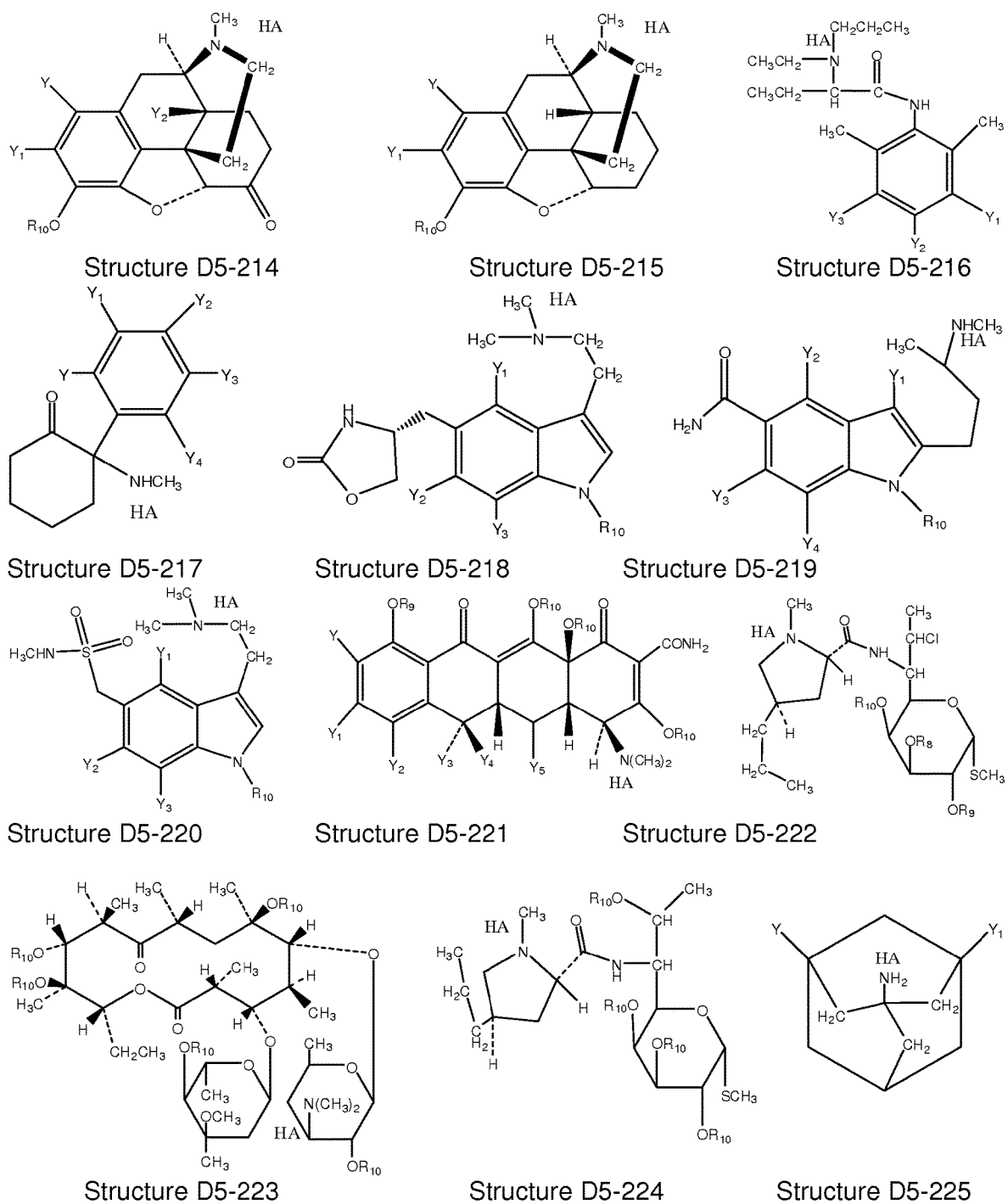
Figure 6:
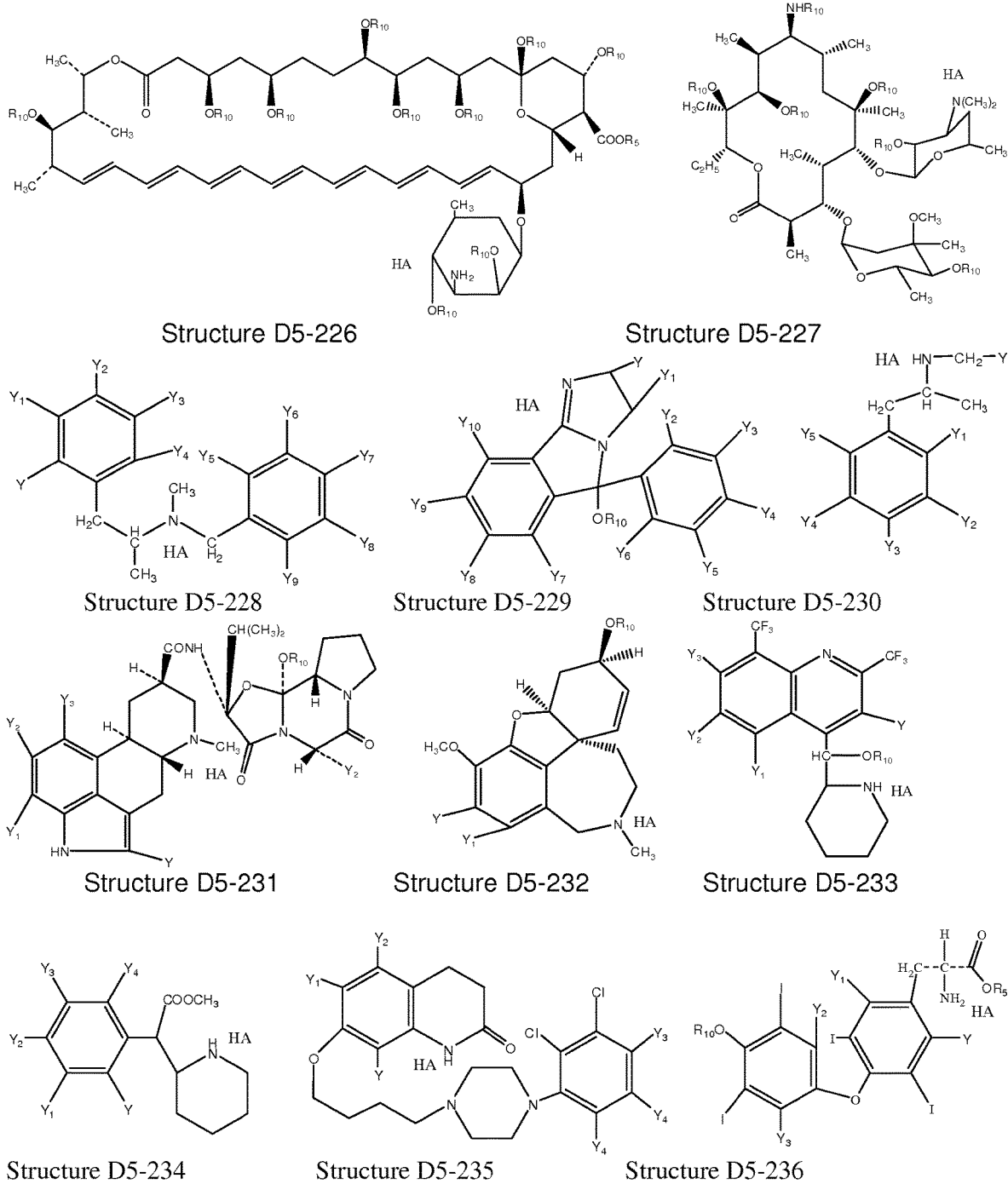
Figure 6:
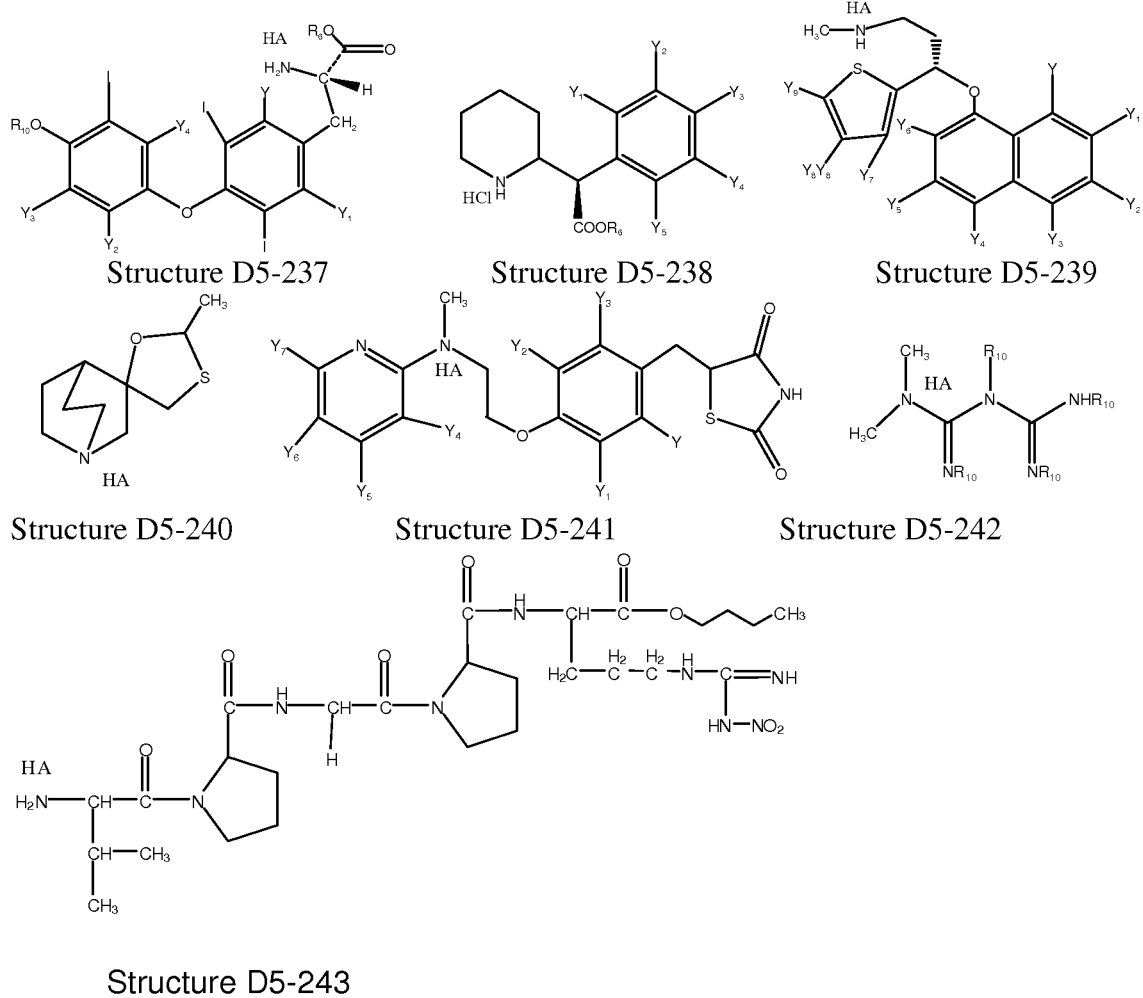

In certain embodiments, the lipophilic portion of a HPC of a parent drug that has both lipophilic portion and a primary, secondary or tertiary amine group is converted from a hydrophilic group by organic synthesis as described supra. In certain embodiments, a HPC is selected from the group consisting of Structure D5-1, Structure D5-2, Structure D5-3, Structure D5-4, Structure D5-5, Structure D5-6, Structure D5-7, Structure D5-8, Structure D5-9, Structure D5-10, Structure D5-11, Structure D5-12, Structure D5-13, Structure D5-14, Structure D5-15, Structure D5-16, Structure D5-17, Structure D5-18, Structure D5-19, Structure D5-20, Structure D5-21, Structure D5-22, Structure D5-23, Structure D5-24, Structure D5-25, Structure D5-26, Structure D5-27, Structure D5-28, Structure D5-29, Structure D5-30, Structure D5-31, Structure D5-32, Structure D5-33, Structure D5-34, Structure D5-35, Structure D5-36, Structure D5-37, Structure D5-38, Structure D5-39, Structure D5-40, Structure D5-41, Structure D5-42, Structure D5-43, Structure D5-44, Structure D5-45, Structure D5-46, Structure D5-47, Structure D5-48, Structure D5-49, Structure D5-50, Structure D5-51, Structure D5-52, Structure D5-53, Structure D5-54, Structure D5-55, Structure D5-56, Structure D5-57, Structure D5-58, Structure D5-59, Structure D5-60, Structure D5-61, Structure D5-62, Structure D5-63, Structure D5-64, Structure D5-65, Structure D5-66, Structure D5-67, Structure D5-68, Structure D5-69, Structure D5-70, Structure D5-71, Structure D5-72, Structure D5-73, Structure D5-74, Structure D5-75, Structure D5-76, Structure D5-77, Structure D5-78, Structure D5-79, Structure D5-80, Structure D5-81, Structure D5-82, Structure D5-83, Structure D5-84, Structure D5-85, Structure D5-86, Structure D5-87, Structure D5-88, Structure D5-89, Structure D5-90, Structure D5-91, Structure D5-92, Structure D5-93, Structure D5-94, Structure D5-95, Structure D5-96, Structure D5-97, Structure D5-98, Structure D5-99, Structure D5-100, Structure D5-101, Structure D5-102, Structure D5-103, Structure D5-104, Structure D5-105, Structure D5-106, Structure D5-107, Structure D5-108, Structure D5-109, Structure D5-110, Structure D5-111, Structure D5-112, Structure D5-113, Structure D5-114, Structure D5-115, Structure D5-116, Structure D5-117, Structure D5-118, Structure D5-119, Structure D5-120, Structure D5-121, Structure D5-122, Structure D5-123, Structure D5-124, Structure D5-125, Structure D5-126, Structure D5-127, Structure D5-128, Structure D5-129, Structure D5-130, Structure D5-131, Structure D5-132, Structure D5-133, Structure D5-134, Structure D5-135, Structure D5-136, Structure D5-137, Structure D5-138, Structure D5-139, Structure D5-140, Structure D5-141, Structure D5-142, Structure D5-143, Structure D5-144, Structure D5-145, Structure D5-146, Structure D5-147, Structure D5-148, Structure D5-149, Structure D5-150, Structure D5-151, Structure D5-152, Structure D5-153, Structure D5-154, Structure D5-155, Structure D5-156, Structure D5-157, Structure D5-158, Structure D5-159, Structure D5-160, Structure D5-161, Structure D5-162, Structure D5-163, Structure D5-164, Structure D5-165, Structure D5-166, Structure D5-167, Structure D5-168, Structure D5-169, Structure D5-170, Structure D5-171, Structure D5-172, Structure D5-173, Structure D5-174, Structure D5-175, Structure D5-176, Structure D5-177, Structure D5-178, Structure D5-179, Structure D5-180, Structure D5-181, Structure D5-182, Structure D5-183, Structure D5-184, Structure D5-185, Structure D5-186, Structure D5-187, Structure D5-188, Structure D5-189, Structure D5-190, Structure D5-191, Structure D5-192, Structure D5-193, Structure D5-194, Structure D5-195, Structure D5-196, Structure D5-197, Structure D5-198, Structure D51-199, Structure D5-200, Structure D5-201, Structure D5-202, Structure D5-203, Structure D5-204, Structure D5-205, Structure D5-206, Structure D5-207, Structure D5-208, Structure D5-209, Structure D5-210, Structure D5-211, Structure D5-212, Structure D5-213, Structure D5-214, Structure D5-215, Structure D5-216, Structure D5-217, Structure D5-218, Structure D5-219, Structure D5-220, Structure D5-221, Structure D5-222, Structure D5-223, Structure D5-224, Structure D5-225, Structure D5-226, Structure D5-227, Structure D5-228, Structure D5-229, Structure D5-230, Structure D5-231, Structure D5-232, Structure D5-233, Structure D5-234, Structure D5-235, Structure D5-236, Structure D5-237, Structure D5-238, Structure D5-239, Structure D5-240, Structure D5-241, Structure D5-242, and Structure D5-243, (FIG. 6), including stereoisomers and salts thereof.

In certain embodiments, a salt of a HPC is a pharmaceutically acceptable salt.

As used herein, the term "pharmaceutically acceptable salt" means those salts of compounds of the present disclosure that are safe for application in a subject. Pharmaceutically acceptable salts include salts of acidic or basic groups present in compounds of the present disclosure. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,11-methylene-bis-(2-hydroxy-3-naphthoate)) salts. Certain compounds of the present disclosure can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1977), incorporated herein by reference.

As used herein, the term "pharmaceutically acceptable acid" means acids that can form salts with compounds of the present disclosure that are safe for application in a subject. Examples of pharmaceutically acceptable acid include, but are not limited to, e.g. hydrochloride, hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid.

As used herein, unless specified otherwise, the term "alkyl" means a branched or unbranched, saturated or unsaturated, monovalent or multivalent hydrocarbon group, including saturated alkyl groups, alkenyl groups and alkynyl groups. Examples of alkyl include, but are not limited to, methyl, ethyl, propyl, isopropyl, butyl, isobutyl, t-butyl, pentyl, hexyl, heptyl, octyl, nonyl, decyl, undecyl, dodecyl, ethenyl, propenyl, butenyl, isobutenyl, pentenyl, hexenyl, heptenyl, octenyl, nonenyl, decenyl, undecenyl, dodecenyl, ethynyl, propynyl, butynyl, isobutynyl, pentynyl, hexynyl, heptynyl, octynyl, nonynyl, decynyl, undecynyl, dodecynyl, methylene, ethylene, propylene, isopropylene, butylene, isobutylene, t-butylene, pentylene, hexylene, heptylene, octylene, nonylene, decylene, undecylene and dodecylene. In certain embodiments, the hydrocarbon group contains 1 to 30 carbons. In certain embodiments, the hydrocarbon group contains 1 to 20 carbons. In certain embodiments, the hydrocarbon group contains 1 to 12 carbons. In certain embodiments, the hydrocarbon group contains 1 to 6 carbons.

As used herein, unless specified otherwise, the term "cycloalkyl" means an alkyl which contains at least one ring and no aromatic rings. In certain embodiments, a cycloalkyl is a saturated cycloalkyl groups. In certain embodiments, a cycloalkyl group comprises unsaturated bonds. Examples of cycloalkyl include, but are not limited to, cyclopropyl, cyclobutyl, cyclopentyl, cyclohexyl, cycloheptyl, cyclooctyl, cyclononyl, cyclodecyl, cycloundecyl and cyclododecyl. In certain embodiments, the hydrocarbon chain contains 1 to 30 carbons. In certain embodiments, the hydrocarbon group contains 1 to 20 carbons. In certain embodiments, the hydrocarbon group contains 1 to 12 carbons. In certain embodiments, the hydrocarbon group contains 1 to 6 carbons.

As used herein, unless specified otherwise, the term "heterocycloalkyl" means a cycloalkyl wherein at least one ring atom is a non-carbon atom. Examples of the non-carbon ring atom include, but are not limited to, S, O and N.

As used herein, unless specified otherwise, the term "alkoxyl" means an alkyl, cycloalkyl or heterocycloalkyl, which contains one or more oxygen atoms. Examples of alkoxyl include, but are not limited to, —$CH_2$—OH, —$OCH_3$, —O-alkyl, -alkyl-OH, -alkyl-O-alkyl-, wherein the two alkyls can be the same or different.

As used herein, unless specified otherwise, the term "alkyl halide" means an alkyl, cycloalkyl or heterocycloalkyl, which contains one or more halogen atoms, wherein the halogen atoms can be the same or different. The term "halogen" means fluorine, chlorine, bromine or iodine. Examples of alkyl halide include, but are not limited to, -alkyl-F, -alkyl-Cl, -alkyl-Br, -alkyl-I, -alkyl(F)—, -alkyl(Cl)—, -alkyl(Br)— and -alkyl(I)—.

As used herein, unless specified otherwise, the term "alkylthio" means an alkyl, cycloalkyl or heterocycloalkyl, which contains one or more sulfur atoms. Examples of alkylthio include, but are not limited to, —$CH_2$—SH, —$SCH_3$, —S-alkyl, -alkyl-SH, -alkyl-S-alkyl-, wherein the two alkyls can be the same or different.

As used herein, unless specified otherwise, the term "alkylamino" means an alkyl, cycloalkyl or heterocycloalkyl, which contains one or more nitrogen atoms. Examples of alkylamino include, but are not limited to, —$CH_2$—NH, —$NCH_3$, —N(alkyl)-alkyl, —N-alkyl, -alkyl-$NH_2$, -alkyl-N-alkyl and -alkyl-N(alkyl)-alkyl wherein the alkyls can be the same or different.

As used herein, unless specified otherwise, the term "alkylcarbonyl" means an alkyl, cycloalkyl or heterocycloalkyl, which contains one or more carbonyl groups. Examples of alkylcarbonyl group include, but are not limited to, aldehyde group (—R'—C(O)—H), ketone group (—R'—C(O)—R"), carboxylic acid group (R'—COOH), ester group (—R"—COO—R'), carboxamide, (—R'''—COO—N(R)R"), enone group (—R''''—C(O)—C(R')=C(R")R'''), acyl halide group (—R'—C(O)—X) and acid anhydride group (—R"—C(O)-β-C(O)—R'), wherein R', R", R''' and R'''' are the same or different alkyl, cycloalkyl, or heterocycloalkyl.

As used herein, unless specified otherwise, the term "perfluoroalkyl" means an alkyl, cycloalkyl or heterocycloalkyl, which contains one or more fluoro group, including, without limitation, perfluoromethyl, perfluoroethyl, perfluoropropyl.

As used herein, unless specified otherwise, the term "aryl" means a chemical structure comprising one or more aromatic rings. In certain embodiments, the ring atoms are all carbon. In certain embodiments, one or more ring atoms are non-carbon, e.g. oxygen, nitrogen, or sulfur ("heteroaryl"). Examples of aryl include, without limitation, phenyl, benzyl, naphthalenyl, anthracenyl, pyridyl, quinoyl, isoquinoyl, pyrazinyl, quinoxalinyl, acridinyl, pyrimidinyl, quinazolinyl, pyridazinyl, cinnolinyl, imidazolyl, benzimidazolyl, purinyl, indolyl, furanyl, benzofuranyl, isobenzofuranyl, pyrrolyl, indolyl, isoindolyl, thiophenyl, benzothiophenyl, pyrazolyl, indazolyl, oxazolyl, benzoxazolyl, isoxazolyl, benzisoxazolyl, thiaxolyl, quanidino and benzothiazolyl.

Examples of HPC of Aspirin and Related Compounds.

In certain embodiments, a HPC has the following Structure P-NSAIA-1 or Structure P-NSAIA-2:

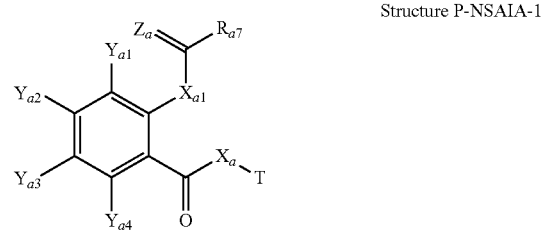

Structure P-NSAIA-1

-continued

Structure P-NSAIA-2

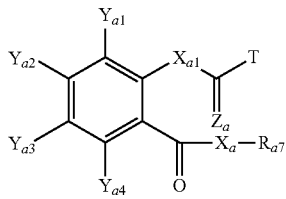

including stereoisomers and salts thereof.

In certain embodiments, a HPC has Structure P-NSAIA1 or Structure P-NSAIA-2, including stereoisomers and salts thereof wherein:

$Z_a$ is selected from the group consisting of O, S, $NOR_{a5}$, and $NR_{a5}$;

$X_a$ is selected from the group consisting of nothing, O, $P(O)OR_{a1}$, NH, $NR_{a1}$ and S;

$R_a$ is selected from the group consisting of nothing, alkyl, cycloalkyl, alkyloxyl, cycloalkyloxyl, alkenyl, cycloalkenyl, perfluoroalkyl, cycloperfluoroalkyl, alkyl halide, cycloalkyl halide, alkynyl, cycloalkynyl, aryl and heteroaryl moieties, wherein, any $CH_2$ may be independently replaced with O, S, CH=CH, C≡C, $CHR_{a5}$, $CR_{a5}R_{a6}$, aryl or heteroaryl moieties, any other moieties which are pharmaceutically acceptable;

$R_{a1}$ and $R_{a2}$ are independently selected from the group consisting of H, alkyl, cycloalkyl, alkyloxyl, cycloalkyloxyl, alkenyl, cycloalkenyl, perfluoroalkyl, cycloperfluoroalkyl, alkyl halide, cycloalkyl halide, alkynyl, cycloalkynyl, aryl and heteroaryl residues, wherein, any $CH_2$ may be independently replaced with O, S, CH=CH, C≡C, $CHR_{a5}$, $CR_{a5}R_{a6}$, aryl or heteroaryl moieties, any other moieties which are pharmaceutically acceptable;

$R_{a5}$ and $R_{a6}$ are independently selected from the group consisting of H, OH, Cl, F, Br, I, alkyl, cycloalkyl, alkyloxyl, cycloalkyloxyl, alkenyl, cycloalkenyl, perfluoroalkyl, cycloperfluoroalkyl, alkyl halide, cycloalkyl halide, alkynyl, cycloalkynyl residues, aryl and heteroaryl moieties;

$R_{a7}$ is selected from the group consisting of alkyl, cycloalkyl, alkyloxyl, cycloalkyloxyl, alkenyl, cycloalkenyl, perfluoroalkyl, cycloperfluoroalkyl, alkyl halide, cycloalkyl halide, alkynyl, and cycloalkynyl residues having aryl or heteroaryl moieties;

T is defined the same as in paragraph 0076;

$X_{a1}$ is selected from the group consisting of O, and the following structures:

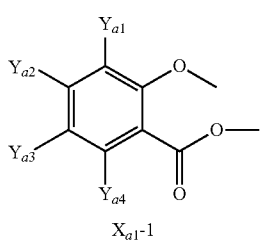

$X_{a1}$-1

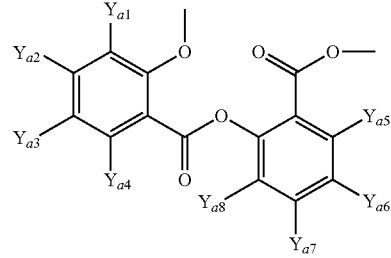

$X_{a1}$-2 each $Y_{a1}$, $Y_{a2}$, $Y_{a3}$, $Y_{a4}$, $Y_{a5}$, $Y_{a6}$, $Y_{a7}$, and $Y_{a8}$ is independently selected from the group consisting of H, HO, $CH_3COO$, $R_8COO$, HS, $NO_2$, CN, $CH_3COS$, $NH_2$, $CH_3CONH$, $R_8CONH$, $CH_3$, $CH_3CH_2$, $C_3H_7$, $C_4H_9$, $CH_3O$, $CH_3CH_2O$, $C_3H_7O$, Cl, F, Br, I, $CH_3S$, $CHF_2O$, $CF_3O$, $CF_3CF_2O$, $C_3F_7O$, $CF_3$, $CF_3CF_2$, $C_3F_7$, $C_4F_9$, $CH_3SO_2$, $R_{a8}SO_2$, $CH_3SO$, $R_{a8}SO$, $CH_3CO$, and $CH_3CH_2CO$;

$R_{a8}$ is selected from the group consisting of alkyl, cycloalkyl, alkyloxyl, cycloalkyloxyl, alkenyl, cycloalkenyl, perfluoroalkyl, cycloperfluoroalkyl, alkyl halide, cycloalkyl halide, alkynyl, and cycloalkynyl residues having aryl or heteroaryl moieties.

In certain embodiments, a HPC of aspirin has the following Structure P-NSAIA-1-a:

Structure P-NSAIA-1a

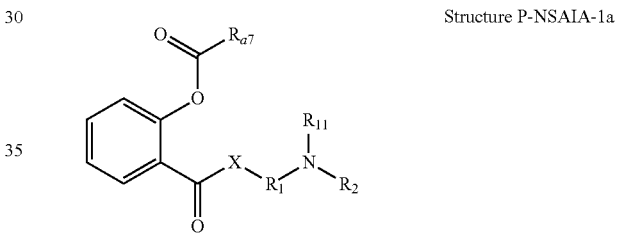

including stereoisomers and salts thereof.

In certain embodiments, a HPC has Structure P-NSAIA-1a, including stereoisomers and salts thereof wherein:

$R_t$, $R_{f1}$ and $R_{f2}$ are defined the same as R, $R_1$ and $R_2$ respectively as in paragraph 0049;

$R_{f7}$ represents $CH_3$, $C_2H_5$, $C_3H_7$, or other lower alkyl groups; and X represents O, S, $NOR_4$, or $NR_4$.

HPC of Ibuprofen and Related Compounds

In certain embodiments, a HPC has the following Structure P-NSAIA-5

Structure P-NSAIA-5

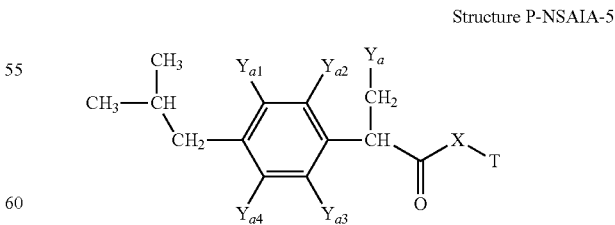

including stereoisomers and pharmaceutically acceptable salts thereof.

In certain embodiments, a HPC has Structure P-NSAIA-5, including stereoisomers and pharmaceutically acceptable salts thereof, wherein:

T is defined the same as in paragraph 0076;

$Y_{a1}$, $Y_{a2}$, $Y_{a3}$, and $Y_{a4}$ are defined the same as in paragraph 98; and $Y_a$ is defined the same as $Y_{a1}$, $Y_{a2}$, $Y_{a3}$, and $Y_{a4}$.

II. Pharmaceutical Compositions Comprising HPCs

Another aspect of the present disclosure relates to a pharmaceutical composition comprising at least a HPC. The pharmaceutical composition further comprises a pharmaceutically acceptable carrier.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a HPC from one location, body fluid, tissue, organ (interior or exterior), or portion of the body, to another location, body fluid, tissue, organ, or portion of the body.

Each carrier is "pharmaceutically acceptable" in the sense of being compatible with the other ingredients, e.g., a HPC, of the formulation and suitable for use in contact with the tissue or organ of a biological subject without excessive toxicity, irritation, allergic response, immunogenicity, or other problems or complications, commensurate with a reasonable benefit/risk ratio.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. acetone and alcohol.

The concentration of HPC in these formulations can vary widely, and will be selected primarily based on fluid volumes, viscosities, body weight and the like in accordance with the particular mode of administration selected and the biological subject's needs. For example, the concentration can be 0.0001% to 100%, 0.01%-100%, 0.1% to 100%, 0.1% to 50%, 1% to 50%, 1%-30%, 1% to 20%, 5% to 10%, 6% to 8% wt.

The compositions of the present disclosure can be administered for prophylactic, therapeutic, and/or hygienic use. Such administration can be topical, mucosal, e.g., oral, nasal, vaginal, rectal, parenteral, transdermal, subcutaneous, intramuscular, intravenous, via inhalation, ophthalmic and other convenient routes. The pharmaceutical compositions can be administered in a variety of unit dosage forms depending upon the method of administration. For example, unit dosage forms suitable for oral administration include powder, tablets, pills, capsules and lozenges.

Thus, a typical pharmaceutical composition for intravenous administration would be about $10^{-9}$ g to about 100 g, about $10^{-6}$ g to about 100 g, about 0.001 g to about 100 g, about 0.01 g to about 10 g, or about 0.01 g to about 1 g per subject per day. Dosages from about 0.01 mg, to about 5 g, per subject per day may be used. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

III. Applications of HPCs i) Methods for Penetrating a Biological Barrier.

Another aspect of the present disclosure relates to a method of using a composition of the present disclosure in penetrating one or more biological barriers in a biological subject. The method comprises a step of administering to a biological subject a HPC, or a pharmaceutical composition thereof. In one embodiment, a HPC exhibits more than 10 times or higher, more than about 50 times or higher, more than about 100 times or higher, more than about 200 time higher, more than about 300 times or higher, more than about 500 times or higher, more than about 1,000 times or higher, more than about 10,000 times or higher penetration rate through one or more biological barriers than its parent drug.

The term "biological barrier" as used herein refers to a biological layer that separates an environment into different spatial areas or compartments, which separation is capable of modulating (e.g. restricting, limiting, enhancing or taking no action in) the passing through, penetrating or translocation of substance or matter from one compartment/area to another. The different spatial areas or compartments as referred to herein may have the same or different chemical or biological environment(s). The biological layer as referred herein includes, but is not limited to, a biological membrane, a cell layer, a biological structure, an inner surface of subjects, organisms, organs or body cavities, an external surface of subjects, organisms, organs or body cavities, or any combination or plurality thereof.

Examples of a biological membrane include a lipid bilayer structure, eukaryotic cell membrane, prokaryotic cell membrane, and intracellular membrane (e.g., nucleus or organelle membrane, such as membrane or envelope of Golgi apparatus, rough and smooth endoplasmic reticulum (ER), ribosomes, vacuoles, vesicles, liposomes, mitochondria, lysosome, nucleus, chloroplasts, plastids, peroxisomes or microbodies).

The lipid bilayer referred to herein is a double layer of lipid-class molecules, including, but not limited to, phospholipids and cholesterol. In a particular embodiment, lipids for bilayer are amphiphilic molecules consisting of polar head groups and non-polar fatty acid tails. The bilayer is composed of two layers of lipids arranged so that their hydrocarbon tails face one another to form an oily core held together by the hydrophobic effect, while their charged heads face the aqueous solutions on either side of the membrane. In another particular embodiment, the lipid bilayer may contain one or more embedded protein and/or sugar molecule(s).

Examples of a cell layer include a lining of eukaryotic cells (e.g., epithelium, lamina propria and smooth muscle or muscularis mucosa (in gastrointestinal tract)), a lining of prokaryotic cells (e.g., surface layer or S-layer which refers to a two dimensional structure monomolecular layer composed of identical proteins or glycoproteins, specifically, an S-layer refers to a part of a cell envelope commonly found in bacteria and archaea), a biofilm (a structured community of microorganisms encapsulated within a self-developed polymeric matrix and adherent to a living or inert surface), and a plant cell layer (e.g., empidermis). The cells may be normal cells or pathological cells (e.g. disease cells, cancer cells).

Examples of biological structures include structures sealed by tight or occluding junctions which provide a barrier to the entry of toxins, bacteria and viruses, e.g. blood milk barrier, blood-cerebrospinal fluid (CSF) barrier, blood-synovial fluid (SF) barrier and blood brain barrier (BBB). In particular, BBB is composed of an impermeable class of endothelium, which presents both a physical barrier through tight junctions adjoining neighboring endothelial cells and a transport barrier comprised of efflux transporters. The biological structure may also include a mixture of cells, proteins and sugars (e.g. blood clots), for example, a myelin sheath, which is a layer around the axon of a neuron formed by a dielectric material, myelin Examples of the inner surface of subjects, organisms, organs or body cavities include buccal mucosa, esophageal mucosa, gastric mucosa, intestinal mucosa, olfactory mucosa, oral mucosa, bronchial mucosa, uterine mucosa and endometrium (the mucosa of the uterus, inner layer of the wall of a pollen grain or the inner wall layer of a spore), or a combination or plurality thereof.

Examples of the external surface of subjects, organisms, organs or body cavities include capillaries (e.g. capillaries in the heart tissue), mucous membranes that are continuous with skin (e.g. such as at the nostrils, the lips, the ears, the genital area, and the anus), outer surface of an organ (e.g. liver, lung, stomach, brain, kidney, heart, ear, eye, nose, mouth, tongue, colon, pancreas, gallbladder, duodenum, rectum stomach, colonrectum, intestine, vein, respiratory system, vascular, the anorectum and pruritus ani), skin, cuticle (e.g., dead layers of epidermal cells or keratinocytes or superficial layer of overlapping cells covering the hair shaft of an animal, a multi-layered structure outside the epidermis of many invertebrates, plant cuticles or polymers cutin and/or cutan), external layer of the wall of a pollen grain or the external wall layer of a spore), and a combination or plurality thereof.

In addition, a biological barrier further includes a sugar layer, a protein layer or any other biological layer, or a combination or plurality thereof. For example, skin is a biological barrier that has a plurality of biological layers. A skin comprises an epidermis layer (outer surface), a demis layer and a subcutaneous layer. The epidermis layer contains several layers including a basal cell layer, a spinous cell layer, a granular cell layer, and a stratum corneum. The cells in the epidermis are called keratinocytes. The stratum corneum ("horny layer") is the outmost layer of the epidermis, wherein cells here are flat and scale-like ("squamous") in shape. These cells contain a lot of keratin and are arranged in overlapping layers that impart a tough and oilproof and waterproof character to the skin's surface.

ii) Methods for Diagnosing a Condition in a Biological Subject.

Another aspect of the present disclosure relates to a method of using a composition of the present disclosure in diagnosing a condition in a biological subject. The method comprises the following steps:

1) administrating a composition comprising a HPC to the biological subject;

2) detecting the presence, location or amount of the HPC, the functional unit of the HPC or a metabolite thereof in the biological subject; and 3) determining a condition in the biological subject.

In certain embodiments, a HPC (or an agent cleaved from the HPC) aggregates in the site of action where a condition occurs. In certain embodiments, the presence, location or amount of a functional unit of a HPC is also detected. In certain embodiments, the onset, development, progress, or remission of a condition (e.g., cancer) associated is also determined.

In certain embodiments, a HPC is labeled with or conjugated to a detectable agent. Alternatively, the HPC is prepared to include radioisotopes for detection.

Numerous detectable agents are available which can be generally grouped into the following categories:

(a) Radioisotopes, such as $^{35}S$, $^{14}C$, $^{13}C$, $^{15}N$, $^{125}I$, $^{3}H$, and $^{131}I$. The diagnostic agent can be labeled with the radioisotope using the techniques known in the art and radioactivity can be measured using scintillation counting; in addition, the diagnostic agent can be spin labeled for electron paramagnetic resonance for carbon and nitrogen labeling.

(b) Fluorescent agents such as BODIPY, BODIPY analogs, rare earth chelates (europium chelates), fluorescein and its derivatives, FITC, 5,6 carboxyfluorescein, rhodamine and its derivatives, dansyl, Lissamine, phycoerythrin, green fluorescent protein, yellow fluorescent protein, red fluorescent protein and Texas Red. Fluorescence can be quantified using a fluorometer.

(c) Various enzyme-substrate agents, such luciferases (e.g., firefly luciferase and bacterial luciferase), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB)); (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

In certain embodiments, a detectable agent is not necessarily conjugated to the diagnostic agent but is capable of recognizing the presence of the diagnostic agent and the diagnostic agent can be detected.

In certain embodiments, a HPC of the present disclosure can be provided in a kit, i.e., a packaged combination of reagents in predetermined amounts with instructions for performing the diagnostic assay. Where the HPC is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

iii) Methods for Screening a Substance for a Desired Character

Another aspect of the present disclosure relates to a method of screening a HPC for a desired character.

In certain embodiments, the method comprises:
1) covalently linking a test functional unit to a transportational unit through a linker to form a test composition (or covalently linking a functional unit to a test transportational unit through a linker, or covalently linking a functional unit to a transportational unit through a test linker)
2) administrating the test composition to a biological subject; and
3) determining whether the test composition has the desired nature or character.

In one embodiment, a desired character may include, for example, 1) the ability of a test functional unit to form a high penetration composition or convert back to a parent drug, 2) the penetration ability and/or rate of a test composition, 3) the efficiency and/or efficacy of a test composition, 4) the transportational ability of a test transportational unit, and 5) the cleavability of a test linker.

iv) Methods for Treating a Condition in a Biological Subject

Another aspect of the present disclosure relates to a method of using a composition of the present disclosure in treating a condition in a biological subject. The method comprises administrating the pharmaceutical composition to the biological subject.

The term "treating" as used herein means curing, alleviating, inhibiting, or preventing. The term "treat" as used herein means cure, alleviate, inhibit, or prevent. The term "treatment" as used herein means cure, alleviation, inhibition or prevention.

The term "biological subject" or "subject" as used herein means an organ, a group of organs that work together to perform a certain task, an organism, or a group of organisms. The term "organism" as used herein means an assembly of molecules that function as a more or less stable whole and has the properties of life, such as animal, plant, fungus, or micro-organism.

The term "animal" as used herein means an eukaryotic organism characterized by voluntary movement. Examples of animal include, without limitation, vertebrata (e.g. human, mammals, birds, reptiles, amphibians, fishes, marsipobranchiata and leptocardia), tunicata (e.g. thaliacea, appendicularia, sorberacea and ascidioidea), articulata (e.g. insecta, myriapoda, malacapoda, arachnida, pycnogonida, merostomata, crustacea and annelida), gehyrea (anarthropoda), and helminthes (e.g. rotifera).

The term "plant" as used herein means organisms belonging to the kindom Plantae. Examples of plant include, without limitation, seed plants, bryophytes, ferns and fern allies. Examples of seed plants include, without limitation, cycads, ginkgo, conifers, gnetophytes, angiosperms. Examples of bryophytes include, without limitation, liverworts, hornworts and mosses. Examples of ferns include, without limitation, ophioglossales (e.g. adders-tongues, moonworts, and grape-ferns), marattiaceae and leptosporangiate ferns. Examples of fern allies include, without limitation, lycopsida (e.g. clubmosses, spikemosses and quillworts), psilotaceae (e.g. lycopodiophyta and whisk ferns) and equisetaceae (e.g. horsetails).

The term "fungus" as used herein means a eukaryotic organism that is a member of the kingdom Fungi. Examples of fungus include, without limitation, chytrids, blastocladiomycota, neocallimastigomycota, zygomycota, glomeromycota, ascomycota and basidiomycota.

The term "micro-organism" as used herein means an organism that is microscopic (e.g. with length scale of micrometer). Examples of micro-organism include, without limitation, bacteria, fungi, archaea, protists and microscopic plants (e.g. green algae) and microscopic animals (e.g. plankton, planarian and amoeba).

Some examples of the conditions the method can treat include conditions that can be treated by the parent drug of the HPC.

v). Methods of Using HPCs and Pharmaceutical Compositions Thereof in Treatments.

Another aspect of the present disclosure relates to a method of using a HPC, of a parent drug or pharmaceutical compositions thereof in treating a condition in a biological subject or subject by administrating a HPC of a parent drug or a pharmaceutical compositions thereof to the biological subject or subject. In certain embodiments, the parent drug of the HPC used in the method is a NSAIA. In certain embodiments, the parent drug of the HPC used in the method is a prostaglandin. In certain embodiments, the parent drug of the HPC used in the method is a mustard. In certain embodiments, the parent drug of the HPC used in the method is a peptide. In certain embodiments, the parent drug of the HPC used in the method is a beta-lactam.

Conditions that can be treated by a method using a HPC of a parent drug or a pharmaceutical composition thereof include conditions that are treatable by the parent drug or a parent drug-related compound. In certain embodiments, a HPC of a parent drug also have new indications due to their enhanced ability to cross biological barrier(s) that the parent drug has difficulties to cross.

In certain embodiments, conditions treatable by a HPC of a parent drug or a pharmaceutical composition thereof include, treating conditions in a site that the parent drug is difficult to reach due to its lack of penetration ability. Examples of such conditions include, without limitation, spinal cord injury, myelin infection and related conditions (e.g. muscle disorders such as amyotrophic lateral sclerosis (ALS), oculopharyngeal muscular dystrophy (OPMD), myotonic dystrophy (MD), Duchenne muscular dystrophy (DMD), polymyositis (PM), dermatomyositis (DM) and inclusion body myositis (IBM)). In certain embodiments, conditions treatable by a HPC include autoimmune disorders (e.g. psoriasis, Crohn's disease, lupus erythematosus, discoid lupus erythematosus, systematic lupus erythematosus, multiple sclerosis, fibrosis (e.g. cystic fibrosis, liver fibrosis, pulmonary fibrosis, pancreas fibrosis, spleen fibrosis, gastrointestinal fibrosis, and fibrosis in other organ)), metabolite disorders (e.g. diabetes (type II), abnormal blood lipid level), thrombosis related conditions (e.g. stroke), neurodegenerative disease (e.g. Alzheimer's diseases and Parkinson's disease), cirrhosis, liver inflammation, hyperthyroidism, gallstones, ageing, undesired skin conditions (e.g. vitiligo, actinic keratosis, abnormal vascular skin lesions, birthmarks, moles (nevi), skin tags, aging spots (liver spots), pus-filled or reddish bumps, comedones, papules, pustules, nodules, epidermoid cysts, keratosis pilaris, sagging skin, wrinkles, crows feet, flesh-colored skin spots, rosacea, post-treatment skin), macular degeneration and age-related macular degeneration (AMD), cough, organ transplant rejection, cancer and tumor (e.g. gastric cancer, multiple myeloma, brain tumor, prostate cancer and bone cancer), grey and/or white hair, hair loss, bold, insufficient hair or eyelashes, pregnancy in women, embryo implantation, brain trama, and conditions in plants that are related to viral, fungus or insect infections.

Examples of the conditions that can be treated by the method using a HPC of a NSAIA include:
1) metabolism disorder, e.g. abnormal blood glucose level, abnormal blood lipid level, diabetes mellitus (type I or/and type II) and diabetes-induced complications, including diabetic retinopathy, necrobiotic ulcers, and diabetic proteinuria;
2) abnormal blood pressure, e.g. hypertension and hypotension;
3) tumor, e.g. benign tumor, breast cancer, colon-rectum cancer, oral cancer, lung or other respiratory system cancers, skin cancers, uterus cancer, pancreatic cancer, prostate cancer, genital cancer, urinary organs cancers, leukemia or other blood and lymph tissues cancer.
4) cardiovascular diseases, e.g. heart attack, unstable angina, peripheral occlusive arterial disease and stroke;
5) neurodegenerative disease, e.g. Alzheimer's diseases and Parkinson's disease;
6) skin condition, e.g. psoriasis and psoriatic disorders, acne, cystic acne, pus-filled or reddish bumps, comedones, papules, pustules, nodules, epidermoid cysts, keratosis pilaris, abnormal vascular skin lesions, birthmarks, moles (nevi), skin tags, scleroderma, vitiligo and related diseases, or aging spots (liver spots);
7) autoimmune disease, e.g. discoid lupus erythematosus, systemic lupus erythematosus (SLE), autoimmune hepatitis, cleroderma, Sjogren's syndrome, rheumatoid arthritis, polymyositis, scleroderma, Hashimoto's thyroiditis, juvenile diabetes mellitus, Addison disease, vitiligo, pernicious anemia, glomerulonephritis, pulmonary fibrosis, multiple sclerosis (MS) and Crohn's disease;
8) eye disease, e.g. glaucoma, ocular hypertension, loss of vision after ophthalmic surgery, vision of a warm-blooded animal impaired by cystoid macular edema and cataract;
9) pain;
10) injuries;
11) inflammation related conditions, e.g. prostate gland inflammation (prostatitis), prostatocystitis, prostate enlarge fibrosis, hemorrhoids, Kawasaki syndrome, gastroenteritis, type-1 membranoproliferative glomerulonephritis, Bartter's syndrome, chronic uveitis, ankylosing spondylitis, hemophilic arthropathy, inflamed hemorrhoids, post irradiation (factitial) proctitis, chronic ulcerative colitis, inflammatory bowel disease, cryptitis, periodontitis, arthritis, and an inflammatory condition in an organ selected from the group consisting of liver, lung, stomach, brain, kidney, heart, ear, eye, nose, mouth, tongue, colon, pancreas, gallbladder, duodenum, rectum stomach, colonrectum, intestine, vein, respiratory system, vascular, the anorectum and pruritus ani;
12) fever;
13) conditions related to platelet aggregation, e.g. thromboembolis after surgery, carotid endarterectomy, the recurrence of stenosis after coronary angioplasty, thromboembolis complications in chronic arterial fibrillation, aortocornonary-artery-bypass graft occlusion, heart attack, stroke, multiinfract dementia, dementia, hemodialysis shunt thrombosis and arterial embolic complications in patients' prosthetic heart valves;
14) dysmenorrheal;
15) allergy;
16) asthma;
17) preeclamptic toxemia in high-risk women,
18) IUD-associated uterine bleeding,
19) radiation-induced conditions, and
20) bone disease, e.g. osteoporosis, Paget's disease and bone metastases.

In certain embodiments, conditions that can be treated by a method of using a HPC of a NSAIA or a pharmaceutical composition thereof further include injuries at locations in a biological subject where a NSAIA has difficulties to reach, e.g. spine cord injury, myelin infection and related conditions such as muscle disorders, e.g. amyotrophic lateral sclerosis (ALS), oculopharyngeal muscular dystrophy (OPMD), myotonic dystrophy (MD), Duchenne muscular dystrophy (DMD), polymyositis (PM), dermatomyositis (DM) and inclusion body myositis (IBM); gray hair, white hair, hair loss and bald; aging, and conditions related to viral, fungus and/or insect in plants.

In certain embodiments, conditions treatable by a NSAIA HPC or a pharmaceutical composition thereof include, but are not limited to, myelin infection and related conditions, cirrhosis, liver inflammation, hyperthyroidism, gallstones, ageing, undesired skin conditions (e.g. actinic keratosis, abnormal vascular skin lesions, birthmarks, moles (nevi), skin tags, aging spots (liver spots), pus-filled or reddish bumps, comedones, papules, pustules, nodules, epidermoid cysts, keratosis pilaris, sagging skin, wrinkles, crows feet, flesh-colored skin spots, rosacea, post-treatment skin), cough, organ transplant rejection, cancer and tumor (e.g. prostate cancer and bone cancer), grey and/or white hair, hair loss, bold, aging, and conditions related to viral, fungus, and/or insect infection in plants.

Examples of conditions or diseases that can be treated by a method using a HPC of a prostaglandin include, without limitation:

1) abnormal birth or reproduction of a human or animal, e.g., inducing childbirth (parturition) or abortion (e.g., $PGE_2$ or $PGF_2$, used with or without mifepristone, which is a progesterone antagonist) and treating egg binding in small birds;
2) peptic ulcers (PGEs and analogs);
3) severe Raynaud's phenomenon or ischemia of a limb (e.g., iloprost, cisaprost);
4) abnormal blood pressure, e.g. hypertension, hypotension, and pulmonary hypertension;
5) cardiovascular conditions or dysfunction, e.g., inhibiting aggregation of platelets, closure of patent ductus arteriosus in newborns with particular cyanotic heart defects (PGE1), heart attack, unstable angina, peripheral occlusive arterial disease and stroke;
6) eye disease, e.g., glaucoma (e.g., in form of bimatoprost ophthalmic solution, which is a synthetic prostamide analog with ocular hypotensive activity), ocular hypertension, loss of vision after ophthalmic surgery, vision of a warm-blooded animal impaired by cystoid macular edema and cataract;
7) sexual dysfunctions, e.g., erectile dysfunction, penile rehabilitation following surgery (e.g., $PGE_1$ as alprostadil) or female sexual dysfunction;
8) bone diseases, e.g. osteoporosis, Paget's disease and bone metastases,
9) gastrointestinal conditions,
10) inflammation,
11) shock, 12) infertility;
13) stimulate hair growth.
14) stimulate eyelash growth Conditions that can be treated by a method of using a HPC of a prostaglandin or a pharmaceutical composition thereof further include brain trauma, stroke, supporting embryo implantation and early pregnancy, treatment of discoid or systemic lupus erythematosus and MS.

Examples of conditions that can be treated by a method of using a HPC of a mustard or a pharmaceutical composition thereof include psoriasis and tumor, e.g., benign tumor, brain tumor, breast cancer, colon-rectum cancer, gastric cancer, oral cancer, lung or other respiratory system cancers, skin cancers, uterus cancer, pancreatic cancer, prostate cancer, genital cancer, urinary organs cancers, myeloma, leukemia or other blood and lymph tissues cancer.

Peptides and amino acids play important roles in all living matter. Any conditions may be treated by amino acid and peptides. Examples of conditions that can be treated by a method of using a HPC of a peptide or a pharmaceutical composition thereof include, without limitation, obesity, pain, and male and female sexual dysfunction.

Conditions that can be treated by a method of using a HPC of a peptide or a pharmaceutical composition thereof further include Alzheimer's disease.

RNA, DNA, nucleosides and nucleotides play an enormous variety of roles in all living matter. Examples of conditions that may be treated by a HPC of RNA, DNA, nucleoside or nucleotide include, without limitation, cancers, tumors, hypertension, obesity, genetic diseases or disorders such as achondroplasia, huntington's disease, neurofibromatosis 1, marfan syndrome, hereditary nonpolyposis colorectal cancer, and hereditary multiple exostoses, congenital anomalies cystic fibrosis, sickle-cell disease, partial sickle-cell disease, Tay-Sachs disease, Niemann-Pick disease, spinal muscular atrophy, tett syndrome, incontinentia pigmenti type 2, aicardi syndrome, klinefelter syndrome, hemophilia A, duchenne muscular dystrophy, red-green color blindness, muscular dystrophy, androgenetic alopecia, male infertility and hypertrichosis pinnae, and Leber's hereditary optic neuropathy.

Examples of conditions that can be treated by a method of using a HPC of a beta-lactam or a pharmaceutical composition thereof include, without limitation, infections related to microorganism and infections related to beta-lactam resistant microorganism, e.g. methicillin-resistant *Staphylococcus aureus* (MRSA)

Examples of conditions that can be treated by a method of using a HPC of a steroid (e.g. progesterone, desogestrel, ethinylestradiol, cholesterol, adrenocorticoids, and sex hormones) or a pharmaceutical composition thereof include, without limitation, rheumatic arthritis, breast cancer, prostate cancer, and other cancers, hypoadrenalism, adrenalectomy, hypophysectomy, rheumatoid diseases, allergic manifestations, bursitis, spontaneous hypoglycemia, gout, sprue, allergy ulcerative colitis, dermatomyositis, periarteritis nodosa, idiopathic pulmonary fibrosis, idiopathic thrombocytopenic purpura, regional ileitis, female contraceptives and abortifacients, progestin antagonists, birth control, acquired hemolytic anemia, nephrosis, cirrhotic ascites, neurodermtitis, psoriasis, pneumonia, peritonitis, typhoid fever, and meningococcemia.

Examples of conditions that can be treated by a method using a HPC of a glibornuride or a pharmaceutical composition thereof include, without limitation, diabetes (type I and II) and related conditions.

Examples of conditions that can be treated by a method using a HPC of Atenolol or a pharmaceutical composition thereof include, without limitation, hypertension and related conditions.

In certain embodiments, a method of treating a condition in a subject using a HPC comprises administering a therapeutic effective amount of the HPC, or a pharmaceutical composition thereof to the subject.

A HPC or a pharmaceutical composition thereof can be administered to a biological subject by any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration. The pharmaceutical compositions can be administered in a variety of unit dosage forms depending upon the method of administration.

A parenteral administration refers to an administration route that typically relates to injection which includes but is not limited to intravenous, intramuscular, intraarterial, intrathecal, intracapsular, intraorbital, intra cardiac, intradermal, intraperitoneal, transtracheal, subcutaneous, subcuticular, intraarticular, subcapsular, subarachnoid, intraspinal, and/or intrasternal injection and/or infusion.

A HPC or a pharmaceutical composition thereof can be given to a subject in the form of formulations or preparations suitable for each administration route. The formulations useful in the methods of the present disclosure include one or more HPCs, one or more pharmaceutically acceptable carriers therefor, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of a HPC which can be combined with a carrier material to produce a pharmaceutically effective dose will generally be that amount of a HPC which produces a therapeutic effect. Generally, out of one hundred percent by weight, this amount of HPC will range from about 0.0001 percent to about 100 percent, from about 0.001 percent to about 99 percent of the HPC, from about 0.001 percent to about 50 percent, from about 0.01 percent to about 30 percent, from about 0.1 percent to about 99.5 percent, from about 0.1 percent to about 50 percent, from about 0.1 percent to about 10 percent, from about 1 percent to about 50 percent, from about 1 percent to about 30 percent, from about 1 percent to about 10 percent, from about 10 percent to about 70 percent, from about 5 percent to about 20 percent, from about 5 percent to about 10 percent, and from about 6 percent to about 8 percent.

Methods of preparing these formulations or compositions include the step of bringing into association a HPC with one or more pharmaceutically acceptable carriers and, optionally, one or more accessory ingredients. In general, the formulations are prepared by uniformly and intimately bringing into association a HPC with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a HPC as an active ingredient. A compound may also be administered as a bolus, electuary, or paste.

In solid dosage forms for oral administration (e.g., capsules, tablets, pills, dragees, powders, granules and the like), the HPC is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate, (5) solution retarding agents, such as paraffin, (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of a HPC therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the HPC(s) only, or preferentially, in a certain portion of the gastrointestinal tract, optionally, in a delayed manner. Examples of embedding compositions which can be used include polymeric substances and waxes. The HPC can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the HPC, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the HPC, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more HPCs with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Formulations which are suitable for vaginal administration also include pessaries, tampons, creams, gels, pastes, foams or spray formulations containing such carriers as are known in the art to be appropriate.

Formulations for the topical or transdermal or epidermal or dermal administration of a HPC composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. The ointments, pastes, creams and gels may contain, in addition to the HPC composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the HPC composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

A HPC or a pharmaceutical composition thereof can be alternatively administered by aerosol. This can be accomplished by preparing an aqueous aerosol, liposomal preparation or solid particles containing the HPCs. A nonaqueous (e.g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches can also be used to deliver HPC compositions to an tumor site. Such formulations can be made by dissolving or dispersing the agent in the proper medium. Absorption enhancers can also be used to increase the flux of the HPC across the skin. The rate of such flux can be controlled by either providing a rate controlling membrane or dispersing the HPC in a polymer matrix or gel.

Ophthalmic formulations, eye ointments, powders, solutions and the like, are also contemplated as being within the scope of this invention.

Formulations suitable for parenteral administration comprise a HPC in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacterostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e.g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of a HPC or in biodegradable polymers such as polylactide-polyglycolide. Depending on the ratio of the HPC to polymer, and the nature of the particular polymer employed, the rate of drug release can be controlled. Examples of other biodegradable polymers include poly (orthoesters) and poly (anhydrides). Depot injectable formulations are also prepared by entrapping the HPC in liposomes or microemulsions which are compatible with body tissue.

In certain embodiments, a HPC, or a pharmaceutical composition thereof is delivered to a disease or tumor site in a therapeutically effective dose. As is known in the art of pharmacology, the precise amount of the pharmaceutically effective dose of a HPC that will yield the most effective results in terms of efficacy of treatment in a given patient will depend upon, for example, the activity, the particular nature, pharmacokinetics, pharmacodynamics, and bioavailability of a particular HPC, physiological condition of the subject (including race, age, sex, weight, diet, disease type and stage, general physical condition, responsiveness to a given dosage and type of medication), the nature of pharmaceutically acceptable carriers in a formulation, the route and frequency of administration being used, and the severity or propensity of a disease caused by pathogenic target microbial organisms, to name a few. However, the above guidelines can be used as the basis for fine-tuning the treatment, e.g., determining the optimum dose of administration, which will require no more than routine experimentation consisting of monitoring the subject and adjusting the dosage. Remington: The Science and Practice of Pharmacy (Gennaro ed. 20.sup.th edition, Williams & Wilkins PA, USA) (2000).

IV. Advantages

In certain embodiments, since a HPC of the present disclosure has enhanced ability of crossing one or more biological barriers, the HPC can be administered locally (e.g., topically or transdermally) to reach a location where a condition occurs without the necessity of a systematic administration (e.g., oral or parenteral administration). A local administration and penetration of a HPC allows the HPC to reach the same level of local concentration of an agent or drug with much less amount or dosage of HPC in comparison to a systematic administration of a parent agent or drug; alternatively, a higher level of local concentration which may not be afforded in the systematic administration, or if possible, requires significantly higher dosage of an agent in the systematic administration. The high local concentration of the HPC or its parent agent if being cleaved enables the treatment of a condition more effectively or much faster than a systematically delivered parent agent and the treatment of new conditions that may not be possible or observed before. The local administration of the HPC may allow a biological subject to reduce potential sufferings from a systemic administration, e.g., adverse reactions associated with the systematic exposure to the agent, gastrointestinal/renal effects. Additionally, the local administration may allow the HPC to cross a plurality of biological barriers and reach systematically through, for example, general circulation and thus avoid the needs for systematic administration (e.g., injection) and obviate the pain associated with the parenteral injection.

In certain embodiments, a HPC or a pharmaceutical composition according to the present disclosure can be administered systematically (e.g., orally or parenterally). The HPC or the active agent (e.g., drug or metabolite) of the HPC may enter the general circulation with a faster rate than the parent agent and gain faster access to the action site a condition. Additionally, the HPC can cross a biological barrier (e.g., blood brain barrier) which has not been penetrated if a parent agent is administered alone and thus offer novel treatment of conditions that may not be possible or observed before.

In certain embodiments, HPCs of NSAIA in the present disclosure demonstrated high penetration rate through a biological barrier (e.g., >about 20 times, >about 100 times, >about 200 times, >about 300 times higher that the NSAIA alone). No gastroduodenal bleeding was observed from the subjects that were orally administered with a HPC of a NSAIA, while gastroduodenal bleeding was observed from the subjects that took the parent NSAIA at the similar dosage.

In certain embodiments, HPCs of prostaglandin of the present disclosure exhibited high penetration rate through a biological barrier (e.g., about >10 times, about >50 times, >about 100 times, about >200 times, about >300 times, about >500 times, about >1,000 times, about >10,000 times or higher than the penetration rate of prostaglandins or prostaglandin analogs if administered alone). No side effect was observed from the subjects to which were administered a HPC of a prostaglandin, while side effects were observed from the subjects to which the parent prostaglandin or a related compound or analog thereof was administered at the similar dosage.

In certain embodiments, HPCs of mustards in the present disclosure demonstrated high penetration rate through a biological barrier (e.g., >about 10 times, >about 50 times, >about 100 times, >about 200 times, >about 300 times higher than if the mustards or mustard-related compounds are administered alone). No or few adverse side effect was observed from the subjects that were administered with a HPC of mustard, while side effects (such as nausea, hair loss, and increased susceptibility to infection) were observed from the subjects that took the parent mustards at the similar dosage.

In certain embodiments, HPCs of peptides in the present disclosure demonstrated penetration rate through a biological barrier (e.g., >about 10 times, >about 50 times, >about 100 times, >about 200 times, >about 500 times, >about 1000 times, >about 10000 times higher than if the peptides or peptide-related compounds are administered alone). No or few adverse side effect was observed from the subjects that took HPC of peptides, while side effects (such as nausea, and increased susceptibility to infection) were observed from the subjects that took the parent peptides at the similar dosage.

In certain embodiments, HPCs of beta-lactam antibiotics in the present disclosure demonstrated high penetration rate through a biological barrier (e.g., >about 10 times, >about 50 times, >about 100 times, >about 200 times, >about 300 times, >about 1000 times higher than if the beta-lactam antibiotics or beta-lactam antibiotics-related compounds are administered alone). No or few adverse side effect was observed from the subjects that took HPC of beta-lactam antibiotics, while side effects were observed from the subjects that took the parent beta-lactam antibiotics at the similar dosage.

In certain embodiments, a HPC of a parent drug is therapeutically effective at a lower dosage comparing to the parent drug. In certain embodiments, a HPC of a parent drug is therapeutically effective at about 50% or lower of the applicable dosage of the parent drug. In certain embodiments, a HPC of a parent drug is therapeutically effective at about 25% or lower of the applicable dosage of the parent drug. In certain embodiments, a HPC of a parent drug is therapeutically effective at about 10% or lower of the applicable dosage of the parent drug. In certain embodiments, a HPC of a parent drug is therapeutically effective at about 5% or lower of the applicable dosage of the parent drug. In certain embodiments, a HPC of a parent drug is therapeutically effective at about 25% or lower of the applicable dosage of the parent drug. In certain embodiments, a HPC of a parent drug is therapeutically effective at about 2% or lower of the applicable dosage of the parent drug. In certain embodiments, a HPC of a parent drug is therapeutically effective at about 1% or lower of the applicable dosage of the parent drug. In certain embodiments, a HPC of a parent drug is therapeutically effective at about 0.1% or lower of the applicable dosage of the parent drug.

V. Examples

The following examples are provided to better illustrate the claimed invention and are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Example 1

Preparation of a HPC from a Parent Drug

Preparation of a HPC from a Parent Drug which Contains at Least One Carboxyl Group In certain embodiments, a parent compound having Structure $F_1$—OH is converted to a HPC having Structure L-1

$F_1$-$L_2$-T                                    Structure L-1 including stereoisomers and pharmaceutically acceptable salts thereof, wherein T is defined as in paragraph 0076.

In certain embodiments, a HPC having Structure L-1 ($F_1$-$L_2$-T) is prepared according to organic synthesis by reacting the parent compounds or derivatives of the parent compounds having a structure of $F_1$—$W_a$ (e.g. acid halides, mixed anhydrides of the parent compounds, etc.) with a compound having a structure of T-$L_2$-H as shown in Scheme 1, wherein $W_a$ is selected from the group consisting of OH, halogen, alkylcarbonyloxy, arylcarbonyloxy, alkoxycarbonyloxy and aryloxycarbonyloxy; and T is defined as in paragraph 0076:

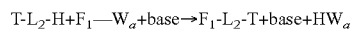

Scheme 1

Preparation of a HPC from a Parent Compound

In certain embodiments, a HPC having Structure L-1 is prepared according to organic synthesis by reacting a salt of a parent compound or a derivative of the parent compound having a structure of F—$O^-B_a^+$ (e.g. sodium salt, potassium salt, triethylamine salt, or polymer bond organic or inorganic base salt, etc.) with a compound having a structure of T-$L_2$-$W_b$.H$W_b$ as shown in Scheme 2, wherein $W_b$ is selected from the group consisting of p-toluenesulphonyl, halogen, alkylcarbonyl, arylcarbonyl, alkoxycarbonyl and aryloxycarbonyloxy; and T is defined as in paragraph 0076:

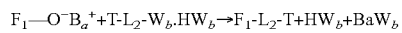

Scheme 2

Preparation of a HPC from a Parent Compound

Preparation of N,N-diethylaminoethyl 9-cis-retinoate.HBr 30 g (0.1 mol) of sodium 9-cis-retinoate was dissolved in 100 ml of acetonitrile. 26.1 g (0.1 mol) of 2-Bromo-N,N-diethylethylamine.HBr was added into the reaction mixture. The mixture was stirred for overnight at RT. The solvents were evaporated off. 200 ml of ethanol was added into the residue. The solid was removed by filtration. The solution was evaporated to dryness. 100 ml of ethyl acetate was added into the reaction mixture. Hexane (100 ml) was added. The solid product was collected by filtration. After drying, it yielded 36 g of the desired product (75%). Hygroscopic product; solubility in water: 30 mg/ml; elementary analysis: $C_{26}H_{42}BrNO_2$; MW: 480.52; calculated % C, 64.99; H, 8.81; Br, 16.63; N, 2.91; O, 6.66. found % C, 65.03; H, 8.80; Br, 16.60; N, 2.89; O, 6.68.

Preparation of a HPC from a Parent Drug which Contains at Least One Hydroxyl Group, or Amino Group In certain embodiments, a parent compound having Structure $F_2$—H is converted to a HPC having Structure L-2

$F_2$-$L_4$-$L_2$-T  Structure L-2 including stereoisomers and pharmaceutically acceptable salts thereof, wherein T is defined as in paragraph 0076.

In certain embodiments, a HPC having Structure L-2 ($F_2$-$L_4$-$L_2$-T) is prepared according to organic synthesis by reacting a parent compound having a structure of $F_2$—H (e.g. an alcohol or amine) with a compound having a structure of T-$L_2$-$L_4$-$W_c$ as shown in Scheme 3, wherein $W_c$ is selected from the group consisting of OH, halogen, alkylcarbonyloxy, arylcarbonyoxy, alkoxycarbonyloxy and aryloxycarbonyloxy; and T is defined as in paragraph 0076:

T-$L_2$-$L_4$-$W_c$+$F_2$—H+base→$F_2$-$L_4$-$L_2$-T+base+$HW_c$

Scheme 3

Preparation of a HPC from a Parent Compound

Preparation of retinyl N,N-dimethyl-2-aminoacetate.HCl 28.6 g (0.1 mol) of retinol was dissolved in 300 ml of acetonitrile. 25 ml of triethylamine was added into the reaction mixture. 16 g of N,N-dimethylaminoacetyl chloride hydrochloride was added into the reaction mixture. The mixture was stirred for 5 h at RT. The solid was removed by filtration. The solution was evaporated to dryness. 500 ml of ethyl acetate was added into the residue. 200 ml of 5% of sodium carbonate solution was added into the mixture with stirring. The organic solution was collected and washed with water. After drying, it yielded 31 g of the desired product (75.5%). Hygroscopic product; elementary analysis: CHCINO; MW: 408.02; calculated % C, 70.65; H, 9.39; Cl, 8.69; N, 3.43; O, 7.84. found % Q70.60; H, 9.46; Cl, 8.71; N, 3.42; O, 7.81.

Preparation of a HPC from a Parent Drug which Contains Both an Amino Group and a Carboxyl Group In certain embodiments, a parent compound having Structure $F_3$—OH is converted to a HPC having Structure L-3

$F_3$-$L_2$-R  Structure L-3 including stereoisomers and pharmaceutically acceptable salts thereof.

In certain embodiments, a HPC having Structure L-3 ($F_3$-$L_2$-R) is prepared according to organic synthesis by reacting a parent compound having a structure of $F_3$—$W_d$ (e.g. acid halides, mixed anhydrides of the parent compounds, etc.) with a compound having a structure of R-$L_2$-H (e.g. an alcohol or amine) as shown in Scheme 4, wherein $W_d$ is selected from the group consisting of OH, halogen, alkylcarbonyloxy, arylcarbonyoxy, alkoxycarbonyloxy and aryloxycarbonyloxy:

R-$L_2$-H+$F_3$—$W_d$+base/acid→$F_3$-$L_2$-R+base/acid+$HW_d$

Scheme 4

Preparation of a HPC from a Parent Compound

Preparation of 3-fluoro-L-phenylalanine isopropyl ester.HCl 18.3 g (0.1 mol) of 3-fluoro-L-phenylalanine was suspended in 150 ml of isopropanol. 25 g of p-toluenesulfonic acid monohydrate and 100 ml of benzene were added into the mixture. The mixture was refluxed until no more water was formed (more fresh benzene and isopropanol may be needed). After cooling to RT, 500 ml of ethyl acetate and 5% $NaHCO_3$ (600 ml) were added into the reaction mixture with stirring. The ethyl acetate layer was collected and washed with 5% $NaHCO_3$ (1×200 ml) and water (3×100 ml). The solution was dried over anhydrous $Na_2SO_4$ and sodium sulfate was removed by filtration and washed with ethyl acetate. The solution was evaporated to dryness. HCl gas (4 g) in ethyl acetate (100 ml) was added into the residue. The solid was collected by filtration and washed with ethyl acetate. After drying, it yielded 23 g of the desired product (87.9%). Elementary analysis: $C_{12}H_{17}ClFNO_2$; MW: 261.73; calculated % C, 55.07; H, 6.55; Cl, 13.54; F, 7.26; N, 5.35; O, 12.23. found % C, 55.02; H, 6.57; Cl, 13.57; F, 7.24; N, 5.33; O, 12.27.

Preparation of a HPC from a Parent Drug which has a Carbonyl Groups Such as a Ketone or Aldehyde In another embodiment, the parent drugs have carbonyl groups such as ketones or aldehydes and a parent drug is linked with transporting unit (T) through an imine bond, oxime bond, or hydrazon bond.

In certain embodiments, a parent compound having Structure $F_4$=O is converted to a HPC having Structure L-4

$F_4$=$L_{41}$-T  Structure L-4 including stereoisomers and pharmaceutically acceptable salts thereof, wherein:

$L_{41}$ is defined as in paragraph 0041; and T is defined as in paragraph 0076;

In certain embodiments, a HPC having Structure L-4 ($F_4$=$L_{41}$-T) is prepared according to organic synthesis by reacting a parent compound having a structure of $F_4$=O (e.g. an aldehyde or ketone) with a compound having a structure of $H_2$-$L_1$-T as shown in Scheme 5, wherein T is defined as in paragraph 0076:

T-$L_1$-$H_2$+$F_4$=O=$F_4$=$L_1$-T+$H_2O$

Scheme 5

Preparation of a HPC from a Parent Compound

Preparation of N-Diethylaminoethyl Progesterone imine.acetic Acid Salt 11.7 g of N,N-Diethylethylenediamine, 8 g of acetic acid, and 31.5 g of progesterone were dissolved in 500 ml toluene.

The mixture was refluxed to remove water. After water was removed, the mixture was evaporated to dryness and yielded 40 g of N-diethylaminoethyl propesterone imine acetic acid salt (85%). $C_{29}H_{48}N_2O_3$. Elementary analysis: $C_{29}H_{48}N_2O_3$; MW: 472.71; calculated % C, 73.68; H, 10.23; N, 5.93; O, 10.15. found % C, 73.62; H, 10.27; N, 5.91; O, 10.28.

Preparation of N—(N,N-dimethylaminopropionoxyl) progesterone imine.acetic acid salt 13.2 g of N—(N',N'-dimethylaminopropionoxyl)amine.acetic acid [$(CH_3)_2NCH_2CH_2COONH_2·CH_3COOH$] and 31.5 g of progesterone were dissolved in 200 ml of acetonitrile. 100 g of dried molecular sieves was added into the mixture. The mixture was stirred for overnight at RT. Molecular sieves were removed and the solution was evaporated to dryness. Yield was 42 g of N—(N,N-dimethylaminopropionoxyl progesterone imine.acetic acid (85.9%). Elementary analysis: $C_{28}H_{44}N_2O_5$; MW: 488.66; calculated % C, 68.82; H, 9.07; N, 5.73; O, 16.37. found % C, 68.78; H, 9.09; N, 5.71; O, 16.42.

Preparation of N-(4-N,N-diethylaminoethoxycarbonyl)phenyl progesterone imine.HCl Salt 25 g of 4-aminobenzoate N,N-diethylaminoethyl ester.HCl salt [$4-(CH_3CH_2)_2NCH_2CH_2OCOC_6H_4NH_2·HCl$] and 31.5 g of progesterone were dissolved in 200 ml of acetonitrile. 100 g of dried molecular sieves was added into the mixture. The mixture was stirred for overnight at RT. Molecular sieves were removed and the solution was evaporated to dryness. Yield was 48 g of N-(4-N,N-diethylaminoethoxycarbonyl)phenyl progesterone imine.HCl salt (84%); Elementary analysis: $C_{34}H_{49}ClN_2O_3$; MW: 569.22; calculated % C, 71.74; H, 8.68; N, 4.92; O, 8.43; Cl: 6.23. found % C, 71.70; H, 8.70; N, 4.89; O, 8.46; Cl, 6.25.

Example 2

HPCs are Capable of Penetrating Biological Barriers

Penetration rates of HPCs through human skin were measured in vitro by Franz cells. A Franz cell has two chambers, a top sample chamber and a bottom receptor chamber. A human skin tissue (360-400 μm thick) that separates the top and the receptor chambers is isolated from the anterior or posterior thigh areas.

Test compounds were diethylaminoethyl N-acetyl-3-(3,4-diacetyloxy-phenyl-L-alanine ester.HCl salt (A), diethylaminopropyl N-acetyl-D-3,5,3',5'-tetraiodothyronine.HCl salt(B), 1-piperidineethyl 2-[4-(4-chlorobenzoyl)phenoxy]-2-methyl-propinate. HCl salt(C), 3-piperidinemethyl 5-(2,5-dimethylphenoxy)-2,2-dimethylpentanoate.HCl salt(D), diethylaminoethyl (S)-3-(benzoylaminomethyl)-5-methylhexanoate.HCl salt(E), N-acetyl-3-(3,4-diacetyloxy-phenyl-L-alanine(F) sodium salt, N-acetyl-D-3,5,3',5'-tetraiodothyronine sodium salt(G), 2-[4-(4-chlorobenzoyl)phenoxy]-2-methyl-propinic acid sodium salt(H), 5-(2,5-dimethylphenoxy)-2,2-dimethylpentanoic acid sodium salt (I), and (S)-3-(benzoylaminomethyl)-5-methylhexanoic acid sodium salt(J).

Figure 8:
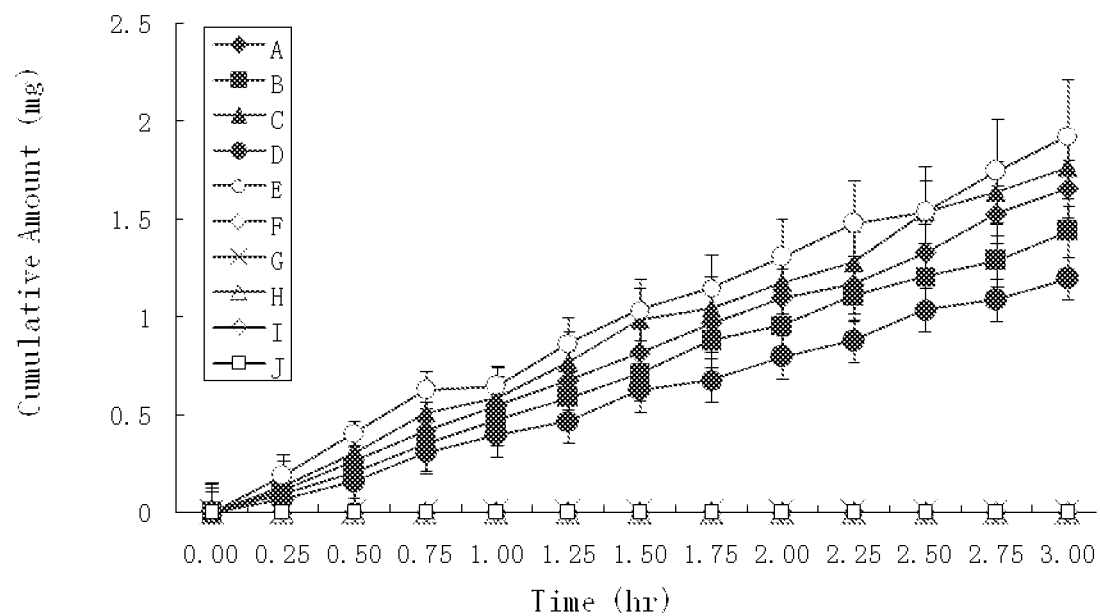
FIG. 8: Cumulative amounts of diethylaminoethyl N-acetyl-3-(3,4-diacetyloxy-phenyl-L-alanine ester.HCl salt (A), diethylaminopropyl N-acetyl-D-3,5,3',5'-tetraiodothyronine.HCl salt(B), 1-piperidineethyl 2-[4-(4-chlorobenzoyl)phenoxy]-2-methyl-propinate. HCl salt(C), 3-piperidinemethyl 5-(2,5-dimethylphenoxy)-2,2-dimethylpentanoate.HCl salt(D), diethylaminoethyl (S)-3-(benzoylaminomethyl)-5-methylhexanoate.HCl salt(E), N-acetyl-3-(3,4-diacetyloxy-phenyl-L-alanine sodium salt (F), N-acetyl-D-3,5,3',5'-tetraiodothyronine sodium salt(G), 2-[4-(4-chlorobenzoyl)phenoxy]-2-methyl-propinic acid sodium salt(H), 5-(2,5-dimethylphenoxy)-2,2-dimethylpentanoic acid sodium salt(I), and (S)-3-(benzoylaminomethyl)-5-methylhexanoic acid sodium salt(J) crossing isolated human skin tissue in Franz cells (n=5). In each case, the vehicle was pure water.

10% solution of the test compound in water was used. The amount of a HPC or its parent drug penetrating a skin was determined by high-performance liquid chromatography method. The results were shown in FIG. 8 and apparent flux values of the HPCs and their corresponding parent drugs were summarized in Table 2.

TABLE 2

In vitro Penetration Rate of HPCs and their Parent Compounds

| HPCs | μg/cm²/h | Parent compounds | μg/cm²/h |
|---|---|---|---|
| diethylaminoethyl N-acetyl-3-(3,4-diacetyloxy-phenyl-L-alanine ester•HCl salt (A) | 550 | N-acetyl-3-(3,4-diacetyloxy-phenyl-L-alanine sodium salt (F) | 1 |
| diethylaminopropyl N-acetyl-D-3,5,3',5'-tetraiodothyronine•HCl salt (B) | 480 | N-acetyl-D-3,5,3',5'-tetraiodothyronine sodium salt (G) | 1 |
| 1-piperidineethyl 2-[4-(4-chlorobenzoyl)phenoxy]-2-methyl-propinate•HCl salt (C) | 590 | 2-[4-(4-chlorobenzoyl)phenoxy]-2-methyl-propinic acid sodium salt (H) | 1 |
| 3-piperidinemethyl 5-(2,5-dimethylphenoxy)-2,2-dimethylpentanoate•HCl salt (D) | 400 | 5-(2,5-dimethylphenoxy)-2,2-dimethylpentanoic acid sodium salt (I) | 1 |
| diethylaminoethyl (S)-3-(benzoylaminomethyl)-5-methylhexanoate•HCl salt (E) | 650 | (S)-3-(benzoylaminomethyl)-5-methylhexanoic acid sodium salt (J) | 1 |

The results suggested that the HPCs diffused through human skin more than 400 times faster than their respective parent drug.

Example 3

Transdermal Administrations of HPC Resulted in In Vivo Distribution of the Parent Drug and Related Compounds The HPC of ibuprofen used in this example was diethylaminoethyl 2-(p-isobutylphenyl)propionate.citric acid. A HPC changed quickly to its parent drug in vivo, so the concentration was the concentration of its parent drug or related compound.

3.1. Transdermal Administrations of HPC of Ibuprofen Resulted in In Vivo Distribution of the Parent Drug and Related Compound in Rats 0.3 mmol/kg HPC of ibuprofen (10% aqueous solution) was applied to the shaved back (10 cm²) of male rats. Table 3 showed the distribution of ibuprofen and diethylaminoethyl 2-(ρ-isobutylphenyl)propionate.HCl (ibuprofenamine) in the rats' organs at 2 hr after the application.

TABLE 3.1

The distribution of ibuprofen and ibuprofenamine in the organs of rats.

| | liver | kidney | stomach | pancreas | heart | brain |
|---|---|---|---|---|---|---|
| Ibuprofen (nmol/g) | 17 ± 11 | 25 ± 8 | 32 ± 9 | 18 ± 7 | 21 ± 7 | 2 ± 0.5 |
| ibuprofenamine (nmol/g) | 0.2 ± 0.2 | 0.4 ± 0.2 | 0.3 ± 0.1 | 0.5 ± 0.3 | 0.5 ± 0.2 | 0.1 ± 0.05 |

3.2 Transdermal Administrations of HPC of Ibuprofen Resulted in Distribution of the Parent Drug and Related Compounds in the Organs of Rabbits.

0.3 mol/kg of HPC of ibuprofen (10% aqueous solution) was applied to the shaved back (30 cm$^2$) of male rabbits (2.5-3.0 kg). Table 3.2 showed the amounts of ibuprofen and ibuprofenamine in the rabbits' organs 2 hr after the application.

TABLE 3.2

The distribution of ibuprofen and ibuprofenamine in the organs of rabbits.

| | brain | Myelin | prostate gland | cartilage pads | testis | heart |
|---|---|---|---|---|---|---|
| Ibuprofen (nmol/g) | 5 ± 1 | 25 ± 8 | 18 ± 7 | 8 ± 2 | 11 ± 4 | 10 ± 5 |
| ibuprofenamine (nmol/g) | 0.4 ± 0.2 | 0.60 ± 0.2 | 0.5 ± 0.3 | 0.4 ± 0.2 | 0.5 ± 0.3 | 0.3 ± 0.1 |

The results show that a HPC penetrated biological barriers to reach prostate, cartilage pads, testis, and myelin and other organs. Therefore, a HPC should be very useful for the treatments of arthritis, prostatitis and prostate enlarge fibrosis, and other conditions such as myelin inflammation related muscle disorders, in a biological subject.

Example 4

A HPC Could Penetrate Biological Barriers Such as Blood-Milk Barrier, Blood-Brain Barrier, Blood-CSF Barrier, and Blood-Synovial Fluid (SF) Barrier A HPC changed quickly to its parent drug in vivo, so the concentration was the concentration of its parent drug or related compound.

4.1. Transdermal Administrations of HPC of Ibuprofen Resulted in Distribution of the Parent Drug and Related Compounds in Milk of Sheep.

0.3 mmol/kg of diethylaminoethyl 2-(p-isobutylphenyl) propionate.citric acid salt (10% aqueous solution) was applied to the back (100 cm$^2$) of female sheep. 30±8 nmol/ml of ibuprofen and 5±3 nmol/ml of ibuprofenamine were found in the milk after 2 hr after the application. The result demonstrated that the HPC could penetrate milk-blood barrier clearly.

4.2: Studies of Penetration of Rat Blood-Brain Barrier of HPC and its Parent Drug.

20 male rats were divided into 4 groups (n=5). 0.5 mmol/kg of diethylaminoethyl acetylsalicylate.HCl salt was administrated into rats intramuscularly (20% in 70% ethanol) or transdermally (10% in 70% ethanol, on the shaved back, 10 cm$^2$) and 0.5 mmol/kg of aspirin was administrated into rats intramuscularly(20% in 70% ethanol) or transdermally (10% in 70% ethanol, on the shaved back, 10 cm$^2$). 30, 60, 120, 240, 480 minutes after the test compound was administrated, rats were decapitated and were perfused with normal Krebs-Henseleit buffer (with Heparin Sodium, pH7.4) (10 mL/min) to remove blood. The brain tissue was homogenized immediately in 3-5 ml of methanol, using a tissue tearor at 30,000 rpm (about 2 min.). The mixture was centrifuged for 5 minutes at 16,000 rpm. The supernatant (2 ml) was collected and evaporated to dryness. The residue was diluted to the appropriate concentrations and the amounts of salicylic acid were determined by LS-MS-MS. The results were shown in Table 4.2a. The results show that HPC of aspirin penetrated blood-brain barrier very efficiently, but aspirin could not.

TABLE 4.2a

The amount of salicylic acid in rat brain tissue.

| Test compounds | 30 min | 60 min | 120 min | 240 min | 480 min |
|---|---|---|---|---|---|
| diethylaminoethyl acetylsalicylate (transdermally) | 3.1 ± 1.1 (nmol/g) | 6.3 ± 2.3 (nmol/g) | 8.2 ± 3.5 (nmol/g) | 9.3 ± 3.3 (nmol/g) | 9.5 ± 4.2 (nmol/g) |
| diethylaminoethyl acetylsalicylate (intramuscularly) | 6.5 ± 2.2 (nmol/g) | 8.2 ± 2.3 (nmol/g) | 9.4 ± 3.1 (nmol/g) | 8.5 ± 2.5 (nmol/g) | 8.2 ± 2.3 (nmol/g) |
| acetylsalicylic acid (intramuscularly) | 0.3 ± 0.1 (nmol/g) | 0.2 ± 0.1 (nmol/g) | 0.2 ± 0.1 (nmol/g) | Not detectable | Not detectable |
| acetylsalicylic acid (transdermally) | Not detectable | Not detectable | Not detectable | Not detectable | Not detectable |

20 male rats were divided into 4 groups (n=5). 0.3 mmol/kg of diethylaminoethyl acetylsalicylate.HCl salt was administrated into rats intramuscularly (20% in 70% ethanol) or transdermally (10% in 70% ethanol, on the shaved back of rat, 10 cm$^2$) and 0.3 mmol/kg of aspirin was administrated into rats intramuscularly (20% in 70% ethanol) or transdermally (10% in 70% ethanol, on the shaved back of rat, 10 cm$^2$). 1, 8, and 18 hours after the test compound was administrated, the rat was killed and 1 ml of plasma and brain were taken out. The plasma or brain tissue (the whole brain was washed with pH 7.4 buffer for 3 times) was homogenized immediately in 3-5 ml of methanol, using a tissue tearor at 30,000 rpm (about 2 min.). Amounts of salicylic acid in rat plasma and brain were determined by LS-MS-MS. The results were shown in Table 4.2b. 1 Hour after aspirin was administrated, most of aspirin stayed in blood system. However, the HPC of aspirin was distributed into other tissues much faster than aspirin. Furthermore, the results show that the HPC of aspirin penetrated blood-brain barrier efficiently, but aspirin could not.

TABLE 4.2b

The amount of salicylic acid in rat plasma and brain.

| Test compounds | Plasma (1 hr) | Brain (1 hr) | Plasma (8 hr) | Brain (8 hr) | Plasma (18 hr) | Brain (18 hr) |
|---|---|---|---|---|---|---|
| diethylaminoethyl acetylsalicylic acid (intramuscularly) | 378 ± 34 (nmol/ml) | 20.2 ± 4.2 (nmol/g) | 123 ± 25 (nmol/ml) | 9.2 ± 3.5 (nmol/g) | 0.9 ± 0.2 (nmol/ml) | 4.2 ± 1.3 (nmol/g) |
| diethylaminoethyl acetylsalicylic acid (transdermally) | 158 ± 21 (nmol/ml) | 10.2 ± 3.1 (nmol/g) | 103 ± 28 (nmol/ml) | 18.4 ± 3.4 (nmol/g) | 1.1 ± 0.2 (nmol/ml) | 11.2 ± 2.1 (nmol/g) |
| acetylsalicylic acid (intramuscularly) | 1424 ± 55 (nmol/ml) | 15.8 ± 4.4 (nmol/g) | 363 ± 29 (nmol/ml) | 4.6 ± 2.5 (nmol/g) | 0.5 ± 0.2 (nmol/ml) | Not detectable |
| acetylsalicylic acid (transdermally) | Not detectable | Not detectable | Not detectable | Not detectable | Not detectable | Not detectable |

0.3 mmol/kg of diethylaminoethyl 2-(ρ-isobutylphenyl) propionate HCl salt was administrated into male rats intramuscularly (20% in 70% ethanol) or transdermally (on the shaved back, 10% in 70% ethanol) and 0.3 mmol/kg of 2-(ρ-isobutylphenyl)propionic acid (ibuprofen) was administrated into male rats intramuscularly (20% in 70% ethanol) or transdermally (10% in 70% ethanol). 1, 8, and 18 hours after the test compound was administrated, the rats were killed and 1 ml of plasma and brain were taken out. The plasma or brain tissue (the whole brain was washed with pH 7.4 buffer for 3 times) was homogenized immediately in 3-5 ml of methanol, using a tissue tearor at 30,000 rpm (about 2 min.). Amounts of ibuprofen in rat plasma and brain were determined by LS-MS-MS. The results were shown in Table 4.2c. 1 Hour after ibuprofen was administrated, most of ibuprofen stayed in blood system. However, the HPC of ibuprofen was distributed into other tissues much faster than ibuprofen. Furthermore, the results show that the HPC of ibuprofen penetrated blood-brain barrier efficiently, but ibuprofen could not.

TABLE 4.2c

The amount of ibuprofen in rat plasma and brain.

| Test compounds | Plasma (1 hr) | Brain (1 hr) | Plasma (8 hr) | Brain (8 hr) | Plasma (18 hr) | Brain (18 hr) |
|---|---|---|---|---|---|---|
| diethylaminoethyl 2-(ρ-isobutyl-phenyl)propionate (intramuscularly) | 438 ± 38 (nmol/ml) | 18.2 ± 4.3 (nmol/g) | 153 ± 29 (nmol/ml) | 8.7 ± 2.5 (nmol/g) | 0.5 ± 0.2 (nmol/ml) | 2.8 ± 0.4 (nmol/g) |
| diethylaminoethyl 2-(ρ-isobutyl-phenyl)propionate (transdermally) | 108 ± 21 (nmol/ml) | 11.2 ± 2.4 (nmol/g) | 113 ± 18 (nmol/ml) | 22.6 ± 3.2 (nmol/g) | 2.9 ± 2 (nmol/ml) | 10.1 ± 0.6 (nmol/g) |
| 2-(ρ-isobutyl-phenyl)propionic acid (intramuscularly) | 1428 ± 68 (nmol/ml) | 12.2 ± 5.2 (nmol/g) | 313 ± 39 (nmol/ml) | 0.8 ± 0.3 (nmol/g) | Not detectable | Not detectable |
| 2-(ρ-isobutyl-phenyl)propionic acid (transdermally) | Not detectable | Not detectable | Not detectable | Not detectable | Not detectable | Not detectable |

4.3. HPC Penetrated Rat Blood-CSF Barrier 27 male rats were divided into 4 groups (n=7). 0.3 mmol/kg of diethylaminoethyl acetylsalicylate HCl salt was administrated into rats intramuscularly (20% in 70% ethanol) or transdermally (10% in 70% ethanol, on the shaved back of rat, 10 cm$^2$) and 0.3 mmol/kg of aspirin was administrated into rats intramuscularly (20% in 70% ethanol) or transdermally (10% in 70% ethanol, on the shaved back of rat, 10 cm$^2$). 1, 8 and 18 hours after the test compound was administrated, the rat was killed and Cerebrospinal fluid (CSF) was taken out. Amounts of salicylic acid in rat CSF were determined. The results were shown in Table 4.3. The results show that a HPC of aspirin penetrated blood-CSF barrier efficiently, but aspirin could not.

TABLE 4.3

The amount of salicylic acid in rat cerebrospinal fluid (CSF)

| Test compounds | 1 hour | 8 hours | 18 hours |
| --- | --- | --- | --- |
| diethylaminoethyl acetylsalicylate (intramuscularly) | 36.4 ± 4.3 (nmol/g) | 28.2 ± 6.5 (nmol/g) | 15.1 ± 4.7 (nmol/g) |
| diethylaminoethyl acetylsalicylate (transdermally) | 38 ± 17 (nmol/g) | 28.4 ± 7.5 (nmol/g) | 22.3 ± 5.4 (nmol/g) |
| acetylsalicylic acid (intramuscularly) | 3.2 ± 1.2 (nmol/g) | 0.5 ± 0.3 (nmol/g) | Not detectable |
| acetylsalicylic acid (transdermally) | Not detectable | Not detectable | Not detectable |

4.4: HPC Penetrated Beagle Dogs Blood-Synovial Fluid (SF) Barrier 12 male Beagle dogs were divided into 4 groups (n=3). 0.3 mmol/kg of diethylaminoethyl 2-(p-isobutyl-phenyl)propionate.HCl salt was administrated into Beagle dogs intramuscularly (20% in 70% ethanol) or transdermally (on the back of dogs, 100 cm$^2$, 10% in 70% ethanol) and 0.3 mmol/kg of 2-(p-isobutyl-phenyl)propionic acid (ibuptofen) was administrated into Beagle dogs intramuscularly (20% in 70% ethanol) or transdermally (on the back of dogs, 100 cm$^2$, 10% in 70% ethanol). 1, 8, and 18 hours after the test compound was administrated, synovial fluid (CF) was taken out and amounts of ibuprofen in Beagle dogs CF were determined respectively. The results were shown in Table 4.4a. The results show that the HPC of ibuprofen penetrated blood-CF barrier efficiently, but ibuprofen could not.

TABLE 4.4a

The amount of ibuprofen in Beagle dogs synovial fluid (CF).

| Test compounds | 1 hour | 8 hours | 18 hours |
| --- | --- | --- | --- |
| diethylaminoethyl 2-(p-isobutyl-phenyl)propionate (intramuscularly) | 28.1 ± 8.1 (nmol/g) | 22.1 ± 4.2 (nmol/g) | 4.2 ± 1.1 (nmol/g) |
| diethylaminoethyl 2-(p-isobutyl-phenyl)propionate (transdermally) | 11.6 ± 4.2 (nmol/g) | 28.2 ± 4.7 (nmol/g) | 11.2 ± 3.2 (nmol/g) |
| 2-(p-isobutyl-phenyl)propionic acid (intramuscularly) | 3.2 ± 0.3 (nmol/g) | 0.3 ± 0.1 (nmol/g) | Not detectable |
| 2-(p-isobutyl-phenyl)propionic acid (transdermally) | Not detectable | Not detectable | Not detectable |

18 hours after the administration of ibuprofen or a HPC of ibuprofen, Beagle dogs were killed and the joint cartilage tissue (the whole joint was washed with pH 7.4 buffer for 3 times) was taken out and homogenized immediately in methanol, using a tissue tearor at 30,000 rpm (about 5 min.). Amounts of ibuprofen in Beagle dog joint cartilage were determined by LS-MS-MS. The results were shown in Table 4.4b.

TABLE 4.4b

Amounts of ibuprofen in Beagle dogs cartilage tissue

| | diethylaminoethyl 2-(p-isobutyl-phenyl)propionate (intramuscularly) | diethylaminoethyl 2-(p-isobutyl-phenyl)propionate (transdermally) | 2-(p-isobutyl-phenyl)propionic acid (intramuscularly) | 2-(p-isobutyl-phenyl)propionic acid (transdermally) |
| --- | --- | --- | --- | --- |
| Amount of ibuprofen (nmol/g) | 17.2 ± 6.1 | 22.5 ± 4.5 | Not detectable | Not detectable |

Example 5

Figure 9:
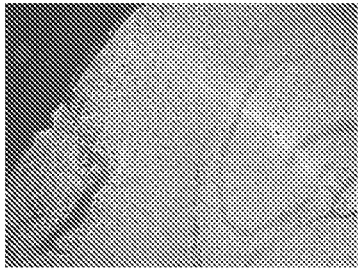
FIG. 9: The HE stained tissues (picture 1: brain, picture 2: muscle, picture 3: liver) 15 minutes after 30 mg of the HPC, N-2-diethylaminoethyl 5-dimethylamino-1-naphthalenesulfonamide.HCl salt in 0.5 ml of 75% ethanol was applied to the back of rats; The HE stained tissues (picture 4: brain, picture 5: muscle, picture 6: liver) 3 hours after 30 mg of the HPC, N-2-diethylaminoethyl 5-dimethylamino-1-naphthalenesulfonamide.HCl salt in 0.5 ml of 75% ethanol was applied to the back of rats; HE stained tissues (picture 7: brain, picture 8: muscle, picture 9: liver) 3 hours after 30 mg of 5-(dimethylamino)naphthalene-1-sulfonic acid in 0.5 ml of 75% ethanol was applied to the back of rats.
Figure 9:
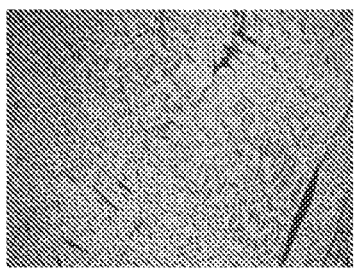
Figure 9:
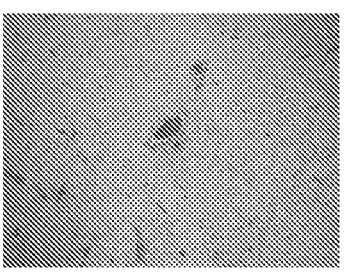
Figure 9:
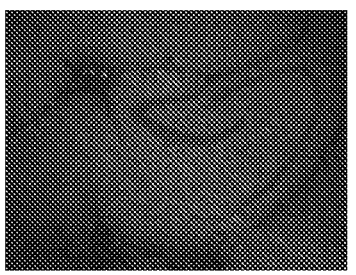
Figure 9:
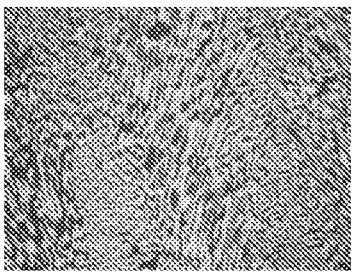
Figure 9:
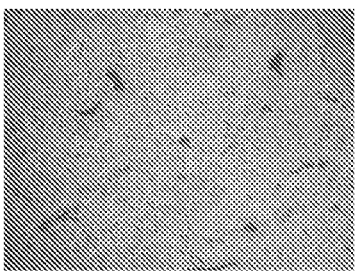
Figure 9:
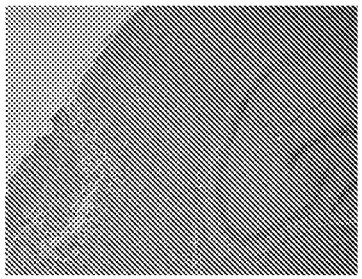
Figure 9:
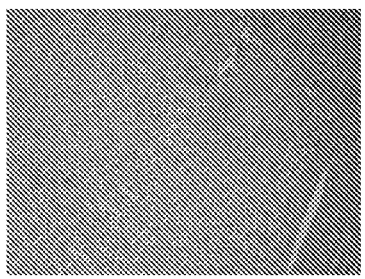
Figure 9:
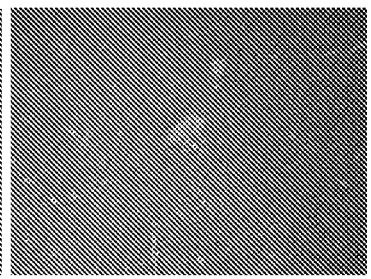

Fluorescence Microscopy Studies of HPC Crossing Rat Skin, Brain and Other Organs For fluorescence microscopy studies, 30 mg of 5-(dimethylamino)naphthalene-1-sulfonic acid or its HPC, N-2-diethylaminoethyl 5-dimethylamino-1-naphthalenesulfonamide.HCl salt was dissolved in 0.5 ml of 75% ethanol and applied to the shaved back of rats (3×3 cm). 15 minutes or 3 hours later, the rat was killed and organs were taken out and frozen. The frozen tissues (brain, liver, and muscle) were sliced and stained with Haematoxylin and eosin (H&E) staining. Results were shown picture 1-9 in FIG. 9.

The results show that only 15 minutes after 30 mg of N-2-diethylaminoethyl 5-dimethylamino-1-naphthalene-sulfonamide.HCl salt in 0.5 ml of 70% ethanol, large amount of the fluorescence chemical had entered the brain, muscle, and liver, but even 3 hours after 30 mg of 5-(dimethylamino)naphthalene-1-sulfonic acid in 0.5 ml of 70% ethanol was applied to the back of rats, none of the fluorescence chemical had entered the brain, muscle, and liver. The HPC showed an enhanced ability than its parent drug to penetrate skin, blood-brain, and other biological barriers.

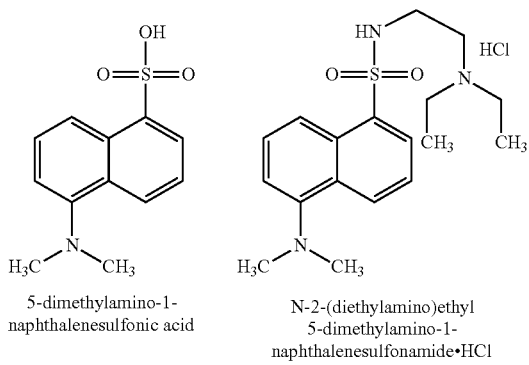 [SMILES: CN(C)c1cccc2c(S(=O)(=O)O)cccc12 ; CCN(CC)CCNS(=O)(=O)c1cccc2c(N(C)C)cccc12 ; Cl]

5-dimethylamino-1-naphthalenesulfonic acid

N-2-(diethylamino)ethyl 5-dimethylamino-1-naphthalenesulfonamide•HCl

Example 6

Transdermal Administrations of Compositions Comprising a HPC Result in Whole Body Distribution of the HPC and Related Compounds in the Absence of General Circulation 0.3 mmol/kg of diethylaminoethyl acetylsalicylate HCl salt (10% in pure water) was applied to the back of rats (10 cm$^2$) which were killed with $CO_2$. The rats were shaken for 5 hrs, then the HPCs and parent drugs in organs of rats were determined. The results (Table 6) show that the HPCs distributed to the whole body of a biological subject through the intercellular and intracellular fluids and not necessary through the general circulation.

blood-brain, blood-milk, and other biological barriers efficiently. The membrane penetration rates of drugs were increased hundreds of times, the pharmacological effect and the clinical response of drugs could be increased dramatically, thus reducing required drug dosage and the side effects dramatically and providing new indications.

Study A: Rats received a sterilized *E. coli* suspension as a pyrogen. 2 hours later, ibuprofen (100 mg/kg, orally, group B), diethylaminoethyl 2-(ρ-isobutylphenyl) propionate.HCl salt (the HPC of ibuprofen, 100 mg/kg, orally, group C), ibuprofen (50 mg/kg, orally, group D), diethylaminoethyl 2-(ρ-isobutylphenyl) propionate.HCl salt (50 mg/kg, orally, group E), ibuprofen (20 mg/kg, orally, group F), diethylaminoethyl 2-(ρ-isobutylphenyl) propionate.HCl salt (20 mg/kg, orally G), ibuprofen (100 mg/kg, transdermally, group H), diethylaminoethyl 2-(ρ-isobutylphenyl) propionate.HCl salt (100 mg/kg, transdermally, group I), ibuprofen (50 mg/kg, transdermally, group J), diethylaminoethyl 2-(ρ-isobutylphenyl) propionate. HCl salt (50 mg/kg, transdermally, group K), ibuprofen (20 mg/kg, transdermally, group L), and diethylaminoethyl 2-(ρ-isobutylphenyl) propionate.HCl salt (20 mg/kg, transdermally, group M) were administered. Group A was the control group. The body temperature of rats was taken at 90 min. intervals before and after the administration of the test compounds. The results are shown in Table 7a.

TABLE 6

The distribution of diethylaminoethyl acetylsalicylate and metabolites in the organs of rats which were killed with $CO_2$(in vivo, the HPC will change to parent drug in a very short time, so the concentration is the concentration of parent drug).

| | Leg muscle | liver | kidney | stomach | pancreas |
|---|---|---|---|---|---|
| diethylaminoethyl acetylsalicylic acid | 5.2 ± 3.2 (nmol/g) | 1.2 ± 1.1 (nmol/g) | 3.1 ± 1.4 (nmol/g) | 4.3 ± 1.1 (nmol/g) | 2.7 ± 1.3 (nmol/g) |
| diethylaminoethyl salicylic acid | 6.2 ± 3.2 (nmol/g) | 1.5 ± 1.2 (nmol/g) | 3.1 ± 1.6 (nmol/g) | 3.2 ± 1.3 (nmol/g) | 3.1 ± 1.1 (nmol/g) |
| acetylsalicylic acid | 6.7 ± 2.1 (nmol/g) | 2.1 ± 1.0 (nmol/g) | 3.5 ± 2.1 (nmol/g) | 4.7 ± 2.5 (nmol/g) | 4.1 ± 1.3 (nmol/g) |
| salicylic acid | 41.4 ± 11.2 (nmol/g) | 12.2 ± 6.1 (nmol/g) | 21.2 ± 7.6 (nmol/g) | 25.1 ± 2.4 (nmol/g) | 14.1 ± 1.2 (nmol/g) |

Example 7

Transdermal or Oral Administrations of a HPC of Ibuprofen or Aspirin Showed Stronger Antipyretic Activities than its Corresponding Parent Drug The results in the present disclosure showed that the HPCs that penetrated skin very efficiently also penetrated TABLE 7a

| Antipyretic Activity of ibuprofen and its HPC. | | | | |
|---|---|---|---|---|
| Compound | t = 0 min. | t = 90 min. | t = 180 min. | t = 270 min. |
| A (Control group) | 37.5 ± 0.4 | 37.7 ± 0.3 | 37.8 ± 0.4 | 37.9 ± 0.3 |
| B (100 mg/kg, orally) | 37.5 ± 0.3 | 37.4 ± 0.4 | 36.8 ± 0.3 | 36.7 ± 0.3 |
| C (100 mg/kg, orally) | 37.5 ± 0.4 | 36.5 ± 0.3 | 36.4 ± 0.3 | 36.4 ± 0.2 |
| D (50 mg/kg, orally) | 37.5 ± 0.3 | 37.6 ± 0.3 | 37.2 ± 0.3 | 37.1 ± 0.3 |

TABLE 7a-continued

Antipyretic Activity of ibuprofen and its HPC.

| Compound | t = 0 min. | t = 90 min. | t = 180 min. | t = 270 min. |
|---|---|---|---|---|
| E (50 mg/kg, orally) | 37.6 ± 0.3 | 36.6 ± 0.3 | 36.5 ± 0.3 | 36.4 ± 0.2 |
| F (20 mg/kg, orally) | 37.5 ± 0.2 | 37.6 ± 0.3 | 37.5 ± 0.3 | 37.4 ± 0.3 |
| G (20 mg/kg, orally) | 37.6 ± 0.3 | 37.1 ± 0.3 | 36.9 ± 0.3 | 36.8 ± 0.2 |
| H (100 mg/kg, transdermally) | 37.6 ± 0.4 | 37.9 ± 0.4 | 37.8 ± 0.3 | 37.8 ± 0.2 |
| I (100 mg/kg, transdermally) | 37.5 ± 0.3 | 36.5 ± 0.2 | 36.4 ± 0.3 | 36.5 ± 0.2 |
| J (50 mg/kg, transdermally) | 37.6 ± 0.3 | 37.8 ± 0.3 | 37.9 ± 0.3 | 38.1 ± 0.3 |
| K (50 mg/kg, transdermally) | 37.5 ± 0.4 | 36.5 ± 0.3 | 36.4 ± 0.3 | 36.5 ± 0.2 |
| L (20 mg/kg, transdermally) | 37.5 ± 0.3 | 37.5 ± 0.5 | 37.8 ± 0.4 | 37.9 ± 0.3 |
| M (20 mg/kg, transdermally) | 37.6 ± 0.2 | 36.7 ± 0.4 | 36.6 ± 0.5 | 36.5 ± 0.3 |

The results show that the HPCs demonstrated stronger antipyretic activity than the corresponding parent drug, ibuprofen. In oral administration, 20 mg/kg of the HPC of ibuprofen (equal to 12 mg of ibuprofen) had almost the same effect as 100 mg/kg of ibuprofen. In transdermal administration, ibuprofen did not show any antipyretic activity because ibuprofen could penetrate skin; but the HPC of ibuprofen had stronger antipyretic activity when it was administrated transdermally than orally.

Study B: Rats received a sterilized *E. coli* suspension as a pyrogen. 2 hours later, aspirin (100 mg/kg, orally, group B), diethylaminoethyl acetylsalicylate.HCl salt (the HPC of aspirin, 100 mg/kg, orally, group C), aspirin (50 mg/kg, orally, group D), diethylaminoethyl acetylsalicylate.HCl salt (50 mg/kg, orally, group E), aspirin (20 mg/kg, orally, group F), diethylaminoethyl acetylsalicylate.HCl salt (20 mg/kg, orally G), aspirin (50 mg/kg, transdermally, group H), diethylaminoethyl acetylsalicylate.HCl salt (50 mg/kg, transdermally, group I), aspirin (20 mg/kg, transdermally, group J), diethylaminoethyl acetylsalicylate.HCl salt (20 mg/kg, transdermally, group K), aspirin (10 mg/kg, transdermally, group L), and diethylaminoethyl acetylsalicylate.HCl salt (10 mg/kg, transdermally, group M) were administered. Group A was the control group. The body temperature of rats was taken at 90 min. intervals before and after the administration of the test compounds. The results were shown in Table 7b.

TABLE 7b

Antipyretic Activity of Aspirin and Its HPC.

| Compound | t = 0 min. | t = 90 min. | t = 180 min. | t = 270 min. |
|---|---|---|---|---|
| A (Control group) | 37.4 ± 0.5 | 37.8 ± 0.3 | 37.7 ± 0.4 | 37.9 ± 0.4 |
| B (100 mg/kg, orally) | 37.5 ± 0.2 | 37.3 ± 0.4 | 36.7 ± 0.3 | 36.8 ± 0.4 |
| C (100 mg/kg, orally) | 37.6 ± 0.4 | 36.6 ± 0.4 | 36.5 ± 0.3 | 36.4 ± 0.3 |
| D (50 mg/kg, orally) | 37.5 ± 0.3 | 37.7 ± 0.3 | 37.1 ± 0.3 | 37.0 ± 0.4 |
| E (50 mg/kg, orally) | 37.6 ± 0.3 | 36.7 ± 0.3 | 36.5 ± 0.2 | 36.4 ± 0.3 |
| F (20 mg/kg, orally) | 37.5 ± 0.2 | 37.7 ± 0.3 | 37.4 ± 0.3 | 37.4 ± 0.4 |
| G (20 mg/kg, orally) | 37.6 ± 0.3 | 37.1 ± 0.4 | 36.8 ± 0.2 | 36.5 ± 0.3 |
| H (50 mg/kg, transdermally) | 37.6 ± 0.3 | 37.9 ± 0.3 | 37.8 ± 0.4 | 37.7 ± 0.5 |
| I (50 mg/kg, transdermally) | 37.5 ± 0.3 | 36.5 ± 0.2 | 36.3 ± 0.3 | 36.4 ± 0.2 |
| J (20 mg/kg, transdermally) | 37.6 ± 0.3 | 37.8 ± 0.4 | 37.7 ± 0.4 | 38.0 ± 0.3 |
| K (20 mg/kg, transdermally) | 37.5 ± 0.4 | 36.7 ± 0.2 | 36.4 ± 0.2 | 36.4 ± 0.2 |
| L (20 mg/kg, transdermally) | 37.5 ± 0.3 | 37.6 ± 0.5 | 37.8 ± 0.3 | 37.9 ± 0.3 |
| M (20 mg/kg, transdermally) | 37.6 ± 0.2 | 36.5 ± 0.4 | 36.4 ± 0.3 | 36.5 ± 0.2 |

In oral administration, 20 mg/kg of the HPC of aspirin (equal to 11.4 mg of aspirin) showed almost the same antipyretic activity as 100 mg/kg of aspirin. In transdermal administration, aspirin did not show any antipyretic activity because aspirin could not penetrate skin; but the HPC of aspirin showed stronger antipyretic activity when it was administrated transdermally than orally.

Example 8

Transdermal or Oral Administrations of HPC of Ibuprofen Showed Stronger Anti-Inflammatory Activities than its Parent Drug Ibuprofen Aqueous solutions of diethylaminoethyl 2-(ρ-isobutylphenyl) propionate.citric acid are administered transdermally to the foot pads of the rats in group C (2 mg/kg of the HPC), D (5 mg/kg of the HPC), E (10 mg/kg of the HPC), and F (20 mg/kg of the HPC) respectively and 100 mg/kg of ibuprofen(group B), 100 mg/kg (group G) and 50 mg/kg (group H) of diethylaminoethyl 2-(ρ-isobutylphenyl) propionate.citric acid were administered orally. 1 Hour later, 0.05 ml of a carrageenin solution was administered subcutaneously to the foot pads of the rats. 1 Hour later, aqueous solutions of diethylaminoethyl 2-(ρ-isobutylphenyl) propionate.citric acid were administered transdermally to the foot pads of the rats in group C (2 mg/kg of the HPC), D (5 mg/kg of the HPC), E (10 mg/kg of the HPC), and F (20 mg/kg of the HPC) respectively.

Figure 10:
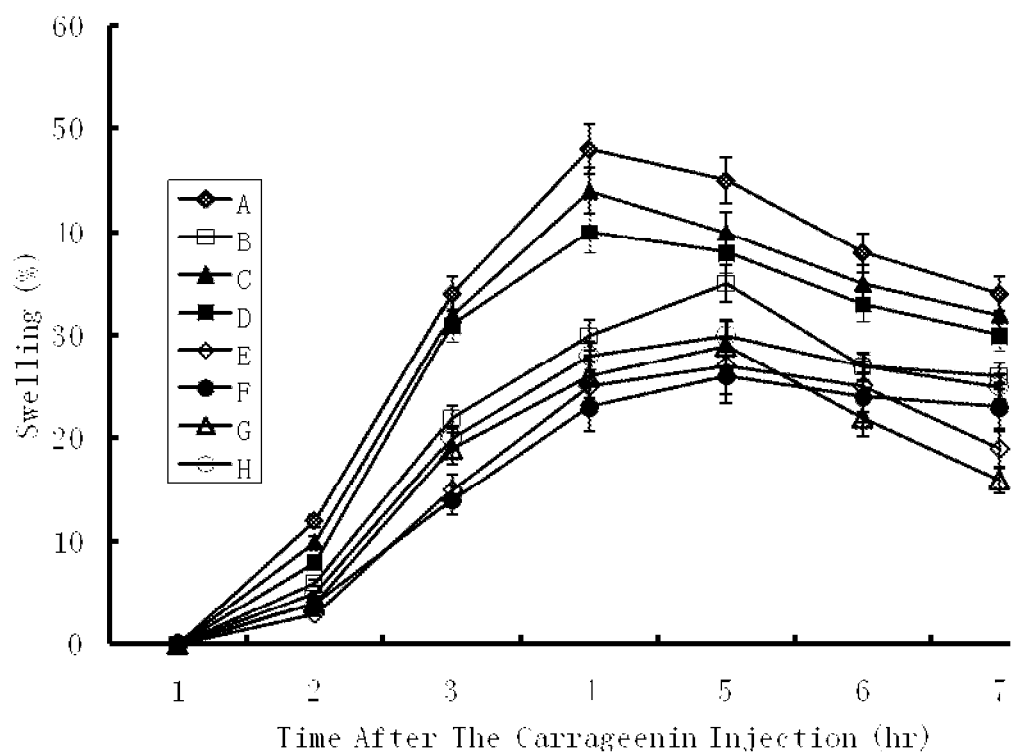
FIG. 10: Rate of swelling (%) after a carrageenin injection. 1 hour before the carrageenin injection, 100 mg/kg of ibuprofen (B) 100 mg/kg (G) and 50 mg/kg (H) of diethylaminoethyl 2-(ρ-isobutylphenyl) propionate.citric acid were administered orally (B), 1 mg/kg (C), 2 mg/kg, 5 mg/kg (D), 10 mg/kg (E), and 20 mg/kg (F) of diethylaminoethyl 2-(ρ-isobutylphenyl) propionate.citric acid were administered transdermally. A was the control group.

The volume of the hind paw was measured at every hour after the administration of the carrageenin and the rate of increase in the volume of the paw was calculated and designated as the rate of swelling (%). The results were shown in FIG. 10.

The anti-inflammatory activity of 20 mg/kg(2×10 mg) of diethylaminoethyl 2-(ρ-isobutylphenyl) propionate.citric acid (MW:497.5, transdermally) [equates to ~8 mg/kg of ibuprofen(MW: 206.2)] and 50 mg/kg of diethylaminoethyl 2-(ρ-isobutylphenyl) propionate.citric acid (orally) [equates to ~20 mg/kg of ibuprofen] were much stronger than that of 100 mg/kg of ibuprofen (oral). Similar results have been demonstrated in other animal models.

Transdermal or oral administrations of compositions comprising a HPC of ibuprofen showed more than 5 times stronger anti-inflammatory activities than its parent drug, ibuprofen.

Example 9

HPC of Aspirin Showed Stronger Anti-Diabetic Activities than Aspirin

Studies of the hypoglycemic effects of aspirin and its HPC, diethylaminoethyl acetylsalicylate.HCl salt, were carried out in type 2 diabetes rat models [SLAC/GK(Goto and Kakisaki)]. 300 mg/kg, 200 mg/kg, 100 mg/kg, and 50 mg/kg of aspirin and diethylaminoethyl acetylsalicylate.HCl salt (HPC) were administered into the GK rats (n=5×8) orally and 100 mg/kg, 50 mg/kg, and 30 mg/kg (10% in 70% ethanol) of aspirin and diethylaminoethyl acetylsalicylate.HCl salt were administered transdermally to the backs (about 7 cm$^2$) of rats [(n=5×6) fur was shaved off] once per day for 6 weeks. The blood glucose levels were measured three times every week (no fasting) from the third week to the sixth week. The results were shown in Table 9.

TABLE 9

Anti-diabetes (type II) activity of aspirin and diethylaminoethyl acetylsalicylate•HCl salt. in GK rats (12-14 weeks old).

| Test compounds | Blood Glucose Levels at day 1 (mg/dL, no fasting, n = 5) | Blood Glucose Levels at day 42 (mg/dL, no fasting, n = 5) |
|---|---|---|
| Control group | 212.4 ± 28.5 | 252.4 ± 23.6 |
| Aspirin (300 mg/kg, orally) | 215.6 ± 22.4 | 165.4 ± 22.1 |
| HPC (300 mg/kg, orally) | 217.4 ± 25.5 | 115.4 ± 18.2 |
| Aspirin (200 mg/kg, orally) | 213.5 ± 21.5 | 195.4 ± 23.4 |
| HPC (200 mg/kg, orally) | 214.4 ± 26.5 | 125.4 ± 26.8 |
| Aspirin (100 mg/kg, orally) | 211.3 ± 21.5 | 219.4 ± 19.9 |
| HPC (100 mg/kg, orally) | 216.4 ± 18.5 | 133.4 ± 23.1 |
| Aspirin (50 mg/kg, orally) | 213.7 ± 20.5 | 243.4 ± 26.7 |
| HPC (50 mg/kg, orally) | 215.6 ± 19.5 | 172.4 ± 21.5 |
| Aspirin(200 mg/kg, transdermally) | 216.4 ± 21.9 | 247.4 ± 27.8 |
| HPC (200 mg/kg, transdermally) | 219.4 ± 23.5 | 111.4 ± 23.2 |
| Aspirin(100 mg/kg, transdermally) | 217.4 ± 18.9 | 255.4 ± 24.6 |
| HPC (100 mg/kg, transdermally) | 219.8 ± 20.4 | 115.4 ± 16.7 |
| Aspirin (50 mg/kg, transdermally) | 216.6 ± 17.3 | 258.2 ± 17.4 |
| HPC (50 mg/kg, transdermally) | 217.3 ± 19.7 | 135.4 ± 19.8 |

The results show that the HPC of aspirin had much stronger (more than 5 times in oral administration) anti-diabetic effect than that of aspirin. Aspirin did not show any anti-diabetic effect in transdermal administration, but the transdermal administration of HPC was more effective than oral administration for HPC.

Example 10

Anti-Diabetes (type II) Activity of the HPCs of NSAIAs

A HPC in the present disclosure lowered blood glucose levels in rat models (SLAC/GK, type 2 diabetes, n=7). 30 mg/kg of 8% diethylaminoethyl acetylsalicylate.HCl salt (P-1, in 25% ethanol); 4-acetamidophenyl salicylyldimethylaminobutyrate.HCl (P-6, in 25% ethanol), diethylaminoethyl 5-(2,4-difluorophenyl)acetylsalicylate.5-(2,4-difluorophenyl)acetylsalicylic acid salt (P-8, in 25% ethanol), diethylaminoethyl salicylsalicylate.HCl salt (P-9, in 25% ethanol), diethylaminoethyl salicylate.AcOH(P-10, in 25% ethanol), diethylaminoethyl 5-acetamido-acetylsalicylate.HCl(P-58, in 25% ethanol), diethylaminoethyl acetylsalicylsalicylate. HCl salt (P-59, in 25% ethanol), diethylaminoethyl acetylsalicylsalicylsalicylate. HCl salt (P-60, in 25% ethanol) were administered transdermally to the backs (6 cm$^2$, fur was shaved) of GK rats (SLAC/GK, 14-16 weeks old) and normal SD rats (SLAC/SD, 14-16 weeks old) once per day (at 8 am) for 6 weeks.

The blood glucose levels were measured once every 3 days at 4:30 pm (no fasting) from the third week to the sixth week as shown in Table 10a and 10b. The results showed that the HPC of NSAIAs lowered blood glucose levels in diabetes rats effectively and did not affect the blood glucose levels in normal rats. Moreover, the blood glucose levels of the rats stayed at normal level (6-9 mmol/L, no fasting) after the treatment was stopped for 40 days. It suggested that the HPC may also have cured diabetes in the rats.

TABLE 10a

Anti-diabetes (type II) activity of the HPCs of NSAIAs

| | HPCs | Control (mmol/L) | P-1 (mmol/L) | P-6 (mmol/L) | P-8 (mmol/L) | P-9 (mmol/L) |
|---|---|---|---|---|---|---|
| GK rats | Day 1 | 16.7 ± 3.2 | 17.1 ± 2.8 | 16.8 ± 3.0 | 16.9 ± 2.8 | 16.4 ± 2.3 |
| | Average (Week 2-5) | 18.9 ± 2.2 | 6.4 ± 2.4 | 9.2 ± 2.7 | 8.3 ± 2.1 | 9.4 ± 2.7 |
| SD rats | Day 1 | 5.6 ± 1.4 | 5.8 ± 1.5 | 5.7 ± 1.3 | 5.6 ± 1.5 | 5.5 ± 1.3 |
| | Average (Week 2-5) | 5.5 ± 1.3 | 5.7 ± 1.3 | 5.8 ± 1.1 | 5.7 ± 1.2 | 5.6 ± 1.2 |

TABLE 10b

Anti-diabetes (type II) activity of the HPCs of NSAIAs

| HPCs | | P-10 (mmol/L) | P-58 (mmol/L) | P-59 (mmol/L) | P-60 (mmol/L) |
|---|---|---|---|---|---|
| GK rats | Day 1 | 16.7 ± 3.2 | 17.1 ± 2.8 | 16.8 ± 3.0 | 15.9 ± 2.8 |
| | Average (Week 2-5) | 9.1 ± 2.2 | 9.4 ± 3.0 | 8.2 ± 2.7 | 9.3 ± 2.9 |
| SD rats | Day 1 | 5.8 ± 1.2 | 5.9 ± 1.2 | 5.7 ± 1.3 | 5.6 ± 1.3 |
| | Average (Week 2-5) | 5.7 ± 1.3 | 5.8 ± 1.1 | 5.8 ± 1.0 | 5.7 ± 1.1 |

HPCs in the present disclosure lowered blood glucose levels and blood lipid levels in mice models (SLAC/DB/DB, obese mice, n=7). 30 mg/kg of 8% diethylaminoethyl acetylsalicylate.HCl salt (P-1, in 25% ethanol); 4-acetamidophenyl salicylyldimethylaminobutyrate.HCl (P-6, in 25% ethanol), diethylaminoethyl 5-(2,4-difluorophenyl)acetylsalicylate.5-(2,4-difluorophenyl)acetylsalicylic acid salt (P-8, in 25% ethanol), diethylaminoethyl salicylsalicylate.HCl salt (P-9, in 25% ethanol), diethylaminoethyl salicylsalicylate.AcOH(P-10, in 25% ethanol), diethylaminoethyl 5-acetamido-acetylsalicylate.HCl(P-58, in 25% ethanol), diethylaminoethyl acetylsalicylsalicylate.HCl salt (P-59, in 25% ethanol), diethylaminoethyl acetylsalicylsalicylsalicylate.HCl salt (P-60, in 25% ethanol) were administered transdermally to the backs (4 cm², fur was shaved) of DB/DB mice(SLAC/DB/DB, 10-12 weeks old) once per day (at 8 am) for 5 weeks. The blood glucose levels were measured once per week and blood lipid levels were measured once every other week. The results are shown in table 10c, 1d, 10e, and 10f.

TABLE 10c

Anti-diabetes activity of the HPCs of NSAIAs in DB/DB mice.

| HPCs | Control (mmol/L) | P-1 (mmol/L) | P-6 (mmol/L) | P-8 (mmol/L) | P-9 (mmol/L) |
|---|---|---|---|---|---|
| Day 1 | 14.5 ± 2.5 | 14.1 ± 2.6 | 14.2 ± 2.0 | 14.5 ± 2.7 | 14.1 ± 2.5 |
| Week 5 | 17.1 ± 3.0 | 6.8 ± 2.8 | 9.5 ± 2.8 | 8.4 ± 2.1 | 8.7 ± 2.3 |

TABLE 10d

Anti-diabetes activity of the HPCs of NSAIAs in DB/DB mice.

| HPCs | P-10 (mmol/L) | P-58 (mmol/L) | P-59 (mmol/L) | P-60 (mmol/L) |
|---|---|---|---|---|
| Day 1 | 15.1 ± 3.7 | 15.6 ± 2.9 | 14.2 ± 2.2 | 14.8 ± 2.7 |
| Week 5 | 9.2 ± 2.3 | 9.3 ± 2.1 | 8.1 ± 2.4 | 9.0 ± 2.1 |

TABLE 10e

Blood lipid-lowering activity of the HPCs of NSAIAs in DB/DB mice

| HPCs | | Control (mmol/L) | P-1 (mmol/L) | P-6 (mmol/L) | P-8 (mmol/L) | P-9 (mmol/L) |
|---|---|---|---|---|---|---|
| Cholesterol (total) | Day 1 | 7.4 ± 0.5 | 7.1 ± 0.4 | 7.0 ± 0.4 | 6.8 ± 0.4 | 7.7 ± 0.5 |
| | Week 5 | 8.6 ± 0.7 | 4.1 ± 0.4 | 4.9 ± 0.5 | 5.0 ± 0.2 | 4.9 ± 0.5 |
| Triglycerides | Day 1 | 4.1 ± 0.4 | 4.1 ± 0.5 | 4.4 ± 0.5 | 4.4 ± 0.4 | 4.1 ± 0.4 |
| | Week 5 | 5.6 ± 0.3 | 1.5 ± 0.3 | 2.5 ± 0.3 | 2.2 ± 0.4 | 2.1 ± 0.3 |

TABLE 10f

Blood lipid-lowering activity of the HPCs of NSAIAs in DB/DB mice

| HPCs | | P-10 (mmol/L) | P-58 (mmol/L) | P-59 (mmol/L) | P-60 (mmol/L) |
|---|---|---|---|---|---|
| Cholesterol (total) | Day 1 | 6.8 ± 0.4 | 7.1 ± 0.3 | 6.6 ± 0.4 | 7.0 ± 0.8 |
| | Week 5 | 4.7 ± 0.5 | 5.1 ± 0.6 | 4.7 ± 0.4 | 5.0 ± 0.4 |
| Triglycerides | Day 1 | 4.8 ± 0.9 | 4.9 ± 0.4 | 4.6 ± 0.4 | 4.3 ± 0.5 |
| | Week 5 | 2.3 ± 0.3 | 4.3 ± 0.5 | 4.6 ± 0.5 | 4.3 ± 0.5 |

The results show that the HPCs of NSAIAs can lower blood glucose level and blood lipid levels (total cholesterol and triglycerides) in obese mice models (SLAC/DB/DB) very effectively.

Example 11

Anti-Diabetes (Type I) Activity of the HPCs of NSAIAs

HPCs showed strong anti-diabetes (type 1) activities in rat models (SLAC:NOD-IDDM, type 1 diabetes, n=7). 10% aqueous solution of diethylaminoethyl acetylsalicylate.acetylsalicylic acid salt (P-1, in acetone); 4-acetamidophenyl salicylyldimethylaminobutyrate. HCl (P-6), diethylaminoethyl 5-(2,4-difluorophenyl)acetylsalicylate.5-(2,4-difluorophenyl)acetylsalicylic acid salt (P-8), diethylaminoethyl salicylsalicylate.AcOH(P-9), diethylaminoethyl 5-acetamido-acetylsalicylate. HCl (P-58), diethylaminoethyl 2-(p-isobutylphenyl) propionate.citric acid (P-59), diethylaminoethyl acetylsalicylsalicylate. acetylsalicylsalicylic acid salt (P-60) (equal to of 20 mg/kg of NSAIAs) were administered transdermally to the shaved back (about 1.5 cm²) of mice twice per day (at 8 am and 5 pm) for 7 weeks.

The blood glucose levels were measured once every 3 days at 4:30 pm (no fasting) from the fourth week to the seventh week as shown in Table 11. The results showed that the HPC of NSAIAs lowered blood glucose levels in diabetic (type I) mouse models effectively.

TABLE 11

Anti-diabetes (type I) activity of the HPCs of NSAIAs

| HPC | Control mmol/L | P-1 mmol/L | P-6 mmol/L | P-8 mmol/L | P-9 mmol/L | P-10 mmol/L | P-58 mmol/L | P-59 mmol/L | P-60 mmol/L |
|---|---|---|---|---|---|---|---|---|---|
| Baseline | 18.6 ± 4.2 | 18.1 ± 4.5 | 18.9 ± 4.3 | 19.4 ± 3.1 | 16.5 ± 3.6 | 18.8 ± 3.4 | 17.9 ± 3.2 | 19.1 ± 3.2 | 17.5 ± 3.3 |
| Average | 32.9 ± 5.5* | 7.5 ± 1.8 | 9.5 ± 2.1 | 9.7 ± 1.4 | 8.4 ± 1.9 | 8.6 ± 1.8 | 8.1 ± 1.9 | 8.9 ± 1.7 | 8.8 ± 1.9 |

*The data are from the fourth week. All mice in the control groups died before the sixth week.

Example 12

Treatment of Diabetes (Type II)

About 0.8 ml of 8% diethylaminoethyl acetylsalicylate.HCl in 25% ethanol is sprayed to any part skin of the body (rotating the location every time to avoid harm to the skin) twice per day. The process is continued until the diabetes is cured (maybe lifelong).

Example 13

Prevention of Diabetes (Type II)

For people with high risk to get diabetes (type II), such as overweight people, people who have family history of diabetes (type II), people with mutant genes related to diabetes (type II), about 0.3 ml of 8% diethylaminoethyl acetylsalicylate.HCl in 25% ethanol is sprayed to any part skin of the body (rotating the location every time to avoid harm to the skin) once or twice per day.

Example 14

Treatment of Diabetes (type I)

About 0.8 ml of 8% diethylaminoethyl acetylsalicylate.HCl in 25% ethanol is sprayed to any part skin of the body (rotating the location every time to avoid harm to the skin) twice per day. The process is continued until the diabetes is cured (maybe lifelong).

Example 15

Prevention of Diabetes (Type I)

For people with high risk to get diabetes (type I), such as people having a twin sister, or brother with diabetes (type I), people who have family history of diabetes (type II), people with mutant genes related to diabetes (type II), about 0.4 ml of 8% diethylaminoethyl acetylsalicylate.HCl in 25% ethanol is sprayed to any part skin of the body (rotating the location every time to avoid harm to the skin) once or twice per day.

Example 16

Treatment of Abnormal Blood Lipid Levels
(Abnormal Blood Cholesterol Levels and/or
Abnormal Blood Triglycerides Levels)

About 0.8 ml of 8% diethylaminoethyl acetylsalicylate.HCl in 25% ethanol is sprayed to any part skin of the body (rotating the location every time to avoid harm to the skin) twice per day. The process is continued until the abnormal blood lipid levels is cured (maybe lifelong).

Example 17

Prevention of Abnormal Blood Lipid Levels
(Abnormal Blood Cholesterol Levels and/or
Abnormal Blood Triglycerides Levels)

For people with high risk to get abnormal blood lipid levels, such as people having a twin sister, or brother with abnormal blood lipid levels, people who have family history of abnormal blood lipid levels, people with mutant genes related to abnormal blood lipid levels, about 0.3 ml of 8% diethylaminoethyl acetylsalicylate.HCl in 25% ethanol is sprayed to any part skin of the body (rotating the location every time to avoid harm to the skin) once or twice per day Example 18

Anti-Psoriasis Activity of the HPCs of NSAIAs

Without being bound by a particular mechanism, COX-1 and COX-2 play a very important role in animal immune-responses. NSAIAs inhibit COX-1 and COX-2. HPCs of NSAIAs may be very useful for treating psoriasis, discoid lupus erythematosus, systemic lupus erythematosus (SLE), and other autoimmune diseases.

Heavy suspensions of Malassezia [Rosenberg, E. W., et al., Mycopathologia, 72, 147-154 (1980)] were applied to the shaved skin on the backs of Chinese white rabbits (n=4×6) twice (at 8 am and 5 pm) per day for 2 weeks to generate lesions similar to psoriasis. HPCs (5%, aq.) were applied to the same areas 3 hours (10 am and 6 pm) after the application of Malassezia (7 am and 3 pm). The lesions healed 10 days after the application of one HPC selected from the group of 3-piperidinemethyl 2-(p-isobutylphenyl) propionate.HCl, diethylaminoethyl 1-methyl-5-(4-methyl-benzoyl)-1H-pyrrole-2-acetate.HCl, diethylaminoethyl 5-(4-Chlorobenzoyl)-1,4-dimethyl-1H-pyrrole-2-acetate. HCl, diethylaminoethyl 1,8-diethyl-1,3,4,9-tetrahydropyrano-[3,4-b]indole-1-acetate.HCl, diethylaminoethyl 2-amino-3-(4-bromo-benzoyl)benzeneacetate.HCl, diethylaminoethyl 3-chloro-4-(2-propenyloxy)benzeneacetate. HCl, diethylaminoethyl 1-(4-chlorobenzoyl-5-methoxy-2-methyl-1H-indole-3-acetoxyacetate. HCl, diethylaminoethyl 4-(4-chlorophenyl)-2-phenyl-5-thiazoleacetate.HCl, and diethylaminoethyl 3-(4-chlorophenyl)-1-phenyl-1H-pyrazole-4-acetate.HCl Example 19

Treatment of Psoriasis

About 1.5 ml (depended on the area size of psoriasis) of 8% N,N-diethylaminoethyl acetylsalicylate.HCl in 25% ethanol is sprayed to the skin with psoriasis or around the psoriasis areas twice per day. The treatment is continued until the psoriasis disappeared (that may be lifelong).

Example 20

Treatment of Acne Vulgaris and Other Skin Disorders

About 1 ml (depended on the affected area size) of 8% N,N-diethylaminoethyl acetylsalicylate.HCl in 25% ethanol is applied to the skin with acne vulgaris or around the acne vulgaris areas twice per day. The treatment is continued until the acne vulgaris disappeared.

Example 21

Prevention of Psoriasis and/or any Other Skin Disorders

For people with high risk to get psoriasis and/or any other skin disorders, such as people having a twin sister or brother with psoriasis and/or any other skin disorders, people who have family history of psoriasis and/or any other skin disorders, about 0.3 ml of 8% diethylaminoethyl acetylsalicylate.HCl in 25% ethanol is sprayed to any part skin of the body (rotating the location every time to avoid harm to the skin) once or twice per day

Example 22

Use of HPCs of NSAIAs to Soften and Shrink Scars in Rabbits

25 Chinese white rabbits were cut on the shaved back to generate wounds of the same size. The rabbits were divided into two groups, one group was treated with the HPCs and the other group was the control group with no treatment. For the treated group, the HPCs (5%, aq.) were applied to the nearby area of the wounds (5×5 $cm^2$). The average scar area of the treated rabbits as one-third of that of that of the untreated rabbits, and the scars were as soft as normal unscarred tissues.

The HPCs tested were 3-piperidinemethyl 2-(ρ-isobutylphenyl) propionate. HCl, diethylaminoethyl 1-methyl-5-(4-methylbenzoyl)-1H-pyrrole-2-acetate.HCl, diethylaminoethyl 5-(4-Chlorobenzoyl)-1,4-dimethyl-1H-pyrrole-2-acetate. HCl, diethylaminoethyl 1,8-diethyl-1,3,4,9-tetrahydropyrano-[3,4-b]indole-1-acetate. HCl, diethylaminoethyl 2-amino-3-(4-bromo-benzoyl)benzeneacetate. HCl, diethylaminoethyl 3-chloro-4-(2-propenyloxy)benzeneacetate. HCl, diethylaminoethyl 1-(4-chlorobenzoyl-5-methoxy-2-methyl-1H-indole-3-acetoxyacetate. HCl, diethylaminoethyl 4-(4-chlorophenyl)-2-phenyl-5-thiazoleacetate.HCl, and diethylaminoethyl 3-(4-chlorophenyl)-1-phenyl-1H-pyrazole-4-acetate.HCl.

Example 23

Treatment of Wound (Cuts, Burns, or Other Injuries)

About 0.7 ml (depended on the affected area size) of 5% diethylaminoethyl 1-methyl-5-(4-methylbenzoyl)-1H-pyrrole-2-acetate.HCl in 25% ethanol is applied to the skin around the wound twice per day. The treatment is continued until the condition disappeared.

Example 24

Application of HPCs to Treat a Spinal Cord Injury

Most NSAIAs cannot penetrate the scar barrier in a therapeutic effective amount, but HPCs in the present disclosure can penetrate the scar barrier, have anti-inflammatory activity, and can help wound healing.

A paralyzed rat was produced by anesthetizing with chloral hydrate first, and then hitting at its spinal cord to induce spinal cord injuries. On the next day, 20 completely paralyzed rats were divided into 2 groups. In group A (n=10), 0.2 ml of pure water was applied transdermally to the area of injury (~2×3 $cm^2$) twice per day for 1 months. In group B (n=10), 5 mg of diethylaminopropyl acetylsalicylate.HCl in 0.2 ml of pure water was applied to the area of injury (~2×3 $cm^2$) twice per day for 1 months. After the treatment, all rats (10/10) in group A were still completely paralyzed. While all rats (10/10) in group B could walk. 4 Rats of group B acted completely normal and the other 6 rats walked more slowly and less confidently than before their injury.

Example 25

Treatment of a Spinal Cord Injury

About 0.8 ml of 8% diethylaminoethyl acetylsalicylate.HCl in 25% ethanol is sprayed to the neck, face, or any part skin of the body twice per day. The process is continued until the spinal cord injury is cured (maybe lifelong).

Example 26

Anti-Lupus Erythematosus Activity of diethylaminoethyl acetylsalicylate Citric Acid (diethylaminoethyl acetylsalicylate HPC)

Inflammation—where the body's immune system attacks its own cells—is linked to discoid lupus erythematosus, systemic lupus erythematosus (SLE), multiple sclerosis (MS), psoriasis, and other autoimmune diseases.

A HPC, diethylaminoethyl acetylsalicylate.HCl (10%, aq., 30 mg/kg) was applied to the back skin (~5 $cm^2$) of SLAC/MRL/LPR mice twice per day (8:00 am and 6:00 pm). Progression of lupus was monitored once a week by measurement of hematuria, body weight and survival rate. The experiments were carried out in two groups of mice. One group of mice were 8 weeks old and had not shown SLE characteristics (Table 26a). The other group of mice were 16 weeks old, and had shown SLE characteristics (Table 26b).

The results show that diethylaminoethyl acetylsalicylate (a HPC of aspirin) prevent MRL/LPR mice from developing lupus completely when the mice were treated since 8 weeks old. Diethylaminoethyl acetylsalicylate HPC treatment reversed lupus in MRL/LPR mice when the mice are treated after 16 weeks old The results suggested that the HPCs of NSAIAs are promising agents for the treatment of psoriasis, discoid lupus erythematosus, systemic lupus erythematosus (SLE), multiple sclerosis (MS, caused by myelin inflammation and the HPCs of NSAIAs in the present disclosure can penetrate the outside membrane of myelin) and other autoimmune diseases in human.

TABLE 26a

Effect of Diethylaminoethyl acetylsalicylate Treatment on MRL/LPR mice of 8 weeks old.

| Time (week) | Untreated Group (n = 10) | | | Diethylaminoethyl acetylsalicylate Treated Group(n = 10) | | |
|---|---|---|---|---|---|---|
| | Body Weight (g) | Hematuria (0-4) | Survival Rate | Body Weight (g) | Hematuria (0-4) | Survival Rate |
| 8  | 31.5 ± 2.2 | 0 | 10/10 | 30.5 ± 2.6 | 0 | 10/10 |
| 9  | 34.2 ± 2.4 | 0 | 10/10 | 33.5 ± 2.1 | 0 | 10/10 |
| 10 | 37.5 ± 2.1 | 0 | 10/10 | 36.2 ± 2.7 | 0 | 10/10 |
| 11 | 41.5 ± 2.8 | 0 | 10/10 | 39.9 ± 2.1 | 0 | 10/10 |
| 12 | 43.9 ± 2.7 | 0 | 10/10 | 42.7 ± 2.3 | 0 | 10/10 |
| 13 | 45.5 ± 2.0 | 0 | 10/10 | 44.7 ± 2.4 | 0 | 10/10 |
| 14 | 49.1 ± 1.9 | 0.80 ± 0.20 | 10/10 | 47.1 ± 1.8 | 0 | 10/10 |
| 15 | 48.2 ± 2.1 | 1.10 ± 0.28 | 10/10 | 48.9 ± 2.6 | 0 | 10/10 |
| 16 | 45.5 ± 2.2 | 1.50 ± 0.43 | 10/10 | 49.6 ± 2.1 | 0 | 10/10 |
| 17 | 44.3 ± 2.6 | 1.70 ± 0.43 | 10/10 | 50.2 ± 2.5 | 0 | 10/10 |
| 18 | 44.1 ± 2.8 | 1.78 ± 0.52 | 9/10 | 50.6 ± 2.4 | 0 | 10/10 |
| 19 | 40.3 ± 2.6 | 1.75 ± 0.49 | 8/10 | 50.9 ± 2.3 | 0 | 10/10 |
| 20 | 36.0 ± 2.7 | 2.13 ± 0.55 | 8/10 | 51.1 ± 2.0 | 0 | 10/10 |
| 21 | 34.6 ± 3.1 | 2.00 ± 0.58 | 7/10 | 50.9 ± 2.3 | 0 | 10/10 |
| 22 | 31.8 ± 2.5 | 2.20 ± 0.49 | 5/10 | 50.4 ± 2.2 | 0 | 10/10 |
| 23 | 31.4 ± 2.6 | 2.60 ± 0.60 | 5/10 | 50.9 ± 2.1 | 0 | 10/10 |
| 24 | 33.3 ± 5.8 | 2.00 ± 0.58 | 3/10 | 51.2 ± 2.5 | 0 | 10/10 |
| 25 | 31.7 ± 4.7 | 2.33 ± 0.88 | 3/10 | 50.8 ± 2.2 | 0 | 10/10 |
| 26 | 32.5 ± 5.5 | 2.50 ± 1.50 | 2/10 | 50.7 ± 2.6 | 0 | 10/10 |
| 27 | 34.2 | 2.00 | 1/10 | 50.3 ± 2.1 | 0 | 10/10 |
| 28 | 30.5 | 3.00 | 1/10 | 50.6 ± 2.0 | 0 | 10/10 |
| 29 | 26.3 | 3.00 | 1/10 | 50.1 ± 2.0 | 0 | 10/10 |
| 30 | | | 0/10 | 49.8 ± 2.1 | 0 | 10/10 |
| 31 | | | | 50.4 ± 1.9 | 0 | 10/10 |
| 32 | | | | 50.8 ± 2.0 | 0 | 10/10 |
| 33 | | | | 50.6 ± 2.1 | 0 | 10/10 |
| 34 | | | | 50.8 ± 2.3 | 0 | 10/10 |
| 35 | | | | 50.3 ± 2.4 | 0 | 10/10 |
| 36 | | | | 50.7 ± 2.3 | 0 | 10/10 |
| 37 | | | | 50.9 ± 2.0 | 0 | 10/10 |
| 38 | | | | 51.1 ± 2.6 | 0 | 10/10 |
| 39 | | | | 50.6 ± 2.2 | 0 | 10/10 |
| 40 | | | | 50.7 ± 2.0 | 0 | 10/10 |
| 41 | | | | 51.2 ± 2.1 | 0 | 10/10 |
| 42 | | | | 51.1 ± 2.6 | 0 | 10/10 |
| 43 | | | | 50.7 ± 2.2 | 0 | 10/10 |
| 44 | | | | 50.3 ± 2.6 | 0 | 10/10 |
| 45 | | | | 50.7 ± 2.0 | 0 | 10/10 |
| 46 | | | | 50.6 ± 2.3 | 0 | 10/10 |
| 47 | | | | 50.1 ± 2.0 | 0 | 10/10 |
| 48 | | | | 50.3 ± 2.5 | 0 | 10/10 |
| 49 | | | | 50.7 ± 2.4 | 0 | 10/10 |
| 50 | | | | 51.2 ± 2.1 | 0 | 10/10 |

TABLE 26b

Effect of Diethylaminoethyl acetylsalicylate Treatment MRL/LPR mice of 16 weeks old.

| Time (week) | Untreated Group (n = 10) | | | Diethylaminoethyl acetylsalicylate Treated Group(n = 10) | | |
|---|---|---|---|---|---|---|
| | Body Weight(g) | Hematuria (0-4) | Survival Rate | Body Weight(g) | Hematuria (0-4) | Survival Rate |
| 16 | 45.5 ± 2.2 | 1.50 ± 0.43 | 10/10 | 42.6 ± 2.1 | 1.70 ± 0.26 | 10/10 |
| 17 | 44.3 ± 2.6 | 1.70 ± 0.43 | 10/10 | 44.2 ± 2.0 | 1.50 ± 0.17 | 10/10 |
| 18 | 44.1 ± 2.8 | 1.78 ± 0.52 | 9/10 | 46.6 ± 2.4 | 1.30 ± 0.15 | 10/10 |
| 19 | 40.3 ± 2.6 | 1.75 ± 0.49 | 8/10 | 47.9 ± 2.5 | 0.80 ± 0.13 | 10/10 |
| 20 | 36.0 ± 2.7 | 2.13 ± 0.55 | 8/10 | 46.8 ± 2.0 | 0.80 ± 0.13 | 10/10 |
| 21 | 34.6 ± 3.1 | 2.00 ± 0.58 | 7/10 | 47.2 ± 2.2 | 0.80 ± 0.13 | 10/10 |
| 22 | 31.8 ± 2.5 | 2.20 ± 0.49 | 5/10 | 47.6 ± 1.9 | 0.80 ± 0.20 | 10/10 |
| 23 | 31.4 ± 2.6 | 2.60 ± 0.60 | 5/10 | 47.1 ± 2.3 | 0.80 ± 0.20 | 10/10 |
| 24 | 33.3 ± 5.8 | 2.00 ± 0.58 | 3/10 | 46.8 ± 2.1 | 0.80 ± 0.20 | 10/10 |
| 25 | 31.7 ± 4.7 | 2.33 ± 0.88 | 3/10 | 47.2 ± 2.0 | 0.70 ± 0.15 | 10/10 |
| 26 | 32.5 ± 5.5 | 2.50 ± 1.50 | 2/10 | 46.9 ± 2.6 | 0.70 ± 0.15 | 10/10 |
| 27 | 34.2 | 2.00 | 1/10 | 47.3 ± 2.0 | 0.60 ± 0.22 | 10/10 |
| 28 | 30.5 | 3.00 | 1/10 | 47.6 ± 2.4 | 0.70 ± 0.15 | 10/10 |

TABLE 26b-continued

Effect of Diethylaminoethyl acetylsalicylate Treatment MRL/LPR mice of 16 weeks old.

| | Untreated Group (n = 10) | | | Diethylaminoethyl acetylsalicylate Treated Group(n = 10) | | |
|---|---|---|---|---|---|---|
| Time (week) | Body Weight(g) | Hematuria (0-4) | Survival Rate | Body Weight(g) | Hematuria (0-4) | Survival Rate |
| 29 | 26.3 | 3.00 | 1/10 | 47.2 ± 2.5 | 0.70 ± 0.15 | 10/10 |
| 30 | | | 0/10 | 46.4 ± 2.1 | 0.60 ± 0.22 | 10/10 |
| 31 | | | | 47.1 ± 2.2 | 0.80 ± 0.20 | 10/10 |
| 32 | | | | 46.6 ± 2.4 | 0.70 ± 0.15 | 10/10 |
| 33 | | | | 47.3 ± 2.1 | 0.50 ± 0.17 | 10/10 |
| 34 | | | | 47.6 ± 2.0 | 0.70 ± 0.15 | 10/10 |
| 35 | | | | 47.2 ± 2.0 | 0.70 ± 0.15 | 10/10 |
| 36 | | | | 46.9 ± 2.1 | 0.50 ± 0.17 | 10/10 |
| 37 | | | | 47.4 ± 2.7 | 0.70 ± 0.15 | 10/10 |
| 38 | | | | 46.9 ± 2.3 | 0.60 ± 0.22 | 10/10 |
| 39 | | | | 47.2 ± 2.0 | 0.50 ± 0.17 | 10/10 |
| 40 | | | | 47.6 ± 2.3 | 0.70 ± 0.15 | 10/10 |
| 41 | | | | 47.7 ± 2.2 | 0.60 ± 0.22 | 10/10 |
| 42 | | | | 46.9 ± 2.0 | 0.70 ± 0.15 | 10/10 |
| 43 | | | | 47.5 ± 2.8 | 0.60 ± 0.22 | 10/10 |
| 44 | | | | 47.6 ± 2.0 | 0.70 ± 0.15 | 10/10 |
| 45 | | | | 47.9 ± 2.5 | 0.50 ± 0.17 | 10/10 |
| 46 | | | | 47.6 ± 2.4 | 0.70 ± 0.15 | 10/10 |
| 47 | | | | 47.3 ± 2.8 | 0.60 ± 0.22 | 10/10 |
| 48 | | | | 46.6 ± 2.8 | 0.50 ± 0.17 | 10/10 |
| 49 | | | | 46.9 ± 2.1 | 0.60 ± 0.22 | 10/10 |
| 50 | | | | 47.1 ± 2.7 | 0.50 ± 0.17 | 10/10 |

Example 27

Treatment of Discoid Lupus Erythematosus

About 2 ml (depended on the affected area size) of 8% N,N-diethylaminoethyl acetylsalicylate.HCl in 25% ethanol is sprayed to the skin with discoid lupus erythematosus or around the discoid lupus erythematosus areas twice per day. The treatment is continued until the discoid lupus erythematosus disappeared (may be lifelong)

Example 28

Treatment of Systemic Lupus Erythematosus

About 1.5 ml of 8% N,N-diethylaminoethyl acetylsalicylate.HCl in 25% ethanol is sprayed to the skin near the affected organs or the skin on any part of the body twice per day. The treatment is continued until the condition disappeared (may be lifelong).

Example 29

Prevention of Discoid or Systemic Lupus Erythematosus

For people with high risk to get discoid or systemic lupus erythematosus, such as people having a twin sister or brother with discoid or systemic lupus erythematosus, people who have family history of discoid or systemic lupus erythematosus, people with mutant genes related to discoid or systemic lupus erythematosus, about 0.3 ml of 8% diethylaminoethyl acetylsalicylate.HCl in 25% ethanol is sprayed to any part skin of the body (rotating the location every time to avoid harm to the skin) once or twice per day Example 30

Treatment of Multiple Sclerosis (MS)

About 0.7 ml of 8% N,N-diethylaminoethyl acetylsalicylate.HCl in 25% ethanol is sprayed to the skin near the multiple sclerosis affected organs or the skin on any part of the body twice per day. The treatment is continued until the condition (MS) disappeared (may be lifelong).

Example 31

Prevention of Multiple Sclerosis (MS)

For people with high risk to get multiple sclerosis, such as people having a twin sister or brother with multiple sclerosis, people who have family history of multiple sclerosis, people with mutant genes related to multiple sclerosis, about 0.3 ml of 8% diethylaminoethyl acetylsalicylate.HCl in 25% ethanol is sprayed to any part skin of the body (rotating the location every time to avoid harm to the skin) once or twice per day.

Example 32

Anti-Tumor Activity of the HPCs of NSAIAs

The relationship between inflammation and cancer is well known. Dr. Thea D. Tlsty described in his speech (Keystone Symposia: Inflammation and Cancer, Breckenridge, Colo., USA, Feb. 27-Mar. 3, 2005) that cyclooxygenase-2 (COX-2) stimulates aromatase activity, angiogenesis, proliferation, invasion, and prostaglandin synthesis. The increase in prostaglandins leads to an inhibition of apoptosis. Aspirin and other NSAIAs inhibit COX-1 and COX-2. The overall relative risk of colorectal cancer, oesophageal cancer, ovarian cancer or other cancers is reduced in people taking long term aspirin. However, cancer cells may change their membrane structure to keep the NSAIAs from entering the cancer cells. The novel HPCs in the present disclosure can penetrate any membrane barriers and can be applied topically to the outside skin area of the location of the cancer and large amounts of the HPCs will enter the cancer cells with very little systemic exposure.

A) Human Breast Cancer Cells

Human breast cancer cells (BCAP-37, 2-3 mm$^3$ of tumor tissue was used in each mouse) were subcutaneously xenografted into nude mice (BALB, 12 groups, 7 mice each group). After 14 days, the tumors growed to the size of 50±10 mm$^3$ (0.05 ml). 50 μl of 5% (equal to 2.5 mg of the HPCs) diethylaminoethyl acetylsalicylate.HCl (P-1, in pure water); 1-piperidinepropyl 2[(2,6-dichlorophenyl)amino]benzene acetate.HCl (P-2, in water), 1-pyrrolidinepropyl 2-(3-benzoylphenyl) propionate.HCl (P-3, in water), 4-piperidinemethyl 2-(3-phenoxyphenyl)propionate.HCl (P-4, in water), 3-piperidinemethyl 2-(ρ-isobutylphenyl) propionate.HCl (P-5, in water), diethylaminoethyl 1-(p-chlorobenzoyl)-5-methoxy-2-methylindole 3-acetate.HCl (P-11, in water), 2-(4-morpholinyl)ethyl (Z)-5-fluoro-2-methyl-1-[(4-methylsulfinyl)phenylmethylene]-1H-indene-3-acetate.HCl (P-12, in water), diethylaminoethyl 2-(2,4-dichlorophenoxy)benzeneacetate.HCl (P-19, in water), diethylaminoethyl 2-(8-methyl-10,11-dihydro-11-oxodibenz(b,f)oxepin-2-yl)propionate.HCl (P-37, in water), 1-pyrrolidinepropyl 2-[[(3-(trifluoromethyl)phenyl)amino]benzoate.HCl (P-48, in water), 4-N,N-dimethylaminobutyryloxy-2-methyl-N-2-pyridinyl-2H,1,2-benzothiazine-3-carboxamide 1,1-dioxide.HCl (P-51, in water) were topically applied to the human breast cancer cells-implanted area (near the front leg) every 8 hours. At day 42, the tumors sizes and weight data shown in Table 32a-1 and Table 32a-2 indicated that the HPCs were effective anti-tumor agents with low side effects such as weight loss TABLE 32a-1

The tumors sizes and the weights of the control group and the drug-treated groups of nude mice at day 42.

| HPC | Control | P-1 | P-2 | P-3 | P-4 | P-5 |
|---|---|---|---|---|---|---|
| Size (mm$^3$) | 850 ± 110 | 140 ± 50 | 160 ± 50 | 210 ± 60 | 190 ± 55 | 180 ± 55 |
| Weight | 23 ± 2 | 24 ± 3 | 23 ± 2 | 22 ± 3 | 23 ± 3 | 23 ± 2 |

TABLE 32a-2

The tumors sizes and the weights of the drug-treated groups of nude mice at day 42.

| HPC | P-11 | P-12 | P-19 | P-37 | P-48 | P-51 |
|---|---|---|---|---|---|---|
| Size (mm$^3$) | 230 ± 105 | 240 ± 60 | 260 ± 55 | 270 ± 70 | 280 ± 50 | 390 ± 55 |
| Weight | 23 ± 2 | 23 ± 3 | 22 ± 2 | 23 ± 3 | 22 ± 3 | 23 ± 2 |

B) Human Colon Cancer Cells

Human colon cancer cells (LS174J, 2-3 mm$^3$ of tumor tissue was used in each mouse) were subcutaneously xenografted into nude mice (BALB). After 7 days, the tumors grow to the size of 65±10 mm$^3$ (0.065 ml). About 50 μl of 5% (equal to 1.5 mg of the HPCs) diethylaminoethyl acetylsalicylate.HCl salt (P-1, in water); 1-piperidinepropyl 2[(2,6-dichlorophenyl)amino]benzene acetate.HCl (P-2, in water), 1-pyrrolidinepropyl 2-(3-benzoylphenyl) propionate.HCl (P-3, in water), 4-piperidinemethyl 2-(3-phenoxyphenyl)propionate.HCl (P-4, in water), 3-piperidinemethyl 2-(ρ-isobutylphenyl) propionate.HCl (P-5, in water), diethylaminoethyl 1-methyl-5-(4-methylbenzoyl)-1H-pyrrole-2-acetate.HCl (P-13, in water), 2-(4-morpholinyl)ethyl 2-amino-3-benzoylbenzeneacetate.HCl (P-16, in water), diethylaminoethyl 2-(10,11-dihydro-10-oxodibenzo(b,f)thiepin-2-yl)propionate.HCl (P-36), diethylaminoethyl 2-[(2,3-dimethylphenyl)amino]benzoate.HCl (P-46, in water), diethylaminoethyl 2-[(2,6-dichloro-3-methylphenyl)amino]benzoate.HCl (P-47, in water), N-(2-thiazoyl)-4-N,N-dimethylaminobutyryloxy-2-methyl-2H,1,2-benzothiazine-3-carboxamide 1,1-dioxide.HCl (P-52, in water) were topically applied to the human colon cancer cells-implanted area (near the front leg) every 12 hours. At day 30, the tumors sizes and weight data shown in Table 32b-1 and Table 32b-2 indicated that the HPCs are effective anti-tumor agents with low side effects such as weight loss TABLE 32b-1

The tumors sizes and the weights of the control group and the drug-treated groups of nude mice at day 30.

| HPC | Control | P-1 | P-2 | P-3 | P-4 | P-5 |
|---|---|---|---|---|---|---|
| Size (mm$^3$) | 1500 ± 380 | 480 ± 130 | 520 ± 170 | 550 ± 190 | 550 ± 128 | 520 ± 140 |
| Weight | 22 ± 2 | 23 ± 3 | 22 ± 2 | 23 ± 2 | 22 ± 3 | 23 ± 2 |

TABLE 32b-2

The tumors sizes and the weights of the drug-treated groups of nude mice at day 30.

| HPC | P-13 | P-16 | P-36 | P-46 | P-47 | P-52 |
|---|---|---|---|---|---|---|
| Size (mm$^3$) | 690 ± 250 | 590 ± 350 | 480 ± 180 | 650 ± 250 | 590 ± 350 | 720 ± 280 |
| Weight | 23 ± 3 | 23 ± 2 | 21 ± 2 | 23 ± 3 | 22 ± 2 | 23 ± 3 |

Example 33

Treatment of Breast Cancer

About 0.8 ml of 8% diethylaminoethyl acetylsalicylate.HCl in 25% ethanol is sprayed on the breast with cancers twice per day. The process is continued until the tumor disappeared.

Example 34

Treatment of Breast Cancer

After the breast cancer is removed surgically or shrunk with other therapy, About 0.8 ml of 8% diethylaminoethyl acetylsalicylate.HCl in 25% ethanol is applied to the skin nearby the cancer or any part skin of the body twice per day. The process is continued until that it is sure that cancer is not come back (may be lifelong).

Example 35

Treatment of Prostate Cancer

About 0.8 ml of 8% diethylaminoethyl acetylsalicylate.HCl in 25% ethanol is applied to the skin nearby the cancer twice per day. The process is continued until the cancer is cured.

Example 36

Treatment of Prostate Cancer

After the cancer is removed surgically or shrunk with other therapy, About 0.8 ml of 8% diethylaminoethyl acetylsalicylate.HCl in 25% ethanol is applied to the skin nearby the cancer or any part skin of the body twice per day.

Example 37

Treatment of Lung Cancer

About 0.8 ml of 8% diethylaminoethyl acetylsalicylate.HCl in 25% ethanol is applied to the skin on the chest twice per day and the treatment is continued until the cancer is cured.

Example 38

Treatment of Lung Cancer

After the cancer is removed surgically or shrunk with other therapy, About 0.8 ml of 8% diethylaminoethyl acetylsalicylate.HCl in 25% ethanol is applied to the skin on the chest twice per day and the treatment is continued until the cancer is cured.

Example 39

Treatment of Colon Cancer

About 0.8 ml of 8% diethylaminoethyl acetylsalicylate.HCl in 25% ethanol is applied to the skin nearby anus, or any part skin of the body twice per day. The process is continued until the cancer is cured.

Example 40

Treatment of Colon Cancer

After the cancer is removed surgically or shrunk with other therapy, About 0.8 ml of 8% diethylaminoethyl acetylsalicylate.HCl in 25% ethanol is applied to the skin nearby anus, or any part skin of the body twice per day. The process is continued until the cancer is cured.

Example 41

Treatment of Skin Cancer

About 0.8 ml of 8% diethylaminoethyl acetylsalicylate.HCl in 25% ethanol is applied to the skin with cancer or nearby twice per day. The process is continued until the cancer is cured.

Example 42

Treatment of Skin Cancer

After the cancer is removed surgically or shrunk with other therapy, About 0.8 ml of 8% diethylaminoethyl acetylsalicylate.HCl in 25% ethanol is applied to the skin with cancer or nearby twice per day. The process is continued until the cancer is cured.

Example 43

Treatment of Bone Cancer

About 0.8 ml of 8% diethylaminoethyl acetylsalicylate.HCl in 25% ethanol is applied to the skin near by the bone cancer nearby twice per day. The process is continued until the cancer is cured.

Example 44

Treatment of Bone Cancer

After the cancer is removed surgically or shrunk with other therapy, About 0.8 ml of 8% diethylaminoethyl acetylsalicylate.HCl in 25% ethanol is applied to the skin near the bone cancer or any part skin of the body twice per day. The process is continued until the cancer is cured.

Example 45

Treatment of any Kind of Cancers

About 0.8 ml of 8% diethylaminoethyl acetylsalicylate.HCl in 25% ethanol is applied to the skin near the cancer or any part skin of the body twice per day. The process is continued until the cancer is cured.

Example 46

Treatment of any Kind of Cancers

After the cancer is removed surgically or shrunk with other therapy, about 0.8 ml of 8% diethylaminoethyl acetylsalicylate.HCl in 25% ethanol is applied to the skin near the cancer or any part skin of the body twice per day. The process is continued until the cancer is cured.

Example 47

Prevention of any Kind of Cancers

For people with high risk to get cancers, such as people having a twin sister or brother with cancer, smokers, people who have family history of cancer, people with mutant genes related to cancer, about 0.5 ml of 8% diethylaminoethyl acetylsalicylate.HCl in 25% ethanol is sprayed to any part skin of the body (rotating the location every time to avoid harm to the skin) once or twice per day.

Example 48

Anti-Thrombosis Activity of HPCs of NSAIAs

Eighteen Chinese White rabbits weighing between 3.0 and 3.5 kg (aged 6-7 months) were selected and divided into three groups (control, P-1 and P-10 groups, n=6). One hour before the experiment, thrombi were made by aspirating venous blood (1 ml) into a sterilized bottle to clot. To avoid fragmentation and slow lysis, the autologous blood clots were stabilized in temperature-controlled (70° C.) distilled water for 10 min. After anesthesia, the femoral veins were exposed and distally isolated, and autologous blood clots (0.05 g/kg) were injected through an indwelling catheter (20GA), which had been placed in the femoral vein isolated earlier. 50 mg/kg of diethylaminoethyl acetylsalicylate.HCl salt (P-1, 10% in 25% ethanol) and diethylaminoethyl acetylsalicylsalicylate.HCl salt (P-59, 10% in 25% ethanol) were topically applied to the back of the rabbits twice per day. After 5 days, rabbits were euthanized with an excessive intravenous injection of sodium amobarbital (60 mg/kg). The lungs and hearts were isolated to observe whether thrombi were present in the pulmonary arteries. The lungs were immersed in 10% formalin for 24 h. Consecutive transverse sections along the obstructed pulmonary arteries were paraffin-embedded and stained with hematoxylin-eosine.

In the control group, platelet thrombus and mixed thrombus surrounded the infused clots, which were present in large-sized vessels as well and stretched the vessel walls in both proximal and distal directions. There was excessive proliferation of endothelial cells and fibrocytes in these vessels. Additionally, there was acute pulmonary congestion. In the P-1 and P-59 groups, both lung tissue and vascular walls were normal. The results show that thrombotic activity and embolization-associated thrombus propagation were prevented by these HPCs of NSAIAs. HPCs can be very useful for preventing and treating blood clots—a major cause of strokes, heart attacks and organ transplant rejection.

Example 49

Anti-Thrombosis Activity of diethylaminoethyl acetylsalicylate.citric Acid Salt Recent data suggests that inflammation is linked to cardiac diseases and aspirin is widely used for preventing cardiac diseases.

Thrombosis was induced by electrical stimulation (1 mA for 3 minutes) of the carotid artery in rats by using a thrombosis formation instrument (YLS-14A, Shandong Academy of Medical Sciences, Shandong, China). The rats (Spragu Dawley, 25 weeks old, 380-450 g) were divided into 3 groups, group A was the control group, groups B and C were the diethylaminoethyl acetylsalicylate-treated group. In group B, 100 mg/kg of diethylaminoethyl acetylsalicylate.HCl salt (10% in water) was applied to the shaved back skin of the rats (~9 cm$^2$, fur was cut off) 2 hour before the operation and 1 hour after the operation, then 50 mg/kg of the HPC was applied to the back of the rats twice per day. In group C, 50 mg/kg of diethylaminoethyl acetylsalicylate.HCl was applied to the back of the rats twice per day starting from 24 hours after the operation. The recovery of motor functions of rats was evaluated every day. The results were shown in Tables 49a and 49b. The results in Table 49a show that aspirin protected rats from stroke without bleeding problem. The results in Table 49b show diethylaminoethyl acetylsalicylate.HCl reversed paralysis from post-stroke in rat model without bleeding problem.

TABLE 49a

Anti-stroke activity by diethylaminoethyl acetylsalicylate

| | Stroke-free rats (2 hours) | Stroke-free rats (1 day) | Stroke-free rats (7 days) |
|---|---|---|---|
| Control group (A) | 0/10 | 0/8 | 0/8 (1 died) |
| Treated group (B) | 8/10 | 9/10 | 10/10 |

TABLE 49b

Alleviation of the effects of strokes by diethylaminoethyl acetylsalicylate

|  | Stroke-free rats (3 hrs) | Stroke-free rats (2 day) | Weight Loss (3 days) | Stroke-free rats (7 day) | Weight Loss (7 days) | Stroke-free rats (14 days) | Weight Loss (14 days) |
|---|---|---|---|---|---|---|---|
| Control group | 0/10 | 0/10 | −25 +/− 8% (2 died) | 0/10 | −22 +/− 5% (1 more died) | 1/10 | −18 +/− 6% |
| Treated group | 0/10 | 4/10 | −13 +/− 7% | 9/10 | −7 +/− 4% | 10/10 | −4 +/− 2% |

Example 50

Treatment of Stroke

About 0.8 ml of 8% diethylaminoethyl acetylsalicylate.HCl in 25% ethanol is sprayed to the neck, chest, legs, arms, or any other part skin (rotating the location every time to avoid harm to the skin) twice per day. The process is continued until stroke is cured (maybe lifelong).

Example 51

Prevention of Stroke

For people with high risk to get stroke, such as overweight people, people having a twin sister, or brother with stroke, people who have family history of stroke, people with mutant genes related to stroke, about 0.5 ml of 8% diethylaminoethyl acetylsalicylate.HCl in 25% ethanol is sprayed to any part skin of the body (rotating the location every time to avoid harm to the skin) once or twice per day.

Example 52

Treatment of Heart Attack

About 1.5 ml of 8% diethylaminoethyl acetylsalicylate.HCl in 25% ethanol is sprayed to the neck, chest, legs, or any other part skin (rotating the location every time to avoid harm to the skin) twice per day. The process is continued until stroke is cured (maybe lifelong).

Example 53

Prevention of Heart Attack

For people with high risk to get heart attack, such as overweight people, people having a twin sister, or brother with heart attack, people who have family history of heart attack, people with mutant genes related to heart attack, about 0.3 ml of 8 diethylaminoethyl acetylsalicylate.HCl in 25% ethanol is sprayed to any part skin of the body (rotating the location every time to avoid harm to the skin) once or twice per day Example 54

Anti-Hypertensive Activity

A) Diethylaminoethyl acetylsalicylate.citric acid (diethylaminoethyl acetylsalicylate citric acid salt)

20 spontaneously hypertensive rats (SLAC/SHR, 19 weeks old, 300-350 g) were divided into 2 groups randomly. In group A, pure water (0.5 ml) was applied to the rats' back skin (~5 cm$^2$, fur was cut off) once per day for 6 weeks. In groups B, 50 mg/kg of diethylaminoethyl acetylsalicylate citric acid salt (10% in water) was applied to the rats' back skin (~5 cm$^2$, fur was cut off) once per day. The results were shown in table 54a. The results showed that HPC of diethylaminoethyl acetylsalicylate had very strong anti-hypertensive activity.

TABLE 54a

Anti-hypertensive activity of diethylaminoethyl acetylsalicylate•citric acid

|  | Blood pressure (mmHg) (week 0) | | Blood pressure (mmHg) (week 2 to week 6) | |
|---|---|---|---|---|
|  | Systolic | diastolic | Systolic | diastolic |
| Group A | 181.4 ± 16.7 | 115.2 ± 15.1 | 183.1 ± 15.7 | 116.2 ± 13.3 |
| Group B | 184.6 ± 15.1 | 118.2 ± 13.1 | 115.4 ± 14.6 | 83.5 ± 12.1 |

B) Atenolol.HCl Salt

Anti-hypertension patients' blood pressure was controlled by transdermally administering 100 mg of atenolol HCl salt in 1 ml of pure water per day without side effect of hypotention. 20 Hypertension patents were divided to 2 groups. Group A was control group (n=10, 1 ml of water was administrated to the chest of patients once per day) and group B was atenolol treated group (n=10, 100 mg of atenolol HCl salt was administrated to the chest of patients once per day). The results were shown in Table 54b.

TABLE 54b

Anti-hypertensive effect of atenolol HPC via transdermal administration

|  | Blood Pressure (mmHg) (before treatment) | Blood pressure(mmHg) (2 weeks after treatment) |
|---|---|---|
| Group A | 162 ± 27/110 ± 21 | 163 ± 28/113 ± 23 |
| Group B | 160 ± 22/110 ± 20 | 128 ± 15/81 ± 12 |

Example 55

Treatment of Hypertension

About 0.8 ml of 8% diethylaminoethyl acetylsalicylate.HCl in 25% ethanol is sprayed to the neck, chest, legs, or any other part skin (rotating the location every time to avoid harm to the skin) twice per day. The process is continued until hypertension is cured (maybe lifelong).

Example 56

Treatment of Hypertension

About 1 ml of 10% atenolol in 25% ethanol (pH is adjusted to 4-7 with HCl) is sprayed to the neck, chest, legs, or any other part skin (rotating the location every time to avoid harm to the skin) twice per day.

Example 57

Prevention of Hypertension

For people with high risk to get hypertension, such as overweight people, people having a twin sister, or brother with hypertension, people who have family history of hypertension, people with mutant genes related to hypertension, about 0.5 ml of 8 diethylaminoethyl acetylsalicylate.HCl in 25% ethanol is sprayed to any part skin of the body (rotating the location every time to avoid harm to the skin) once or twice per day.

Example 58

Treatment of Amyotrophic Lateral Sclerosis (ALS), Oculopharyngeal Muscular Dystrophy (OPMD), Myotonic Dystrophy (MD), Duchenne Muscular Dystrophy (DMD), Polymyositis (PM), Dermatomyositis (DM), Inclusion Body Myositis (IBM), and Other Muscle Disorders The pathogenesis of cell death in amyotrophic lateral sclerosis (ALS) may involve glutamate-mediated excitotoxicity, oxidative damage, and apoptosis. Cyclooxygenase-2, present in spinal neurons and astrocytes, catalyzes the synthesis of prostaglandin $E_2$. Prostaglandin $E_2$ stimulates glutamate release from astrocytes, whereas cyclooxygenase-2 also plays a key role in the production of pro-inflammatory cytokines, reactive oxygen species, and free radicals. Treatment with a selective cyclooxygenase-2 inhibitor, celecoxib, markedly inhibited production of prostaglandin $E_2$ in the spinal cords of ALS mice. Celecoxib treatment significantly delayed the onset of weakness and weight loss and prolonged survival by 25%. Spinal cords of treated ALS mice showed significant preservation of spinal neurons and diminished astrogliosis and microglial activation (Merit. E. Cudkowicz, et al., Annals of neurology, 52, 771-778, 2002). These results suggest that cyclooxygenase-2 inhibition may benefit ALS patients. HPCs of NSAIAs in the present disclosure can penetrate skin and nerve cell membrane barriers in very high rates (most NSAIAs cannot penetrate nerve cells effectively) and can be administered transdermally without hurting the GI tract, so these HPC are very promising agents for the treatment of amyotrophic lateral sclerosis (ALS), oculopharyngeal muscular dystrophy (OPMD), myotonic dystrophy (MD), Duchenne muscular dystrophy (DMD), polymyositis (PM), dermatomyositis (DM), inclusion body myositis (IBM), and other muscle disorders.

For treatment of amyotrophic lateral sclerosis (ALS), oculopharyngeal muscular dystrophy (OPMD), myotonic dystrophy (MD), Duchenne muscular dystrophy (DMD), polymyositis (PM), dermatomyositis (DM), inclusion body myositis (IBM), and other muscle disorders, about 0.8 ml of 8% diethylaminoethyl acetylsalicylate.HCl in 25% ethanol is sprayed to the neck, chest, legs, or any other part skin (rotating the location every time to avoid harm to the skin) twice per day.

Example 59

Prevention of Amyotrophic Lateral Sclerosis (ALS), Oculopharyngeal Muscular Dystrophy (OPMD), Myotonic Dystrophy (MD), Duchenne Muscular Dystrophy (DMD), Polymyositis (PM), Dermatomyositis (DM), Inclusion Body Myositis (IBM), and Other Muscle Disorders For people with high risk to get amyotrophic lateral sclerosis (ALS), oculopharyngeal muscular dystrophy (OPMD), myotonic dystrophy (MD), Duchenne muscular dystrophy (DMD), polymyositis (PM), dermatomyositis (DM), inclusion body myositis (IBM), and other muscle disorders, such as people having a twin sister, or brother with any one or more these diseases, people who have family history of any one or more these diseases, people with mutant genes related to any one or more these diseases, about 0.5 ml of 8% diethylaminoethyl acetylsalicylate.HCl in 25% ethanol is sprayed to any part skin of the body (rotating the location every time to avoid harm to the skin) once or twice per day

Example 60

Anti-Hair Loss and Bald Activity of diethylaminoethyl acetylsalicylate.HCl Salt 30 Lesional Dundee experimental bald rats (DEBR) were allocated to 3 groups. Group A (n=10) rats received 2 ml of pure water on whole body once per day for 10 weeks. Group B (n=10) rats received 50 mg/kg of diethylaminoethyl acetylsalicylate citric acid (1% in pure water) on whole body once per day for 10 weeks. Group C (n=10) received orally administered cyclosporine A (CsA) (10 mg/kg daily) for 10 weeks. In the untreated control group A, no hair growth was seen as a result of vehicle application and hair loss continued. In the diethylaminoethyl acetylsalicylate citric acid treated group B, hair regrew over the whole body with 2-4 weeks. In the oral CsA group C, hair regrew over the whole body with 2-4 weeks in a much lower rate (~40%) of that of group B.

Example 61

Treatment of Bald

About 0.3 ml of 8% diethylaminoethyl acetylsalicylate.HCl in 25% ethanol is sprayed to the top skin of head once or twice per day. The process is continued until bald is cured (maybe lifelong).

Example 62

Treatment of Hair Loss

About 0.3 ml of 8% diethylaminoethyl acetylsalicylate.HCl in 25% ethanol is sprayed to the top skin of head once or twice per day. The process is continued until hair loss is cured (maybe lifelong).

Example 63

Anti-Vitiligo Activity of diethylaminopropyl acetylsalicylate.HCl Salt

20 Smyth chickens (animal models of vitiligo) were allocated to 2 groups. Group A (n=10) chickens received 1 ml of pure water on discoloured lesions once per day for 10 weeks. Group B (n=10) Smyth chicken received 50 mg/kg of diethylaminoethyl acetylsalicylate citric acid (5% in pure water) on discoloured lesions once per day for 10 weeks. In the untreated control group A, the lesions were worse and feather loss continued. In the diethylaminoethyl acetylsalicylate citric acid treated group B, the discoloured lesions disappeared and feathers regrew with 3-6 weeks.

Example 64

Treatment of Vitiligo

About 0.8 ml of 8% diethylaminoethyl acetylsalicylate.HCl in 25% ethanol is sprayed to the skin or hair with vitiligo twice per day. The process is continued until vitiligo is cured (maybe lifelong).

Example 65

Prevention of Vitiligo

For people with high risk to get vitiligo, such as people having a twin sister, or brother with vitiligo, people who have family history of vitiligo, people with mutant genes related to vitiligo, about 0.3 ml of 8% diethylaminoethyl acetylsalicylate.HCl in 25% ethanol is sprayed to any part skin of the body (rotating the location every time to avoid harm to the skin) once or twice per day.

Example 66

Anti-Alzheimer Disease Activity of Diethylaminopropyl acetylsalicylate.HCl Tested with Tg2576 Mouse Model of Alzheimer Disease Inflammatory mechanisms have been proposed as important mediators in the pathogenetic cascade of Alzheimer's disease (McGeer P L, McGeer E G. The inflammatory response system of brain implications for the therapy of Alzheimer and other neurodegenerative diseases. Brain Res. Rev., 1995; 21: 195-218). In the study by in't Veld et al. (the New England Journal of Medicine, 2001; 345, 1515), they followed almost 7000 person at risk of Alzheimer's disease for nearly seven years. Their results suggested that NSAIAs can reduce the relative risk for those whose cumulative use of NSAIAs was at least two years and two or more years before the onset of dementia. If the neuroprotective capacity of NSAIAs ceases in the years just before the onset of dementia, then these compounds would offer no protection against progression among most persons with the prodromal stage of diseases. We believe that the reason for this is that the tissues around the damaged nerve cells will form scars to protect the nerve cells from damaging farther. Most of NSAIAs have very low brain-blood and nerve cell barriers penetration rate and cannot penetrate the scar barrier. HPCs in the present disclosure have very high skin, blood-brain, nerve cell membrane, and scar barriers penetration rates and are very promising agents for the treatment of Alzheimer's disease, Parkinson's diseases, and other progressive neurodegenerative diseases.

The pathology of Alzheimer's disease (AD) shows a significant correlation between β-amyloid peptide (ADP) conformation and the clinical severity of dementia. For many years, efforts have been focused on the development of inhibitors of β-amyloid (Aβ) formation and its related neurotoxic effects. To determine the effect of diethylaminopropyl acetylsalicylate. HCl on in vivo AD accumulation, we administered transdermally diethylaminopropyl acetylsalicylate. HCl (50 mg/kg in water) to the Tg2576 mouse model of AD over 2 months resulted in a significant, non-overlapping 70-80% reduction in the number of senile plaques, one of the pathological hallmarks of AD. Three-month-old female transgenic mice overexpressing the human APP gene containing the Swedish mutation that causes familial AD (Tg2576 line) were used for testing the effects of diethylaminopropyl acetylsalicylate.HCl in vivo. 20 Tg2576 mice were divided into 2 groups. In group A (n=10), 0.2 ml of pure water was applied transdermally to the back of mouse once per day for 2 months. In group B (n=10), 50 mg/kg of diethylaminopropyl acetylsalicylate.HCl in 0.2 ml of pure water was applied to the back of mouse once per day for 2 months. Then the animals were killed and their brains were removed for analysis. For Aβ analysis, hemibrains were dounce homogenized in 70% formic acid at 150 mg tissue/ml formic acid solution. Homogenates were transferred to a chilled ultracentrifuge and were then spun at 100,000 g for 1 h at 4° C. Supernatants were collected and neutralized with formic acid neutralization buffer (1.0 M Tris base, 0.5 M $NaH_2PO_4$, and 0.05% $NaN_3$; 1:20) for Aβ quantitation by ELISA. Aβ40 and Aβ42 were assayed by ELISA. Four individual experiments were performed. To compare across studies, the values for an individual study were normalized using the values obtained for the control animals included in each study. Values represent the mean±SE for the n number shown, after normalizing. As shown in table 66a. The transdermal treatment of diethylaminopropyl acetylsalicylate.HCl (50 mg/kg) resulted in a significant reduction (70%) in Aβ42 concentration in the brain.

TABLE 66a

The effect of diethylaminopropyl acetylsalicylate•HCl on the Aβ42 concentration.

| Group | Control (pure water) | diethylaminopropyl acetylsalicylate•HCl (50 mg/kg) |
|---|---|---|
| Aβ42 concentration (pmol/g tissue) | 7.8 ± 0.4 | 2.3 ± 0.3 |

Studies in the Tg2576 mouse model have indicated that transdermally administered 50 mg/kg of diethylaminopropyl acetylsalicylate.HCl results in a significant reduction (70%) the amount of Aβ detected in the brains of these animals at 2 months administration. To determine if the transdermal administration of diethylaminopropyl acetylsalicylate.HCl has beneficial functional consequences, we tested 2 months of diethylaminopropyl acetylsalicylate.HCl (50 mg/kg) in the transgenic model for Alzheimer's disease in which mice develop learning deficits as amyloid accumulates. The results showed that diethylaminopropyl acetylsalicylate.HCl protected transgenic mice from the learning and age-related memory deficits that normally occur in this mouse model for Alzheimer's disease. In the diethylaminopropyl acetylsalicylate.HCl (50 mg/kg) treated group, all mice performed superbly on the radial-arm water-maze test of working memory and untreated transgenic mice show memory deficits. The diethylaminopropyl acetylsalicylate.HCl treated transgenic mice showed cognitive performance superior to that of the control transgenic mice and, ultimately, performed as well as nontransgenic mice. This therapeutic approach can thus prevent and treat Alzheimer's dementia.

Example 67

Treatment of Alzheimer's Disease and Other Neurodegenerative Diseases

About 0.8 ml of 8% diethylaminoethyl acetylsalicylate.HCl in 25% ethanol is sprayed to the skin or hair with vitiligo twice per day. The process is continued until vitiligo is cured (maybe lifelong).

Example 68

Prevention of Alzheimer's Disease and Other Progressive Neurodegenerative Diseases For people with high risk to get Alzheimer's disease and other progressive neurodegenerative diseases, such as people having a twin sister, or brother with Alzheimer's disease and other progressive neurodegenerative diseases, people who have family history of Alzheimer's disease and other progressive neurodegenerative diseases, people with mutant genes related to Alzheimer's disease and other progressive neurodegenerative diseases, about 0.3 ml of 8% diethylaminoethyl acetylsalicylate.HCl in 25% ethanol is sprayed to any part skin of the body (rotating the location every time to avoid harm to the skin) once or twice per day.

Example 69

Anti-Parkinson's Disease Activity of Diethylaminoethyl acetylsalicylate.HCl Salt was Tested with MPTP-Induced Parkinson's Disease Mice Male C57/BL6 mice (24-26 g) were divided into 3 groups. Group A mice were ip injected 0.4% sodium carboxymethylcellulos (15 ml/kg per day) for 7 days. Group B and C mice were ip injected N-methyl-4-phenyl-1,2,3,6-tetrahydropyridine (MPTP, 30 mg/kg per day) for 7 days. The mice were divided into 2 groups. In groups A and B, 0.1 ml of pure water was applied transdermally to the neck of mice once per day for 14 days. In group C, 30 mg/kg of diethylaminoethyl acetylsalicylate.HCl salt in 0.1 ml of water was applied transdermally to the neck of mice once per day for 14 days. All mice were killed after the last treatment and the brain tissues were quickly freezed at −80° C. The contents of dopamine (DA) in the striatum were determined with spectrofluorophotometer ($\lambda_{Ex}$=310 nm, $\lambda_{Em}$=390 nm, RF-5000), 5-HT ($\lambda_{Ex}$=355 nm, $\lambda_{Em}$=495 nm), and noradrenaline (NA) ($\lambda_{Ex}$=400 nm, $\lambda_{Em}$=500 nm). The contents of malondialdehyde (MDA) in the SN were measured with the thiobarbituric acid-reaction to indicate the LPO, and contents of glutathione (GSH) in the substantia nigra (SN) were based on the dithionitrobenzonic acid (DTNB) determination. The contents of GABA and Glu in the striatum and SN were shown by high performance amino acid auto-analyser. The results were shown in table 69a. Effects of diethylaminoethyl acetylsalicylate.citric acid on the contents of DA, NA, and 5-HT The content of DA, NA, and 5-HT in the striatum was significantly decreased in MPTP group compared with control group (P<0.05, n=10). Diethylaminoethyl acetylsalicylate.citric acid (30 mg/kg transdermally) increased DA, NA, and 5-HT contents compared with model group (P<0.05, n=10) (Table 69a).

TABLE 69a

Effects of diethylaminoethyl acetylsalicylate•citric acid on the concentration DA, NA, and 5-HT in the striatum of PD mice induced by MPTP.

| Group | DA | NA | 5-HT |
|---|---|---|---|
| | μg/g wet tissue | | |
| Control | 885 ± 86 | 618 ± 55 | 306 ± 17 |
| MPTP + water | 515 ± 103 | 419 ± 57 | 248 ± 22 |
| MPTP + diethylaminoethyl acetylsalicylate (30 mg/kg) | 817 ± 89 | 602 ± 55 | 302 ± 29 | n = 10. Mean ± SD. $^b$P < 0.05 vs the control group. $^e$P < 0.05 vs MPTP group.

Effects of diethylaminoethyl acetylsalicylate.citric Acid on the Contents of MDA and GSH.

The level of nigral GSH in model group was markedly decreased (P<0.01, n=10) and the contents of nigral MDA was increased compared with those in control group (P<0.01, n=10). Diethylaminoethyl acetylsalicylate.citric acid markedly lowered the MDA level while relatively increased the GSH level in PD model (P<0.01, n=10). The results were shown in table 69b.

TABLE 69b

Effects of diethylaminoethyl acetylsalicylate•citric acid on the concentration GSH (μg/g protein) and MDA (μmol/g protein) in the substantia nigra of PD mice induced by MPTP.

| Group | GSH | MDA |
|---|---|---|
| Control | 152 ± 12 | 13 ± 3 |
| MPTP + water | 101 ± 17 | 21 ± 4 |
| MPTP + diethylaminoethyl acetylsalicylate (30 mg/kg) | 143 ± 13 | 14 ± 4 | n = 10. Mean ± SD. P < 0.01 vs control group P < 0.01 vs MPTP group.

Effect of diethylaminoethyl acetylsalicylate.citric Acid on the Contents of GABA and Glu.

MPTP markedly increased the striatal GABA level (P<0.01, n=10) while decreased GABA in the SN (P<0.05, n=10) compared with control group, which were reversed by diethylaminoethyl acetylsalicylate.citric acid (30 mg/kg). However, modafinil did not change the increase of nigrostriatal Glu release induced by MPTP (Table 69c).

TABLE 69c

Effects of diethylaminoethyl acetylsalicylate•citric acid on the concentration of GABA (μmol/g wet tissue) and Glu in the substantia nigra and striatum of PD mouse induced by MPTP.

| | Substantia nigra | | Striatum | |
|---|---|---|---|---|
| Group | GABA | Glu | GABA | Glu |
| Control | 5.1 ± 0.5 | 27.1 ± 2.5 | 4.7 ± 1.7 | 24.1 ± 2.6 |
| MPTP + water | 2.2 ± 0.4 | 34.5 ± 2.7 | 8.4 ± 1.7 | 33.2 ± 4.5 |
| MPTP + diethylaminoethyl acetylsalicylate(30 mg/kg) | 4.7 ± 0.5 | 29.5 ± 2.4 | 4.9 ± 1.6 | 26.5 ± 2.7 | n = 10. Mean ± SD. P < 0.01 vs control group. P > 0.05, P < 0.05, P < 0.01 vs MPTP group.

The results showed that the contents of striatal NA and 5-HT in the MPTP mice were markedly lower than those of the normal mice, and diethylaminoethyl acetylsalicylate increased striatal DA, NA, and 5-HT levels. It can improve or reverse the progress of Parkinson's disease. Our results also showed that diethylaminoethyl acetylsalicylate inhibited striatal GABA release in PD model. In conclusion, diethylaminoethyl acetylsalicylate prevented against the neurotoxicity of MPTP by anti-oxidation and modulation of the striatal NA and 5-HT and nigrostriate GABAergic activity. Thereby diethylaminoethyl acetylsalicylate may be a valuable neuroprotective agent for the treatment of Parkinson's disease.

Example 70

Treatment of Parkinson's Disease and Related Diseases

About 0.8 ml of 8% diethylaminoethyl acetylsalicylate.HCl in 25% ethanol is sprayed to the neck, face, or any part skin of the body twice per day. The process is continued until the disease is cured (maybe lifelong).

Example 71

Prevention of Parkinson's Disease and Related Diseases

For people with high risk to get Parkinson's disease and related diseases, such as people having a twin sister, or brother with Parkinson's disease and related diseases, people who have family history of Parkinson's disease and related diseases, people with mutant genes related to Parkinson's disease and related diseases, about 0.3 ml of 8% diethylaminoethyl acetylsalicylate.HCl in 25% ethanol is sprayed to any part skin of the body (rotating the location every time to avoid harm to the skin) once or twice per day.

Example 72

Anti-Glaucoma Activity of diethylaminoethyl acetylsalicylate.HCl

The ability of diethylaminoethyl acetylsalicylate.HCl to reduce intraocular pressure (IOP) was evaluated in cats with ocular hypertension produced by previously done laser trabeculoplastry. IOP was determined with a pneumatonometer after light corneal anesthesia with dilute proparacaine. 14 Cats were divided into 2 groups. Baseline IOP was determined prior to treatment with the test compound aqueous solution. In group A, 0.5 ml of water was applied transdermally to the area around eye (outside) of cat twice per day for 10 days. In group B, 30 mg/kg of diethylaminoethyl acetylsalicylate.HCl was applied to the area around eye (outside) of cat twice per day for 10 days. The results as shown in Table 72 showed that the HPC diethylaminoethyl acetylsalicylate.HCl had strong anti-glaucoma activity in animal model.

TABLE 72

Intraocular pressure reduction by diethylaminoethyl acetylsalicylate•HCl.

| Group | Base-line | End of treatment (day 10) |
|---|---|---|
| A (pure water) | 23.2 ± 0.6 | 22.2 ± 0.5 |
| B (drug treated) | 24.1 ± 0.7 | 16.1 ± 0.5 |

Diethylaminoethyl acetylsalicylate.HCl showed very strong anti-glaucoma activity in animal model.

Example 73

Treatment of Glaucoma

About 0.3 ml of 8% diethylaminoethyl acetylsalicylate.HCl in 25% ethanol is applied to the skin nearby the eyes twice per day. The process is continued until glaucoma is cured (maybe lifelong).

Example 74

The Treatment for Cataract

About 0.3 ml of 8% diethylaminoethyl acetylsalicylate.HCl in 25% ethanol is applied to the skin nearby the eyes twice per day. The process is continued until cataract is cured (maybe lifelong).

Example 75

Prevention of Cataract

For people with high risk to get cataract, such as people having a twin sister or brother with cataract, people who have family history of cataract, people with mutant genes related to cataract, about 0.3 ml of 8% diethylaminoethyl acetylsalicylate.HCl in 25% ethanol is applied the skin nearby the eyes once or twice per day.

Example 76

HPCs of NSAIAs Increase the Lifespan of Mice

NSAIAs are not very effective for treatment of the conditions described above or have serious side effects because they cannot penetrate the cell membrane, especially the brain cells and nerve cells, very effectively and stay the general circulation too long, thus most of drugs will be metabolized by intestinal mucosa, liver, kidney, and lung before they reach the "site of action." This situation not only produces very low pharmacologic effect, but also causes toxic burden on intestinal mucosa, liver, kidneys, lungs, and other parts of the body. HPCs in the present disclosure are capable of penetrating across biological barriers and are more effective than the parent drugs. A few tenths or hundredths of the normal drug dosage is needed and much less side effects will be caused. This will benefit not only transdermal drug delivery, but also any drug delivery system (such as oral, subcutaneous, intramuscular, inhalation, and nasal) and can treat many conditions better than they can be treated by their respective parent drugs and even some conditions which cannot be treated by their respective parent drugs.

Increased inflammation and slowed metabolism are believed to be two primary contributors to the human and animal aging process. HPCs of aspirin and other NSAIAs that can penetrate one or more biological membranes and show very strong anti-inflammatory activity should increase the lifespan of animals.

60 mice (10 weeks old, 30.3±3.5 g) were divided into groups A and B. In group A (n=30), 0.05 ml of distilled water (~2 cm$^2$) was applied to the back of mice once per day. In group B (n=30), 0.5 mg of diethylaminoethyl acetylsalicylate citric acid (the HPC of aspirin) in 0.05 ml of water (10%) was applied to the back of mice (~2 cm²) once per day. The results showed that the aspirin HPC increased 27% of the lifespan of mice (Table 76).

TABLE 76

Anti-aging effect of diethylaminoethyl acetylsalicylate citric acid which was administrated transdermally

| | Lifespan (month) |
|---|---|
| Group A | 30.2 ± 4.2 |
| Group B | 38.2 ± 4.6 |

Example 77

The Treatment for Anti-Aging and Increasing the Lifespan

About 0.4 ml of 8% diethylaminoethyl acetylsalicylate.HCl in 25% ethanol is sprayed to the any part skin of the body twice per day. The process is continued for lifelong.

Example 78

Treatment of Crohn's Disease and Other Autoimmune Diseases

About 0.7 ml of 8% N,N-diethylaminoethyl acetylsalicylate.HCl in 25% ethanol is sprayed to around anus, abdomen, or any part of the body twice per day. The treatment is continued until the conditions disappeared (may be lifelong).

Example 79

Prevention of Crohn's Disease and Other Autoimmune Diseases

For people with high risk to get Crohn's disease and other autoimmune diseases, such as people having a twin sister or brother with Crohn's disease and other autoimmune diseases, people who have family history of Crohn's disease and other autoimmune diseases, people with mutant genes related to Crohn's disease and other autoimmune diseases, about 0.3 ml of 8% diethylaminoethyl acetylsalicylate.HCl in 25% ethanol is sprayed to any part skin of the body (rotating the location every time to avoid harm to the skin) once or twice per day Example 80

Treatment of Hyperthyroidism

About 0.7 ml of 8% N,N-diethylaminoethyl acetylsalicylate.HCl in 25% ethanol is sprayed to neck or any part of the body twice per day. The treatment is continued until the hyperthyroidism condition disappeared (may be lifelong).

Example 81

Prevention of Hyperthyroidism

For people with high risk to get hyperthyroidism, such as people having a twin sister or brother with hyperthyroidism and other autoimmune diseases, people who have family history of hyperthyroidism and other autoimmune diseases, people with mutant genes related to hyperthyroidism and other autoimmune diseases, about 0.3 ml of 8% diethylaminoethyl acetylsalicylate.HCl in 25% ethanol is sprayed to any part skin of the body (rotating the location every time to avoid harm to the skin) once or twice per day Example 82

Treatment of Autoimmune Liver Inflammation, Liver Fibrosis and/or Cirrhosis

About 0.7 ml of 8% N,N-diethylaminoethyl acetylsalicylate.HCl in 25% ethanol is sprayed to abdomen or any part of the body twice per day. The treatment is continued until autoimmune liver inflammation, liver fibrosis and/or cirrhosis conditions disappeared (may be lifelong).

Example 83

Prevention of Autoimmune Liver Inflammation, Liver Fibrosis and/or Cirrhosis

For people with high risk to get autoimmune liver inflammation, liver fibrosis and cirrhosis, such as people having a twin sister or brother with autoimmune liver inflammation, liver fibrosis and/or cirrhosis, people who have family history of autoimmune liver inflammation, liver fibrosis and/or cirrhosis, people with mutant genes related to autoimmune liver inflammation, liver fibrosis and/or cirrhosis, about 0.3 ml of 8 diethylaminoethyl acetylsalicylate.HCl in 25% ethanol is sprayed to abdomen or any part skin of the body (rotating the location every time to avoid harm to the skin) once or twice per day.

Example 84

Treatment of Cystic Fibrosis, Pulmonary Fibrosis, Pancreas Fibrosis, Spleen Fibrosis, Gastrointestinal Fibrosis, and Other Organs' Fibrosis About 0.7 ml of 8% N,N-diethylaminoethyl acetylsalicylate.HCl in 25% ethanol is sprayed to the skin near the affected organs or any part of the body twice per day. The treatment is continued until cystic fibrosis, pulmonary fibrosis, pancreas fibrosis, spleen fibrosis, gastrointestinal fibrosis, and other organs' fibrosis conditions disappeared (may be lifelong).

Example 85

Prevention of Cystic Fibrosis, Pulmonary Fibrosis, Pancreas Fibrosis, Spleen Fibrosis, Gastrointestinal Fibrosis, and Other Organs' Fibrosis For people with high risk to get cystic fibrosis, pulmonary fibrosis, pancreas fibrosis, spleen fibrosis, gastrointestinal fibrosis, and other organs' fibrosis, such as people having a twin sister or brother with cystic fibrosis, pulmonary fibrosis, pancreas fibrosis, spleen fibrosis, gastrointestinal fibrosis, and other organs' fibrosis, people who have family history of cystic fibrosis, pulmonary fibrosis, pancreas fibrosis, spleen fibrosis, gastrointestinal fibrosis, and other organs' fibrosis, people with mutant genes related to cystic fibrosis, pulmonary fibrosis, pancreas fibrosis, spleen fibrosis, gastrointestinal fibrosis, and other organs' fibrosis, about 0.3 ml of 8 diethylaminoethyl acetylsalicylate.HCl in 25% ethanol is sprayed to any part skin of the body (rotating the location every time to avoid harm to the skin) once or twice per day.

Example 86

Treatment of Gallstones

Cholesterol gallstones develop when bile contains too much cholesterol and not enough bile salts. Bile duct inflammation may play a very important role in the formation of gallstones. The HPCs of NSAIAs can lower blood lipid levels and have anti-inflammatory activity. One of the treatments of gallstones is: about 0.7 ml of 8% N,N-diethylaminoethyl acetylsalicylate.HCl in 25% ethanol is sprayed to abdomen or any part of the body twice per day. The treatment is continued until the gallstones disappear.

Example 87

Treatment of Actinic Keratosis

About 0.7 ml of 8% N,N-diethylaminoethyl acetylsalicylate.HCl in 25% ethanol is sprayed to the skin with actinic keratosis or any part of the body twice per day. The treatment is continued until the actinic keratosis is cured.

Example 88

Prevention of Actinic Keratosis

For people with high risk to get actinic keratosis, such as people having a twin sister or brother with actinic keratosis, people who work a long time out door, about 0.4 ml of 8% diethylaminoethyl acetylsalicylate.HCl in 25% ethanol is sprayed to any part skin of the body (rotating the location every time to avoid harm to the skin) once or twice per day

Example 89

Treatment of Abnormal Vascular Skin Lesions, Birthmarks, Moles (Nevi), Skin Tags, Aging Spots (Liver Spots), and Other Skin Disorders About 0.7 ml of 8% N,N-diethylaminoethyl acetylsalicylate.HCl in 25% ethanol is sprayed to the affected skin or any part of the body twice per day. The treatment is continued until the skin disorders are cured.

Example 90

Treatment of Allergic Rhinitis (Nasal Allergies), Allergic Eyes, Allergic Eczema (Atopic Dermatitis), Hives, Allergic Shock (Anaphylaxis or Anaphylactic Shock), and/or Other Allergies (they May be Caused by Pollens, Dust Mite, Molds, Danders, Foods, Drugs, and/or Other Allergens)

About 0.7 ml of 8% N,N-diethylaminoethyl acetylsalicylate.HCl in 25% ethanol is sprayed to the affected areas or any part of the body twice per day. The treatment is continued until allergic rhinitis (nasal allergies), allergic eyes, allergic eczema (atopic dermatitis), hives, allergic shock (anaphylaxis or anaphylactic shock), and/or other allergies (they may be caused by pollens, dust mite, molds, danders, foods, drugs, and/or other allergens) are cured.

Example 91

Treatment for a Longer Healthier Life

About 0.4 ml of 8% N,N-diethylaminoethyl acetylsalicylate.HCl in 25% ethanol is sprayed to any part of the body twice per day. The treatment is continued for whole life.

Example 92

Treatment of Acne, Cystic Acne, Pus-Filled or Reddish Bumps, Comedones, Papules, Pustules, Nodules, Epidermoid Cysts, Keratosis Pilaris, and Other Skin Disorders About 0.5 ml of 8% N,N-diethylaminoethyl acetylsalicylate.HCl in 25% ethanol is sprayed to the affected skin or any part of the body twice per day. The treatment is continued until acne, cystic acne, pus-filled or reddish bumps, comedones, papules, pustules, nodules, epidermoid cysts, keratosis pilaris, and other skin disorders are cured.

Example 93

Treatment of Sagging Skin, Wrinkles, Crows Feet, Flesh-Colored Skin Spots, Rosacea, Post-Treatment Skin, and Other Skin Disorders About 0.7 ml of 8% N,N-diethylaminoethyl acetylsalicylate.HCl in 25% ethanol is sprayed to the affected skin or any part of the body twice per day. The treatment is continued until sagging skin, wrinkles, crows feet, flesh-colored skin spots, rosacea, post-treatment skin, and other skin disorders are cured.

Example 94

Treatment for a Healthier Skin

About 0.4 ml of 8% N,N-diethylaminoethyl acetylsalicylate.HCl in 25% ethanol is sprayed to any part of the body twice per day. The treatment is continued for whole life.

Example 95

Treatment for Macular Degeneration and Age-Related Macular Degeneration (AMD)

About 0.7 ml of 8% N,N-diethylaminoethyl acetylsalicylate.HCl in 25% ethanol is sprayed to the skin near the affected area or any part of the body twice per day. The treatment is continued until the conditions are cured.

Example 96

Treatment for Both Acute and Chronic Cough

About 0.7 ml of 8% N,N-diethylaminoethyl acetylsalicylate.HCl in 25% ethanol is sprayed to the neck (near throat) or any part of the body twice per day. The treatment is continued until the condition is cured.

Example 97

Treatment of Amyotrophic Lateral Sclerosis (ALS), Oculopharyngeal Muscular Dystrophy (OPMD), Myotonic Dystrophy (MD), Duchenne Muscular Dystrophy (DMD), Polymyositis (PM), Dermatomyositis (DM), Inclusion Body Myositis (IBM), and Other Muscle Disorders The pathogenesis of cell death in amyotrophic lateral sclerosis (ALS) may involve glutamate-mediated excitotoxicity, oxidative damage, and apoptosis. Cyclooxygenase-2, present in spinal neurons and astrocytes, catalyzes the synthesis of prostaglandin $E_2$. Prostaglandin $E_2$ stimulates glutamate release from astrocytes, whereas cyclooxygenase-2 also plays a key role in the production of pro-inflammatory cytokines, reactive oxygen species, and free radicals. Treatment with a selective cyclooxygenase-2 inhibitor, celecoxib, markedly inhibited production of prostaglandin E2 in the spinal cords of ALS mice. Celecoxib treatment significantly delayed the onset of weakness and weight loss and prolonged survival by 25%. Spinal cords of treated ALS mice showed significant preservation of spinal neurons and diminished astrogliosis and microglial activation (Merit. E. Cudkowicz, et al., Annals of neurology, 52, 771-778, 2002). These results suggest that cyclooxygenase-2 inhibition may benefit ALS patients. HPCs of NSAIAs in the present disclosure can penetrate skin and nerve cell membrane barriers in very high rates (most NSAIAs cannot penetrate nerve cells effectively) and can be administered transdermally without hurting the GI tract, so these HPC are very promising agents for the treatment of amyotrophic lateral sclerosis (ALS), oculopharyngeal muscular dystrophy (OPMD), myotonic dystrophy (MD), Duchenne muscular dystrophy (DMD), polymyositis (PM), dermatomyositis (DM), inclusion body myositis (IBM), and other muscle disorders. One of the treatments for these diseases is: About 0.7 ml of 8% N,N-diethylaminoethyl acetylsalicylate.HCl in 25% ethanol is sprayed to the neck, head, face, chest, or any part of the body twice per day. The treatment is continued until the conditions disappeared (may be lifelong).

Example 98

Prevention of Amyotrophic Lateral Sclerosis (ALS), Oculopharyngeal Muscular Dystrophy (OPMD), Myotonic Dystrophy (MD), Duchenne Muscular Dystrophy (DMD), Polymyositis (PM), Dermatomyositis (DM), Inclusion Body Myositis (IBM), and Other Muscle Disorders For people with high risk to get amyotrophic lateral sclerosis (ALS), oculopharyngeal muscular dystrophy (OPMD), myotonic dystrophy (MD), Duchenne muscular dystrophy (DMD), polymyositis (PM), dermatomyositis (DM), inclusion body myositis (IBM), and other muscle disorders., such as people having a twin sister or brother with amyotrophic lateral sclerosis (ALS), oculopharyngeal muscular dystrophy (OPMD), myotonic dystrophy (MD), Duchenne muscular dystrophy (DMD), polymyositis (PM), dermatomyositis (DM), inclusion body myositis (IBM), and other muscle disorders, people who have family history of amyotrophic lateral sclerosis (ALS), oculopharyngeal muscular dystrophy (OPMD), myotonic dystrophy (MD), Duchenne muscular dystrophy (DMD), polymyositis (PM), dermatomyositis (DM), inclusion body myositis (IBM), and other muscle disorders., people with mutant genes related to amyotrophic lateral sclerosis (ALS), oculopharyngeal muscular dystrophy (OPMD), myotonic dystrophy (MD), Duchenne muscular dystrophy (DMD), polymyositis (PM), dermatomyositis (DM), inclusion body myositis (IBM), and other muscle disorders., about 0.3 ml of 8% diethylaminoethyl acetylsalicylate.HCl in 25% ethanol is sprayed to any part skin of the body (rotating the location every time to avoid harm to the skin) once or twice per day.

Example 99

Treatment of Organ Transplant Rejection

Transplant rejection occurs when a transplanted organ or tissue is not accepted by the body of the transplant recipient. This is explained by the concept that the immune system of the recipient attacks the transplanted organ or tissue. This is expected to happen, because the immune system's purpose is to distinguish foreign material within the body and attempt to destroy it, just as it attempts to destroy infecting organisms such as bacteria and viruses. When possible, transplant rejection can be reduced through serotyping to determine the most appropriate donor-recipient match and through the use of immunosuppressant drugs that have serious side effects. Acute rejection usually begins one week after transplantation (as opposed to hyperacute rejection, which is immediate). The risk of acute rejection is highest in the first three months after transplantation. However, acute rejection can also occur months to years after transplantation. A single episode of acute rejection is not a cause for concern if recognized and treated promptly, and rarely leads to organ failure. But recurrent episodes are associated with chronic rejection the rejection is due to a chronic inflammatory and immune response against the transplanted tissue. The long-term use of immunosuppressant drugs will cause serious side effects. Normal NSAIAs have a little use and high dosage of NSAIAs will cause serious side effects too. HPC of NSAIAs in the present disclosure should be good choices for the treatment of organ Transplant rejection.

A). The Treatment and Prevention of Arm Transplant Rejection

About 0.7 ml of 8% N,N-diethylaminoethyl acetylsalicylate.HCl in 25% ethanol and 0.1 ml of 1% of N,N-diethylaminoethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate.HCl salt (the HPC of Montelukast) in 25% ethanol are sprayed to the arm or other part skin of the body twice per day. The treatment is continued until the rejection stops (that may be lifelong).

B) The Treatment and Prevention of Arm Transplant Rejection

About 0.7 ml of 8% N,N-diethylaminoethyl acetylsalicylate.HCl in 25% ethanol is sprayed to the arm or other part skin of the body twice per day. The treatment is continued until the rejection stops (that may be lifelong).

C). The Treatment and Prevention of Leg Transplant Rejection

About 0.7 ml of 8% N,N-diethylaminoethyl acetylsalicylate.HCl in 25% ethanol and 0.1 ml of 1% of N,N-diethylaminoethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate.HCl salt (the HPC of Montelukast) in 25% ethanol are sprayed to the leg or other part skin of the body twice per day. The treatment is continued until the rejection stops (that may be lifelong).

D) The Treatment and Prevention of Face Transplant Rejection

About 0.7 ml of 8% N,N-diethylaminoethyl acetylsalicylate.HCl in 25% ethanol is sprayed to the face or other part skin of the body twice per day. The treatment is continued until the rejection stops (that may be lifelong).

E) The Treatment and Prevention of Skin Transplant Rejection

About 0.7 ml of 8% N,N-diethylaminoethyl acetylsalicylate.HCl in 25% ethanol is sprayed to the transplanted skin or other part skin of the body twice per day. The treatment is continued until the rejection stops (that may be lifelong).

F). The Treatment and Prevention of Lung Transplant Rejection

About 0.7 ml of 8% N,N-diethylaminoethyl acetylsalicylate.HCl in 25% ethanol and 0.1 ml of 1% of N,N-diethylaminoethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate.HCl salt (the HPC of Montelukast) in 25% ethanol are sprayed to the chest or other part skin of the body twice per day. The treatment is continued until the rejection stops (that may be lifelong).

G) The Treatment and Prevention of Lung Transplant Rejection

About 0.7 ml of 8% N,N-diethylaminoethyl acetylsalicylate.HCl in 25% ethanol and 1 mg of N,N-diethylaminoethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate.HCl salt (the HPC of Montelukast) are inhaled into the lung and/or upper respiratory tract twice per day. The treatment is continued until the rejection stops (that may be lifelong).

H). The Treatment and Prevention of Liver Transplant Rejection

About 0.7 ml of 8% N,N-diethylaminoethyl acetylsalicylate.HCl in 25% ethanol and 0.1 ml of 1% of N,N-diethylaminoethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate.HCl salt (the HPC of Montelukast) in 25% ethanol are sprayed to the skin around the liver or other part skin of the body twice per day. The treatment is continued until the rejection stops (that may be lifelong).

I). The Treatment and Prevention of Kidney Transplant Rejection

About 0.7 ml of 8% N,N-diethylaminoethyl acetylsalicylate.HCl in 25% ethanol is sprayed to the skin around kidney or other part skin of the body twice per day. The treatment is continued until the rejection stops (that may be lifelong).

Example 100

Treatment of Osteoporosis

Osteoporosis is a disease of bone that leads to an increased risk of fracture. In osteoporosis the bone mineral density (BMD) is reduced, bone microarchitecture is disrupted, and the amount and variety of proteins in bone is altered. Local production of eicosanoids and interleukins is thought to participate in the regulation of bone turnover, and excess or reduced production of these mediators may underlie the development of osteoporosis [Raisz L (2005). *J Clin Invest* 115 (12): 3318-25]. Bone formation and bone resorption are physiologically controlled by the activities of osteoblasts and osteoclasts imbalances in these activities can arise from a variety of hormonal or inflammatory perturbations, resulting in skeletal abnormalities characterized by decreased bone mass, as in osteoporosis, or increased bone mass, in osteopetrosis [Yang, S., Chen, W., Stashenko, P. and Li, Y-P, Journal of Cell Science. October. 1; 120:3362-71, (2007)]. Oral infections such as periodontitis and pulpal/periapical disease eclicit innate and adaptive immune responses that protect the host against more widespread infection, but do so at the cost of localized tissue and bone destruction. Bone loss in these and other conditions is mediated by osteoclasrs [Battaglino R, etc. J. Cell Biochem. 200(6):1387-94 (2007)]. NSAIAs have anti-inflammatory activities, so HPCs of NSAIAs can be used for the treatment of osteoporosis, Paget's disease, bone metastases, periodontitis, and rheumatoid arthritis in humans and animals. Emerging clinical and molecular evidence suggests that inflammation also exerts significant influence on bone turnover, inducing osteoporosis. Numerous proinflammatory cytokines have been implicated in the regulation of osteoblasts and osteoclasts, and a shift towards an activated immune profile has been hypothesized as important risk factor. Chronic inflammation and the immune system remodeling characteristic of ageing, as well as of other pathological conditions commonly associated with osteoporosis, may be determinant pathogenetic factors [Lia Ginaldi, Maria Cristina Di Benedetto, and Massimo De Martinis (2005). Immunity & ageing, 2:14]. HPc of NSAIAs can be used for the treatment of osteoporosis without or with little side effects.

Example 101

Treatment of Osteoporosis

About 0.8 ml of 8% diethylaminoethyl acetylsalicylate.HCl in 25% ethanol is sprayed to legs, arms, or any other part skin (rotating the location every time to avoid harm to the skin) twice per day. The process is continued until osteoporosis is cured (maybe lifelong).

Example 102

Treatment of Osteoporosis

About 0.8 ml of 8% diethylaminoethyl 2-(ρ-isobutylphenyl) propionate.HCl in 25% ethanol is sprayed to legs, arms, or any other part skin (rotating the location every time to avoid harm to the skin) twice per day. The process is continued until osteoporosis is cured (maybe lifelong).

Example 103

Treatment of Osteoporosis

About 0.8 ml of 8% diethylaminoethyl 1-methyl-5-(4-methylbenzoyl)-1H-pyrrole-2-acetate.HCl salt in 25% ethanol is sprayed to legs, arms, or any other part skin (rotating the location every time to avoid harm to the skin) twice per day. The process is continued until osteoporosis is cured (maybe lifelong).

Example 104

Prevention of Osteoporosis

For people with high risk to get osteoporosis, such as old people, people having a twin sister, or brother with osteoporosis, people who have family history of osteoporosis, people with mutant genes related to osteoporosis, about 0.3 ml of 8% diethylaminoethyl acetylsalicylate.HCl in 25% ethanol is sprayed to any part skin of the body (rotating the location every time to avoid harm to the skin) once or twice per day.

Example 105

Antiviral, Anti-Fungus, and Anti-Insect Activity of N,N-diethylaminoethyl acetylsalicylate and/or N,N-diethylaminoethyl jasmonate.citric Acid in Peach Trees 240 Peach trees were divided into 4 groups. All field operations concerning land preparation and the uses of fertilizers were same for all groups. Group A (n=60) was control group with no chemical treatments. Group B (n=60) was normal fungicides and insecticides-treated group. Group C (n=60) was treated with N,N-diethylaminoethyl acetylsalicylate plus some insecticides. Group D (n=60) was N,N-diethylaminoethyl acetylsalicylate and N,N-diethylaminoethyl jasmonate.citric acid treated group. In group A, Peach Leaf Curl, Peach Scab, Brown Rot, Black Knot and other fungal diseases were found and different scale insects, Shothole Borer, Peach tree Borer, Lesser Peachtree Borer, fruit Moth and other diseases and insects were found. No any good (edible) fruits were harvested. In group B, 100 g of ferbam [iron tris(dimethyldithiocarbamate)] 76% Wettable Powder (WP) in 50 kg of water was applied to the group B Peach trees in November 15; 160 g of agricultural lime and 80 g of Sulfur 95% WP in 50 kg of water was applied to the group B Peach trees in December 15; 100 g of Daconil 2787 (chlorothalonil) in 50 kg of water was applied to the group B Peach trees in March 1; 80 g of difenoconazole [30% emulsifiable concentrate (EC)] and 80 g of propiconazole (30% EC) in 50 kg of water was applied to the group B Peach trees on March 15, 125 g of Captan 50% WP, 95 g of Ferbam 76% Wettable Powder, 80 g of Sulfur 95% Wettable Powder, 60 g of thiophanate-methyl 50% WP in 50 kg of water was applied to the group B Peach trees on April 2 (early pink), 125 g of Malathion 50% EC, 125 g of 1-naphthyl methylcarbamate 50% WP and 100 g of dimethomorph 50% WP in 50 kg of water was applied to the group B Peach trees on April 15; 125 g of Captan 50% WP and 60 g of thiophanate-methyl 50% WP in 50 kg of water was applied to the group B Peach trees on April 20; 1.5 kg of M-Pede 49% liquid in 50 kg of water was applied to the group B Peach trees on april 25; 125 g of Captan 50% WP, 100 g of Ferbam 76% Wettable Powder, 80 g of Sulfur 95% Wettable Powder, and 60 g of thiophanate-methyl 50% WP in 50 kg of water was applied to the group B Peach trees on May 8, 125 g of Malathion 50% EC, 125 g of 1-naphthyl methylcarbamate 50% WP and 50 g of myclobutanil (12.5% EC) in 50 kg of water was applied to the group B Peach trees on May 15; 125 g of Captan 50% Wettable Powder, 100 g of Ferbam 76% Wettable Powder, 80 g of Sulfur 95% Wettable Powder, and 60 g of thiophanate-methyl 50% WP in 50 kg of water was applied to the group B Peach trees on June 8, 125 g of Malathion 50% EC, 125 g of 1-naphthyl methylcarbamate 50% WP and 100 g of dimethomorph 50% WP in 50 kg of water was applied to the group B Peach trees on June 16; 125 g of Captan 50% WP and 60 g of thiophanate-methyl 50% WP in 50 kg of water was applied to the group B Peach trees on June 26; Yield 2500 kg of good (edible) peach. Group C was N,N-diethylaminoethyl acetylsalicylate-treated group. 50 g of N,N-diethylaminoethyl acetylsalicylate in 50 kg of water was applied to the group C Peach trees on November 15, March 1, March 20, and June 20, 50 g of N,N-diethylaminoethyl acetylsalicylate, 125 g of Malathion 50% EC, 125 g of 1-naphthyl methylcarbamate 50% WP and 60 g of thiophanate-methyl 50% WP in 50 kg of water was applied to the group C peach trees on April 1, April 20, May 10, and May 30. Yield 3000 kg of good (edible) peaches. Group D was the N,N-diethylaminoethyl acetylsalicylate.HCl and N,N-diethylaminoethyl jasmonate.citric acid-treated group, 50 g of N,N-diethylaminoethyl acetylsalicylate in 50 kg of water was applied to the group C peach trees on November 15, March 1, and March 20.50 g of N,N-diethylaminoethyl acetylsalicylate, 125 g of Malathion 50% EC, and 25 g of N,N-diethylaminoethyl jasmonate.citric acid in 50 kg of water was applied to the group C peach trees on April 1, April 20, May 10, May 30, and June 20. Yielded 3200 kg of good (edible) peaches. The results show that diethylaminoethyl acetylsalicylate.HCl and N,N-diethylaminoethyl jasmonate.citric acid had strong antiviral, anti-fungus, and anti-insect activity in peach trees. Only a few of insecticides and fungicides were needed and the yield was much higher in group C and D than other groups. The labor costs of groups C and D were much less and the harvest dates of groups C and D were 1 week earlier.

Example 106

Antiviral, Anti-Fungus, and Anti-Insect Activity of N,N-diethylaminoethyl acetylsalicylate and N,N-diethylaminoethyl jasmonate.citric Acid in Red Grape Vine 2 Acres of grape vine was divided into 4 groups (½ acre each). All field operations concerning land preparation and the uses of fertilizers were same for all groups. Group A was control group treated with no chemicals. Group B was normal fungicides and insecticides-treated group. Group C was N,N-diethylaminoethyl acetylsalicylate treated group. Group D was N,N-diethylaminoethyl acetylsalicylate and N,N-diethylaminoethyl jasmonate.citric acid treated group. In group A, black rot, downy mildew, powdery mildew, anthracnose, *Phomopsis* Blight, and other fungal diseases were found and Grape Berry Moth, Grape Root Borer, Rose Chafer, Japanese beetle, grape tomato gall, and other diseases and insects were found. Yield nothing of good (edible) grapes. In group B, 200 g of Ferbam 76% WP in 100 kg of water was applied to the group B grape vines in November 15; 160 g of sulfur 95% WP and 600 g of hydrated lime in 100 kg of water was applied to the group B grape vines in December 15; 200 g of Daconil 2787 in 100 kg of water was applied to the group B grape vines in March 10; 250 g of Captan 50% WP and 200 g of dimethomorph 50% WP in 100 kg of water was applied to the group B grape vines in March 20; 30 g of (4"R)-4"-deoxy-4"-(methylamino)avermectin B1 benzoate [proclaim R (banleptm)] 2% WP and 120 g of thiophanate-methyl 50% WP in 100 kg of water was applied to the group B grape vines on March 30; 200 g of dimethomorph 50% WP and 200 g of Mancozeb 80% WP in 100 kg of water was applied to the group B grape vines on April 10; 160 g of difenoconazole [30% emulsifiable concentrate (EC)] and 160 g of propiconazole (30% EC) in 100 kg of water was applied to the group B grape vines on April 20, 30 g of (4"R)-4"-deoxy-4"-(methylamino)avermectin B1 benzoate [proclaim R (banleptm)] 2% WP, 250 g of 1-naphthyl methylcarbamate 50% WP and 100 g of thiophanate-methyl 50% WP in 100 kg of water was applied to the group B grape vines on April 30; 160 g of difenoconazole [30% emulsifiable concentrate (EC)] and 160 g of propiconazole (30% EC) in 100 kg of water was applied to the group B grape vines on May 10; 250 g of Malathion 50% EC, 250 g of 1-naphthyl methylcarbamate 50% WP and 120 g of thiophanate-methyl 50% WP in 100 kg of water was applied to the group B grape vines on May 20; 250 g of Captan 50% Wettable Powder and 30 g of (4"R)-4"-deoxy-4"-(methylamino)avermectin B1 benzoate [proclaim R (banleptm)] 2% WP in 100 kg of water was applied to the group B grape vines on May 30; 250 g of Malathion 50% EC, 250 g of 1-naphthyl methylcarbamate 50% WP and 120 g of thiophanate-methyl 50% WP in 100 kg of water was applied to the group B grape vines on June 8; 250 g of Captan 50% Wettable Powder and 200 g of Ferbam 76% Wettable Powder in 100 kg of water was applied to the group B grape vines on June 18; 160 g of Sulfur 95% Wettable Powder and 120 g of thiophanate-methyl 50% WP in 100 kg of water was applied to the group B grape vines on June 25; 250 g of Malathion 50% EC, 250 g of 1-naphthyl methylcarbamate 50% WP and 120 g of thiophanate-methyl 50% WP in 100 kg of water was applied to the group B grape vines on July 2; 160 g of difenoconazole [30% emulsifiable concentrate (EC)] and 160 g of propiconazole (30% EC) in 100 kg of water was applied to the group B grape vines on July 10; 250 g of Captan 50% Wettable Powder, 200 g of Ferbam 76% Wettable Powder, 160 g of Sulfur 95% Wettable Powder, and 120 g of thiophanate-methyl 50% WP in 50 kg of water was applied to the group B grape vines on July 17, 250 g of Malathion 50% EC, 250 g of 1-naphthyl methylcarbamate 50% WP and 120 g of thiophanate-methyl 50% WP in 100 kg of water was applied to the group B grape vine on July 24; 250 g of Captan 50% Wettable Powder, 200 g of Ferbam 76% Wettable Powder, 160 g of Sulfur 95% Wettable Powder, and 120 g of thiophanate-methyl 50% WP in 100 kg of water was applied to the group B grape vines on July 30. Yield 5000 kg of good (edible) grapes. Group C was N,N-diethylaminoethyl acetylsalicylate-treated group, 100 g of N,N-diethylaminoethyl acetylsalicylate.HCl in 100 kg of water was applied to the group C grape vine on November 15, February 20, March 15, April 5, May 15, and July 25; 100 g of N,N-diethylaminoethyl acetylsalicylate.HCl and 200 g of Malathion 50% Emulsifiable Concentrate in 100 kg of water was applied to the group C grapes on April 25, June 5, and June 30; Yield 6300 kg of good (edible) grapes. Group D was N,N-diethylaminoethyl acetylsalicylate and N,N-diethylaminoethyl jasmonate.citric acid-treated group. 100 g of N,N-diethylaminoethyl acetylsalicylate.HCl in 100 kg of water was applied to the group C grape vine on November 1, February 20, and March 20; 100 g of N,N-diethylaminoethyl acetylsalicylate.HCl and 50 g of N,N-diethylaminoethyl jasmonate.citric acid in 100 kg of water was applied to the group D grapes on April 5, April 20, May 5, May 20, June 5, June 20, July 5, and July 25. Yield 6700 kg of good (edible) grapes. The results show that N,N-diethylaminoethyl acetylsalicylate.HCl and N,N-diethylaminoethyl jasmonate.citric acid had strong antiviral, anti-fungus, and anti-insect activity in grape vine. Only a few of insecticides and fungicide were needed and the yield was much higher in group C and D than other groups. Labor costs of groups C and D were much less and the harvest dates of Groups C and D were 10 days earlier.

Example 107

Antiviral, Anti-Fungus, and Anti-Insect Activity of N,N-diethylaminoethyl acetylsalicylate in Rice 2 Acres of rice was divided into 4 groups (½ acre each). All field operations concerning land preparation and the uses of fertilizers were same for all groups. Group A was control group treated with no chemicals, Group B was normal fungicides and insecticides-treated group, Group C was N,N-diethylaminoethyl acetylsalicylate.HCl-treated group and Group D was N,N-diethylaminoethyl acetylsalicylate.HCl and N,N-diethylaminoethyl jasmonate.citric acid-treated group. In group A, Rice blast, rice sheath blight, sheath spot, sheath rot, stem rot, brown leaf spot, leaf smut, narrow brown leaf spot, kernel smut, panicle blast, and other diseases and insects were found. Yield 200 kg of not good rice. In group B, 200 g of validamycin A 5% aqueous solution in 100 kg of water was applied to the group B rice in July 1; 30 g of imidacloprid 10% WP in 100 kg of water was applied to the group B rice in July 5; 30 g of imidacloprid 10% WP and 200 g of Carbendazim 50% WP in 100 kg of water was applied to the group B rice in July 12; 250 g of Malathion 50% EC and 120 g of propiconazole (11.7%) in 100 kg of water was applied to the group B rice in July 20; 200 g of validamycin A 5% aqueous solution in 100 kg of water was applied to the group B rice on July 30, 180 g of chlorothalonil 70% WP in 100 kg of water was applied to the group B rice on August 8, 250 g of Malathion 50% EC and 200 g of validamycin A 5% aqueous solution in 100 kg of water was applied to the group B rice on August 17; 30 g of imidacloprid 10% WP and 200 g of Carbendazim 50% WP in 100 kg of water was applied to the group B rice on August 26 and September 8; 250 g of Malathion 50% EC and 200 g of validamycin A 5% aqueous solution in 100 kg of water was applied to the group B rice on September 20 and October 10. Yield 1500 kg of good rice. Group C was N,N-diethylaminoethyl acetylsalicylate.HCl-treated group. 30 g of imidacloprid 10% WP and 100 g of N,N-diethylaminoethyl acetylsalicylate.HCl in 100 kg of water was applied to the group C rice on July 1, July 12, July 25, August 10, August 25, September 10 and September 25; Yield 1800 kg of good rice. Group D was N,N-diethylaminoethyl acetylsalicylate.HCl and N,N-diethylaminoethyl jasmonate.citric acid-treated group, 50 g of N,N-diethylaminoethyl jasmonate.citric acid and 100 g of N,N-diethylaminoethyl acetylsalicylate.HCl in 100 kg of water was applied to the group C rice on July 1, July 12, July 25, August 10, August 25, September 10 and September 25; Yield 1850 kg of good rice. The results show that N,N-diethylaminoethyl acetylsalicylate.HCl and N,N-diethylaminoethyl jasmonate-.citric acid had strong antiviral, anti-fungus, and anti-insect activity in rice. Only a few of insecticides and fungicides were needed and the yield was much higher in groups C and D than other groups. The harvest dates of group C and D were 5 days earlier.

Example 108

Application of HPCs of Prostaglandins to Stimulate Hair Growth and Eyelash Growth About 0.2 ml of 1% of HPC of N,N-diethylaminoethyl 11,15-dihydroxy-9-oxoprost-13-en-1-oate.HBr (the HPC of prostaglandin $E_1$), N,N-diethylaminoethyl (Z)-7-{[(1R,2R,3R,5S)-3,5-Dihydroxy-2-[1E,3S]-3-hydroxy-5-phenyl-1-pentenyl]cyclopentyl}-5-N-ethylheptenoate.HBr(the HPC of bimatoprost), (13,14-dihydro-17-phenyl-18,19,20-trinor $PGF_{2\alpha}$N,N-diethylaminoethyl ester, N,N-diethylaminoethyl (Z)-7-[(1R,2R,3R,5S)-3,5-dihydroxy-2-[(1E,3R)-3-hydroxy-4-[(α,α,α-trifluoro-m-tolyl)oxy]-1-butenyl]cyclopentyl]-5-heptenoate.HBr, or 13,14-dihydro-15-keto-20-ethyl $PGF_{2\alpha}$N,N-diethylaminoethyl ester in pure water is applied to the skin area close to the eyelashes (0.1 ml solution for each eye). After more than 1 month treatment, the eyelashes will grow longer and fuller.

About 1 ml of 1% of HPC of N,N-diethylaminoethyl 11,15-dihydroxy-9-oxoprost-13-en-1-oate.HBr (the HPC of prostaglandin $E_1$), N,N-diethylaminoethyl (Z)-7-{[(1R,2R,3R,5S)-3,5-Dihydroxy-2-[1E,3S]-3-hydroxy-5-phenyl-1-pentenyl]cyclopentyl}-5-N-ethylheptenoate.HBr(the HPC of bimatoprost), (13,14-dihydro-17-phenyl-18,19,20-trinor $PGF_{2\alpha}$N,N-diethylaminoethyl ester, N,N-diethylaminoethyl (Z)-7-[(1R,2R,3R,5S)-3,5-dihydroxy-2-[(1E,3R)-3-hydroxy-4-[(α,α,α-trifluoro-m-tolyl)oxy]-1-butenyl]cyclopentyl]-5-heptenoate.HBr, or 13,14-dihydro-15-keto-20-ethyl $PGF_{2\alpha}$N,N-diethylaminoethyl ester in pure water is applied to the skin (frontal and parietal areas) on the head skull. After more than 1 month treatment, the hairs will grow longer and fuller.

The above HPCs of prostaglandins and other HPCs of prostaglandins can stimulate hair growth and eyelash growth, and may be very useful in cosmetic industry.

Example 109

Applications of HPCs of Progesterone

Progesterone plays many roles relating to the development of the fetus, nervous system, immune system and many other systems. It can act as an anti-inflammatory agent and regulates the immune response. Because of the poor bio-availability of progesterone when taken orally, the transdermal administration of it is favorable. Vaginal and rectal application is also effective, ENDOMETRIN (progesterone) Vaginal insert 100 mg, approved by the FDA in June 2007 to support embryo implantation and early pregnancy, Other products are CRINONE and PROCHIEVE bioadhessive progesterone vaginal gels, approved by FDA for use in infertility and during pregnancy. Progesterone can be given by injection. It may be used in treating multiple sclerosis, since the characteristic deterioration of nerve myelin insulation halts during pregnancy, when progesterone levels are raised. It may be used for preventing preterm birth in women at risk for preterm birth. It may be used for keeping females and males youth. It has been observed in animal models that females have reduced susceptibility to traumatic brain injury [Roof R L, Hall E D (May 2000). "gender differences in acute CNS trauma and Stroke: neuroprotective effects of estrogen and progesterone". J. Neurotrauma 17(5): 367-88.]. Encouraging results have also been reported in human clinical trials [Wright D W, et.al. (2007), Ann Emerg Med 49 (4): 391-402, 402 e1-2.; Xiao G, et. al. (2008) Crit Care 12(2): R61.]. The mechanism of progesterone protective effects may be the reduction of inflammation which follows brain trauma. [Pan D S, et. al. (2007), Biomed. Environ. Sci. 20(5): 432-8.]]

A). Treatment of Brain Trauma

About 0.5 ml of 2% of N-(4-N,N-diethylaminoethoxycarbonyl)phenyl progesterone imine.HCl salt in isopropanol is sprayed on the neck, chest, face, or any part of skin three time per day. The process is continued until the brain injury is cured.

B). Treatment of Stroke

About 0.5 ml of 2% of N-(4-N,N-diethylaminoethoxycarbonyl)phenyl progesterone imine.HCl salt in isopropanol is sprayed on the neck, chest, face, or any part of skin three time per day. The process is continued until stroke is cured.

C). Supporting Embryo Implantation and Early Pregnancy

About 0.3 ml of 2% of N-(4-N,N-diethylaminoethoxycarbonyl)phenyl progesterone imine.HCl salt in isopropanol is sprayed on any part of skin three times per day. The process is continued as necessary.

D). Treatment of Discoid Lupus Erythematosus

About 0.3 ml of 2% of N-(4-N,N-diethylaminoethoxycarbonyl)phenyl progesterone imine.HCl salt in isopropanol is sprayed on the affected skin three time per day. The process is continued until discoid lupus erythematosus is cured E). Treatment of Systemic Lupus Erythematosus About 0.5 ml of 2% of N-(4-N,N-diethylaminoethoxycarbonyl)phenyl progesterone imine.HCl salt in isopropanol is sprayed on the skin near by the affected organs three time per day. The process is continued until systemic lupus erythematosus is cured F). Treatment of Multiple Sclerosis (MS).

About 0.5 ml of 2% of N-(4-N,N-diethylaminoethoxycarbonyl)phenyl progesterone imine.HCl salt in isopropanol is sprayed on the skin near by the affected organs three time per day. The process is continued until MS is cured.

Example 110

In Vivo Transportation of HPC and Application of HPC of Mustards and Related Compounds in Treating Cancer Study A: Blocking Human Gastric Cancer HGC-27 cell Proliferation with Chlorambucil and N,N-diethylaminoethyl 4-[bis(2-chloroethyl)amino]benzenebutyrate.HCl salt The inhibition of cellular proliferation was measured by the modified dimethyl thiazolyl diphenyl tetrazolium salt (MTT) [3-(4,5-dimethylthiazol-2-yl)-2,5-diphenyltetrazolium bromide] assay, based on the ability of live cells to converting thiazolyl blue to dark blue formazan. Approximately 3500 cells of HGC-27 (in 100 μl culture solution) were seeded into 96-well culture plates and were cultured for 16 hours at 37° C. Different concentration solution (100 μl) of Taxol (positive control), chlorambucil, or N,N-diethylaminoethyl 4-[bis(2-chloroethyl)amino]benzenebutyrate.HCl salt (HPC of chlorambucil) were added and incubation continued for 72 hours at 37° C. Then MTT were added and incubation continued at 37° C. for 4 h, and 100 μl DMSO was pipetted to solubilize the formazan product for 30 min at room temperature. The absorbency at 570 nm was measured using Bio-Rad micro-plate reader stored at −20° C. until use for electrophoresis. Results were shown in table 110a.

TABLE 110a

HGC-27 cell growth inhibition rates for chlorambucil and its HPC (the HPC).

| Concentration | Chlorambucil (100%) | HPC of chlorambucil (100%) |
| --- | --- | --- |
| 0.5 μM | 0.3 | 15.6 |
| 2.0 μM | 1.6 | 28.7 |
| 5.0 μM | 12.5 | 42.1 |
| 25 μM | 31.5 | 61.6 |
| 50 μM | 39.4 | 82.1 |
| 75 μM | 41.5 | 96.5 |
| 100 μM | 53.1 | 98.1 |
| 200 μM | 62.1 | 97.2 |
| 500 μM | 81.0 | 98.2 |

The results showed that the HPC of chlorambucil had much stronger cancer cell growth inhibition than the parent drug, chlorambucil.

Study B: For evaluation of antitumor activity, a human myeloma cell line derived from the ascites of a patient with multiple myeloma was implanted into mice. The experiment was carried out on 17 groups of mice. Control group (A, orally), chlorambucil (group $B_1$: 1 mg/kg, orally, group $B_2$, 3 mg/kg, orally, group $B_3$:1 mg/kg, transdermally, and group $B_4$: 3 mg/kg, transdermally), melphalan (group $C_1$: 1 mg/kg, orally, group $C_2$, 3 mg/kg, orally, group $C_3$:1 mg/kg, transdermally, and group $C_4$: 3 mg/kg, transdermally), N,N-diethylaminoethyl 4-[bis(2-chloroethyl)amino]benzenebutyrate.HBr (the HPC of chlorambucil (group $D_1$: 1 mg/kg, orally, group $D_2$, 3 mg/kg, orally, group $D_3$:1 mg/kg, transdermally, and group $D_4$: 3 mg/kg, transdermally), and 4-[bis(2-chloroethyl)amino]-N-acetyl-L-phenylalanine N,N-diethylaminoethyl ester hydrobromide (the HPC of melphalan) (group $E_1$: 1 mg/kg, orally, group $E_2$, 3 mg/kg, orally, group $E_3$:1 mg/kg, transdermally, and group $E_4$: 3 mg/kg, transdermally). The results are shown in table 110b.

TABLE 110b

Extension of survival period of mice with multiple myeloma by use of mustards and their HPCs (novel HPCs).

| Compounds | Dose (mg/kg) Perday | n | Survival Period (days) | Life Elongation Rate (%) |
|---|---|---|---|---|
| Control (A) | — | 5 | 45.5 ± 3.6 | 100 |
| $B_1$ | 1 mg | 5 | 48.7 ± 5.3 | 107 |
| $B_2$ | 3 mg | 5 | 68.5 ± 4.2 | 151 |
| $B_3$ | 1 mg | 5 | 46.1 ± 3.6 | 99 |
| $B_4$ | 3 mg | 5 | 44.6 ± 3.6 | 98 |
| $C_1$ | 1 mg | 5 | 48.1 ± 5.3 | 106 |
| $C_2$ | 3 mg | 5 | 70.5 ± 3.2 | 155 |
| $C_3$ | 1 mg | 5 | 44.7 ± 3.6 | 98 |
| $C_4$ | 3 mg | 5 | 45.6 ± 3.6 | 100 |
| $D_1$ | 1 mg | 5 | 71.7 ± 3.3 | 158 |
| $D_2$ | 3 mg | 5 | 88.5 ± 3.2 | 194 |
| $D_3$ | 1 mg | 5 | 85.7 ± 4.4 | 188 |
| $D_4$ | 3 mg | 5 | 91.5 ± 4.7 | 201 |
| $E_1$ | 1 mg | 5 | 68.7 ± 5.1 | 151 |
| $E_1$ | 3 mg | 5 | 85.2 ± 4.3 | 187 |
| $E_1$ | 1 mg | 5 | 86.7 ± 4.5 | 190 |
| $E_4$ | 3 mg | 5 | 87.5 ± 4.2 | 192 |

The results showed that the HPCs demonstrated much stronger antitumor activity than their parent drugs and transdermal administration of the HPCs is better than oral administration.

Example 111

Antitumor Activity of the HPCs of Mustards

There are very few differences between cancer and normal cells according to present knowledge. Almost every cancer drug destroys both of cancer and normal cells, especially the rapidly dividing normal body cells such as hair follicles, cells lining the gastrointestinal tract, and bone marrow cells involved in the immune defense system. The most common side effects of present chemotherapy are nausea, hair loss, and increased susceptibility to infection. In addition, there are many other side effects that cancer patients experience.

HPCs in the present disclosure can be administered transdermally. Transdermal cancer drug delivery has several advantages. This method helps to avoid cancer drugs directly hurting the gastro-intestinal tract and liver and inactivation of the drugs caused by first pass metabolism in the liver and gastro-intestinal tract. It can provide local delivery of appropriate concentrations of a drug to the intended site of action without systemic exposure. Topical drug delivery methods may use a much smaller amount of drugs than the amount used for the systemic method and thus reduce the side effects of cancer drugs.

A human myeloma cell line derived from the ascites of a patient with multiple myeloma was implanted into mice. The mice was divided into 11 groups: control group (A, orally), melphalan ($B_1$ and $B_2$, orally), chlorambucil ($C_1$ and $C_2$, orally), N,N-diethylaminoethyl 4-[bis(2-chloroethyl)amino]benzenebutyrate.HBr ($D_1$ and $D_2$, transdermally), 4-[bis(2-chloroethyl)amino]-N-acetyl-L-phenylalanine N,N-diethylaminoethyl ester hydrobromide ($E_1$ and $E_2$, transdermally in 5% aqueous solution), and diethylaminoethyl 4-[bis(2-methylsulfonylethyl)amino]benzenebutyrate.HCl ($F_1$ and $F_2$, transdermally in 5% aqueous solution). The body weight loss of mice was determined on day 21.

The results (Table 111) show that the HPCs of mustards had strong antitumor activity at 1.5 mg/kg dose and caused less side effects (less weight loss) when the HPCs are administered transdermally.

TABLE 111

Extension of survival period and weight loss of cancer mice by use of mustards and their HPCs.

| Compounds | Dose (mg/kg) perday | n | Survival Period (days) | Life Elongation Rate (%) | None Disease Rate | Weight Loss (%) |
|---|---|---|---|---|---|---|
| Control (A) | — | 7 | 43.5 ± 5.6 | 100 | 0/7 | — |
| $B_1$ | 1.5 mg | 7 | 52.7 ± 4.3 | 121 | 0/7 | 10% |
| $B_2$ | 3 mg | 7 | 83.5 ± 5.8 | 192 | 2/7 | 20% |
| $C_1$ | 1.5 mg | 7 | 54.8 ± 5.5 | 126 | 2/7 | 10% |
| $C_2$ | 3 mg | 7 | 87.2 ± 6.9 | 200 | 3/7 | 17% |
| $D_1$ | 1.5 mg | 7 | 122.5 ± 7.3 | 282 | 4/7 | 7% |
| $D_2$ | 3 mg | 7 | 117.2 ± 6.1 | 269 | 4/7 | 10% |
| $E_1$ | 1.5 mg | 7 | 118.5 ± 7.6 | 272 | 4/7 | 5% |
| $E_2$ | 3 mg | 7 | 115.2 ± 6.8 | 265 | 3/7 | 9% |
| $F_1$ | 1.5 mg | 7 | 112.5 ± 8.7 | 259 | 4/7 | 7% |
| $F_2$ | 3 mg | 7 | 111.2 ± 5.9 | 256 | 3/7 | 11% |

Example 112

Treatment of Multiple Myeloma

About 0.2 ml of 2% N,N-diethylaminoethyl 4-[bis(2-chloroethyl)amino]benzenebutyrate.HBr in 50% ethanol is sprayed to the skin of any part of the body (apply to a different location every time to avoid hurting the skin repeatedly) twice per day. The treatment is continued until the condition (multiple myeloma) disappeared (may be lifelong).

Example 113

Treatment of Brain Tumors

About 0.1 ml of 2% N,N-diethylaminoethyl 4-[bis(2-chloroethyl)amino]benzenebutyrate.HBr in 50% ethanol is applied to the skin of the head near the tumor (apply to a different location every time to avoid hurting the skin repeatedly) twice per day. The treatment is continued until the brain tumor disappeared.

Example 114

Treatment of Brain Tumors

About 0.01 ml of 5% N,N-diethylaminoethyl 4-[bis(2-chloroethyl)amino]benzenebutyrate.HBr in pure water is injected into the tumor twice per week. The treatment is continued until the brain tumor disappeared.

Example 115

Treatment of Skin Cancers

About 0.5 ml of 0.1% N,N-diethylaminoethyl 4-[bis(2-chloroethyl)amino]benzenebutyrate.HBr in 50% ethanol is applied to the skin with tumor or nearby the skin cancers twice per day. The treatment is continued until the brain tumor disappeared.

Example 116

N,N-diethylaminoethyl 4-[bis(2-chloroethyl)amino] benzenebutyrate.HBr for the Treatment of Breast Cancer 0.2 ml of 5% N,N-diethylaminoethyl 4-[bis(2-chloroethyl)amino]benzenebutyrate.HBr in pure water (or 50% ethanol) is directly applied to the surface skin of where the breast tumor is and this process is repeated every 3 days. 0.2 ml of 20% N,N-diethylaminoethyl acetylsalicylate in pure water (or 50% ethanol) is applied to the same area twice per day (without mixing it with the first medicine).

Example 117

N,N-diethylaminoethyl 4-[bis(2-chloroethyl)amino] benzenebutyrate.HBr for the treatment of leukemias 0.2 ml of 20% N,N-diethylaminoethyl 4-[bis(2-chloroethyl)amino]benzenebutyrate.HBr in pure water (or 50% ethanol) is directly applied to the skin on any part of the body twice perweek (always applying to a different area to avoid hurting the same patch of skin over prolonged exposure).

Example 118

Anti-Obesity of HPCs

Anti-Obesity of HPCs in Sprague Dawley Rats.

Peptides play an enormous variety of roles in all living matter. Peptide hormone is the largest group of hormones. They have a fascinating role in processes that control life. Unfortunately, peptides and related compounds are rapidly proteolysized by proteolytic enzymes. When peptides are taken orally, they are destroyed in a few minutes. In the case of injection, the administration of peptides is painful, and in many cases requires frequent and costly office visits to treat chronic conditions.

Enterostatins [Val-Pro-Asp-Pro-Arg (VPDPR), Val-Pro-Gly-Pro-Arg (VPGPR), and Ala-Pro-Gly-Pro-Arg (APGPR)] are pentapeptides derived from the $NH_2$-terminus of procolipase after tryptic cleavage and belong to the family of gut-brain peptides. They regulate fat intake and may be used for the treatment of obesity (Erlanson-Albertsson C, York D, Obes. Rev. 1997 July; 5(4): 360-72 and Sorhede M, Mei J, Erlanson-Albertsson C., J Physiol. 87:273-275, 1993).

20 Female Sprague Dawley (SD) rats (20 weeks old, 320-345 g) were divided into 2 groups. In group A, 0.2 ml of water was administered to the back of rat (n=10) twice per day for 30 days. In Group B, 10 mg/kg of H-Val-Pro-Gly-Pro-Arg($NO_2$)—$OCH_2CH_2CH_2CH_3$.HCl in 0.2 ml of water was administered transdermally to the backs of rats (n=10) twice per day for 30 days. The results were shown in table 118a.

TABLE 118a

| | Anti-obesity of H-Val-Pro-Gly-Pro-Arg($NO_2$)—$OCH_2CH_2CH_2CH_3$•HCl in Sprague Dawley rats. | | |
|---|---|---|---|
| Group | Weight (g) (Day1) | Food intake (per day & per rat) | Weight (g) (Day 30) |
| A | 330.5 ± 4.3 | 20.5 ± 1.2 | 350.5 ± 4.1 |
| B | 333.5 ± 4.2 | 17.5 ± 1.2 | 301.4 ± 3.7 |

The results showed that peptide H-Val-Pro-Gly-Pro-Arg($NO_2$)—$OCH_2CH_2CH_2CH_3$.HCl reduced the body weight of rats effectively. The rats of the control group were about 17% heavier than the rats in the peptide treated group.

Anti-Obesity of Peptide HPC in Obese Mice (SLAC/DB/DB).

20 obese DB/DB mice (SLAC/DB/DB) mice (16 weeks old, 55-60 g) were divided into 2 groups. In group A, 0.1 ml of water was administered to the back of mouse (n=10) twice per day for 30 days. In Group B, 15 mg/kg of H-Val-Pro-Gly-Pro-Arg($NO_2$)—$OCH_2CH_2CH_2CH_3$.HCl in 0.2 ml of water was administered transdermally to the backs of rats (n=10) twice per day for 30 days. The results were shown in table 118b.

TABLE 118b

| | Anti-obesity of H-Val-Pro-Gly-Pro-Arg($NO_2$)—O $OCH_2CH_2CH_2CH_3$•HCl in obese mice (SLAC/DB/DB). | | |
|---|---|---|---|
| Group | Weight (g) (Day1) | Food intake (per day & per rat) | Weight (g) (Day 30) |
| A | 56.5 ± 2.2 | 4.8 ± 0.3 | 67.5 ± 2.1 |
| B | 57.1 ± 1.8 | 3.9 ± 0.3 | 53.4 ± 4.7 |

The results showed that peptide H-Val-Pro-Gly-Pro-Arg($NO_2$)—$OCH_2CH_2CH_2CH_3$.HCl reduced the body weight of obese mice very effectively. The mice of the control group were about 26% heavier than the mice in the peptide treated group.

Example 119

The Treatment for Obese

About 0.3 ml of 5% H-Ala-Pro-Gly-Pro-Arg($NO_2$)—$OCH_2CH_2CH_2CH_3$.HCl in 25% ethanol is applied to the neck, face, back, or any other part skin three times per day. The dosage should be adjusted to reach the health weight.

Example 120

HCl.H-Asn-Ala-Pro-Val-Ser-Ile-Pro-Gln-$OCH_2CH_3$ for the Treatment of Alzheimer's Disease 20 mg of H-Asn-Ala-Pro-Val-Ser-Ile-Pro-Gln-$OCH_2CH_3$HCl salt is dissolved in 0.5 ml of pure water. The solution is applied transdermally to the neck, face, or any part of the body twice everyday for the treatment of Alzheimer's disease.

Example 121

Minimum Inhibitory Concentrations (MICs) of Antimicrobials and HPCs of Antimicrobials Minimum inhibitory concentrations (MICs) of the antimicrobials and their HPCs were assessed according to Jennifer M. Andrews, Journal of Antimicrobial Chemotherapy 48, suppl. S1, 5-16 (2001). The results (Tables 21) showed that the HPCs of antimicrobials were able to overcome β-lactam resistance in methicillin-resistant *Staphylococcus aureus* (MRSA) according to Minimum inhibitory concentrations (MICs) and much better than their parent drug. The test compounds are: 6-phenoxyacetacetamidopenicillanic acid 1-piperidineethyl ester hydrochloride (penicillin V-PEE), penicillin V, 6-(2,6-dimethoxybenzamido)penicillinic acid 2-pyrrolidinemethyl ester hydrochloride (methicillin-PME), methicillin, 7-[[(2-acetylamino-4-thiazolyl)(methoxyimino)acetyl]amino]-8-oxo-5-thia-1-azabicyclo[4.2.0]oct-2-ene-2-carboxylic acid 2-diethylaminoethyl ester hydrochloride (ceftizoxime-DEE), and ceftizoxime). The HPCs showed much stronger anti-antimicrobial effects than their parent drugs.

TABLE 121

MICs (mg/L) of various antimicrobials and their HPCs to methicillin-resistant *Staphylococcus aureus* (MRSA)

| | Penicillin V | Penicillin V-PEE | Methicillin | Methicillin-PME | Ceftizoxime | Ceftizoxime-DEE |
|---|---|---|---|---|---|---|
| MIC (mg/L) | 1824 | 12 | 1156 | 19 | 986 | 2.5 |

Example 122

Glibornuridyl-N,N-dimethylaminoacetate.HCl for the Treatment of Diabetes

A. Preparation of Glibomuridyl-N,N-dimethylaminoacetate.HCl 367 g of glibornuride 1N-[[(3-hydroxy-4,7,7-trimethylbicyclo[2.2.1]hept-2-yl)amino]carbonyl]-4-methylbenzenesulfonamide and 120 ml of triethylamine is dissolved in ethyl acetate (2 lit). 150 g of N,N-dimethylaminoacetyl chloride is added into the reaction mixture. The mixture is stirred for 2 h. The mixture is washed with water (1×1 lit), 5% NaHCO$_3$ (1×1 lit), water (1×1 lit), 10% citric acid (1×1 lit), and water (3×1 lit). The solution is dried over sodium sulfate. After sodium sulfate is removed, 35 g of HCl gas is bubbled into the solution and the solid is collected by filtration and washed with ethyl acetate (3×).

B. Controlled Drug Releasing System 1 ml of 20% Glibornuridyl-N,N-dimethylaminoacetate.HCl in pure water (or 50% ethanol) is put into a reservoir, which can be wore around the arms, legs or any other part of the body and has a permeable bottom (the area is about 4 cm$^2$) facing the skin. By controlling the rate of release of the solution, this system enables glibornuridyl-N,N-dimethylaminoacetate.HCl to reach constantly optimal therapeutic blood levels to keep the blood glucose at optimal level.

Example 123

Atenolol for the Management of Hypertension 100 mg of Atenolol HCl salt is dissolved in 1 ml of pure water in a reservoir, which can be weared around the arms or legs and has a permeable bottom (the area is 4 cm$^2$) facing the skin. By controlling the rate of release of the solution, this system enables atenolol to reach constantly optimal therapeutic blood levels to keep the blood pressure at optimal level.

Example 124

Desogestrelyl-N,N-dimethylaminoacetate.HCl and ethinyl estradiolyl-N,N-dimethylaminoacetate.HCl for the Prevention of Pregnancy in Women 2 mg of desogestrelyl-N,N-dimethylaminoacetate.HCl and 0.4 mg of ethylnyl estradialyl-N,N-dimethylaminoacetate.HCl is mixed with polyethylene glycol to form a gel. This gel is loaded on a patch (about 3 cm$^2$) to deliver a constantly optimal therapeutic blood level of desogestrel and ethinyl estradiol for the prevention of pregnancy in women.

Example 125

Application of HPC of NSAIA in Treatment of ALS

Without being bound by a mechanism, the pathogenesis of cell death in amyotrophic lateral sclerosis (ALS) may involve glutamate-mediated excitotoxicity, oxidative damage, and apoptosis. Cyclooxygenase-2, present in spinal neurons and astrocytes, catalyzes the synthesis of prostaglandin E2. Prostaglandin E2 stimulates glutamate release from astrocytes, whereas cyclooxygenase-2 also plays a key role in the production of pro-inflammatory cytokines, reactive oxygen species, and free radicals. Treatment with a selective cyclooxygenase-2 inhibitor, celecoxib, markedly inhibited production of prostaglandin E2 in the spinal cords of ALS mice. Celecoxib treatment significantly delayed the onset of weakness and weight loss and prolonged survival by 25%. Spinal cords of treated ALS mice showed significant preservation of spinal neurons and diminished astrogliosis and microglial activation (Merit. E. Cudkowicz, et al., Annals of neurology, 52, 771-778, 2002). These results suggest that cyclooxygenase-2 inhibition may benefit ALS patients.

HPCs of NSAIAs in the present disclosure can penetrate skin and nerve cell membrane barriers in very high rates and can be administered transdermally without hurting the GI tract, so these HPC are promising agents for the treatment of amyotrophic lateral sclerosis (ALS), oculopharyngeal muscular dystrophy (OPMD), myotonic dystrophy (MD), Duchenne muscular dystrophy (DMD), polymyositis (PM), dermatomyositis (DM), inclusion body myositis (IBM), and other muscle disorders.

Example 126

Treatment of Gray Hairs or White Hairs

About 0.3 ml of 8% diethylaminoethyl acetylsalicylate.HCl salt in 25% ethanol was sprayed to the skin under hairs or around the hairs twice per day. The treatment is continued until the color of hairs change back to the natural color.

What is claimed is:

1. A compound of Structure P4-3:

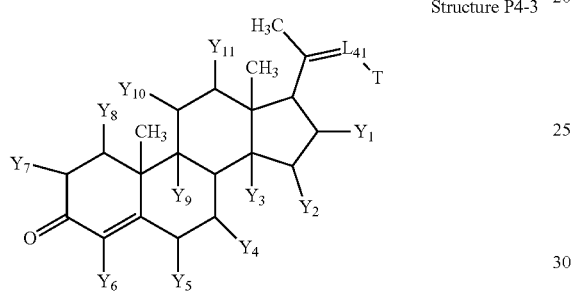

Structure P4-3 wherein:

T is selected from the group consisting of

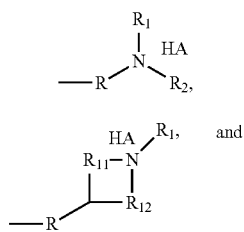

T-1

T-2

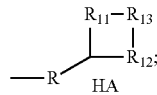

T-3

$L_{41}$ is selected from the group consisting of N and $N\text{-}L_3$;

wherein $L_3$ is selected from the group consisting of $C_1\text{-}C_{12}$ alkylene, $C_3\text{-}C_{12}$ cycloalkylene, $C_3\text{-}C_{12}$ heterocycloalkylene, arylene, heteroarylene, $C_1\text{-}C_{12}$ alkoxylene, $C_1\text{-}C_{12}$ alkylenethio, $C_1\text{-}C_{12}$ perfluoroalkylene, and $C_1\text{-}C_{12}$ alkylene halide;

each $Y1\text{-}Y_{11}$ is independently selected from the group consisting of H, Cl, F, Br, I, CN, $CH_3C\!\!=\!\!C$, $CF_3$, $CH_3$, $CF_3CF_2$, $CH_3CH_2$, $CH_3CH_2CH_2$, $(CH_3)_2CH$, $(CH_3)_2CHCH_2$, $CH_3CH_2CH(CH_3)$, $(CH_3)_3C$, $C_5H11$, $CH_3CO$, $CH_3CH_2CO$, $CH_3OC(\!\!=\!\!O)$, $CH_3CH_2OC(\!\!=\!\!O)$, $CH_3COO$, $CH_3COS$, $CH_3O$, HO, $CF_3CH_2SCH_2$, $CHCl_2$, $CH_3S$, HS, $CH_3OCH_2CH_2$, $C_2H_5OCONH$, $CH_3OCONH$, $CH_3SO_2$, $CH_3SO$, $NH_2SO_2$, $C_6H_5CH_2$, $NH_2$, cyclobutyl, cyclopropyl, 4-chlorophenyl, 4-fluorophenyl, $CH_2\!\!=\!\!CH$, $CH_2\!\!=\!\!CHCH_2$, $CH_3CH\!\!=\!\!CH$, and $NO_2$;

R is selected from the group consisting of $C_1\text{-}C_{12}$ alkylene, $C_3\text{-}C_{12}$ cycloalkylene, $C_3\text{-}C_{12}$ heterocycloalkylene, arylene, heteroarylene, $C_1\text{-}C_{12}$ alkoxylene, $C_1\text{-}C_{12}$ alkylenethio, $C_1\text{-}C_{12}$ perfluoroalkylene, and $C_1\text{-}C_{12}$ alkylene halide;

each $R_1$ and $R_2$ is independently selected from the group consisting of H, $C_1\text{-}C_{12}$ alkyl, $C_3\text{-}C_{12}$ cycloalkyl, $C_3\text{-}C_{12}$ heterocycloalkyl, aryl, heteroaryl, $C_1\text{-}C_{12}$ alkoxyl, $C_1\text{-}C_{12}$ alkylthio, $C_1\text{-}C_{12}$ alkylamino, $C_1\text{-}C_{12}$ perfluoroalkyl, and $C_1\text{-}C_{12}$ alkyl halide;

each $R_{11}\text{-}R_{13}$ is independently selected from the group consisting of nothing, $C_1\text{-}C_{12}$ alkylene, $C_3\text{-}C_{12}$ cycloalkylene, $C_3\text{-}C_{12}$ heterocycloalkylene, arylene, heteroarylene, $C_1\text{-}C_{12}$ alkoxylene, $C_1\text{-}C_{12}$ alkylenethio, $C_1\text{-}C_{12}$ alkyleneamino, $C_1\text{-}C_{12}$ perfluoroalkylene, and $C_1\text{-}C_{12}$ alkylene halide; and HA is a pharmaceutically acceptable acid.

2. The compound according to claim 1, wherein T is T-1.
3. The compound according to claim 1, wherein T is T-2.
4. The compound according to claim 1, wherein T is T-4.
5. A composition comprising the compound according to claim 1 and a pharmaceutically acceptable carrier.

* * * * *